United States Patent
Zischinsky et al.

(10) Patent No.: US 8,927,534 B2
(45) Date of Patent: Jan. 6, 2015

(54) COMPOUNDS FOR THE INHIBITION OF INTEGRINS AND USE THEREOF

(75) Inventors: Gunther Zischinsky, Berlin (DE); Roland Stragies, Berlin (DE); Frank Osterkamp, Berlin (DE); Dirk Scharn, Berlin (DE); Gerd Hummel, Berlin (DE); Holger Kalkhof, Berlin (DE); Grit Zahn, Berlin (DE); Doerte Vossmeyer, Berlin (DE); Claudia Christner-Albrecht, Berlin (DE); Ulrich Reineke, Berlin (DE)

(73) Assignee: Shire Orphan Therapies GmbH, Berlin (DE)

( * ) Notice: Subject to any disclaimer, the term of this patent is extended or adjusted under 35 U.S.C. 154(b) by 1472 days.

(21) Appl. No.: 12/162,798

(22) PCT Filed: Jan. 31, 2007

(86) PCT No.: PCT/EP2007/000832
§ 371 (c)(1),
(2), (4) Date: Jul. 31, 2008

(87) PCT Pub. No.: WO2007/088041
PCT Pub. Date: Aug. 9, 2007

(65) Prior Publication Data
US 2009/0104116 A1 Apr. 23, 2009

(30) Foreign Application Priority Data
Jan. 31, 2006 (EP) .................................... 06002005

(51) Int. Cl.
*C07D 401/12* (2006.01)
*C07D 471/04* (2006.01)

(52) U.S. Cl.
CPC ............ *C07D 401/12* (2013.01); *C07D 471/04* (2013.01)
USPC ..................... 514/210.2; 514/228.8; 514/278; 514/300; 514/309; 514/326; 514/331; 514/340; 514/343; 544/96; 544/321; 546/15; 546/16; 546/122; 546/141; 546/194; 546/199; 546/210; 546/268.1; 546/278.4; 546/283.4

(58) Field of Classification Search
None
See application file for complete search history.

(56) References Cited

U.S. PATENT DOCUMENTS

| | | | |
|---|---|---|---|
| 6,388,084 B1 | 5/2002 | Kaplan et al. | |
| 6,420,558 B1 * | 7/2002 | Ishikawa et al. | ............... 544/330 |
| 6,521,666 B1 | 2/2003 | Sircar et al. | |
| 2003/0220268 A1 | 11/2003 | Makino et al. | |
| 2004/0106622 A1 | 6/2004 | Morie et al. | |
| 2005/0192279 A1 | 9/2005 | Barbay et al. | |
| 2006/0223836 A1 | 10/2006 | Makino et al. | |
| 2007/0043113 A1 | 2/2007 | Ward et al. | |
| 2009/0203745 A1 | 8/2009 | Zischinsky et al. | |

FOREIGN PATENT DOCUMENTS

| | | | | |
|---|---|---|---|---|
| EP | 1 288 205 A1 | 3/2003 | | |
| EP | 1 371 646 A1 | 12/2003 | | |
| WO | WO 99/20606 | * 4/1999 | ............ | C07D 211/00 |
| WO | WO 03/089410 | * 10/2003 | .......... | C07D 207/327 |
| WO | WO 03/089410 A1 | 10/2003 | | |
| WO | WO 2005/061440 | 7/2005 | | |
| WO | WO 2005/090329 A1 | 9/2005 | | |
| WO | WO 2007/060408 A2 | 5/2007 | | |
| WO | WO 2007/060409 A1 | 5/2007 | | |
| WO | WO 2007/131764 | 11/2007 | | |

OTHER PUBLICATIONS

Golub et al. Science (1999), vol. 286, pp. 531-536.*
Huff, Joel R. HIV Protease: A novel chemotherapeutic target for AIDS. Journal of Medicinal Chemistry, 34(8) (1991), 2305-2314.*
Lala et al. Cancer and Metastasis Reviews (1998), 17(1), 91-106.*
Morissette et al. Advanced Drug Delivery Reviews 2004, 56, 275-300.*
Vippagunta et al. Advanced Drug Delivery Reviews 2001, 48, 3-26, abstract.*
Houtman, J., J.,FASEB, Breakthroughs in Bioscience, Angiogenesis, 2010.*
Starkov et al, 2005, Biochemistry (Mosc.) 70, 200-214.*
Ex parte Quayle Office Action for U.S. Appl. No. 12/300,530 (listed on SB/08 as US 2009/0203745), mailed Mar. 23, 2012.
International Search Report for International Application PCT/EP2007/000832, dated Jun. 27, 2007.
International Search Report for International Application PCT/EP2007/004283, dated Oct. 18, 2007.
Non-Final Office Action for U.S. Appl. No. 12/300,530 (listed on SB/08 as US 2009/0203745), mailed Aug. 30, 2011.
Notice of Allowance for U.S. Appl. No. 12/300,530 (listed on SB/08 as US 2009/0203745), mailed Jun. 21, 2012.

* cited by examiner

*Primary Examiner* — Alicia L Otton
(74) *Attorney, Agent, or Firm* — Lisa M. Treannie, Esq.; Morse, Barnes-Brown & Pendleton, P.C.

(57) ABSTRACT

The present invention is related to a compound of formula (I), wherein A is a nonaromatic heterocyclic ring, Ar is either absent or phenylene; Ψ is a radical of formula (II), $R_2$ is a hydrophobic moiety; and G is a radical containing one or more moieties selected from the group consisting of NH, OH and a basic moiety. The compounds are inhibitors of integrins, especially antagonists of the fibronectin receptor alpha5beta1, useful as anti-angiogenic agents.

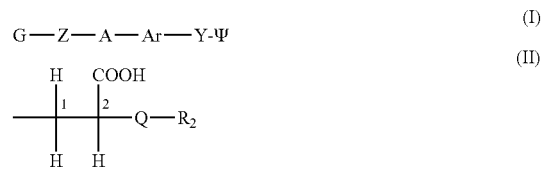

4 Claims, 11 Drawing Sheets

$X = B(OH)_2, Cl, Br, I, OTf$ $X = I, Br, Cl, OTos$

COMPOUNDS FOR THE INHIBITION OF INTEGRINS AND USE THEREOF

CROSS REFERENCE TO RELATED APPLICATION

This application is a 35 U.S.C. 371 National Phase Entry Application from PCT/EP2007/000832, filed Jan. 31, 2007, which claims the benefit of European Patent Application No. 06002005.4 filed on Jan. 31, 2006, the disclosure of which is incorporated herein in its entirety by reference.

The present invention is related to new compounds and the use of said compounds for the manufacture of medicaments and diagnostics.

Angiogenesis, also called neovascularization, is a fundamental process whereby new blood vessels are formed. Under normal physiological conditions angiogenesis is highly regulated and essential for reproduction, embryonic development and wound healing (Folkman and Shing, 1992, J. Biol. Chem., 267, 10931). However, angiogenesis also occurs under various pathological conditions including ocular neovascularization such as in diabetic retinopathy, age related macular degeneration and various other eye diseases, inflammatory disorders like rheumatoid arthritis, tumor growth and metastasis (Folkman and Shing, 1992, J. Biol. Chem., 267, 10931).

Angiogenesis is a highly regulated process which occurs in response to various proangiogenic stimuli like growth factors, cytokines and other physiological molecules as well as to other factors like hypoxia and low pH (Folkman and Shing, 1992, J. Biol. Chem., 267, 10931). The angiogenic cascade for development of new blood vessels requires the cooperation of a variety of molecules that regulate necessary cellular processes such as extracellular matrix (ECM) remodelling, invasion, migration, proliferation, differentiation and tube formation (Brooks, 1996, Eur. J. Cancer, 32A, 2423). After an initiation phase, proangiogenic molecules like VEGF, bFGF, PDGF and others activate endothelial cells via stimulation of their cell surface receptors such as, e.g., VEGFR2-Flk1/KDR. These activated cells undergo a process of cellular proliferation, elevated expression of cell adhesion molecules, increased secretion of proteolytic enzymes and increased cellular migration and invasion. A number of distinct molecules are involved to promote proliferation and invasion, including members of the integrin, selectin and immunoglobulin gene super family for adhesion as well as proteolytic enzymes such as matrix metalloproteinases and serine proteinases for degrading the ECM (Brooks, 1996, Eur. J. Cancer, 32A, 2423). Finally, a complex cascade of biochemical signals derived from cell surface receptors interacting with ECM components and soluble factors is triggered, leading to lumen formation and differentiation into mature blood vessels.

Inhibition of different molecules involved in the angiogenic cascade has been shown to prevent angiogenesis and results in efficacious treatment of neovascular diseases in animal models and clinical studies (Madhusudan, 2002, Curr. Op. Pharm., 2, 403; Folkman, 2001, Thromb Haemost, 86, 23; Eyetech Study Group, 2003, Opthalmology, 110, 979; Ferrara, 2002, Semin Oncol. 6 Suppl 16, 10) for cancer and age related macular degeneration (AMD). Most of these angiogenic inhibitors are directed towards blocking the initial growth factor mediated activation step induced by VEGF or PDGF. These approaches target only one molecule or a small set out of the multiple set of pro-angiogenic stimuli. However, angiogenesis takes place in response to various growth factors such as VEGF, bFGF, PDGF and others (Folkman and Shing, 1992, J. Biol. Chem., 267, 10931). Therefore, a more general approach for inhibiting angiogenesis based on interference with this whole variety of stimuli would be more beneficial.

Inhibition of cell adhesion to the ECM, the fundamental step for activation, survival, targeting and migration of activated endothelial cells (EC), is a promising target mechanism for anti-angiogenesis. Most of these interactions are mediated by integrins, a family of multifunctional cell adhesion receptors.

Members of the integrin family are non-covalently associated alpha/beta heterodimers that mediate cell-cell, cell-extracellular matrix and cell-pathogene interactions. These type I transmembrane proteins are expressed on a variety of cells and require bivalent cations for their physiological function. Until now, 19 different integrin alpha subunits and 8 different beta subunits are known that combine to form at least 25 different alpha/beta heterodimers with different ligand specificity. The ligands for the extracellular domain of many integrins are the proteins of the extracellular matrix, whereby mostly a consensus motif with the amino acid sequence RGD (arginine-glycine-aspartate) is recognized. The intracellular domains of the integrins are either directly or indirectly connected to intracellular components such as kinases and the cytoskeleton. Integrins serve as bidirectional signalling receptors, whereupon protein activities and gene expression are changed in response to ligand binding to the extracellular integrin domain, which is also referred to as outside-in signalling. On the other hand, the affinity of the integrins is modulated in response to intracellular changes such as binding of proteins to the intracellular domain of the integrin, which is referred to as inside-out signalling (Humphries, 2000, Biochem. Soc. Trans., 28, 311; Hynes, 2002, Cell 110, 673).

A multitude of studies on the integrin pattern on activated endothelial cells, mice gene knockouts and inhibition studies in angiogenic animal models with antibodies, peptides and small molecules provided information about the integrins and ECM proteins involved in critical steps of angiogenesis (Brooks, 1994, Science, 264, 569; Brooks, 1996, Eur. J. Cancer, 32A, 2423; Mousa, 2002, Curr. Opin. Chem. Biol, 6, 534; Hynes, 2002, Cell, 110, 673; Hynes, 2002, Nature Medicine, 8, 918; Kim, 2000, Am. J. Path., 156, 1345). Thereby it becomes clear that above all the vitronectin receptors alphavbeta3, alphavbeta5 and the fibronectin receptor alpha5beta1 play a critical role in angiogenesis. Gene deletion studies of integrins attributed essential roles to almost all integrins. The deletion driven defects suggest widespread contributions of the various integrins to both the maintenance of tissue integrity and the promotion of cellular migration. However, only the deletion of alpha5 and beta1 and its ligand fibronectin, leads to embryogenic lethality with major vascular defects, whereas ablation of alphav, beta3 and beta5 genes fail to block angiogenesis and in some cases even enhance angiogenesis (Hynes, 2002, Nature Medicine, 8, 918). Also, alpha5beta1 is poorly expressed in quiescent endothelium but strongly expressed in proliferating endothelium. Its expression is significantly upregulated on blood vessels in human tumors and after stimulation with growth factors (Kim, 2000, Am. J. Path, 156, 1345; Collo, 1999, J. Cell Sc., 112, 569). The alpha5beta1 fibronectin interaction facilitates the survival of entdothelial cells in vivo and in vitro (Kim, 2002, J. Clin. Invest., 110, 933; Kim, 2000, J. Biol. Chem., 275, 33920). Additionally, experimental studies established a fundamental role of alpha5beta1 in the regulation of alphavbeta3 mediated angiogenesis (Kim, 2000, J. Biol. Chem., 275, 33920).

Only alpha5beta1 genetic and pharmacological data are consistent and confirm the fundamental role of alpha5beta1 for angiogenesis. Therefore, alpha5beta1 is a preferred target for the development of anti-angiogenic drugs. Consequently, antagonists of integrin alpha5beta1 have a great therapeutic potential for the treatment of neovascularization in tumors, in the eye and of inflammatory processes. Angiogenesis induced by multiple growth factors in several models was blocked with alpha5beta1 antagonists (Varner, 1998, 98 (suppl), 1-795, 4166; Kim, 2000, Am. J. Path, 156, 1345). Additionally, these antagonists also inhibit tumor angiogenesis, thereby causing regression of human tumors in animal models (Kim, 2000, Am. J. Path, 156, 1345)

In the light of these scientific findings on the importance of integrins in angiogenesis, serious efforts have been undertaken to develop respective inhibitors.

There are at least three major classes of reagents developed as integrin, especially alpha5beta1 integrin antagonists. These include antibodies such as monoclonal antibodies, polyclonal antibodies, and antibody fragments (Kim, 2000, Am. J. Path., 156, 1345, WO2005/092073, WO2004/056308), natural peptides such as venom derived "disintegrin" peptides (Marcinkiewicz, 1999, Biochemistry, 38, 13302), synthetic peptides (Koivunen, 1994, J. Biol. Chem., 124, 373) and non-peptidic small molecules such as spiro compounds (WO97/33887).

Although these compounds are in principle suitable as alpha5beta1 antagonists, they have some drawbacks. For example, antibodies are complex biological molecules with usually high activity and specificity for the targeted molecule. But the non-human source of antibodies could cause an immune response during later treatment of humans or the molecules have to be humanized by special additional procedures. Additionally, the human immune system can develop antibodies against the antigen binding region of the therapeutic antibody (anti-idiotypic antibodies). The development of an immune response against the therapeutic antibody could cause immunological problems in humans and could decrease or inhibit the efficacy of the antibody. Moreover the production of antibodies requires special treatment to avoid any contaminants such as prions or other proteinaceous material, which might have a detrimental effect upon application to a patient. Additionally, the high molecular weight of these molecules constricts the possible administration routes of the medicament in the treatment of patients, usually through the intravenous route. Due to the high molecular weight the tissue penetration may be limited which can cause unsufficiant drug delivery. This could be a drawback for the treatment of certain diseases such as solid tumors due to the increased interstitial fluid pressure, or fibrotic disorders due to the dense extracellular matrix within the affected tissue.

There are several peptidic alpha5beta1 inhibitors known that are based on the RGD-sequence derived from the natural ligand, However, these inhibitors show mostly no or only limited specificity against other integrins. Furthermore, peptidic molecules are generally disadvantageous concerning their application as a medicament. One aspect thereof resides in the limited stability against naturally occurring proteases. Another one is the limitation of possible administration routes due to their hydrophilic nature.

One fibronectin derived peptide (U.S. Pat. No. 6,001,965) proposed to act via alpha5beta1, showed anti-metastatic activity in mouse tumor models (Stoeltzing, 2003, Int. J. Cancer 104, 496) and inhibition of cell invasion (Livant, 2000, Cancer Res., 60, 309), but no direct inhibition of alpha5beta1-fibronectin interaction could be shown. The peptide only binds to alpha5beta1 without effecting the fibronectin binding, and to alphavbeta3 integrin (Cianfrocca, conference talk at 6th International Symposium on Anti-Angiogenic Agents, San Diego, 30 Jan.-1 Feb. 2004). Therefore, the molecular mechanism of action and the specificity remain unclear and shed some further doubt on the usage of peptides derived from this postulated second, so called synergistic, integrin binding site in fibronectin as inhibitors for alpha5beta1.

The small molecules synthesized in the art are, e.g., described in the international patent application WO 97/33887 which discloses compounds comprising a spiro moiety as a core element which is presenting three moieties obviously needed for integrin binding. However, due to the spiro moiety contained in these compounds they are difficult to synthesize and, owing to the three moieties attached to the core, they provide relatively high molecular weights.

The small molecules disclosed in international patent application WO 2005/090329 are comprising a cyclic core structure that is also bearing three moieties necessary for exhaustive interaction with the integrin.

International patent application WO 95/32710 discloses the use of a benzyl residue as a core element. These compounds, however, seem to lack the required specificity for an integrin which is particularly relevant in the pathological mechanism of the aforementioned diseases.

Thus, the objective of the present invention is to provide chemical compounds which are suitable to interact with integrins, more particularly specifically interact with certain integrin species such as integrin alpha5beta1. A further objective of the present invention is to provide antagonists for alpha5beta1, which preferably show enhanced activity, stability, selectivity, and synthetic accessibility. A further objective of the present invention is to provide new modes of treatment for diseases, preferably for diseases involving integrin mediated effects and processes.

The problem underlying the present invention is solved in a first aspect by a compound of formula (I), which is preferably a first embodiment,

wherein

A is a radical selected from the group comprising nonaromatic heterocyclic and homocyclic ring systems;

Ar is a radical which is either absent or present, whereby
 if Ar is present, Ar is selected from the group comprising 3- to 9-membered rings, or
 if Ar is present, Ar is a polycyclic ring system selected from the group comprising 4,4-membered rings, 4,5-membered rings, 4,6-membered rings, 5,5-membered rings, 5,6-membered rings, 6,6-membered rings, 6,7-membered rings, 7,7-membered rings, 6,5,6-membered rings, 6,6,6-membered rings, 6,7,6-membered rings;

Z and Y are radicals individually and independently selected from the group comprising $(CH_2)_n$-E-$(CH_2)_m$-L-$(CH_2)_k$ and $(CH_2)_m$-L-$(CH_2)_k$, wherein
 E is a radical which is either absent or present, whereby if E is present, E is selected from the group comprising O, S, NH, $NR^a$, CO, SO, $SO_2$, substituted ethylene and acetylene;
 L is a radical which is either absent or present, whereby if L is present, L is individually and independently selected from the group comprising O, S, NH, $NR^b$, CO, SO, $SO_2$, substituted ethylene and acetylene; and
 k, m and n are individually and independently 0, 1, 2 or 3;

Ψ is a radical of formula (II)

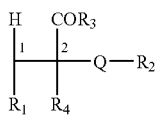

wherein

Q is a radical selected from the group comprising a direct bond, C=O, C=S, O, S, CR$^a$R$^b$, NR$^a$—NR$^b$, N=N, CR$^a$=N, N=CR$^a$, (C=O)—O, O—(C=O), SO$_2$, NR$^a$, (C=O)—NR$^a$, NR$^a$—(C=O)—NR$^b$, NR$^c$—(C=O), O—(C=O)—NR$^c$, NR$^c$—(C=O)—O, NR$^c$—(C=S), (C=S)—NR$^c$, NR$^c$—(C=S)—NR$^d$, NR$^c$—SO$_2$ and SO$_2$—NR$^c$.

R$_1$, R$^a$, R$^b$, R$^c$ and R$^d$ are radicals which are individually and independently selected from the group comprising H, alkyl, substituted alkyl, cycloalkyl, substituted cycloalkyl, heterocycloyl, substituted heterocycloyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxy, alkyloxyalkyl, substituted alkyloxyalkyl, alkyloxycycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl and substituted alkylthiocycloalkyl, hydroxy, substituted hydroxy, oxo, thio, substituted thio, aminocarbonyl, substituted aminocarbonyl, formyl, substituted formyl, thioformyl, substituted thioformyl, amino, substituted amino, hydroxyl, substituted hydroxyl, mercapto, substituted mercapto, hydrazino, substituted hydrazino, diazene, substituted diazene, imine, substituted imine, amidino, substituted amidino, iminomethylamino, substituted iminomethylamino, ureido, substituted ureido, formylamino, substituted formylamino, aminocarbonyloxy, substituted aminocarbonyloxy, hydroxycarbonylamino, substituted hydroxycarbonylamino, hydroxycarbonyl, substituted hydroxycarbonyl, formyloxy, substituted formyloxy, thioformylamino, substituted thioformylamino, aminothiocarbonyl, substituted aminothiocarbonyl, thioureido, substituted thioureido, sulfonyl, substituted sulfonyl, sulfonamino, substituted sulfonamino, aminosulfonyl, substituted aminosulfonyl, cyano, halogen;

R$_2$ is a hydrophobic moiety;

R$_3$ is a radical selected from the group comprising OH, C1-C8alkyloxy and aryl C0-C6alkyloxy;

R$_4$ is a radical selected from the group comprising hydrogen, halogen and C1-C4alkyl; and G is a radical containing one or more moieties, whereby such moiety is selected from the group comprising NH, OH and a basic moiety.

In an embodiment, which is preferably a second embodiment, which is preferably a further embodiment of the first embodiment of the first aspect, any of R$_1$, R$^a$, R$^b$, R$^c$ and R$^d$ is a radical individually and independently selected from the group comprising hydrogen, alkyl, substituted alkyl, halogen, cyano, hydroxy, alkyloxy, substituted alkyloxy, oxo, aryl, substituted aryl, arylalkyl, substituted arylalkyl, amino, substituted amino.

In an embodiment, which is preferably a third embodiment, which is preferably a further embodiment of the first and second embodiment of the first aspect any of R$_1$, R$^a$, R$^b$, R$^c$ and R$^d$ is a radical individually and independently selected from the group comprising hydrogen, fluoro, chloro, bromo, methyl, ethyl, propyl, tert-butyl, phenyl, benzyl, hydroxyl, methoxy, oxo, amino, acetylamino, cyano.

In an embodiment, which is preferably a fourth embodiment, which is preferably a further embodiment of the first to the third embodiment, preferably of the second and third embodiment of the first aspect, Ar is either absent or present, whereby if Ar is present, Ar is an aromatic mono- or bicyclic ring system comprising ring atoms whereby the ring system contains 0, 1, 2, 3 or 4 heteroatoms, whereby the heteroatom(s) is/are individually and independently selected from the group comprising N, O and S and if a or the heteroatom of the ring system is S, each S is optionally individually and independently substituted with 0, 1 or 2 oxygen atoms, and one or several of the ring atoms is/are optionally individually and independently substituted with a substituent, whereby the substituent is R$_5$ and whereby R$_5$ is individually and independently selected from the group comprising H, benzyl, substituted benzyl, phenyl, substituted phenyl, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, cycloalkylalkyl, substituted cycloalkylalkyl, heterocyclylalkyl, substituted heterocyclylalkyl, alkyloxyalkyl, substituted alkyloxyalkyl, alkyloxycycloalkyl, substituted alkyloxycycloalkyl, alkyloxyheterocyclyl, substituted alkyloxyheterocyclyl, alkyloxyaryl, substituted alkyloxyaryl, alkyloxyheteroaryl, substituted alkyloxyheteroaryl, alkylthioalkyl, substituted alkylthioalkyl, alkylthiocycloalkyl and substituted alkylthiocycloalkyl, (C=O)—NHR$^a$, (C=O)R$^a$, (C=S)R$^a$, NHR$^a$, OR$^a$, SR$^a$, CH$_2$R$^a$, CR$^a$R$^b$R$^c$NH—NHR$^a$, N=NR$^a$, CH=NR$^a$, N=CHR$^a$, NH—(C=O)—NHR$^a$, NH—(C=O)R$^a$, O—(C=O)—NHR$^a$, NH—(C=O)—OR$^a$, (C=O)—OR$^a$, O—(C=O)R$^a$, NH—(C=S)R$^a$, (C=S)—NHR$^a$, NH—(C=S)—NHR$^a$, SO$_2$R$^a$, NH—SO$_2$R$^a$, SO$_2$—NHR$^a$, NR$^c$R$^a$, (C=O)—NR$^c$R$^a$, NR$^c$R$^a$, NR$^c$—(C=O)—NHR$^a$, NH—(C=O)—NR$^c$R$^a$, NR$^c$—(C=O)—NR$^d$R$^a$, NR$^c$—(C=O)R$^a$, O—(C=O)—NR$^c$R$^a$, NR$^c$—(C=O)—OR$^a$, NR$^c$—(C=S)R$^a$, (C=S)—NR$^c$R$^a$, NR$^c$—(C=S)—NHR$^a$, NH—(C=S)—NR$^c$R$^a$, NR$^c$—(C=S)—NR$^d$R$^a$, NR$^c$—SO$_2$R$^a$, SO$_2$—NR$^c$R$^a$, SCHF$_2$, OCHF$_2$, CN, halogen, CF$_3$, CCl$_3$ and OCF$_3$, whereby any of R$^a$, R$^b$, R$^c$ and R$^d$ is as defined in any of the first to third embodiment.

In an embodiment, which is preferably a fifth embodiment, which is preferably a further embodiment of the fourth embodiment of the first aspect, R$_5$ is selected from the group comprising hydrogen, alkyl, aryl, arylalkyl, halogen, hydroxy, amino, alkoxy, alkylamino, dialkylamino, alkylcarbonyl, alkylaminocarbonyl, dialkylaminocarbonyl, alkyloxycarbonyl, cylcoalkyl, alkylcarbonylamino, aminocarbonyl, cyano and alkylthio.

In an embodiment, which is preferably a sixth embodiment, which is preferably a further embodiment of the fifth embodiment of the first aspect, $R_5$ is selected from the group comprising hydrogen, fluoro, chloro, bromo, cyano, amino, methylamino, dimethylamino, methoxycarbonyl, aminocarbonyl, methylaminocarbonyl, dimethylaminocarbonyl, acetylamino, phenyl, benzyl, methyl, ethyl, propyl, tert-butyl, hydroxy, methoxy, trifluoromethyl, trifluoromethyloxy, difluoromethyloxy, acetyl, and methylthio.

In an embodiment, which is preferably a seventh embodiment, which is preferably a further embodiment of the sixth embodiment of the first aspect, $R_5$ is hydrogen, fluoro, chloro, cyano, methylamino, dimethylamino, methylaminocarbonyl, acetylamino, phenyl, benzyl, methyl, tert-butyl, hydroxy, methoxy, trifluoromethyl.

In an embodiment, which is preferably an eighth embodiment, which is preferably a further embodiment of the first to seventh embodiment, preferably of the fourth to seventh embodiment, more preferably of the fifth to the seventh embodiment and even more preferably of the sixth and the seventh embodiment of the first aspect, Ar is either absent or present, whereby
    if Ar is present, Ar is a 5- or 6-membered aromatic ring or a condensed 5,5-, 5,6- or 6,6-ring system comprising ring atoms represented by formulas (III) to (VII)

 (III)

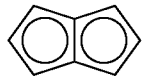 (IV)

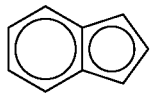 (V)

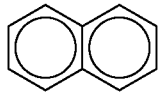 (VI)

 (VII)

whereby
    individually and independently in any of formulas (III) to (VII), 0, 1, 2, 3 or 4 ring carbon atoms are hetero atoms which are individually and independently selected from the group comprising N, O and S;
    one or several of the ring atoms is/are optionally individually and independently substituted with a substituent, whereby if substituted, the substituent is $R_5$; and
    if a or the hetero atom is S, each S is optionally substituted with 0, 1 or 2 oxygen atoms.

In an embodiment, which is preferably a nineth embodiment, which is preferably a further embodiment of the first to the eighth embodiment, preferably of the eighth embodiment of the first aspect, Ar is a radical selected from the group comprising furyl, thienyl, pyrrolyl, pyrazolyl, imidazolyl, 1,2,3-triazolyl, 1,2,4-triazolyl, oxazolyl, isoxazolyl, thiazolyl, isothiazolyl, phenyl, pyridyl, pyrimidinyl, indolyl, indazolyl, benzotriazolyl, benzooxazolyl, benzoisoxazolyl, benzothiophenyl, benzothiazolyl, benzoisothiazolyl and naphthyl,
    whereby one or several of the ring atoms is/are optionally individually and independently substituted with a substituent, whereby if substituted, the substituent is $R_5$; and
    whereby the 6-membered rings in the 5,6- and 6,6-membered ring systems optionally contain 0, 1 or 2 N-atoms.

In an embodiment, which is preferably a tenth embodiment, which is preferably a further embodiment of the nineth embodiment of the first aspect, Ar is a radical selected from the group comprising phenyl, pyridyl and thienyl,
    whereby one or several of the ring atoms is/are optionally individually and independently substituted with $R_5$;
    whereby $R_5$ is defined as in the fifth to the seventh embodiment, preferably the sixth embodiment and more preferably the seventh embodiment.

In an embodiment, which is preferably an eleventh embodiment, which is preferably a further embodiment of the tenth embodiment of the first aspect, Ar is phenyl,
    whereby A and Y are connected to Ar in the positions para to each other.

In an embodiment, which is preferably a twelfth embodiment, which is preferably a further embodiment of the first to the eleventh embodiment, preferably of the tenth or the eleventh embodiment, more preferably of the eleventh embodiment of the first aspect, A is a saturated or unsaturated heterocyclic or homocyclic 3- to 9-membered nonaromatic ring of formula (VIII)

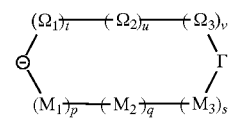 (VIII)

wherein
    $\Theta$ and $\Gamma$ are each a radical and independently and individually selected from the group comprising C, $CR^a$ and N;
    $M_1$, $M_2$, $M_3$, $\Omega_1$, $\Omega_2$ and $\Omega_3$ are each a radical and independently and individually selected from the group comprising $CR^aR^b$, $CR^a$, C, O, N, $NR^a$, CO, S, SO and $SO_2$;
        whereby any of $R^a$ and $R^b$ is as defined in the first embodiment, more preferably as defined in the second embodiment and even more preferably as defined in the third embodiment;
    p, q, s, t, u and v are independently and individually selected from 0, 1, 2 or 3;
    bonds within the ring may be either single or double bonds, provided that each combination of bonds results in a radical that is chemically stable at room temperature and is a nonaromatic system; and
    A is connected to Z and Ar via $\Theta$ and $\Gamma$.

In an embodiment, which is preferably a thirteenth embodiment, which is preferably a further embodiment of the twelfth embodiment of the first aspect, A is a saturated or unsaturated heterocyclic 3- to 9-membered nonaromatic ring of formula (IX) containing at least one N-atom

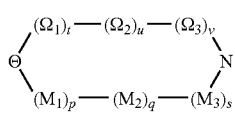
(IX)

wherein
Θ is a radical and independently and individually selected from the group comprising C, CR$^a$ and N; and
A is connected to Z via Θ and to Ar at the or a ring N-atom.

In an embodiment, which is preferably a fourteenth embodiment, which is preferably a further embodiment of the thirteenth embodiment of the first aspect,
A is a heterocyclic 3- to 7-membered ring comprising ring atoms and is selected from the group consisting of formulas (X)-(XIV)

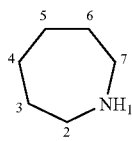
(X)

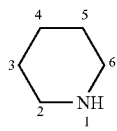
(XI)

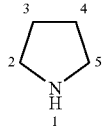
(XII)

(XIII)

(XIV)

whereby
in any of formulas (X) to (XIV) individually and independently 0, 1, 2 or 3 ring carbon atoms are replaced by a heteroatom or moiety individually and independently selected from the group comprising N, O and S, SO, SO$_2$, CO;
bonds within formulas (X) to (XIV) may be either single or double bonds, provided that each combination of bonds results in a radical that is chemically stable at room temperature and is a nonaromatic system;
any of the ring atoms is individually and independently substituted with 0, 1 or 2 R$^a$ as defined in the first embodiment, preferably in the second embodiment and even more preferably in the third embodiment;
A is connected to Ar at the N-atom;
A is connected to Z via ring atom number 3 in formulas (XII) to (XIV); and
A is connected to Z via ring atom number 3 or number 4 in formulas (X) and (XI).

In an embodiment, which is preferably a fifteenth embodiment, which is preferably a further embodiment of the fourteenth embodiment of the first aspect,
A is
(a) a 3- or 4-membered nitrogen containing ring selected from the group consisting of aziridine, azetidin and azetidin-2-one, whereby
ring atoms are individually and independently substituted with 0, 1 or 2 R$^a$; and
A is connected to Ar at the or a N-atom;
(b) a 5-membered nitrogen containing ring selected from the group consisting of pyrrolidine, pyrrolidin-2-one, pyrrolidin-2-thione, pyrrolidin-2,5-dione, imidazolidin-2-one, imidazolidin-2-thione, oxazolidin-2-one, oxazolidin-2-thione, thiazolidin-2-one, thiazolidin-2-thione, 3H-oxazol-2-one, 1,3-dihydro-imidazol-2-one, 1,3-dihydro-pyrrol-2-one, isoxazolidin-3-one, pyrazolidin-3-one, imidazolidine-2,4-dione, imidazolidin-4-one, imidazolidine-4,5-dione, 2,3-dihydro-[1,3,4]oxadiazole, isothiazolidin-3-one, isothiazol-3-one, 4,5-dihydro-1H-[1,2,3]triazole, 4,5-dihydro-1H-imidazole, [1,2,5]thiadiazolidine-1,1-dioxide, isothiazolidine 1,1-dioxide, whereby
ring atoms are individually and independently substituted with 0, 1 or 2 R$^a$;
A is connected to Ar at the or a N-atom;
(c) a 6-membered nitrogen containing ring selected from the group consisting of tetrahydro-pyrimidin-2-one, [1,3]oxazinan-2-one, [1,3]thiazinan-2-one, [1,3]oxazinane-2-thione, tetrahydro-pyrimidine-2-thione, piperidine, piperidine-2-one, piperidine-2-thione, piperidine-2,6-dione, piperazine, piperazine-2-one, piperazine-2-thione, piperazin-2,5-dione, piperazin-2,6-dione, [1,2]thiazinane-1,1-dioxide, [1,2,6]thiadiazinane-1,1-dioxide, tetrahydro-pyridazin-3-one, [1,2,4]triazinan-3-one, [1,2,5]oxadiazinan-6-one, 3,4-dihydro-1H-pyrazin-2-one, morpholine, thiomorpholine, 1,4,5,6-tetrahydro-pyrimidine, 5,6-dihydro-3H-pyrimidin-4-one, [1,3,5]triazinane-2,4,6-trione
whereby
ring atoms are individually and independently substituted with 0, 1 or 2 R$^a$;
A is connected to Ar at the or a N-atom; or
(d) a 7-membered nitrogen containing ring selected from the group consisting of azepane, azepan-2-on, azepan-2,7-dion, [1,4]diazepane-2,5-dione, [1,4]diazepane-2,3-dione, [1,4]diazepane-2,7-dione, [1,3]oxazepan-2-one, [1,3]thiazepan-2-one, [1,3]diazepan-2-one and
ring atoms are individually and independently substituted with 0, 1 or 2 R$^a$;
A is connected to Ar at the or a N-atom; and
whereby any R$^a$ in (a) to (d) is defined as in the first to the third embodiment, preferably in the second embodiment and more preferably in the third embodiment.

In an embodiment, which is preferably a sixteenth embodiment, which is preferably a further embodiment of the fifteenth embodiment of the first aspect,
A is selected from the group comprising
azetidine, pyrrolidine, pyrrolidin-2-one, imidazolidin-2-one, oxazolidin-2-one, isoxazolidin-3-one, 4,5-dihydro-1H-imidazole, 2,4-dihydro-pyrazol-3-one, 4,5-dihydro-1H-[1,2,3]triazole, [1,3]oxazinan-2-one, piperidine, piperidine-2-one, piperidine-2,6-dione, piperazine, piperazine-2-one, piperazin-2,5-dione, 1,4,5,6-tetrahydro-pyrimidine, piperazin-2,6-dione, morpholine, azepane, azepan-2-one,
whereby
ring atoms are individually and independently substituted with 0, 1 or 2 $R^a$
whereby
$R^a$ is defined as in the first to third embodiment, preferably in the second embodiment and more preferably in the third embodiment.

In an embodiment, which is preferably a seventeenth embodiment, which is preferably a further embodiment of the sixteenth embodiment of the first aspect,
A is selected from the group comprising azetidine, pyrrolidine, pyrrolidin-2-one, [1,3]oxazinan-2-one, piperidine and piperidin-2-one,
wherein
ring atoms are individually and independently substituted with 0, 1 or 2 $R^a$ as defined in the first to the third embodiment, preferably in the second embodiment and more preferably in the third embodiment; and
A is connected to Ar at the ring N-atom.

In an embodiment, which is preferably an eighteenth embodiment, which is preferably a further embodiment of the seventeenth embodiment of the first aspect,
A is piperidine,
whereby
A is connected to Ar via the ring N-atom; and
A is connected to Z via the ring atom in position 4.

In an embodiment, which is preferably a nineteenth embodiment, which is preferably a further embodiment of the twelfth embodiment of the first aspect,
A is a heterocyclic 5- or 6-membered ring of formula (XV)

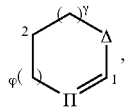

(XV)

wherein
Π is a radical selected from the group comprising N and $CR^a$;
Δ is a radical selected from the group comprising $CR^aR^b$, $NR^c$, O and S;
γ and φ are individually and independently 0, 1 or 2; and
Ar and Z are connected to A via the ring atoms number 1 and 2 in formula (XV) or vice versa.

In an embodiment, which is preferably a twentieth embodiment, which is preferably a further embodiment of the nineteenth embodiment of the first aspect,
A is a heterocyclic 5- or 6-membered ring selected from the group comprising 4,5-dihydro-oxazole, 1-methyl-4,5-dihydro-1H-imidazole, 4,5-dihydro-thiazole, 3,4-dihydro-2H-pyrrole, 5,6-dihydro-4H-[1,3]oxazine, 5,6-dihydro-4H-[1,3]thiazine, 2,3,4,5-tetrahydro-pyridine, 1-methyl-1,4,5,6-tetrahydro-pyrimidine.

In an embodiment, which is preferably a twenty-first embodiment, which is preferably a further embodiment of the first to twentieth embodiment of the first aspect, wherein Ar is preferably as defined in any of the eighth to the eleventh embodiment, more preferably as in the eleventh embodiment and A is preferably as defined in any of the twelfth to the twentieth embodiment, more preferably as in the fifteenth to the eighteenth embodiment and in the twentieth embodiment, even more preferably as in the eighteenth embodiment,
wherein
G is $R_9$—NH
whereby
$R_9$ is a radical selected from the group comprising
(a) 5- or 6-membered aromatic rings and 5- or 7-membered nonaromatic rings comprising ring atoms whereby
any of the rings contains 0, 1, 2, 3 or 4 heteroatoms whereby the heteroatoms are individually and independently selected from the group comprising N, O and S; and
any or several of the ring atoms is/are optionally and individually and independently substituted with one or several substituents, whereby the substituent is $R_5$;
(b) 5,5-, 5,6- or 6,6-membered aromatic, nonaromatic or combined aromatic/nonaromatic bicyclic ring systems comprising ring atoms whereby
any of the ring systems contains 0, 1, 2, 3 or 4 heteroatoms whereby the heteroatoms are individually and independently selected from the group comprising N, O and S; and
one or several of the ring atoms is/are optionally and individually and independently substituted with one or several substituents, whereby the substituent is $R_5$; and
(c) (C=O)—$NR^b$—$R^a$, (C=$NR^c$)—$NR^b$—$R^a$, (C=$NR^a$)—$R^b$, (C=O)—$R^a$, (C=S)—$R^a$, $NR^b$—$R^a$, O—$R^a$, $CH_2$—$R^a$, (C=O)—O—$R^a$, (C=S)—$NR^b$—$R^a$, $SO_2OR^a$ and $SO_2$—$NR^b$—$R^a$;
whereby
any $R_5$ of (a) to (c) is defined as in the fifth to the seventh embodiment, preferably in the sixth embodiment and more preferably in the seventh embodiment; and
any of $R^a$, $R^b$ and $R^c$ of (a) to (c) is each and independently a radical as defined in the first to the third embodiment, preferably in the second embodiment and more preferably in the third embodiment.

In an embodiment, which is preferably a twenty-second embodiment, which is preferably a further embodiment of the twenty-first embodiment of the first aspect,
$R_9$ is a 5-membered aromatic or nonaromatic heterocyclic ring containing 1, 2 or 3 N-atoms
whereby
said ring is substituted or unsubstituted with one or more $R_5$ as defined in the fifth to the seventh embodiment, preferably in the sixth embodiment and more preferably in the seventh embodiment.

In an embodiment, which is preferably a twenty-third embodiment, which is preferably a further embodiment of the twenty-second embodiment of the first aspect,
$R_9$ is connected to the NH group of G adjacent to one of said ring N-atoms.

In an embodiment, which is preferably a twenty-fourth embodiment, which is preferably a further embodiment of the twenty-first embodiment of the first aspect,
$R_9$ is a 6-membered aromatic or nonaromatic heterocyclic ring containing 1, 2 or 3 N-atoms,
whereby
said ring is substituted or unsubstituted with one or more substituents $R_5$ each and independently as defined in the fifth to the seventh embodiment, preferably in the sixth embodiment and more preferably in the seventh embodiment.

In an embodiment, which is preferably a twenty-fifth embodiment, which is preferably a further embodiment of the twenty-fourth embodiment of the first aspect,
$R_9$ is connected to the NH group of G adjacent to one of said ring N-atoms.

In an embodiment, which is preferably a twenty-sixth embodiment, which is preferably a further embodiment of the twenty-second to the twenty-fifth embodiment, preferably of the twenty-third to the twenty-fifth embodiment of the first aspect, G is a radical selected from the group comprising thiazol-2-ylamino, 4,5,6,7-tetrahydro-1H-benzoimidazol-2-ylamino, 3a,4,5,6,7,7a-hexahydro-1H-benzoimidazol-2-ylamino, 3H-indol-2-ylamino, 3,4-dihydro-quinolin-2-ylamino, 3H-pyrrolo[2,3-b]pyridin-2-ylamino, 3,4-dihydro-[1,8]naphthyridin-2-ylamino, 3H-imidazol-4-ylamino, pyridin-2-ylamino, pyrimidin-2-ylamino, 1H-imidazol-2-ylamino, 4,5-dihydro-1H-imidazol-2-ylamino, 1,4,5,6-tetrahydro-pyrimidin-2-ylamino, 4,5,6,7-tetrahydro-1H-[1,3]diazepin-2-ylamino, 4,5-dihydro-3H-pyrrol-2-ylamino, 3,4,5,6-tetrahydro-pyridin-2-ylamino, 4,5,6,7-tetrahydro-3H-azepin-2-ylamino, 1H-benzoimidazol-2-ylamino, 1H-indol-2-ylamino, pyrazin-2-ylamino, 5,6-dihydro-1H-pyrimidin-4-one-2-ylamino, 1,5-dihydro-imidazol-4-one-2-ylamino, oxazol-2-ylamino, 1H-[1,8]naphthyridin-4-one-2-amino, 4,5-dihydro-thiazol-2-ylamino, 4,5-dihydro-oxazol-2-ylamino and pyrimidin-4-ylamino, whereby
each radical is attached to Z at the amino group of G; and
each radical is unsubstituted or substituted with one or more $R_5$ as defined in the fifth to the seventh embodiment, preferably in the sixth embodiment and more preferably in the seventh embodiment.

In an embodiment, which is preferably a twenty-seventh embodiment, which is preferably a further embodiment of the first to twentieth embodiment of the first aspect, wherein Ar is preferably as defined in any of the eighth to the eleventh embodiment, more preferably as in the eleventh embodiment and A is preferably as defined in any of the twelfth to the twentieth embodiment, more preferably as in the fifteenth to the eighteenth embodiment and in the twentieth embodiment, even more preferably as in the eighteenth embodiment, G is a radical selected from the group comprising
(a) 5- or 6-membered aromatic rings and 5- or 7-membered nonaromatic rings comprising ring atoms, whereby
any of the rings contains 0, 1, 2, 3 or 4 heteroatoms, whereby
the heteroatoms are individually and independently selected from the group comprising N, O and S;
any or several of the ring atoms is/are optionally and individually and independently substituted with one or several substituents, whereby the substituent is $R_5$;
(b) 5,5-, 5,6- or 6,6-membered aromatic, nonaromatic or combined aromatic/nonaromatic bicyclic ring systems comprising ring atoms,
whereby
any of the ring systems contains 0, 1, 2, 3 or 4 heteroatoms, whereby the heteroatoms are individually and independently selected from the group comprising N, O and S;
one or several of the ring atoms is/are optionally and individually and independently substituted with one or several substituents, whereby the substituent is $R_5$; and
(c) (C=O)—$NR^b$—$R^a$, (C=$NR^c$)—$NR^b$—$R^a$, (C=$NR^a$)—$R^b$, (C=O)—$R^a$, (C=S)—$R^a$, $NR^b$—$R^a$, O—$R^a$, $CH_2$—$R^a$, (C=O)—O—$R^a$, (C=S)—$NR^b$—$R^a$, $SO_2$—$R^a$ and $SO_2$—$NR^b$—$R^a$;

whereby
any $R_5$ of (a) to (c) is defined as in the fifth to the seventh embodiment, preferably in the sixth embodiment and more preferably in the seventh embodiment; and
any of $R^a$, $R^b$ and $R^c$ of (a) to (c) is each and independently a radical as defined in the first to the third embodiment, preferably in the second embodiment and more preferably in the third embodiment.

In an embodiment, which is preferably a twenty-eighth embodiment, which is preferably a further embodiment of the twenty-seventh embodiment of the first aspect, G is a heterocyclic 1, 2, 3 or 4 N-atoms containing ring or ring system selected from the group comprising aromatic and nonaromatic 5- or 6-membered rings and bicyclic aromatic and nonaromatic as well as combined aromatic/nonaromatic 5,5-, 5,6- or 6,6-membered ring systems, whereby
said rings or ring systems are unsubstituted or substituted with one or more $R_5$ as defined in the fifth to seventh embodiment, preferably in the sixth embodiment and even more preferably in the seventh embodiment; and
G is connected to Z at a ring atom adjacent to one of said ring N-atoms.

In an embodiment, which is preferably a twenty-nineth embodiment, which is preferably a further embodiment of the twenty-eighth embodiment of the first aspect, G is a radical from the group comprising 1,2,3,4-tetrahydro-[1,8]naphthyridin-2-yl, 1,2,3,4-tetrahydro-[1,8]naphthyridine-7-yl, 1H-pyrrolo[2,3-b]pyridin-2-yl, 1H-pyrrolo[2,3-b]pyridin-6-yl, 1,3,4,6,7,8-hexahydro-2H-pyrimido[1,2-a]pyrimidin-2-yl, 2,3,5,6,7,8-hexahydro-imidazo[1,2-a]pyrimidin-7-yl, 5,6,7,8-tetrahydro-imidazo[1,2-a]pyrimidin-7-yl, 5,6,7,8-tetrahydro-imidazo[1,2-a]pyrimidin-2-yl, 4,5,6,7-tetrahydro-3H-imidazo[4,5-b]pyridin-2-yl, 5,6,7,8-tetrahydro-imidazo[1,2-a]pyrimidin-2-yl, 3H-imidazo[4,5-b]pyridin-5-yl, 1H-pyrazolo[3,4-b]pyridin-6-yl, 2,3-dihydro-1H-imidazo[1,2-a]imidazol-6-yl, 2,3-dihydro-1H-pyrrolo[2,3-b]pyridine-6-yl, 2-methylaminopyridin-6-yl, 4-methylaminothiazol-2-yl, 2-methylamino-1H-pyrrol-5-yl, 2-methylamino-1H-imidazol-5-yl and 4-methylamino-1H-imidazol-2-yl;

wherein
each radical is unsubstituted or substituted with one or more substituents $R_5$ each and individually as defined in the fifth to the seventh embodiment, preferably in the sixth embodiment and even more preferably in the seventh embodiment.

In an embodiment, which is preferably a thirtieth embodiment, which is preferably a further embodiment of the twenty-sixth to twenty-nineth embodiment of the first aspect, G is a radical selected from the group comprising pyridin-2-ylamino, 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 1,2,3,4-tetrahydro-[1,8]naphthyridine-7-yl, 5,6-dihydro-1H-pyrimidin-4-one-2-ylamino, 1,5-dihydro-imidazol-4-one-2-ylamino, 2,3-dihydro-1H-pyrrolo[2,3-b]pyridine-6-yl, 2-methylaminopyridin-6-yl, 4-methylpyridin-2-ylamino, 5-methylpyridin-2-ylamino, 4-methoxypyridin-2-ylamino, 4-fluoropyridin-2-ylamino and 2-methylamino-1H-imidazol-5-yl.

In an embodiment, which is preferably a thirty-first embodiment, which is preferably a further embodiment of the twenty-first to the twenty-seventh embodiment, preferably the embodiments of the twenty-first embodiment as described in section (c) thereof and the twenty-seventh embodiment as described in section (c) thereof of the first aspect, G is a radical selected from the group comprising formylamino, aminocarbonyl, amidino, ureido, hydroxycarbonylamino, aminocarbonyloxy, sulfonamino, aminomethyleneamino and guanidino;
whereby
each radical is individually and independently substituted or unsubstituted with $R^a$, $R^b$ and $R^c$ as defined in the first to the third embodiment, preferably in the second embodiment and more preferably in the third embodiment.

In an embodiment, which is preferably a thirty-second embodiment, which is preferably a further embodiment of the thirty-first embodiment of the first aspect, G is a radical selected from the group comprising butyramido, N'-propylureido, N'-cyclobutylureido, N'-cyclopropylureido, N'-benzylureido, N'-(2,2,2-trifluoroethyl)ureido, N'-(3,3,3,2,2-pentafluoropropyl)ureido, N'-cyclopropylmethylureido, N'-phenylureido, guanidino, amidino and amino(phenylmethylene)amino.

In an embodiment, which is preferably a thirty-third embodiment, which is preferably a further embodiment of the first to thirty-second embodiment of the first aspect, wherein Ar is preferably as defined in any of the eighth to the eleventh embodiment, more preferably as in the eleventh embodiment; A is preferably as defined in any of the twelfth to the twentieth embodiment, more preferably as in the fifteenth to eighteenth embodiment and in the twentieth embodiment, even more preferably as in the eighteenth embodiment; G is preferably as defined in any of the twenty-first to thirty-second embodiment, more preferably as in the twenty-sixth, twenty-ninth and thirty-first embodiment, even more preferably as in the thirtieth and thirty-second embodiment, Z is a direct bond, $CH_2$ or CO.

In an embodiment, which is preferably a thirty-fourth embodiment, which is preferably a further embodiment of the first to the thirty-second embodiment of the first aspect, wherein Ar is preferably as defined in any of the eighth to the eleventh embodiment, more preferably as in the eleventh embodiment; A is preferably as defined in any of the twelfth to the twentieth embodiment, more preferably as in the fifteenth to eighteenth embodiment and in the twentieth embodiment, even more preferably as in the eighteenth embodiment; G is preferably as defined in any of the twenty-first to thirty-second embodiment, more preferably as in the twenty-sixth, twenty-ninth and thirty-first embodiment, even more preferably as in the thirtieth and thirty-second embodiment, $R_2$ is a radical selected from the group comprising phenyl, substituted phenyl, heterocyclyl, substituted heterocyclyl, aryl, substituted aryl, heteroaryl, substituted heteroaryl, cycloalkyl and substituted cycloalkyl
whereby Q is attached to $R_2$ at one of the ring atoms of $R_2$.

In an embodiment, which is preferably a thirty-fifth embodiment, which is preferably a further embodiment of the thirty-fourth embodiment of the first aspect, $R_2$ is a radical of formula (XVI)

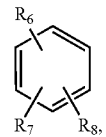

(XVI)

wherein
0 or 1 ring carbon atom in formula (XVI) is substituted by a nitrogen atom;
$R_6$, $R_7$ and $R_8$ are each radicals and individually and independently selected from the group comprising hydrogen, halogen, cyano, alkyl, substituted alkyl, alkoxy, substituted alkoxy, aryl, substituted aryl, heteroaryl, and substituted heteroaryl; and
$R_2$ is attached to Q via a ring atom of the radical of formula (XVI).

In an embodiment, which is preferably a thirty-sixth embodiment, which is preferably a further embodiment of the thirty-fifth embodiment of the first aspect,
$R_2$ is a radical of formula (XVII)

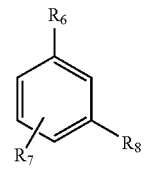

(XVII)

wherein
0 or 1 ring carbon atom in formula (XVII) is substituted by a nitrogen atom;
$R_6$, $R_7$ and $R_8$ are each radicals and individually and independently selected from the group comprising hydrogen, fluoro, chloro, bromo, methyl, ethyl, propyl, tert-butyl, phenyl, benzyl, hydroxyl, methoxy, oxo, amino, acetylamino, cyano, nitro, benzyloxy, trifluoromethyl, 1-oxoethyl, dimethylaminocarbonyl, methylaminocarbonyl, aminocarbonyl, trifluoromethoxy, trichloromethyl, methoxycarbonyl, methylsulfonyl, trifluoromethylsulfonyl, methylthio, aminosulfonyl, methylaminosulfonyl, dimethylaminosulfonyl, 2-oxazolyl, 2-imidazolyl, 1-imidazolyl and 4,5-dihydro-oxazol-2-yl; and
Q is attached to the ring of formula (XVII) in a position ortho to $R_6$ and $R_8$.

In an embodiment, which is preferably a thirty-seventh embodiment, which is preferably a further embodiment of the thirty-sixth embodiment of the first aspect, $R_2$ is a radical selected from the group comprising phenyl, 2,4,6-trimethylphenyl, 2,6-dimethylphenyl, 4-cyanophenyl, 2,4,6-tribromophenyl, 2-bromo-6-methylphenyl, 4-benzyloxyphenyl, 2-methylphenyl, 2-ethyl-6-methylphenyl, 2-methyl-6-trifluoromethylphenyl, 4-fluoro-2-ethyl-6-methylphenyl, 4-chloro-2-ethyl-6-methylphenyl, 4-cyano-2-ethyl-6-methylphenyl, 4-trifluoromethyl-2-ethyl-6-methylphenyl, 4-(1-oxoethyl)-2-ethyl-6-methylphenyl, 4-dimethylcarbamoyl-2-ethyl-6-methyl-phenyl, 4-methylcarbamoyl-2-ethyl-6-methyl-phenyl, 4-carbamoyl-2-ethyl-6-methyl-phenyl, 4-trifluoromethoxy-2-ethyl-6-methyl-phenyl, 4-(1H-imidazo-1-yl)-2-ethyl-6-methylphenyl, 4-fluoro-2,6-dimethylphenyl, 4-chloro-2,6-dimethylphenyl, 4-cyano-2,6-dimethylphenyl, 4-trifluoromethyl-2,6-dimethylphenyl, 4-(1-oxoethyl)-2,6-dimethylphenyl, 4-trifluoromethoxy-2,6-dimethylphenyl, 4-(1H-imidazo-1-yl)-2,6-dimethylphenyl, pyridine-3-yl, 2-methyl-pyridine-3-yl, 2-methyl-4-trifluoromethylpyridine-3-yl, 2,4-dimethyl-pyridine-3-yl, 4-chloro-2-methyl-6-methylthio-phenyl, 4-fluoro-2-methyl-6-methylthio-phenyl, 2-methyl-6-methylthio-phenyl, 4-fluoro-2-(2-propyl)-6-methylphenyl, 4-cyano-2-methyl-6-methylthio-phenyl, 4-trifluoromethyl-2-methyl-6-methylthio-phenyl, 2-isopropyl-6-methylphenyl, 4-fluoro-2-(2-propyl)-6-methylphenyl, 2-ethyl-4-methyl-pyridine-3-yl, 4-trichloromethyl-2-ethyl-6-methylphenyl, 4-nitro-2-ethyl-6-methylphenyl, 4-methyloxycarbonyl-2-ethyl-6-methylphenyl, 4-methylsulfonyl-2-ethyl-6-methylphenyl, 4-trifluoromethylsulfonyl-2-ethyl-6-methylphenyl, 4-aminosulfonyl-2-ethyl-6-methylphenyl, 4-methylaminosulfonyl-2-ethyl-6-methylphenyl, 4-dimethylaminosulfonyl-2-ethyl-6-methylphenyl, 4-methylaminocarbonyl-2-ethyl-6-methylphenyl, 4-dimethylaminocarbonyl-2-ethyl-6-methylphenyl, 4-aminocarbonyl-2-ethyl-6-methylphenyl, 2-ethyl-6-methyl-4-(2-oxazolyl)phenyl, 2-ethyl-6-methyl-4-(2-imidazolyl)phenyl, 4-trifluormethylcarbonyl-2-ethyl-6-methylphenyl, 4-trichloromethyl-2,6-dimethylphenyl, 4-nitro-2,6-dimethylphenyl, 4-methyloxycarbonyl-2,6-dimethylphenyl, 4-methylsulfonyl-2,6-dimethylphenyl, 4-trifluoromethylsulfonyl-2,6-dimethylphenyl, 4-aminosulfonyl-2,6-dimethylphenyl, 4-methylaminosulfonyl-2,6-dimethylphenyl, 4-dimethylaminosulfonyl-2,6-dimethylphenyl, 4-methylaminocarbonyl-2,6-dimethylphenyl, 4-dimethylaminocarbonyl-2,6-dimethylphenyl, 4-aminocarbonyl-2,6-dimethylphenyl, 2,6-dimethyl-4-(2-oxazolyl)phenyl, 2,6-dimethyl-4-(2-imidazolyl)phenyl and 4-trifluormethylcarbonyl-2,6-dimethylphenyl.

In an embodiment, which is preferably a thirty-eighth embodiment, which is preferably a further embodiment of the thirty-fourth embodiment of the first aspect,
$R_2$ is a radical of formula (XVIII)
wherein

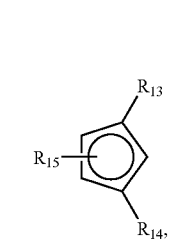

(XVIII)

1, 2 or 3 ring atoms in formula (XVIII) are hetero atoms selected from the group comprising N, O and S;
$R_{13}$, $R_{14}$ and $R_{15}$ are each radicals and individually and independently selected from the group comprising hydrogen, halogen, cyano, alkyl, substituted alkyl, alkoxy, substituted alkoxy, aryl, substituted aryl, heteroaryl, and substituted heteroaryl; and
Q is attached to the ring in formula (XVIII) in a position ortho to $R_{13}$ and $R_{14}$.

In an embodiment, which is preferably a thirty-nineth embodiment, which is preferably a further embodiment of the thirty-eighth embodiment of the first aspect,
$R_2$ is a radical selected from the group comprising 3,5-dimethylisoxazol-4-yl, 5-methyl-3-trifluoromethylisoxazol-4-yl, 3-isopropyl-5-methylisoxazol-4-yl, 5-methyl-3-phenylisoxazol-4-yl, 3,5-diethylisoxazol-4-yl, 2-methyl-4,5,6,7-tetrahydrobenzofuran-3-yl, 2,4-dimethylfuran-3-yl, 1,3,5-trimethyl-1H-pyrazol-4-yl, 1-tert-butyl-3,5-dimethyl-1H-pyrazol-4-yl, 1-benzyl-3,5-dimethyl-1H-pyrazol-4-yl, 2,4-dimethylthiophen-3-yl and 3-ethyl-5-methylisoxazol-4-yl.

In an embodiment, which is preferably a fortieth embodiment, which is preferably a further embodiment of the thirty-fourth embodiment of the first aspect,
$R_2$ is a cycloalkyl radical selected from the group comprising cyclohexyl, cyclopentyl, 1-phenylcyclopentyl, 1-methylcyclohexyl, 1-phenylcyclohexyl, bicyclo[3.2.1]octane-6-yl, adamantan-1-yl, 2,2,6,6-tetramethylcyclohexyl, 2,4,6-trimethylcyclohexyl, and 2-methylcyclohexyl.

In an embodiment, which is preferably a fourty-first embodiment, which is a further embodiment of the first to the thirty-second embodiment of the first aspect, wherein Ar is preferably as defined in any of the eighth to the eleventh embodiment, more preferably as in the eleventh embodiment; A is preferably as defined in any of the twelfth to the twentieth embodiment, more preferably as in the fifteenth to eighteenth embodiment and in the twentieth embodiment, even more preferably as in the eighteenth embodiment; G is preferably as defined in any of the twenty-first to the thirty-second embodiment, more preferably as in the twenty-sixth, twenty-nineth and thirty-first embodiment, even more preferably as in the thirtieth and thirty-second embodiment,
$R_2$ is a radical selected from the group comprising H, alkyl, branched alkyl, substituted branched alkyl, substituted alkyl, benzyl, substituted benzyl, arylalkyl, substituted arylalkyl, heteroarylalkyl, substituted heteroarylalkyl, cycloalkylalkyl, substituted cycloalkylalkyl, heterocyclylalkyl and substituted heterocyclylalkyl,
whereby
$R_2$ is preferably selected from the group comprising arylalkyl, substituted arylalkyl, branched alkyl, substituted branched alkyl; and
$R_2$ is attached to Q at its alkyl moiety.

In an embodiment, which is preferably a fourty-second embodiment, which is preferably a further embodiment of the fourty-first embodiment of the first aspect,
$R_2$ is a substituted alkyl radical selected from the group comprising 1,1-dimethylethyl, 1,1-dimethylpropyl, 1-methyl-1-phenylethyl, 1-phenylpropyl, 2-methyl-1-phenylpropyl, 1-methylbutyl, 1-ethyl-1-methylpropyl, 1-ethylpropyl, and 1-isopropyl-2-methylpropyl.

In an embodiment, which is preferably a fourty-third embodiment, which is preferably a further embodiment of the first to the fourty-second embodiment of the first aspect, wherein Ar is preferably as defined in any of the eighth to the eleventh embodiment, more preferably as in the eleventh embodiment; A is preferably as defined in any of the twelfth to the twentieth embodiment, more preferably as in the fifteenth to the eighteenth embodiment and in the twentieth embodiment, even more preferably as in the eighteenth embodiment; G is preferably as defined in any of the twenty-first to the thirty-second embodiment, more preferably as in the twenty-sixth, twenty-nineth and thirty-first embodiment, even more preferably as in the thirtieth and thirty-second embodiment; $R_2$ is preferably as defined in any of the thirty-fourth to fourty-second embodiment, more preferably as in the thirty-seventh, thirty-nineth, fourtieth and fourty-second embodiment,
Q is selected from the group comprising NHCO, CONH and NHSO$_2$.

In an embodiment, which is preferably a fourty-fourth embodiment, which is preferably a further embodiment of the first to thirty-third embodiment of the first aspect,
Q is a direct bond;
$R_2$ is a lactame radical selected from the group comprising azetidine-2-ones, pyrrolidine-2-ones, and piperidine-2-ones, whereby
any of the radicals is either
geminal substituted with $R^a$ and $R^b$,
whereby $R^a$ and $R^b$ are individually and independently selected; or ortho-fused with an aromatic or nonaromatic 5- or 6-membered ring or spiro-fused with a nonaromatic 5- or 6-membered ring;
whereby
ring atoms of the ortho- or spiro-fused non-lactame rings are individually and independently substituted with 0, 1, 2, 3 or 4 $R^c$;
$R^a$, $R^b$ and $R^c$ are defined as in the first to the third embodiment, preferably in the second embodiment and more preferably in the third embodiment; and
said lactames are directly bound at their ring N-atom to C-atom number 2 in formula (II).

In an embodiment, which is preferably a fourty-fifth embodiment, which is preferably a further embodiment of the fourty-fourth embodiment of the first aspect,
$R_2$ is a radical selected from the group comprising formulas (XIX) to (XXIV)

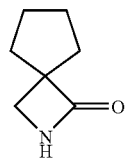

(XIX)

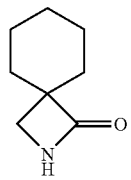

(XX)

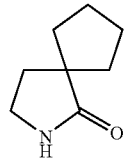

(XXI)

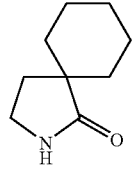

(XXII)

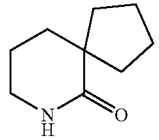

(XXIII)

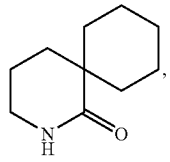

(XXIV)

whereby
any of the formulas (XIX) to (XXIV) is directly bound to C-atom number 2 in formula (II) at the ring N-atom of the respective formulas (XIX) to (XXIV);
the cycloalkyl rings spiro-fused to the heterocycles in any of the formulas (XIX) to (XXIV) are optionally ortho-fused with an aromatic 5- or 6-membered ring; and
any of the formulas (XIX) to (XXIV) is individually and independently substituted with 0, 1 or 2 $R^a$;
whereby
$R^a$ is defined as in the first embodiment, preferably in the second embodiment and even more preferably in the third embodiment.

In an embodiment, which is preferably a fourty-sixth embodiment, which is preferably a further embodiment of the fourty-fourth embodiment of the first aspect,
$R_2$ is a radical selected from the group comprising formulas (XXV)-(XXIX)

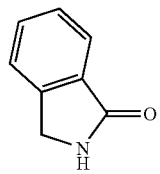

(XXV)

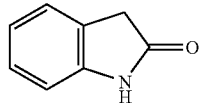

(XXVI)

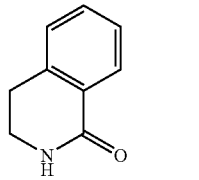

(XXVII)

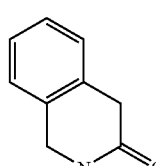

(XXVIII)

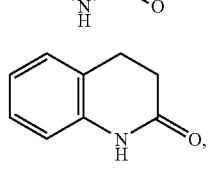

(XXIX)

whereby
any of the formulas (XXV) to (XXIX) is directly bound to C-atom number 2 in formula (II) at the ring N-atom of the respective formulas (XXV) to (XXIX); and
any of the formulas (XXV) to (XXIX) is independently and individually substituted with 0, 1 or 2 $R_5$ as defined in the fourth embodiment, preferably as defined in the fifth embodiment, more preferably as defined in the sixth embodiment, and even more preferably as defined in the seventh embodiment.

In an embodiment, which is preferably a fourty-seventh embodiment, which is preferably a further embodiment of the fourty-fourth embodiment of the first aspect,
$R_2$ is a radical selected from the group comprising formulas (XXX) to (XXXIV)

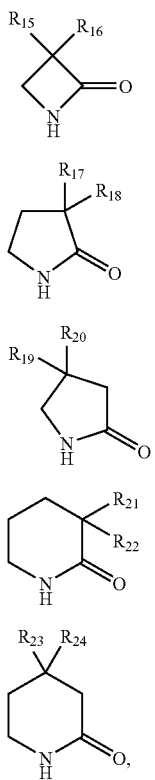

(XXX)

(XXXI)

(XXXII)

(XXXIII)

(XXXIV)

whereby
any of the formulas (XXX)-(XXXIV) is directly bound to C-atom number 2 in formula (II) at the ring N-atom; and $R_{15}$, $R_{16}$, $R_{17}$, $R_{18}$, $R_{19}$, $R_{20}$, $R_{21}$, $R_{22}$, $R_{23}$ and $R_{24}$ are each radicals and are individually and independently selected from the group comprising hydrogen, halogen, C1-C6alkyl, C3-C6cycloalkyl, substituted C3-C6cycloalkyl, phenyl, substituted phenyl, benzyl, and substituted benzyl.

In a second aspect the problem underlying the present invention is solved by a compound having formula (XXXV), which is preferably a first embodiment of the second aspect and optionally a further embodiment of the first aspect, preferably excluding the nineteenth and twentieth embodiment of the first aspect,

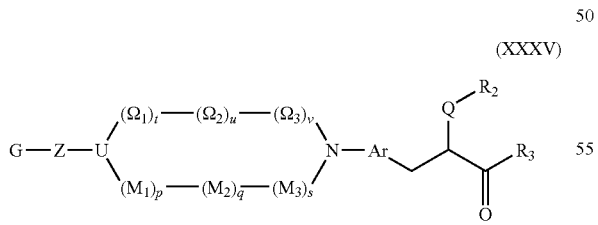

(XXXV)

wherein

Ar is a radical selected from the group comprising phenyl, pyridine and thiophene;

Q is selected from the group comprising a direct bond, NH—CO, CO—NH and $NHSO_2$;

U is a radical and independently and individually selected from the group comprising C, $CR^a$ and N;

$M_1$, $M_2$, $M_3$, $\Omega_1$, $\Omega_2$ and $\Omega_3$ are each a radical and independently and individually selected from the group comprising $CR^aR^b$, $CR^a$, C, O, N, $NR^a$, CO, S, SO and $SO_2$ whereby
any of $R^a$ and $R^b$ is as defined in the first embodiment, preferably as defined in the second embodiment and more preferably as defined in the third embodiment of the first aspect;

p, q, s, t, u and v are an integer independently and individually selected from 0, 1, 2 or 3, whereby the resulting ring is a 3- to 7-membered ring;

bonds within the N-heterocycle connected to Ar in formula (XXXV) may be either single or double bonds, provided that each combination of bonds results in a radical that is chemically stable at room temperature and is an nonaromatic system;

$R_2$ is a radical as defined in any of thirty-fourth to the fourty-seventh embodiment of the first aspect;

$R_3$ is a radical selected from the group comprising OH, OMe and OEt;

Z is selected from the group comprising a direct bond, $CH_2$, $CH_2$—$CH_2$ and CO; and G is a radical as defined in any of the twenty-first to the thirty-second embodiment of the first aspect.

In an embodiment, which is preferably a second embodiment of the second aspect, which is preferably a further embodiment of the first embodiment of the second aspect, the compound has formula (XXXVI)

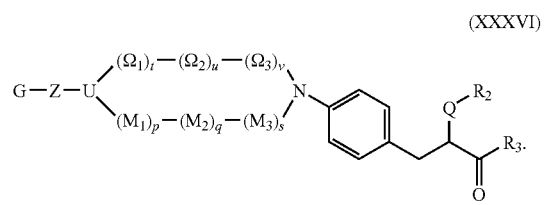

(XXXVI)

In an embodiment, which is preferably a third embodiment of the second aspect, which is preferably a further embodiment of the second embodiment of the second aspect, the compound has formula (XXXVII)

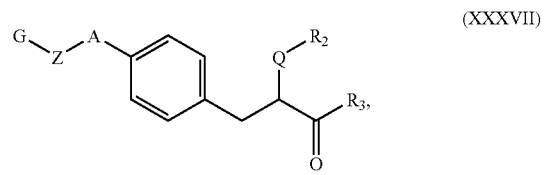

(XXXVII)

wherein

A is a radical selected from the group comprising
(a) a 3- or 4-membered nitrogen containing ring selected from the group consisting of aziridine, azetidin and azetidin-2-one;
(b) a 5-membered nitrogen containing ring selected from the group comprising pyrrolidine, pyrrolidin-2-one, pyrrolidin-2-thione, pyrrolidin-2,5-dione, imidazolidin-2-one, imidazolidin-2-thione, oxazolidin- 2-one, oxazolidin-2-thione, thiazolidin-2-one, thiazolidin-2-thione, oxazolidine-2-thione, 3H-oxazol-2-one, 1,3-dihydro-imidazol-2-one, 1,3-dihydro-pyrrol-2-one, isoxazolidin-3-one, pyrazolidin-3-one, imidazolidine-2,4-dione, imidazolidin-4-one, imidazolidine-4,5-dione, 2,3-dihydro-[1,3,4]oxadiazole, isothiazolidin-3-one, isothiazol-3-one, 4,5-dihydro-1H-[1,2,3]triazole, 4,5-dihydro-1H-imidazole, [1,2,5]thiadiazolidine-1,1-dioxide, and isothiazolidine-1,1-dioxide;

(c) a 6-membered nitrogen containing ring selected from the group comprising tetrahydro-pyrimidin-2-one, [1,3]oxazinan-2-one, [1,3]thiazinan-2-one, [1,3]oxazinane-2-thione, tetrahydro-pyrimidine-2-thione, piperidine, piperidine-2-one, piperidine-2-thione, piperidine-2,6-dione, piperazine, piperazine-2-one, piperazine-2-thione, piperazin-2,5-dione, piperazin-2,6-dione, [1,2]thiazinane-1,1-dioxide, [1,2,6]thiadiazinane-1,1-dioxide, tetrahydro-pyridazin-3-one, [1,2,4]triazinan-3-one, [1,2,5]oxadiazinan-6-one, 3,4-dihydro-1H-pyrazin-2-one, morpholine, thiomorpholine, 1,4,5,6-tetrahydro-pyrimidine, 5,6-dihydro-3H-pyrimidin-4-one, and [1,3,5]triazinane-2,4,6-trione; and (d) a 7-membered nitrogen containing ring selected from the group comprising azepane, azepan-2-on, azepan-2,7-dion, [1,4]diazepane-2,5-dione, [1,4]diazepane-2,3-dione, [1,4]diazepane-2,7-dione, [1,3]oxazepan-2-one, [1,3]thiazepan-2-one, and [1,3]diazepan-2-one, whereby for any of (a) to (d)

ring atoms are individually and independently substituted with 0, 1 or 2 substituents $R^a$ whereby $R^a$ is defined as in the first embodiment, preferably in the second embodiment and even more preferably in the third embodiment of the first aspect; and A is connected to the phenyl ring at the or a ring N-atom In an embodiment, which is preferably a fourth embodiment of the second aspect, which is preferably a further embodiment of the third embodiment of the second aspect, Q is selected from the group comprising a direct bond, NH—CO and NHSO$_2$;

A is selected from the group comprising azetidine, pyrrolidin, pyrrolidin-2-one, imidazolidin-2-one, oxazolidin-2-one, isoxazolidin-3-one, 4,5-dihydro-1H-imidazole, 4,5-dihydro-1H-[1,2,3]triazole, [1,3]oxazinan-2-one, piperidine, piperidine-2-one, piperidine-2,6-dione, piperazine, piperazine-2-one, piperazin-2,5-dione, 1,4,5,6-tetrahydro-pyrimidine, piperazin-2,6-dione, morpholine, azepane and azepan-2-on, whereby A is connected to the phenyl ring at the or a ring N-atom and ring atoms are individually and independently substituted with 0, 1 or 2 substituents $R^a$;

Z is selected from the group comprising a direct bond, CH$_2$ and CO;

In an embodiment, which is preferably a fifth embodiment of the second aspect, which is preferably a further embodiment of the fourth embodiment of the second aspect, the compound has formula (XXXVIII)

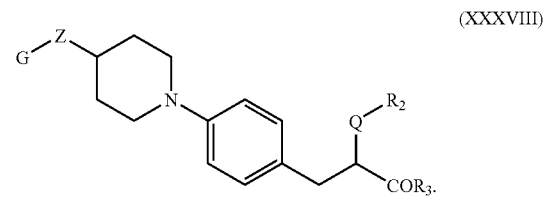

(XXXVIII)

In an embodiment, which is preferably a sixth embodiment of the second aspect, which is preferably a further embodiment of the fifth embodiment of the second aspect, the compound has formula (XXXIX)

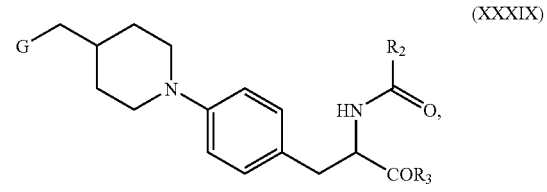

(XXXIX)

wherein

R$_2$ is a radical selected from the groups defined in any of the thirty-seventh, thirty-nineth, fourtieth and fourty-second embodiment of the first aspect, preferably in the thirty-seventh embodiment; and G is a radical selected from the group comprising pyridin-2-ylamino, 1H-imidazol-2-ylamino, 4,5-dihydro-1H-imidazol-2-ylamino, 1,4,5,6-tetrahydro-pyrimidin-2-ylamino, 4,5-dihydro-3H-pyrrol-2-ylamino, 3,4,5,6-tetrahydro-pyridin-2-ylamino, 1H-benzoimidazol-2-ylamino, 5,6-dihydro-1H-pyrimidin-4-one-2-ylamino, 1,5-dihydro-imidazol-4-one-2-ylamino, 4-methylpyridin-2-ylamino, 5-methylpyridin-2-ylamino, 4-methoxypyridin-2-ylamino, and 4-fluoropyridin-2-ylamino.

In an embodiment, which is preferably a seventh embodiment of the second aspect, which is preferably a further embodiment of the fifth embodiment of the second aspect, the compound has formula (XL)

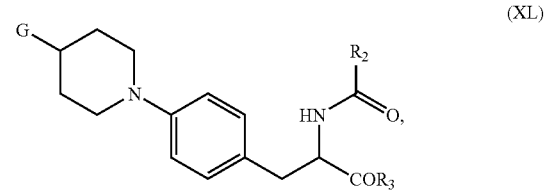

(XL)

wherein

R$_2$ is a radical selected from the groups defined in any of the thirty-seventh, thirty-nineth, fourtieth and fourty-second embodiment, preferably in the thirty-seventh embodiment of the first aspect; and G is a radical selected from the group comprising 1,2,3,4-tetrahydro-[1,8]naphthyridin-2-yl, 1,2,3,4-tetrahydro-[1,8]naphthyridine-7-yl, 1H-pyrrolo[2,3-b]pyridin-2-yl, 1H-pyrrolo[2,3-b]pyridin-6-yl, 1,3,4,6,7,8-hexahydro-2H-pyrimido[1,2-a]pyrimidin-2-yl, 2,3,5,6,7,8-hexahydro-imidazo[1,2-a]pyrimidin-7-yl, 5,6,7,8-tetrahydro-imidazo[1,2-a]pyrimidin-7-yl, 5,6,7,8-tetrahydro-imidazo[1,2-a]pyrimidin-2-yl, 4,5,6,7- tetrahydro-3H-imidazo[4,5-b]pyridin-2-yl, 5,6,7,8-tetrahydro-imidazo[1,2-a]pyrimidin-2-yl, 3H-imidazo[4,5-b]pyridin-5-yl, 1H-pyrazolo[3,4-b]pyridin-6-yl, 2,3-dihydro-1H-imidazo[1,2-a]imidazol-6-yl, 2,3-dihydro-1H-pyrrolo[2,3-b]pyridine-6-yl, 2-methylaminopyridin-6-yl, 4-methylaminothiazol-2-yl, 2-methylamino-1H-pyrrol-5-yl, 2-methylamino-1H-imidazol-5-yl and 4-methylamino-1H-imidazol-2-yl.

In an embodiment, which is preferably an eighth embodiment of the second aspect, which is preferably a further embodiment of the fifth embodiment of the second aspect, Q is a direct bond;

$R_2$ is a radical selected from the groups defined in any of the fourty-fourth to fourty-seventh embodiment, preferably in the fourty-fifth to fourty-seventh embodiment, and more preferably the fourty-fifth and fourty-seventh embodiment of the first aspect; and G is a radical as defined in the thirtieth embodiment of the first aspect.

In an embodiment, which is preferably a nineth embodiment of the second aspect, which is preferably a further embodiment of the fourth embodiment of the second aspect, the compound has formula (XLI)

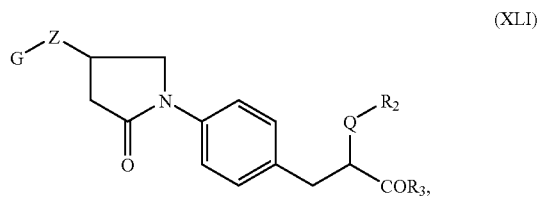

(XLI)

wherein $R_2$ is a radical as defined in any of the thirty-seventh, thirty-nineth, fourtieth, fourty-second and fourty-fifth to fourty seventh embodiment of the first aspect; and G is a radical selected from the groups defined in any of the twenty-sixth, twenty-nineth, thirtieth and thirty-second embodiment, preferably the thirtieth embodiment of the first aspect.

In an embodiment, which is preferably a tenth embodiment of the second aspect, which is preferably a further embodiment of the fourth embodiment of the second aspect, the compound has formula (XLII)

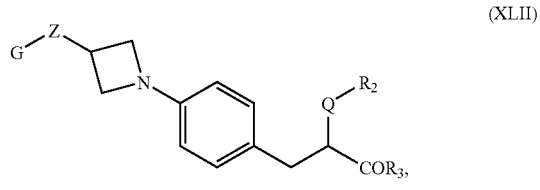

(XLII)

wherein $R_2$ is a radical as defined in any of the thirty-seventh, thirty-nineth, fourtieth, fourty-second and fourty-fifth to fourty seventh embodiment of the first aspect; and G is a radical selected from the groups defined in any of the twenty-sixth, twenty-nineth, thirtieth and thirty-second embodiment, preferably the thirtieth embodiment of the first aspect.

In an embodiment, which is preferably an eleventh embodiment of the second aspect, which is preferably a further embodiment of the fourth embodiment of the second aspect, the compound has formula (XLIII)

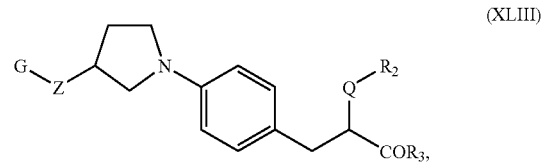

(XLIII)

wherein $R_2$ is a radical as defined in any of the thirty-seventh, thirty-nineth, fourtieth, fourty-second and fourty-fifth to the fourty seventh embodiment of the first aspect; and G is a radical selected from the groups defined in any of the twenty-sixth, twenty-nineth, thirtieth and thirty-second embodiment, preferably the thirtieth embodiment of the first aspect.

In an embodiment, which is preferably a twelfth embodiment of the second aspect, which is preferably a further embodiment of the fourth embodiment of the second aspect, the compound has formula (XLIV)

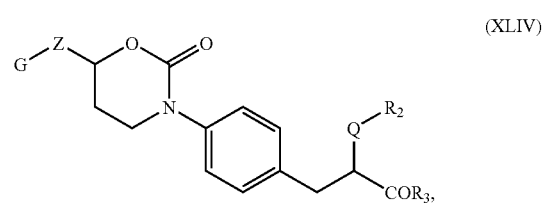

(XLIV)

wherein $R_2$ is a radical selected from the groups defined in the thirty-seventh, thirty-nineth, fourtieth, fourty-second and fourty-fifth to the fourty seventh embodiment of the first aspect; and G is a radical selected from the groups defined in any of the twenty-sixth, twenty-nineth, thirtieth and thirty-second embodiment, preferably the thirtieth embodiment of the first aspect.

In an embodiment, which is preferably a thirteenth embodiment of the second aspect, which is preferably a further embodiment of the fourth embodiment of the second aspect, the compound has formula (XLV)

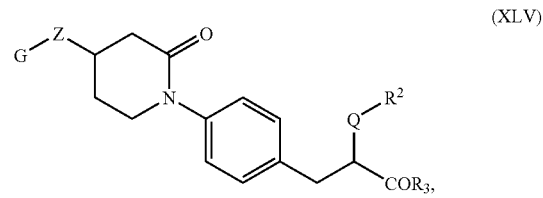

(XLV)

wherein $R_2$ is a radical as defined in any of the thirty-seventh, thirty-nineth, fourtieth, fourty-second and fourty-fifth to fourty seventh embodiment of the first aspect; and G is a radical selected from the groups defined in any of the twenty-sixth, twenty-nineth, thirtieth and thirty-second embodiment, preferably the thirtieth embodiment of the first aspect.

The problem underlying the present invention is solved in a third aspect by a compound
having formula (XLVI), which is preferably a first embodiment of the third aspect and optionally a further embodiment of the first aspect excluding the thirteenth to eighteenth embodiment of the first aspect,

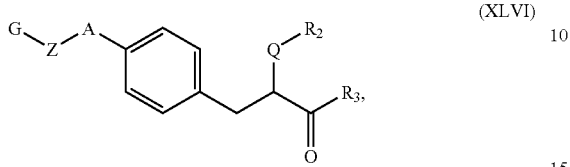

(XLVI)

wherein
Q is selected from the group comprising a direct bond, NH—CO, CO—NH and $NHSO_2$;
$R_2$ is a radical as defined in any of the thirty-seventh, thirty-nineth, fourtieth, fourty-second and fourty-fifth to the fourty seventh embodiment of the first aspect;
A is a radical selected from the group comprising 4,5-dihydro-oxazole, 1-methyl-4,5-dihydro-1H-imidazole, 4,5-dihydro-thiazole, 3,4-dihydro-2H-pyrrole, 5,6-dihydro-4H-[1,3]oxazine, 5,6-dihydro-4H-[1,3]thiazine, 2,3,4,5-tetrahydro-pyridine, and 1-methyl-1,4,5,6-tetrahydro-pyrimidine;
whereby
A is connected to the phenyl ring via the imine C-atom in position 2 of the heterocycles represented by A; and
each and any of the ring atoms are individually and independently substituted with 0, 1 or 2 $R^a$,
whereby
$R^a$ is as defined in the first to the third embodiment, preferably as defined in the second embodiment and more preferably as defined in the third embodiment of the first aspect;
Z is selected from the group comprising a direct bond, CO, $CH_2$ and $CH_2$—$CH_2$; and
G is a radical selected from the groups defined in the twenty-first to the thirty-second embodiment of the first aspect.

In an embodiment, which is preferably a second embodiment of the third aspect, which is preferably a further embodiment of the first embodiment of the third aspect,
the compound has formula (XLVII)

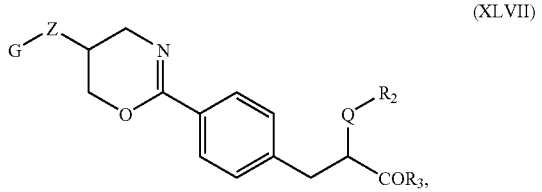

(XLVII)

wherein
Q is a direct bond, NHCO or $NHSO_2$;
Z is selected from the group comprising a direct bond, CO and $CH_2$; and
G is a radical selected from the groups defined in any of the twenty-sixth, twenty-nineth, thirtieth and thirty-second embodiment, preferably the thirtieth embodiment of the first aspect.

In an embodiment, which is preferably a third embodiment of the third aspect, which is preferably a further embodiment of the first embodiment of the third aspect,
the compound has formula (XLVIII)

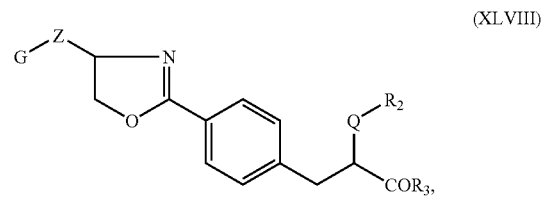

(XLVIII)

wherein
Q is a direct bond, NHCO or $NHSO_2$;
Z is selected from the group comprising a direct bond, CO and $CH_2$; and
G is a radical selected from the groups defined in any of the twenty-sixth, twenty-nineth, thirtieth and thirty-second embodiment, preferably the thirtieth embodiment.

The problem underlying the present invention is solved in a fourth aspect by a compound
having formula (XLVIX), which is preferably a first embodiment of the fourth aspect and optionally a further embodiment of the first aspect, preferably excluding the nineth to eleventh embodiments,

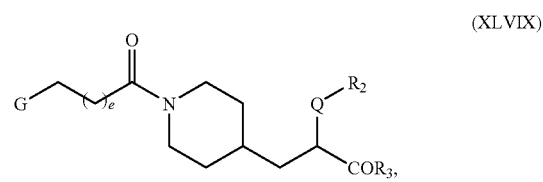

(XLVIX)

wherein
e is any integer of 0, 1, 2 or 3;
Q is a direct bond, NHCO or $NHSO_2$;
$R_2$ is a radical as defined in any of the thirty-seventh, thirty-nineth, fourtieth, fourty-second and fourty-fifth to fourty seventh embodiment;
$R_3$ is a radical selected from the group comprising OH, OMe and OEt; and
G is a radical selected from the groups defined in any of the twenty-sixth, twenty-nineth, thirtieth and thirty-second embodiment, preferably the thirtieth embodiment of the first aspect.

In an embodiment of the first to the fourth aspect
the compound is selected form the group consisting of
compound (5): 3-(4-(4-((pyridin-2-ylamino)methyl)piperidin-1-yl)phenyl)-2-(2,4,6-trimethylbenzamido)propanoic acid
compound (8): 3-(4-(4-((4-methylpyridin-2-ylamino)methyl)piperidin-1-yl)phenyl)-2-(2,4,6-trimethylbenzamido)propanoic acid
compound (11): 3-(4-(3-((pyridin-2-ylamino)methyl)azetidin-1-yl)phenyl)-2-(2,4,6-trimethylbenzamido)propanoic acid
compound (16): 3-(4-{4-[(4-methyl-pyridin-2-ylamino)methyl]-2-oxo-pyrrolidin-1-yl}phenyl)-2-(2,4,6-trimethylbenzoylamino)propionic acid
compound (18): 3-{4-[4-(4,5-Dihydro-1H-imidazol-2-ylcarbamoyl)piperidin-1-yl]phenyl}-2-(2-ethyl-4-fluoro-6-methyl-benzoylamino)propionic acid compound (20): 3-(4-(4-((1H-benzo[d]imidazol-2-ylamino)methyl)piperidin-1-yl)phenyl)-2-(2,4,6-trimethylbenzamido)propanoic acid compound (23): 3-(4-(4-(5,6,7,8-tetrahydro-1,8-naphthyridin-2-yl)piperidin-1-yl)phenyl)-2-(2,4,6-trimethylbenzamido)propanoic acid compound (27): 2-[(1-methyl-cyclohexanecarbonyl)-amino]-3-[1-(2-5,6,7,8-tetrahydro-[1,8]naphthyridin-2-yl-acetyl)piperidin-4-yl]propionic acid compound (29): 2-(1-methylcyclohexanecarboxamido)-3-(1-(3-(5,6,7,8-tetrahydro-1,8-naphthyridin-2-yl)propanoyl)piperidin-4-yl)propanoic acid compound (31): 2-(1-methylcyclohexanecarboxamido)-3-(4-(3-((pyridin-2-ylamino)methyl)azetidin-1-yl)phenyl)propanoic acid compound (32): 2-(2,2-dimethylbutanamido)-3-(4-(4-((pyridin-2-ylamino)methyl)piperidin-1-yl)phenyl)propanoic acid compound (33): 2-(picolinamido)-3-(4-(4-((pyridin-2-ylamino)methyl)piperidin-1-yl)phenyl)propanoic acid compound (34): 2-(1-oxo-2-azaspiro[3.4]octan-2-yl)-3-(4-(4-((pyridin-2-ylamino)methyl)piperidin-1-yl)phenyl)propanoic acid compound (35): 2-(1-methylcyclohexanecarboxamido)-3-(4-(4-((pyridin-2-ylamino)methyl)-4,5-dihydrooxazol-2-yl)phenyl)propanoic acid compound (36): 2-(1-methylcyclohexanecarboxamido)-3-(4-(3-((pyridin-2-ylamino)methyl)pyrrolidin-1-yl)phenyl)propanoic acid compound (37): 2-(2-ethyl-2-methylbutanamido)-3-(4-(4-((pyridin-2-ylamino)methyl)piperidin-1-yl)phenyl)propanoic acid compound (38): 2-(1-oxoisoindolin-2-yl)-3-(4-(4-((pyridin-2-ylamino)methyl)piperidin-1-yl)phenyl)propanoic acid compound (39): 2-(2-oxoindolin-1-yl)-3-(4-(4-((pyridin-2-ylamino)methyl)piperidin 1-yl)phenyl)propanoic acid compound (40): 2-(2-methylbenzamido)-3-(4-(4-((pyridin-2-ylamino)methyl)piperidin-1-yl)phenyl)propanoic acid compound (41): 2-(2-ethyl-6-methylbenzamido)-3-(4-(3-((pyridin-2-ylamino)methyl)azetidin-1-yl)phenyl)propanoic acid compound (42): 2-(2-methylnicotinamido)-3-(4-(4-((pyridin-2-ylamino)methyl)piperidin-1-yl)phenyl)propanoic acid compound (43): 3-(4-(4-((4-methylpyridin-2-ylamino)methyl)piperidin-1-yl)phenyl)-2-(1-oxo-2-azaspiro[3.4]octan-2-yl)propanoic acid compound (44): 2-(1-oxo-2-azaspiro[3.5]nonan-2-yl)-3-(4-(4-((pyridin-2-ylamino)methyl)piperidin-1-yl)phenyl)propanoic acid compound (45): 2-(1-oxo-2-azaspiro[4.4]nonan-2-yl)-3-(4-(4-((pyridin-2-ylamino)methyl)piperidin-1-yl)phenyl)propanoic acid compound (46): 2-(3,5-dimethylisoxazole-4-carboxamido)-3-(4-(4-((pyridin-2-ylamino)methyl)piperidin-1-yl)phenyl)propanoic acid compound (47): 2-(1-methylcyclohexanecarboxamido)-3-(4-(4-((pyridin-2-ylamino)methyl)piperidin-1-yl)phenyl)propanoic acid compound (48): 2-(3,3-diethyl-2-oxopyrrolidin-1-yl)-3-(4-(4-((pyridin-2-ylamino)methyl)piperidin-1-yl)phenyl)propanoic acid compound (49): 2-(1-methylcyclohexanecarboxamido)-3-(4-(5-((pyridin-2-ylamino)methyl)-5,6-dihydro-4H-1,3-oxazin-2-yl)phenyl)propanoic acid compound (50): 2-(1-methylcyclohexanecarboxamido)-3-(4-(2-oxo-4-((pyridin-2-ylamino)methyl)pyrrolidin-1-yl)phenyl)propanoic acid compound (51): 2-(4-cyanobenzamido)-3-(4-(4-((pyridin-2-ylamino)methyl)piperidin-1-yl)phenyl)propanoic acid compound (52): 3-{4-[4-(4,5-dihydro-1H-imidazol-2-ylcarbamoyl)piperidin-1-yl]phenyl}-2-[(1-methyl-cyclohexanecarbonyl)-amino]propionic acid compound (53): 3-(4-(4-((4-methylpyridin-2-ylamino)methyl)piperidin-1-yl)phenyl)-2-(1-oxoisoindolin-2-yl)propanoic acid compound (54): 3-(4-(4-((4-methylpyridin-2-ylamino)methyl)piperidin-1-yl)phenyl)-2-(2-oxoindolin-1-yl)propanoic acid compound (55): 2-(1-oxo-3,4-dihydroisoquinolin-2(1H)-yl)-3-(4-(4-((pyridin-2-ylamino)methyl)piperidin-1-yl)phenyl)propanoic acid compound (56): 2-(3-oxo-3,4-dihydroisoquinolin-2(1H)-yl)-3-(4-(4-((pyridin-2-ylamino)methyl)piperidin-1-yl)phenyl)propanoic acid compound (57): 2-(2-oxo-3,4-dihydroquinolin-1(2H)-yl)-3-(4-(4-((pyridin-2-ylamino)methyl)piperidin-1-yl)phenyl)propanoic acid compound (58): 2-(2,6-dimethylbenzamido)-3-(4-(4-((pyridin-2-ylamino)methyl)piperidin-1-yl)phenyl)propanoic acid compound (59): 3-(4-(4-((pyridin-2-ylamino)methyl)-4,5-dihydrooxazol-2-yl)phenyl)-2-(2,4,6-trimethylbenzamido)propanoic acid compound (60): 2-(2-ethyl-6-methylbenzamido)-3-(4-(4-((pyridin-2-ylamino)methyl)-4,5-dihydrooxazol-2-yl)phenyl)propanoic acid compound (61): 3-(4-(3-((pyridin-2-ylamino)methyl)pyrrolidin-1-yl)phenyl)-2-(2,4,6-trimethylbenzamido)propanoic acid compound (62): 2-(2-ethyl-6-methylbenzamido)-3-(4-(3-((pyridin-2-ylamino)methyl)pyrrolidin-1-yl)phenyl)propanoic acid compound (63): 2-(2,4-dimethylnicotinamido)-3-(4-(4-((pyridin-2-ylamino)methyl)piperidin-1-yl)phenyl)propanoic acid compound (64): 3-(4-(4-((4-methylpyridin-2-ylamino)methyl)piperidin-1-yl)phenyl)-2-(1-oxo-2-azaspiro[3.5]nonan-2-yl)propanoic acid compound (65): 3-(4-(4-((4-methylpyridin-2-ylamino)methyl)piperidin-1-yl)phenyl)-2-(1-oxo-2-azaspiro[4.4]nonan-2-yl)propanoic acid compound (66): 2-(1-oxo-2-azaspiro[4.5]decan-2-yl)-3-(4-(4-((pyridin-2-ylamino)methyl)piperidin-1-yl)phenyl)propanoic acid compound (67): 2-(6-oxo-7-azaspiro[4.5]decan-7-yl)-3-(4-(4-((pyridin-2-ylamino)methyl)piperidin-1-yl)phenyl)propanoic acid compound (68): 2-(2-ethyl-4-fluoro-6-methylbenzamido)-3-(4-(3-((pyridin-2-ylamino)methyl)azetidin-1-yl)phenyl)propanoic acid compound (69): 2-(5-ethyl-3-methylisoxazole-4-carboxamido)-3-(4-(4-((pyridin-2-ylamino)methyl)piperidin-1-yl)phenyl)propanoic acid compound (70): 2-(2,4-dimethylthiophene-3-carboxamido)-3-(4-(4-((pyridin-2-ylamino)methyl)piperidin-1-yl)phenyl)propanoic acid compound (71): 2-(1-methylcyclohexanecarboxamido)-3-(4-(4-((4-methylpyridin-2-ylamino)methyl)-2-oxopyrrolidin-1-yl)phenyl)propanoic acid compound (72): 3-{1-[2-(6-Ethylamino-pyridin-2-yl)-acetyl]piperidin-4-yl}-2-(2-ethyl-6-methyl-benzoylamino)propionic acid compound (73): 3-[1-(2-5,6,7,8-Tetrahydro-[1,8]naphthyridin-2-yl-acetyl)piperidin-4-yl]-2-(2,4,6-trimethyl-benzoylamino)propionic acid compound (74): 2-(3,3-diethyl-2-oxopyrrolidin-1-yl)-3-(4-(4-((4-methylpyridin-2-ylamino)methyl)piperidin-1-yl)phenyl)propanoic acid compound (75): 2-(1-methylcyclohexanecarboxamido)-3-(4-(4-((4-methylpyridin-2-ylamino)methyl)piperidin-1-yl)phenyl)propanoic acid compound (76): 2-(4-fluoro-2,6-dimethyl-benzoylamino)-3-[1-(2-5,6,7,8-tetrahydro-[1,8]naphthyridin-2-yl-acetyl)piperidin-4-yl]propionic acid compound (77): 2-(4-cyano-2-ethyl-6-methylbenzamido)-3-(4-(3-((pyridin-2-ylamino)methyl)azetidin-1-yl)phenyl)propanoic acid compound (78): 2-(1-methylcyclohexanecarboxamido)-3-(4-(4-((4-oxo-1,4,5,6-tetrahydropyrimidin-2-ylamino)methyl)piperidin-1-yl)phenyl)propanoic acid compound (79): 2-[(1-methyl-cyclohexanecarbonyl)-amino]-3-{4-[4-(1,4,5,6-tetrahydro-pyrimidin-2-ylcarbamoyl)piperidin-1-yl]phenyl}propionic acid compound (80): 3-(4-(4-((4-methylpyridin-2-ylamino)methyl)piperidin-1-yl)phenyl)-2-(1-oxo-3,4-dihydroisoquinolin-2(1H)-yl)propanoic acid compound (81): 3-(4-(4-((4-methylpyridin-2-ylamino)methyl)piperidin-1-yl)phenyl)-2-(3-oxo-3,4-dihydroisoquinolin-2(1H)-yl)propanoic acid compound (82): 3-(4-(4-((4-methylpyridin-2-ylamino)methyl)piperidin-1-yl)phenyl)-2-(2-oxo-3,4-dihydroquinolin-1(2H)-yl)propanoic acid compound (83): 2-(2-oxo-3-phenylpyrrolidin-1-yl)-3-(4-(4-((pyridin-2-ylamino)methyl)piperidin-1-yl)phenyl)propanoic acid compound (84): 2-(2-ethyl-6-methylbenzamido)-3-(4-(4-((pyridin-2-ylamino)methyl)piperidin-1-yl)phenyl)propanoic acid compound (85): 2-(2-methyl-2-phenylpropanamido)-3-(4-(4-((pyridin-2-ylamino)methyl)piperidin-1-yl)phenyl)propanoic acid compound (86): 3-(4-(5-((pyridin-2-ylamino)methyl)-5,6-dihydro-4H-1,3-oxazin-2-yl)phenyl)-2-(2,4,6-trimethylbenzamido)propanoic acid compound (87): 2-(2-ethyl-6-methylbenzamido)-3-(4-(5-((pyridin-2-ylamino)methyl)-5,6-dihydro-4H-1,3-oxazin-2-yl)phenyl)propanoic acid compound (88): 2-(2-ethyl-6-methylbenzamido)-3-(4-(2-oxo-4-((pyridin-2-ylamino)methyl)pyrrolidin-1-yl)phenyl)propanoic acid compound (89): 2-(2-ethyl-4-methylnicotinamido)-3-(4-(4-((pyridin-2-ylamino)methyl)piperidin-1-yl)phenyl)propanoic acid compound (90): 2-(4-fluoro-2,6-dimethylbenzamido)-3-(4-(4-((pyridin-2-ylamino)methyl)piperidin-1-yl)phenyl)propanoic acid compound (91): 2-(2-ethyl-4-fluoro-6-methylbenzamido)-3-(4-(4-((pyridin-2-ylamino)methyl)-4,5-dihydrooxazol-2-yl)phenyl)propanoic acid compound (92): 2-(2-ethyl-4-fluoro-6-methylbenzamido)-3-(4-(3-((pyridin-2-ylamino)methyl)pyrrolidin-1-yl)phenyl)propanoic acid compound (93): 3-(4-(4-((4-methylpyridin-2-ylamino)methyl)piperidin-1-yl)phenyl)-2-(1-oxo-2-azaspiro[4.5]decan-2-yl)propanoic acid compound (94): 3-(4-(4-((4-methylpyridin-2-ylamino)methyl)piperidin-1-yl)phenyl)-2-(6-oxo-7-azaspiro[4.5]decan-7-yl)propanoic acid compound (95): 2-(1-oxo-2-azaspiro[5.5]undecan-2-yl)-3-(4-(4-((pyridin-2-ylamino)methyl)piperidin-1-yl)phenyl)propanoic acid compound (96): 2-(1-methylcyclohexanecarboxamido)-3-(4-(4-(5,6,7,8-tetrahydro-1,8-naphthyridin-2-yl)piperidin-1-yl)phenyl)propanoic acid compound (97): 3-{4-[4-(4,5-dihydro-1H-imidazol-2-ylcarbamoyl)piperidin-1-yl]phenyl}-2-(2,4,6-trimethyl-benzoylamino)propionic acid compound (98): 2-(3,5-diethylisoxazole-4-carboxamido)-3-(4-(4-((pyridin-2-ylamino)methyl)piperidin-1-yl)phenyl)propanoic acid compound (99): 3-{4-[4-(4,5-Dihydro-1H-imidazol-2-ylcarbamoyl)piperidin-1-yl]phenyl}-2-(2-ethyl-6-methyl-benzoylamino)propionic acid compound (100): 2-(2-ethyl-6-methylbenzamido)-3-(1-(3-(5,6,7,8-tetrahydro-1,8-naphthyridin-2-yl)propanoyl)piperidin-4-yl)propanoic acid compound (101): 3-(1-(3-(5,6,7,8-tetrahydro-1,8-naphthyridin-2-yl)propanoyl)piperidin-4-yl)-2-(2,4,6-trimethylbenzamido)propanoic acid compound (102): 3-(4-(4-((pyridin-2-ylamino)methyl)piperidin-1-yl)phenyl)-2-(2,4,6-trimethylcyclohexanecarboxamido)propanoic acid compound (103): 2-(4-chloro-2-ethyl-6-methylbenzamido)-3-(4-(3-((pyridin-2-ylamino)methyl)azetidin-1-yl)phenyl)propanoic acid compound (104): 3-(4-(4-((4-methoxypyridin-2-ylamino)methyl)piperidin-1-yl)phenyl)-2-(1-methylcyclohexanecarboxamido)propanoic acid compound (105): 2-(2-oxo-1',3'-dihydrospiro[azetidine-3,2'-indene]-1-yl)-3-(4-(4-((pyridin-2-ylamino)methyl)piperidin-1-yl)phenyl)propanoic acid compound (106): 2-(4-fluoro-2,6-dimethylbenzamido)-3-(1-(3-(5,6,7,8-tetrahydro-1,8-naphthyridin-2-yl)propanoyl)piperidin-4-yl)propanoic acid compound (107): 2-(2-Ethyl-4-fluoro-6-methyl-benzoylamino)-3-[1-(2-5,6,7,8-tetrahydro-[1,8]naphthyridin-2-yl-acetyl)piperidin-4-yl]propionic acid compound (108): 2-(4-cyano-2,6-dimethylbenzamido)-3-(4-(4-((pyridin-2-ylamino)methyl)piperidin-1-yl)phenyl)propanoic acid compound (109): 2-(4-cyano-2-ethyl-6-methylbenzamido)-3-(4-(4-((pyridin-2-ylamino)methyl)-4,5-dihydrooxazol-2-yl)phenyl)propanoic acid compound (110): 2-(4-cyano-2-ethyl-6-methylbenzamido)-3-(4-(3-((pyridin-2-ylamino)methyl)pyrrolidin-1-yl)phenyl)propanoic acid compound (111): 3-(4-(4-((4-methylpyridin-2-ylamino)methyl)piperidin-1-yl)phenyl)-2-(2-oxo-3-phenylpyrrolidin-1-yl)propanoic acid compound (112): 2-(4-chloro-2,6-dimethyl-benzoylamino)-3-[1-(2-5,6,7,8-tetrahydro-[1,8]naphthyridin-2-yl-acetyl)piperidin-4-yl]propionic acid compound (113): 2-(4-acetyl-2-ethyl-6-methylbenzamido)-3-(4-(3-((pyridin-2-ylamino)methyl)azetidin-1-yl)phenyl)propanoic acid compound (114): 3-(4-(4-((4-methylpyridin-2-ylamino)methyl)-2-oxopyrrolidin-1-yl)phenyl)-2-(2,4,6-trimethylbenzamido)propanoic acid compound (115): 2-(2-ethyl-6-methylbenzamido)-3-(4-(4-((4-methylpyridin-2-ylamino)methyl)-2-oxopyrrolidin-1-yl)phenyl)propanoic acid compound (116): 2-(2-isopropyl-6-methylbenzamido)-3-(4-(4-((pyridin-2-ylamino)methyl)piperidin-1-yl)phenyl)propanoic acid compound (117): 2-(2-ethyl-6-methylbenzamido)-3-(4-(4-((4-methylpyridin-2-ylamino)methyl)piperidin-1-yl)phenyl)propanoic acid compound (118): 2-(4-cyano-2-ethyl-6-methyl-benzoylamino)-3-[1-(2-5,6,7,8-tetrahydro-[1,8]naphthyridin-2-yl-acetyl)piperidin-4-yl]propionic acid compound (119): 3-(4-(4-((1H-benzo[d]imidazol-2-ylamino)methyl)piperidin-1-yl)phenyl)-2-(1-methylcyclohexanecarboxamido)propanoic acid compound (120): 2-(2-ethyl-4-fluoro-6-methylbenzamido)-3-(4-(4-((pyridin-2-ylamino)methyl)piperidin-1-yl)phenyl)propanoic acid compound (121): 2-(2-ethyl-4-fluoro-6-methylbenzamido)-3-(4-(5-((pyridin-2-ylamino)methyl)-5,6-dihydro-4H-1,3-oxazin-2-yl)phenyl)propanoic acid compound (122): 2-(2-ethyl-4-fluoro-6-methylbenzamido)-3-(4-(2-oxo-4-((pyridin-2-ylamino)methyl)pyrrolidin-1-yl)phenyl)propanoic acid compound (123): 2-(2-methyl-6-(methylthio)benzamido)-3-(4-(4-((pyridin-2-ylamino)methyl)piperidin-1-yl)phenyl)propanoic acid compound (124): 3-(4-(4-((4-methylpyridin-2-ylamino)methyl)piperidin-1-yl)phenyl)-2-(1-oxo-2-azaspiro[5.5]undecan-2-yl)propanoic acid compound (125): 3-(4-(4-((4-oxo-1,4,5,6-tetrahydropyrimidin-2-ylamino)methyl)piperidin-1-yl)phenyl)-2-(2,4,6-trimethylbenzamido)propanoic acid compound (126): 2-(2-ethyl-6-methylbenzamido)-3-(4-(4-((4-oxo-1,4,5,6-tetrahydropyrimidin-2-ylamino)methyl)piperidin-1-yl)phenyl)propanoic acid compound (127): 2-(2-ethyl-6-methyl-benzoylamino)-3-{4-[4-(1,4,5,6-tetrahydro-pyrimidin-2-ylcarbamoyl)piperidin-1-yl]phenyl}propionic acid compound (128): 3-{4-[4-(1,4,5,6-Tetrahydro-pyrimidin-2-ylcarbamoyl)piperidin-1-yl]phenyl}-2-(2,4,6-trimethylbenzoylamino)propionic acid compound (129): 3-(4-(4-((pyridin-2-ylamino)methyl)piperidin-1-yl)phenyl)-2-(2,2,6,6-tetramethylcyclohexanecarboxamido)propanoic acid compound (130): 2-(4-chloro-2-ethyl-6-methylbenzamido)-3-(4-(4-((pyridin-2-ylamino)methyl)-4,5-dihydrooxazol-2-yl)phenyl)propanoic acid compound (131): 2-(4-chloro-2,6-dimethylbenzamido)-3-(4-(4-((pyridin-2-ylamino)methyl)piperidin-1-yl)phenyl)propanoic acid compound (132): 2-(4-chloro-2-ethyl-6-methylbenzamido)-3-(4-(3-((pyridin-2-ylamino)methyl)pyrrolidin-1-yl)phenyl)propanoic acid compound (133): 2-(2-ethyl-4-fluoro-6-methylbenzamido)-3-(1-(3-(5,6,7,8-tetrahydro-1,8-naphthyridin-2-yl)propanoyl)piperidin-4-yl)propanoic acid compound (134): 3-(4-(4-((4-methylpyridin-2-ylamino)methyl)piperidin-1-yl)phenyl)-2-(2-oxo-1',3'-dihydrospiro[azetidine-3,2'-indene]-1-yl)propanoic acid compound (135): 2-(2'-oxo-1,3-dihydrospiro[indene-2,3'-pyrrolidine]-1'-yl)-3-(4-(4-((pyridin-2-ylamino)methyl)piperidin-1-yl)phenyl)propanoic acid compound (136): 2-(4-cyano-2-ethyl-6-methylbenzamido)-3-(4-(5-((pyridin-2-ylamino)methyl)-5,6-dihydro-4H-1,3-oxazin-2-yl)phenyl)propanoic acid compound (137): 2-(4-cyano-2-ethyl-6-methylbenzamido)-3-(4-(2-oxo-4-((pyridin-2-ylamino)methyl)pyrrolidin-1-yl)phenyl)propanoic acid compound (138): 2-(4-cyano-2-ethyl-6-methylbenzamido)-3-(4-(4-((pyridin-2-ylamino)methyl)piperidin-1-yl)phenyl)propanoic acid compound (139): 2-(4-chloro-2,6-dimethylbenzamido)-3-(1-(3-(5,6,7,8-tetrahydro-1,8-naphthyridin-2-yl)propanoyl)piperidin-4-yl)propanoic acid compound (140): 2-(4-chloro-2-ethyl-6-methyl-benzoylamino)-3-[1-(2-5,6,7,8-tetrahydro-[1,8]naphthyridin-2-yl-acetyl)piperidin-4-yl]propionic acid compound (141): 2-(4-acetyl-2-ethyl-6-methylbenzamido)-3-(4-(4-((pyridin-2-ylamino)methyl)-4,5-dihydrooxazol-2-yl)phenyl)propanoic acid compound (142): 2-(4-acetyl-2,6-dimethylbenzamido)-3-(4-(4-((pyridin-2-ylamino)methyl)piperidin-1-yl)phenyl)propanoic acid compound (143): 2-(4-acetyl-2-ethyl-6-methylbenzamido)-3-(4-(3-((pyridin-2-ylamino)methyl)pyrrolidin-1-yl)phenyl)propanoic acid compound (144): 2-(4-carbamoyl-2,6-dimethyl-benzoylamino)-3-{4-[4-(pyridin-2-ylaminomethyl)piperidin-1-yl]phenyl}propionic acid compound (145): 2-(4-cyano-2-ethyl-6-methyl-benzoylamino)-3-{4-[4-(4,5-dihydro-1H-imidazol-2-ylcarbamoyl)piperidin-1-yl]phenyl}propionic acid compound (146): 2-(2-ethyl-6-methylbenzamido)-3-(4-(4-((4-methoxypyridin-2-ylamino)methyl)piperidin-1-yl)phenyl)propanoic acid compound (147): 3-(4-(4-((4-methoxypyridin-2-ylamino)methyl)piperidin-1-yl)phenyl)-2-(2,4,6-trimethylbenzamido)propanoic acid compound (148): 2-(4-cyano-2-ethyl-6-methylbenzamido)-3-(1-(3-(5,6,7,8-tetrahydro-1,8-naphthyridin-2-yl)propanoyl)piperidin-4-yl)propanoic acid compound (149): 2-(2,6-dimethyl-4-nitrobenzamido)-3-(4-(4-((pyridin-2-ylamino)methyl)piperidin-1-yl)phenyl)propanoic acid compound (150): 2-(2-ethyl-4-fluoro-6-methylbenzamido)-3-(4-(4-((4-methylpyridin-2-ylamino)methyl)-2-oxopyrrolidin-1-yl)phenyl)propanoic acid compound (151): 2-(4-fluoro-2-isopropyl-6-methylbenzamido)-3-(4-(4-((pyridin-2-ylamino)methyl)piperidin-1-yl)phenyl)propanoic acid compound (152): 2-(2-ethyl-4-fluoro-6-methylbenzamido)-3-(4-(4-((4-methylpyridin-2-ylamino)methyl)piperidin-1-yl)phenyl)propanoic acid compound (153): 2-(4-acetyl-2-ethyl-6-methyl-benzoylamino)-3-[1-(2-5,6,7,8-tetrahydro-[1,8]naphthyridin-2-yl-acetyl)piperidin-4-yl]propionic acid compound (154): 2-(4-chloro-2-ethyl-6-methylbenzamido)-3-(4-(5-((pyridin-2-ylamino)methyl)-5,6-dihydro-4H-1,3-oxazin-2-yl)phenyl)propanoic acid compound (155): 2-(4-chloro-2-ethyl-6-methylbenzamido)-3-(4-(2-oxo-4-((pyridin-2-ylamino)methyl)pyrrolidin-1-yl)phenyl)propanoic acid compound (156): 2-(4-chloro-2-ethyl-6-methylbenzamido)-3-(4-(4-(pyridin-2-ylamino)methyl)piperidin-1-yl)phenyl)propanoic acid compound (157): 2-(4-fluoro-2-methyl-6-(methylthio)benzamido)-3-(4-(4-(pyridin-2-ylamino)methyl)piperidin-1-yl)phenyl)propanoic acid compound (158): 2-(2-ethyl-4-fluoro-6-methylbenzamido)-3-(4-(4-((4-oxo-1,4,5,6-tetrahydropyrimidin-2-ylamino)methyl)piperidin-1-yl)phenyl)propanoic acid compound (159): 2-(2-ethyl-4-fluoro-6-methyl-benzoylamino)-3-{4-[4-(1,4,5,6-tetrahydro-pyrimidin-2-ylcarbamoyl)piperidin-1-yl]phenyl}propionic acid compound (160): 3-(4-(4-((4-methylpyridin-2-ylamino)methyl)piperidin-1-yl)phenyl)-2-(2'-oxo-1,3-dihydrospiro[indene-2,3'-pyrrolidine]-1'-yl)propanoic acid compound (161): 2-(2-ethyl-4-(1H-imidazol-1-yl)-6-methylbenzamido)-3-(4-(3-((pyridin-2-ylamino)methyl)azetidin-1-yl)phenyl)propanoic acid compound (162): 2-(4-cyano-2-ethyl-6-methylbenzamido)-3-(4-(4-((4-methylpyridin-2-ylamino)methyl)-2-oxopyrrolidin-1-yl)phenyl)propanoic acid compound (163): 3-(4-(4-((1H-benzo[d]imidazol-2-ylamino)methyl)piperidin-1-yl)phenyl)-2-(2-ethyl-6-methylbenzamido)propanoic acid compound (164): 2-(4-cyano-2-ethyl-6-methylbenzamido)-3-(4-(4-((4-methylpyridin-2-ylamino)methyl)piperidin-1-yl)phenyl)propanoic acid compound (165): 2-(4-chloro-2-ethyl-6-methyl-benzoylamino)-3-{4-[4-(4,5-dihydro-1H-imidazol-2-ylcarbamoyl)piperidin-1-yl]phenyl}propionic acid compound (166): 2-(2-methyl-6-(trifluoromethyl)benzamido)-3-(4-(4-((pyridin-2-ylamino)methyl)piperidin-1-yl)phenyl)propanoic acid compound (167): 2-(2-ethyl-6-methyl-4-(trifluoromethyl)benzamido)-3-(4-(3-((pyridin-2-ylamino)methyl)azetidin-1-yl)phenyl)propanoic acid compound (168): 2-(4-chloro-2-ethyl-6-methylbenzamido)-3-(1-(3-(5,6,7,8-tetrahydro-1,8-naphthyridin-2-yl)propanoyl)piperidin-4-yl)propanoic acid compound (169): 2-(2-methyl-4-(trifluoromethyl)nicotinamido)-3-(4-(4-((pyridin-2-ylamino)methyl)piperidin-1-yl)phenyl)propanoic acid compound (170): 2-(4-acetyl-2-ethyl-6-methylbenzamido)-3-(4-(5-((pyridin-2-ylamino)methyl)-5,6-dihydro-4H-1,3-oxazin-2-yl)phenyl)propanoic acid compound (171): 2-(4-acetyl-2-ethyl-6-methylbenzamido)-3-(4-(2-oxo-4-((pyridin-2-ylamino)methyl)pyrrolidin-1-yl)phenyl)propanoic acid compound (172): 2-(4-acetyl-2-ethyl-6-methylbenzamido)-3-(4-(4-((pyridin-2-ylamino)methyl)piperidin-1-yl)phenyl)propanoic acid compound (173): 2-(4-carbamoyl-2-ethyl-6-methyl-benzoylamino)-3-{4-[4-(pyridin-2-ylaminomethyl)piperidin-1-yl]phenyl}propionic acid compound (174): 2-(4-cyano-2-methyl-6-(methylthio)benzamido)-3-(4-(4-((pyridin-2-ylamino)methyl)piperidin-1-yl)phenyl)propanoic acid compound (175): 2-(2,6-dimethyl-4-(methylcarbamoyl)benzamido)-3-(4-(4-((pyridin-2-ylamino)methyl)piperidin-1-yl)phenyl)propanoic acid compound (176): 2-(4-(methoxycarbonyl)-2,6-dimethylbenzamido)-3-(4-(4-((pyridin-2-ylamino)methyl)piperidin-1-yl)phenyl)propanoic acid compound (177): 2-(4-cyano-2-ethyl-6-methylbenzamido)-3-(4-(4-((4-oxo-1,4,5,6-tetrahydropyrimidin-2-ylamino)methyl)piperidin-1-yl)phenyl)propanoic acid compound (178): 2-(4-cyano-2-ethyl-6-methyl-benzoylamino)-3-{4-[4-(1,4,5,6-tetrahydro-pyrimidin-2-ylcarbamoyl)piperidin-1-yl]phenyl}propionic acid compound (179): 2-(2,6-dimethyl-4-trifluoromethyl-benzoylamino)-3-[1-(2-5,6,7,8-tetrahydro-[1,8]naphthyridin-2-yl-acetyl)piperidin-4-yl]propionic acid compound (180): 2-(4-acetyl-2-ethyl-6-methyl-benzoylamino)-3-{4-[4-(4,5-dihydro-1H-imidazol-2-ylcarbamoyl)piperidin-1-yl]phenyl}propionic acid compound (181): 2-(2-ethyl-4-fluoro-6-methylbenzamido)-3-(4-(4-((4-methoxypyridin-2-ylamino)methyl)piperidin-1-yl)phenyl)propanoic acid compound (182): 2-(4-acetyl-2-ethyl-6-methylbenzamido)-3-(1-(3-(5,6,7,8-tetrahydro-1,8-naphthyridin-2-yl)propanoyl)piperidin-4-yl)propanoic acid compound (183): 2-(4-chloro-2-ethyl-6-methylbenzamido)-3-(4-(4-((4-methylpyridin-2-ylamino)methyl)-2-oxopyrrolidin-1-yl)phenyl)propanoic acid compound (184): 2-(4-chloro-2-ethyl-6-methylbenzamido)-3-(4-(4-((4-methylpyridin-2-ylamino)methyl)piperidin-1-yl)phenyl)propanoic acid compound (185): 2-(2-bromo-6-methylbenzamido)-3-(4-(4-((pyridin-2-ylamino)methyl)piperidin-1-yl)phenyl)propanoic acid compound (186): 2-(2-ethyl-4-(1H-imidazol-1-yl)-6-methylbenzamido)-3-(4-(4-((pyridin-2-ylamino)methyl)-4,5-dihydrooxazol-2-yl)phenyl)propanoic acid compound (187): 2-(4-(1H-imidazol-1-yl)-2,6-dimethylbenzamido)-3-(4-(4-((pyridin-2-ylamino)methyl)piperidin-1-yl)phenyl)propanoic acid compound (188): 2-(4-(1H-imidazol-2-yl)-2,6-dimethylbenzamido)-3-(4-(4-((pyridin-2-ylamino)methyl)piperidin-1-yl)phenyl)propanoic acid compound (189): 2-(2-ethyl-4-(1H-imidazol-1-yl)-6-methylbenzamido)-3-(4-(3-((pyridin-2-ylamino)methyl)pyrrolidin-1-yl)phenyl)propanoic acid compound (190): 2-(4-chloro-2-methyl-6-(methylthio)benzamido)-3-(4-(4-((pyridin-2-ylamino)methyl)piperidin-1-yl)phenyl)propanoic acid compound (191): 2-(2,6-dimethyl-4-(oxazol-2-yl)benzamido)-3-(4-(4-((pyridin-2-ylamino)methyl)piperidin-1-yl)phenyl)propanoic acid compound (192): 2-(4-chloro-2-ethyl-6-methylbenzamido)-3-(4-(4-((4-oxo-1,4,5,6-tetrahydropyrimidin-2-ylamino)methyl)piperidin-1-yl)phenyl)propanoic acid compound (193): 2-(4-chloro-2-ethyl-6-methyl-benzoylamino)-3-{4-[4-(1,4,5,6-tetrahydro-pyrimidin-2-ylcarbamoyl)piperidin-1-yl]phenyl}propionic acid compound (194): 2-(2,6-dimethyl-4-(trifluoromethyl)benzamido)-3-(4-(4-((pyridin-2-ylamino)methyl)piperidin-1-yl)phenyl)propanoic acid compound (195): 2-(2-ethyl-6-methyl-4-(trifluoromethyl)benzamido)-3-(4-(4-((pyridin-2-ylamino)methyl)-4,5-dihydrooxazol-2-yl)phenyl)propanoic acid compound (196): 2-(2-ethyl-6-methyl-4-(trifluoromethyl)benzamido)-3-(4-(3-((pyridin-2-ylamino)methyl)pyrrolidin-1-yl)phenyl)propanoic acid compound (197): 2-(4-cyano-2-ethyl-6-methylbenzamido)-3-(4-(4-((4-methoxypyridin-2-ylamino)methyl)piperidin-1-yl)phenyl)propanoic acid compound (198): 2-(2-methyl-4-(trifluoromethoxy)benzamido)-3-(4-(4-((pyridin-2-ylamino)methyl)piperidin-1-yl)phenyl)propanoic acid compound (199): 2-(4-acetyl-2-ethyl-6-methylbenzamido)-3-(4-(4-((4-methylpyridin-2-ylamino)methyl)-2-oxopyrrolidin-1-yl)phenyl)propanoic acid compound (200): 2-(4-acetyl-2-ethyl-6-methylbenzamido)-3-(4-(4-((4-methylpyridin-2-ylamino)methyl)piperidin-1-yl)phenyl)propanoic acid compound (201): 2-(2-ethyl-6-methyl-4-(methylcarbamoyl)benzamido)-3-(4-(4-((pyridin-2-ylamino)methyl)piperidin-1-yl)phenyl)propanoic acid compound (202): 2-(4-(dimethylcarbamoyl)-2,6-dimethylbenzamido)-3-(4-(4-((pyridin-2-ylamino)methyl)piperidin-1-yl)phenyl)propanoic acid compound (203): 3-(4-(4-((1H-benzo[d]imidazol-2-ylamino)methyl)piperidin-1-yl)phenyl)-2-(2-ethyl-4-fluoro-6-methylbenzamido)propanoic acid compound (204): N-(1-carboxy-2-{4-[4-(pyridin-2-ylaminomethyl)piperidin-1-yl]phenyl}ethyl)-3-ethyl-5-methyl-terephthalamic acid methyl ester compound (205): 2-(2-ethyl-4-imidazol-1-yl-6-methyl-benzoylamino)-3-[1-(2-5,6,7,8-tetrahydro-[1,8]naphthyridin-2-yl-acetyl)piperidin-4-yl]propionic acid compound (206): 2-(2,6-dimethyl-4-(trifluoromethyl)benzamido)-3-(1-(3-(5,6,7,8-tetrahydro-1,8-naphthyridin-2-yl)propanoyl)piperidin-4-yl)propanoic acid compound (207): 2-(2-ethyl-6-methyl-4-trifluoromethyl-benzoylamino)-3-[1-(2-5,6,7,8-tetrahydro-[1,8]naphthyridin-2-yl-acetyl)piperidin-4-yl]propionic acid compound (208): 2-(4-chloro-2-ethyl-6-methylbenzamido)-3-(4-(4-(5,6,7,8-tetrahydro-1,8-naphthyridin-2-yl)piperidin-1-yl)phenyl)propanoic acid compound (209): 2-(4-acetyl-2-ethyl-6-methylbenzamido)-3-(4-(4-((4-oxo-1,4,5,6-tetrahydropyrimidin-2-ylamino)methyl)piperidin-1-yl)phenyl)propanoic acid compound (210): 2-(4-acetyl-2-ethyl-6-methyl-benzoylamino)-3-{4-[4-(1,4,5,6-tetrahydro-pyrimidin-2-ylcarbamoyl)piperidin-1-yl]phenyl}propionic acid compound (211): 2-(4-(benzyloxy)benzamido)-3-(4-(4-((pyridin-2-ylamino)methyl)piperidin-1-yl)phenyl)propanoic acid compound (212): 2-(2,6-dimethyl-4-(methylsulfonyl)benzamido)-3-(4-(4-((pyridin-2-ylamino)methyl)piperidin-1-yl)phenyl)propanoic acid compound (213): 3-(4-(4-((1H-benzo[d]imidazol-2-ylamino)methyl)piperidin-1-yl)phenyl)-2-(4-cyano-2-ethyl-6-methylbenzamido)propanoic acid compound (214): 2-(4-chloro-2-ethyl-6-methylbenzamido)-3-(4-(4-((4-methoxypyridin-2-ylamino)methyl)piperidin-1-yl)phenyl)propanoic acid compound (215): 2-(2,6-dimethyl-4-sulfamoyl-benzoylamino)-3-{4-[4-(pyridin-2-ylaminomethyl)piperidin-1-yl]phenyl}propionic acid compound (216): 2-(2-ethyl-4-(1H-imidazol-1-yl)-6-methylbenzamido)-3-(4-(4-((pyridin-2-ylamino)methyl)piperidin-1-yl)phenyl)propanoic acid compound (217): 2-[2-ethyl-4-(1H-imidazol-2-yl)-6-methyl-benzoylamino]-3-{4-[4-(pyridin-2-ylaminomethyl)piperidin-1-yl]phenyl}propionic acid compound (218): 2-(2-ethyl-4-(1H-imidazol-1-yl)-6-methylbenzamido)-3-(4-(5-((pyridin-2-ylamino)methyl)-5,6-dihydro-4H-1,3-oxazin-2-yl)phenyl)propanoic acid compound (219): 2-(2-ethyl-4-(1H-imidazol-1-yl)-6-methylbenzamido)-3-(4-(2-oxo-4-((pyridin-2-ylamino)methyl)pyrrolidin-1-yl)phenyl)propanoic acid compound (220): 2-(2-ethyl-6-methyl-4-(oxazol-2-yl)benzamido)-3-(4-(4-((pyridin-2-ylamino)methyl)piperidin-1-yl)phenyl)propanoic acid compound (221): 2-(2-ethyl-6-methyl-4-(trifluoromethyl)benzamido)-3-(4-(4-((pyridin-2-ylamino)methyl)piperidin-1-yl)phenyl)propanoic acid compound (222): 2-(2-ethyl-6-methyl-4-(trifluoromethyl)benzamido)-3-(4-(5-((pyridin-2-ylamino)methyl)-5,6-dihydro-4H-1,3-oxazin-2-yl)phenyl)propanoic acid compound (223): 2-(2-ethyl-6-methyl-4-(trifluoromethyl)benzamido)-3-(4-(2-oxo-4-((pyridin-2-ylamino)methyl)pyrrolidin-1-yl)phenyl)propanoic acid compound (224): 2-(4-acetyl-2-ethyl-6-methylbenzamido)-3-(4-(4-(5,6,7,8-tetrahydro-1,8-naphthyridin-2-yl)piperidin-1-yl)phenyl)propanoic acid compound (225): 2-(4-(dimethylcarbamoyl)-2-ethyl-6-methylbenzamido)-3-(4-(4-((pyridin-2-ylamino)methyl)piperidin-1-yl)phenyl)propanoic acid compound (226): 3-{4-[4-(4,5-dihydro-1H-imidazol-2-ylcarbamoyl)piperidin-1-yl]phenyl}-2-[2-ethyl-4-(1H-imidazol-2-yl)-6-methyl-benzoylamino]propionic acid compound (227): 2-(4-acetyl-2-ethyl-6-methylbenzamido)-3-(4-(4-((4-methoxypyridin-2-ylamino)methyl)piperidin-1-yl)phenyl)propanoic acid compound (228): 2-(2-ethyl-4-(1H-imidazol-1-yl)-6-methylbenzamido)-3-(1-(3-(5,6,7,8-tetrahydro-1,8-naphthyridin-2-yl)propanoyl)piperidin-4-yl)propanoic acid compound (229): 3-{4-[4-(4,5-dihydro-1H-imidazol-2-ylcarbamoyl)piperidin-1-yl]phenyl}-2-(2-ethyl-6-methyl-4-trifluoromethyl-benzoylamino)propionic acid compound (230): 3-(4-(4-((1H-benzo[d]imidazol-2-ylamino)methyl)piperidin-1-yl)phenyl)-2-(4-chloro-2-ethyl-6-methylbenzamido)propanoic acid compound (231): 2-(2-ethyl-6-methyl-4-(trifluoromethyl)benzamido)-3-(1-(3-(5,6,7,8-tetrahydro-1,8-naphthyridin-2-yl)propanoyl)piperidin-4-yl)propanoic acid compound (232): 2-(2-ethyl-4-methanesulfonyl-6-methyl-benzoylamino)-3-{4-[4-(pyridin-2-ylaminomethyl)piperidin-1-yl]phenyl}propionic acid compound (233): 2-(2-ethyl-4-(1H-imidazol-1-yl)-6-methylbenzamido)-3-(4-(4-((4-methylpyridin-2-ylamino)methyl)-2-oxopyrrolidin-1-yl)phenyl)propanoic acid compound (234): 2-(2-ethyl-4-(1H-imidazol-1-yl)-6-methylbenzamido)-3-(4-(4-((4-methylpyridin-2-ylamino)methyl)piperidin-1-yl)phenyl)propanoic acid compound (235): 3-(4-(4-((1H-benzo[d]imidazol-2-ylamino)methyl)piperidin-1-yl)phenyl)-2-(4-acetyl-2-ethyl-6-methylbenzamido)propanoic acid compound (236): 2-(2,6-dimethyl-4-(2,2,2-trifluoroacetyl)benzamido)-3-(4-(4-(pyridin-2-ylamino)methyl)piperidin-1-yl)phenyl)propanoic acid compound (237): 2-(2-ethyl-6-methyl-4-(trifluoromethyl)benzamido)-3-(4-(4-((4-methylpyridin-2-ylamino)methyl)-2-oxopyrrolidin-1-yl)phenyl)propanoic acid compound (238): 2-(2-ethyl-6-methyl-4-(trifluoromethyl)benzamido)-3-(4-(4-((4-methylpyridin-2-ylamino)methyl)piperidin-1-yl)phenyl)propanoic acid compound (239): 2-(2-ethyl-6-methyl-4-(trifluoromethoxy)benzamido)-3-(4-(4-((pyridin-2-ylamino)methyl)piperidin-1-yl)phenyl)propanoic acid compound (240): 2-(2-ethyl-4-(1H-imidazol-1-yl)-6-methylbenzamido)-3-(4-(4-((4-oxo-1,4,5,6-tetrahydropyrimidin-2-ylamino)methyl)piperidin-1-yl)phenyl)propanoic acid compound (241): 2-[2-ethyl-4-(1H-imidazol-2-yl)-6-methyl-benzoylamino]-3-{4-[4-(1,4,5,6-tetrahydro-pyrimidin-2-ylcarbamoyl)piperidin-1-yl]phenyl}propionic acid compound (242): 2-(2-methyl-6-(methylthio)-4-(trifluoromethyl)benzamido)-3-(4-(4-((pyridin-2-ylamino)methyl)piperidin-1-yl)phenyl)propanoic acid compound (243): 2-(2-ethyl-6-methyl-4-(trifluoromethyl)benzamido)-3-(4-(4-((4-oxo-1,4,5,6-tetrahydropyrimidin-2-ylamino)methyl)piperidin-1-yl)phenyl)propanoic acid compound (244): 2-(2-ethyl-6-methyl-4-trifluoromethyl-benzoylamino)-3-{4-[4-(1,4,5,6-tetrahydro-pyrimidin-2-ylcarbamoyl)piperidin-1-yl]phenyl}propionic acid compound (245): 2-(2-ethyl-6-methyl-4-methylsulfamoyl-benzoylamino)-3-{4-[4-(pyridin-2-ylaminomethyl)piperidin-1-yl]phenyl}propionic acid compound (246): 2-(4-(N,N-dimethylsulfamoyl)-2,6-dimethylbenzamido)-3-(4-(4-(pyridin-2-ylamino)methyl)piperidin-1-yl)phenyl)propanoic acid compound (247): 2-(2-ethyl-6-methyl-4-(trifluoromethyl)benzamido)-3-(4-(4-(5,6,7,8-tetrahydro-1,8-naphthyridin-2-yl)piperidin-1-yl)phenyl)propanoic acid compound (248): 2-[2-ethyl-6-methyl-4-(2,2,2-trifluoro-acetyl)benzoylamino]-3-{4-[4-(pyridin-2-ylaminomethyl)piperidin-1-yl]phenyl}propionic acid
compound (249): 2-(2-ethyl-4-(1H-imidazol-1-yl)-6-methylbenzamido)-3-(4-(4-((4-methoxypyridin-2-ylamino)methyl)piperidin-1-yl)phenyl)propanoic acid
compound (250): 2-(2-ethyl-6-methyl-4-(trifluoromethyl)benzamido)-3-(4-(4-((4-methoxypyridin-2-ylamino)methyl)piperidin-1-yl)phenyl)propanoic acid
compound (251): 2-(2,6-dimethyl-4-(trichloromethyl)benzamido)-3-(4-(4-((pyridin-2-ylamino)methyl)piperidin-1-yl)phenyl)propanoic acid
compound (252): 3-(4-(4-((1H-benzo[d]imidazol-2-ylamino)methyl)piperidin-1-yl)phenyl)-2-(2-ethyl-4-(1H-imidazol-1-yl)-6-methylbenzamido)propanoic acid
compound (253): 3-(4-(4-((1H-benzo[d]imidazol-2-ylamino)methyl)piperidin-1-yl)phenyl)-2-(2-ethyl-6-methyl-4-(trifluoromethyl)benzamido)propanoic acid
compound (254): 2-(4-dimethylsulfamoyl-2-ethyl-6-methyl-benzoylamino)-3-{4-[4-(pyridin-2-ylaminomethyl)piperidin-1-yl]phenyl}propionic acid
compound (255): 2-(2-ethyl-6-methyl-4-trichloromethyl-benzoylamino)-3-{4-[4-(pyridin-2-ylaminomethyl)piperidin-1-yl]phenyl}propionic acid
compound (256): 2-(2,6-dimethyl-4-(trifluoromethylsulfonyl)benzamido)-3-(4-(4-((pyridin-2-ylamino)methyl)piperidin-1-yl)phenyl)propanoic acid
compound (257): 2-(2-ethyl-6-methyl-4-trifluoromethanesulfonyl-benzoylamino)-3-{4-[4-(pyridin-2-ylaminomethyl)piperidin-1-yl]phenyl}propionic acid
compound (258): 3-(4-(4-((pyridin-2-ylamino)methyl)piperidin-1-yl)phenyl)-2-(2,4,6-tribromobenzamido)propanoic acid
compound (259): 2-(2,6-dimethyl-benzoylamino)-3-(4-{4-[(4-methyl-pyridin-2-ylamino)methyl]piperidin-1-yl}phenyl)propionic acid
compound (260): 2-(4-cyano-benzoylamino)-3-(4-{4-[(4-methyl-pyridin-2-ylamino)methyl]piperidin-1-yl}phenyl)propionic acid
compound (261): 3-(4-{4-[(4-methyl-pyridin-2-ylamino)methyl]piperidin-1-yl}phenyl)-2-(2,4,6-tribromo-benzoylamino)propionic acid
compound (262): 2-benzoylamino-3-(4-{4-[(4-methyl-pyridin-2-ylamino)methyl]piperidin-1-yl}phenyl)propionic acid
compound (263): 2-(4-fluoro-2,6-dimethyl-benzoylamino)-3-(4-{4-[(4-methyl-pyridin-2-ylamino)methyl]piperidin-1-yl}phenyl)propionic acid
compound (264): 2-(2-bromo-6-methyl-benzoylamino)-3-(4-{4-[(4-methyl-pyridin-2-ylamino)methyl]piperidin-1-yl}phenyl)propionic acid
compound (265): 2-(2-methyl-benzoylamino)-3-(4-{4-[(4-methyl-pyridin-2-ylamino)methyl]piperidin-1-yl}phenyl)propionic acid
compound (266): 2-(3-methyl-2-phenyl-butyrylamino)-3-(4-{4-[(4-methyl-pyridin-2-ylamino)methyl]piperidin-1-yl}phenyl)propionic acid
compound (267): 2-(2,6-dimethyl-benzoylamino)-3-(4-{4-[(4-methoxy-pyridin-2-ylamino)methyl]piperidin-1-yl}phenyl)propionic acid
compound (268): 2-(4-fluoro-2,6-dimethyl-benzoylamino)-3-(4-{4-[(4-methoxy-pyridin-2-ylamino)methyl]piperidin-1-yl}phenyl)propionic acid
compound (269): 3-(4-{4-[(3-propyl-ureido)methyl]piperidin-1-yl}phenyl)-2-(2,4,6-trimethyl-benzoylamino)propionic acid
compound (270): 3-{4-[4-(3-cyclopropylmethyl-ureidomethyl)piperidin-1-yl]phenyl}-2-(2,4,6-trimethyl-benzoylamino)propionic acid
compound (271): 3-(4-{4-[(3-cyclobutyl-ureido)methyl]piperidin-1-yl}phenyl)-2-(2,4,6-trimethyl-benzoylamino)propionic acid
compound (272): 3-(4-{4-[3-(2,2,2-trifluoro-ethyl)ureidomethyl]piperidin-1-yl}phenyl)-2-(2,4,6-trimethyl-benzoylamino)propionic acid.
compound (273): 3-(4-{4-[3-(2,2,3,3,3-pentafluoro-propyl)ureidomethyl]piperidin-1-yl}phenyl)-2-(2,4,6-trimethyl-benzoylamino)propionic acid In an embodiment of the compounds according to the first to the fourth aspect comprise a further moiety, preferably a moiety which is selected from the group comprising a targeted moiety, a delivery moiety, and a detection moiety.

In a preferred embodiment of the first to the fourth aspect the further moiety is attached or incorporated, preferably conjugated to the compounds according to the first to the fourth aspect.

In a further preferred embodiment of the first to the fourth aspect the detection moiety is a label, whereby preferably the label is selected from the group comprising radionuclide labels, paramagnetic material, X-ray attenuating material, immune labels, colored labels, infrared labels, chemiluminescent labels, luminescent labels, fluorescent labels, enzyme substrates, enzymes, and labels complexing detectable ions.

In a still further preferred embodiment of the first to the fourth aspect the moiety is a targeted moiety, whereby the targeted moiety is preferably a pharmaceutically active moiety, whereby the pharmaceutically active moiety is selected from the group comprising cytotoxins, chemotherapeutics, antibodies, radionuclides and cytotoxic proteins.

In a further preferred embodiment of the first to the fourth aspect the targeted moiety is selected from the group comprising antibodies, linker molecules and liposomes.

The problem underlying the present invention is solved in a fifth aspect by the use of a compound according to the first to the fourth aspect as an inhibitor, which is preferably a first embodiment of the fifth aspect.

In an embodiment, which is preferably a second embodiment of the fifth aspect, which is preferably a further embodiment of the first embodiment of the fifth aspect, the compound is an inhibitor to an integrin.

In an embodiment, which is preferably a third embodiment of the fifth aspect, which is preferably a further embodiment of the second embodiment of the fifth aspect, the integrin is alpha5beta1 integrin.

The problem underlying the present invention is solved in a sixth aspect by the use of a compound according to any of the first to the fourth aspect of the invention for the manufacture of a medicament, preferably a medicament for the treatment and/or prevention of a disease, which is preferably a first embodiment of the sixth aspect.

In an embodiment, which is preferably a second embodiment of the sixth aspect, which is preferably a further embodiment of the first embodiment of the sixth aspect, the medicament is for a disease mediated by or involving alpha5beta1 integrin.

In an embodiment, which is preferably a third embodiment of the sixth aspect, which is preferably a further embodiment of the first and second embodiment of the sixth aspect, the disease is selected from the group comprising diseases based on pathological angiogenesis and/or diseases based on interaction of an integrin with a ligand, whereby preferably the ligand is present on the extracellular matrix and/or on any cell surface.

In an embodiment, which is preferably a fourth embodiment of the sixth aspect, which is preferably a further embodiment of the first to the third embodiment of the sixth aspect, the disease is related to an ocular tissue, the skin, joints, synovial tissue, liver, kidney, lung, heart, bladder, neoplasm, intestinal tissue, blood, connective tissue and/or the bone tissue.

In an embodiment, which is preferably a fifth embodiment of the sixth aspect, which is preferably a further embodiment of the first to the fourth embodiment of the sixth aspect, the disease is a disease of an ocular tissue, preferably diabetic retinopathy, retinopathy of prematurity or macular degeneration, more preferably age related macular degeneration.

In an embodiment, which is preferably a sixth embodiment of the sixth aspect, which is preferably a further embodiment of the first to the fourth embodiment of the sixth aspect, the disease is a disease of the skin, more preferably hemangioma and psoriasis.

In an embodiment, which is preferably a seventh embodiment of the sixth aspect, which is preferably a further embodiment of the first to the fourth embodiment of the sixth aspect, the disease is a disease of or affecting the joints, more preferably primary arthritis including rheumatoid arthritis, psoriatic arthritis, osteoarthritis, and secondary arthritis.

In an embodiment, which is preferably an eighth embodiment of the sixth aspect, which is preferably a further embodiment of the first to the fourth embodiment of the sixth aspect, the disease is a neoplasm, more preferably a malignant neoplasm.

In an embodiment, which is preferably a nineth embodiment of the sixth aspect, which is preferably a further embodiment of the eighth embodiment of the sixth aspect, the malignant neoplasm is selected from the group comprising sarcoma, carcinoma, osteosarcoma, adenocarcinoma, blastoma, myeloma, leukaemia, lymphoma, including but not limited to breast cancer, gynaecological cancers, pancreatic cancer, bladder cancer, mesothelioma, teratocarcinoma, astrocytoma, melanoma, angioma and glioblastoma, renal cancer, prostate cancer, brain cancer, lung cancer, head and neck cancer, parotid cancer, thyroid cancer, fibrosarcoma, gastrointestinal cancer, endocrine cancer, AIDS-related cancers, adrenal cancer, eye cancer, hepatocellular cancer, skin cancer, thymus cancer, and testicular cancer.

In an embodiment, which is preferably a tenth embodiment of the sixth aspect, which is preferably a further embodiment of the first to the third embodiment of the sixth aspect, the disease is based on an interaction of an integrin with a ligand in the extracellular matrix or on the cell surface, preferably the disease is an inflammatory disease.

In an embodiment, which is preferably an eleventh embodiment of the sixth aspect, which is preferably a further embodiment of the first to the third embodiment of the sixth aspect, the disease is based on an interaction of an integrin with a ligand in the extracellular matrix or on the cell surface, preferably the disease is an infectious disease.

In an embodiment, which is preferably a twelfth embodiment of the sixth aspect, which is preferably a further embodiment of the first to fourth and tenth embodiment of the sixth aspect, the inflammatory disease is a disease selected from the group comprising rheumatoid arthritis, juvenile arthritis, psoriatic arthritis, osteoarthritis, glomerulonephritis, gingivitis, inflammatory bowel disease, ulcerative colitis, systemic lupus erythematosus associated glomerulonephritis, irritable bowel syndrome, bronchial asthma, multiple sclerosis, pemphigus, pemphigoid, scleroderma, myasthenia gravis, Wegener's granulomatosis, Churg-Strauss-allergic granulomatosis, Sjögren's syndrome, Sicca syndrome, Goopasture's disease, autoimmune haemolytic and thrombocytopenic states, pulmonary hemorrhage, vasculitis, Crohn's disease, and dermatomyositis, ankylosing spondylitis, burns, lung injury, myocardial infarction, coronary thrombosis, vascular occlusion, post-surgical vascular reocclusion, IgA nephropathy, sarcoidosis, eosinophilic granulomata, midline granuloma, arteritis temporalis, Takayasu's arteritis, pterygia, Kawasaki's disease, atherosclerosis, traumatic central nervous system injury, ischemic heart disease and ischemia-reperfusion injury, acute respiratory distress syndrome, systemic inflammatory response syndrome, multiple organ dysfunction syndrome, tissue graft rejection and hyperacute rejection of transplanted organs, uveitis, psoriasis, rosacea, transplantation and asthma.

In an embodiment, which is preferably a thirteenth embodiment of the sixth aspect, which is preferably a further embodiment of the first to the fourth and tenth to the eleventh embodiment of the sixth aspect, the disease is an infectious disease, more preferably the disease is an infection caused by or involving fungi, bacteria and/or viruses.

In an embodiment, which is preferably a fourteenth embodiment of the sixth aspect, which is preferably a further embodiment of the first to the fourth and tenth to the eleventh embodiment of the sixth aspect, the disease is connected with a non-neoplastic cell proliferation and/or tissue remodelling.

In an embodiment, which is preferably a fifteenth embodiment of the sixth aspect, which is preferably a further embodiment of the first to the fourth and tenth, eleventh and fourteenth embodiment of the sixth aspect, the disease is a non-neoplastic cell proliferative and/or tissue remodelling disorder, preferably this disorder is selected from the group comprising fibrotic disorders, more preferably the fibrotic disorder is fibrosis.

In an embodiment, which is preferably a sixteenth embodiment of the sixth aspect, which is preferably a further embodiment of the first to the fourth, tenth, eleventh, fourteenth and fifteenth embodiment of the sixth aspect, the disease is a hepatic disorder, preferably, liver fibrosis, liver cirrhosis, reperfusion injury after hepatic transplantation or necrotizing hepatitis.

In an embodiment, which is preferably a seventeenth embodiment of the sixth aspect, which is preferably a further embodiment of the first to the fourth, tenth, eleventh, fourteenth and fifteenth embodiment of the sixth aspect, the disease is a renal disorder, preferably renal fibrosis, glomrulonephritis, IgA nephropathy, reperfusion injury after kidney transplantation, chronic renal allograft dysfunction, amyloidosis, diabetic nephropathy, mesangio proliferative glomrulonephritis, nephrosclerosis In an embodiment, which is preferably an eighteenth embodiment of the sixth aspect, which is preferably a further embodiment of the first to the fourth, tenth, eleventh, fourteenth and fifteenth embodiment of the sixth aspect, the disease is a fibrotic disorder, preferably lung fibrosis comprising interstitial pulmonary fibrosis, idiophatic fibrosis, drug-induced fibrosis, sarcoidosis, diffuse alveolar damage disease, pulmonary hypertension, chronic obstructive pulmonary disease, respiratory distress syndrome; skin fibrosis such as scleroderma, keloid, hypertrophic scar, dermatofibroma, chronic wounds, psoriasis, dupuytren's contracture, pemphegoid, burn; stomach and intestinal fibrosis comprising abnormal intestinal motility, hypertrophic pyloric stenosis, Hirschsprung's disease, megacolon of piebaldism, idiopathic obstruction, collagenous colitis, villious atrophy and crypt hyperplasia, polyp formation, fibrosis of Crohn's disease, gastric ulcer; eye fibrosis comprising acute and fibrotic sympathetic ophthalmia, Grave's disease, fibrosis after glaucoma surgery, fibrosis after cataract surgery, anterior capsular cataract, corneal scarring, pemphigoid, diabetic microaneurism, capsule opacification; or any other fibrosis comprising systemic sclerosis, artherosclerosis, restenosis, chronic myeloproliferative disorders, fibrodysplsia ossificans progressive, myelodysplasia, osteoporosis, myelofibrosis, osteosclerosis, rheumatoid pannus formation in rheumatoid arthritis, peritoneal fibrosis, myocardial fibrosis, pancreatic fibrosis, chronic pancreatitis, glial scar tissue formation in HIV associated cognitive motor disease and spongiform encephalopathy, gingival hypertrophy secondary to drugs and fibrocystic disease In an embodiment, which is preferably a nineteenth embodiment of the sixth aspect, which is preferably a further embodiment of the first to the fourth, tenth, eleventh, fourteenth and fifteenth embodiment of the sixth aspect, the disease is an ocular disorder, preferably connected with pathological proliferation and/or transdifferentiation of RPE cells, more preferably proliferative diabetic retinopathy, retinal detachment, age related macular degeneration or proliferative vitreoretinopathy.

The problem underlying the present invention is solved in a seventh aspect by the use of a compound according to the first to the fourth aspect as a diagnostic tool or for the manufacture of a diagnostic tool, whereby preferably such diagnostic tool is useful for in vivo and/or for ex vivo application, which is preferably a first embodiment of the seventh aspect.

In an embodiment, which is preferably a second embodiment of the seventh aspect, which is preferably a further embodiment of the first embodiment of the seventh aspect, the compound comprises a detection moiety, whereby the detection moiety is a label, whereby preferably the label is selected from the group comprising radionuclide labels, paramagnetic material, X-ray attenuating material, immune labels, colored labels. chemiluminescent labels, luminescent labels, fluorescent labels, infrared labels, enzyme substrates, enzymes, and labels complexing detectable ions.

In an embodiment, which is preferably a third embodiment of the seventh aspect, which is preferably a further embodiment of the first and second embodiment of the seventh aspect, the diagnostic tool is used in an in vivo imaging method and/or an ex vivo imaging method, more particularly radionuclide imaging, positron emission tomography, computerized axial tomography, magnetic resonance imaging, X-ray, infrared spectroscopy, luminescence, fluorescence, and chemiluminescence.

The problem underlying the present invention is solved in an eighth aspect by a pharmaceutical composition comprising a compound according to the first to the fourth aspect and a pharmaceutically acceptable carrier, diluent or excipient, which is preferably a first embodiment of the eighth aspect.

In an embodiment, which is preferably a second embodiment of the eighth aspect, which is preferably a further embodiment of the first embodiment of the eighth aspect, the pharmaceutical composition comprises an additional pharmaceutically active compound.

In an embodiment, which is preferably a third embodiment of the eighth aspect, which is preferably a further embodiment of the first and second embodiment of the eighth aspect, the compound is present as a pharmaceutically acceptable salt or a pharmaceutically active solvate.

In an embodiment, which is preferably a fourth embodiment of the eighth aspect, which is preferably a further embodiment of the first to the third embodiment of the eighth aspect, the compound is either alone or in combination with any of the ingredients of the composition present in a multitude of individualised dosages and/or administration forms.

In an embodiment, which is preferably a fifth embodiment of the eighth aspect, which is preferably a further embodiment of the first to the fourth embodiment of the eighth aspect, the disease is selected from diseases mediated by or involving alpha5beta1 integrin.

In an embodiment, which is preferably a sixth embodiment of the eighth aspect, which is preferably a further embodiment of the first to the fifth embodiment of the eighth aspect, the disease is any of the diseases defined in any embodiment of the sixth aspect.

In an embodiment, which is preferably a seventh embodiment of the eighth aspect, which is preferably a further embodiment of the first to the sixth embodiment of the eighth aspect, the pharmaceutical composition is used together with a method of treatment for a disease, preferably a disease defined in any embodiment of the sixth aspect.

In an embodiment, which is preferably an eighth embodiment of the eighth aspect, which is preferably a further embodiment of the seventh embodiment of the eighth aspect, the method of treatment is a sequential or combination therapy with the treatment selected from the group comprising chemotherapy, anti-proliferative, anti-hormone therapy, radiation therapy, photodynamic therapy, surgery, anti-fibrotic therapy, anti-inflammatory therapy, immunosuppressive therapy and anti-angiogenic therapy.

The problem underlying the present invention is solved in a nineth aspect by a method for treating an integrin associated state in a subject comprising administering to said subject an effective amount of a compound according to any of the first to the fourth aspect such that said integrin associated state is treated, which is preferably a first embodiment of the nineth aspect.

In an embodiment, which is preferably a second embodiment of the nineth aspect, which is preferably a further embodiment of the first embodiment of the nineth aspect, the integrin is alpha5beta1 integrin.

The problem underlying the present invention is solved in a tenth aspect by a method for treating a disease in a subject comprising administering to said subject an effective amount of a compound according to any of the first to the fourth aspect such that the disease is treated, which is preferably a first embodiment of the tenth aspect.

In an embodiment, which is preferably a second embodiment of the tenth aspect, which is preferably a further embodiment of the first embodiment of the tenth aspect, the disease is any of the diseases defined in connection with the sixth aspect.

The inventors have surprisingly found that the compounds according to the present invention are particularly suitable to interact with integrins, more particularly with integrin alpha5beta1 which is also referred to herein as alpha5beta1.

Without wishing to be bound by any theory the inventors assume that the structure underlying the compounds according to the present invention, more particularly comprising a central core structure represented by A-Ar in formula (I) and a total of two radii emerging therefrom, namely the radius Z-G, and the radius Y-Ψ, provides for this effect.

It seems that this design surprisingly confers to the compounds according to the present invention the ability to specifically interact with the integrin, typically reflected in a low $IC_{50}$ value. Additionally, this simple core structure provides preferable physicochemical properties, enhanced stability, selectivity and synthetic accessibility.

The compounds according to the present invention seem to be particularly binding to and specific, respectively, for integrin alpha5beta1. However, it is also within the present invention that the compounds of the present invention show cross-reactivity with other compounds, preferably with other integrins.

According to the current understanding of the inventors and without wishing to be bound by any theory, the various radii contributing in a synergistic manner to the binding of the compounds according to the present invention to the integrins and preferably to integrin alpha5beta1, can be assigned the following functions.

According to the present invention the interaction of any of the molecules described herein with integrins requires one basic and one acidic moiety to be present in said molecule. These moieties are represented in the compounds according to the present invention by radius Z-G and radius Y-Ψ, respectively. Insofar, the inventors clearly depart from the design of small molecules of the prior art which interact with integrins and which comprise a tri-radial core such as disclosed in WO 97/33887 and WO 2005/090329.

The basic radius Z-G can interact with carboxylic group(s) of the integrin protein. Basic functional groups like guanidine, amidine or aromatic nitrogen containing heterocycles are widely used as interaction partners. The term "basic" refers in so far to a functional group which is positively charged under physiologic conditions. However, also non-charged functional groups like amide or urea serve this requirement. The further design of this radius may be taken from the respective more detailed disclosure of the present application.

The acidic radius Y-Ψ bears usually a carboxylic acid and interacts with metal ions which are incorporated into the protein structure. Such interaction is also referred to herein as acidic interaction. Esters such as alkyl or aryl esters and amides such as mono- and dialkyl or aryl amides being derivatives of this carboxylic acid group may advantageously be used as prodrugs of the corresponding active compound. Such prodrugs are compounds which undergo biotransformation prior to exhibiting their pharmacological effects and the invention particularly extends to prodrugs of the acid, whereby the prodrug character is conferred by or resides in the acid moiety of the molecule and its derivatization. Such prodrugs are well known in the art and, for example, described in International Patent Application No. WO00/26419, Bodor, N. (Alfred Benzon Symposium, 1982, 17, 156), Singh, G. et al. (J. Sci. Ind. Res., 1996, 55, 497) and Bundgaard, H., (Design of Prodrugs, 1985, Elsevier, Amsterdam). It is thus within the present invention that the compounds according to the present invention also comprise the prodrug form of the compounds disclosed herein.

For this acidic interaction realized by the compounds according to the present invention a carboxylic acid group is preferably used as interaction partner for the interacting group of the integrin. Preferably, the interacting group of the integrin is a counter ion on the integrin and more preferably a metal ion. However, this interaction does not necessarily require a carboxylic acid functional group provided by the compounds according to the present invention. Other functional groups like tetrazole, phosphates and acylsulfonamides can also serve as a binding partner for the interacting group of the integrin interacting with said compound according to the present invention. These other groups which may interact with the interacting group of the integrin, are bioisosteres for the carboxylic group. Respective bioisosters for the carboxylic group in addition to tetrazole, phosphates and acylsulfonamides are known to the ones skilled in the art. Thus the compounds according to the present invention also comprise those compounds where the carboxylic group is replaced by a bioisoster of such carboxylic group.

Each of the following terms, used alone or in conjunction with other terms, is preferably used in the following meaning (except where noted to the contrary). Insofar the definitions given herein are in each and any case only preferred embodiments.

In organic nomenclature radicals are considered formally as derived from parent compounds by the removal of one or more hydrogen atoms from one or more atoms of a parent compound. It should be understood that the term "radical" in this application includes also di- or triradicals. The resulting radicals feature one or more unpaired electrons. An atom of a radical on which an unpaired electron is largely localized, is called radical center. Radical centers represent the positions where the radical moiety is connected to other molecular moieties of compounds disclosed in this application and of compounds according to the present invention. Names of radicals usually contain the suffix "-yl". For reason of simplicity within this application also names or structures/formulas of parent compounds are used synonymously for radicals. For example if "piperidine" is listed in a group of radicals it should be understood, that it can be a mono-, di- or triradical with the radical centers at any reasonable ring position.

The same is true for drawn structures indicated in this application and referred to as radicals. If for example the term "a radical selected from the group comprising structures" is used and the related structures or formulas are drawn without any radical center, it should be understood that this structure represents the parent compound and related radicals as generated by the removal of 1, 2 or 3 hydrogen atoms at any position unless otherwise radical center positions are indicated in the accompanying text.

It should also be clear, that if a moiety is not explicitly referred to as a radical in this application but is nonetheless a molecular part or moiety of a compound disclosed in this application that this moiety is preferably a radical. This is also true for names or structures/formulas of parent compounds used to describe structural properties within this application.

The term "basic moiety" preferably refers to a functional group, chemical species, moiety or molecular entity having an available pair of electrons capable of forming a covalent bond with a proton. The resulting protonated moiety is positively charged. A "basic moiety" can also be called "base". In this application those basic moieties are of special interest that are protonated under physiologic conditions.

The term "acidic moiety" or "acid" preferably refers to a functional group, chemical species, moiety or molecular entity having a tendency to act as a proton donor, i.e., breaking the covalent bond to a proton thereby liberating the proton or donating it to a base. In this application those acidic moieties are of special interest that are completely or to some degree deprotonated in water under physiologic conditions.

If a radical is defined by the term "direct bond" or is said to be a "direct bond", this means, that the radical is replaced or represented by a single bond. For example if in a compound with the hypothetical formula "A-B—C" B is defined as "direct bond", A is directly and covalently connected to C by a single bond and the resulting compound is "A-C".

The term "alkyl" refers, in a preferred embodiment of the present invention, to a saturated aliphatic radical containing from one to ten carbon atoms or a mono- or polyunsaturated aliphatic hydrocarbon radical containing from two to twelve carbon atoms, containing at least one double and triple bound, respectively. Thus in a preferred embodiment, the term alkyl also comprises alkenyl and alkynyl. "Alkyl" refers to both branched and unbranched, i.e., non-linear alkyl groups. Preferred alkyl groups are straight chain alkyl groups containing from one to eight carbon atoms. More preferred alkyl groups are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O). "Substituted alkyl" refers to alkyl groups straight or branched further bearing one or more substituents. One substituent also means mono-substituted and more substitutents mean poly-substituted. It should be understood that any combination term using a "substituted alkyl" prefix refers to analogs according to the above definition of "substituted alkyl". For example, a term such as "substituted alkylaryl" refers to substituted alkyl group linked to an aryl group. Additionally, it is within the present invention that the term alky, particularly in the branched embodiment, also comprises embodiments where the branch of the branched alky residue or moiety is either linear or branched in itself.

The term $C_v$-$C_\xi$ alkyl refers to an alkyl radical consisting of a number of v to 4 carbon atoms according to the above definition of "alkyl". For example C0-C2alkyl refers to an alkyl radical which is either not present or methyl, methylene, methylidyne, ethyl, ethylene, ethylidene, ethylidyne or the related higher radicals.

The term "cycloalkyl" refers, in a preferred embodiment of the present invention, to the cyclic analogue of an alkyl group, as defined above, optionally unsaturated and/or substituted. Preferred cycloalkyl groups are saturated cycloalkyl groups, more particularly those containing from three to eight carbon atoms, and even more preferably three to six carbon atoms. "Substituted cycloalkyl" refers to cycloalkyl groups further bearing one or more substituents. "Mono-unsaturated cycloalkyl" refers to cycloalkyl containing one double bond or one triple bond. "Poly-unsaturated cycloalkyl" refers to cycloalkyl containing at least two double bonds or two triple bonds or a combination of at least one double bond and one triple bond.

The term "alkenyl" refers, in a preferred embodiment of the present invention, to an unsaturated hydrocarbon group containing at least one carbon-carbon double bond, including straight-chain, branched-chain, and cyclic groups. Preferred alkenyl groups have two to twelve carbons. More preferred alkenyl groups have two to six carbons. "Substituted alkenyl" refers to alkenyl groups further bearing one or more substitutents.

The term "cycloalkenyl" refers, in a preferred embodiment of the present invention, to the cyclic analog of an alkenyl group, as defined above, optionally substituted. Preferred cycloalkenyl groups are containing from four to eight carbon atoms. "Substituted cycloalkenyl" refers to cycloalkenyl groups further bearing one or more substituents. "Mono-unsaturated cycloalkenyl" refers to cycloalkenyl containing one double bond. "Poly-unsaturated cycloalkenyl" refers to cycloalkenyl containing at least two double bonds. In a more preferred embodiment the term "cycloalkenyl" comprises also "aryl". In an alternative more preferred embodiment the term "cycloalkenyl" does not comprise "aryl".

The term "alkynyl" refers, in a preferred embodiment of the present invention, to an unsaturated hydrocarbon group containing at least one carbon-carbon triple bond, including straight-chain, branched-chain, and cyclic groups. Preferred alkynyl groups have two to twelve carbons. More preferred alkynyl groups have two to six carbons. "Substituted alkynyl" refers to alkynyl groups further bearing one or more substitutents.

The term "aryl" refers, in a preferred embodiment of the present invention, to aromatic groups having in the range of 6 to 14 carbon atoms and "substituted aryl" refers to aryl groups further bearing one or more substituents. It should be understood that any combination term using an "ar" or "aryl" prefix refers to analogs according to the above definition of "aryl". For example, a term such as "aryloxy" refers to aryl group linked to a second group via an oxygen atom.

Each of the above defined "alkyl", "cycloalkyl", and "aryl" shall be understood to include their halogenated analogs, whereby the halogenated analogs may comprise one or several halogen atoms. The halogenated analogs thus comprise any halogen radical as defined in the following.

The term "halo" refers, in a preferred embodiment of the present invention, to a halogen radical selected from fluoro, chloro, bromo, iodo. Preferred halo groups are fluoro, chloro and bromo.

The term "heteroaryl" refers, in a preferred embodiment of the present invention, to a stable 5 to 8 membered, preferably 5 or 6 membered monocyclic or 8 to 11 membered bicyclic aromatic heterocycle radical. Each heterocycle consists of carbon atoms and from 1 to 4 heteroatoms selected from the group consisting of nitrogen, oxygen, sulfur. The heterocycle may be attached by any atom of the cycle, which preferably results in the creation of a stable structure. Preferred heteroaryl radicals as used herein include, for example, furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthridinyl, pteridinyl, carbazolyl, acridinyl, phenazinyl, phenothiazinyl and phenoxazinyl. "Substituted heteroaryl" refers to heteroaryl groups further bearing one or more substituents.

The term "heterocyclyl" refers to a stable 5 to 8 membered, preferably 5 or 6 membered monocyclic or 8 to 11 membered bicyclic heterocycle radical which may be either saturated or unsaturated, and is non-aromatic. Each heterocycle consists of carbon atom(s) and from 1 to 4 heteroatoms selected from the group consisting of nitrogen, oxygen and sulfur. The heterocycle may be attached by any atom of the cycle, which preferably results in the creation of a stable structure. Preferred heterocycle radicals as used herein include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione. "Mono-unsaturated heterocyclyl" refers to heterocyclyl containing one double bond or one triple bond. "Poly-unsaturated heterocyclyl" refers to heterocyclyl containing at least two double bonds or two triple bonds or a combination of at least one double bond and one triple bond.

The term "substituted heterocyclyl" refers, in a preferred embodiment of the present invention, to heterocyclyl groups further bearing one or more substituents.

The terms "heterocyclyl", "heteroaryl" and "aryl", when associated with another moiety, unless otherwise specified, shall have the same meaning as given above. For example, "aroyl" refers to phenyl or naphthyl linked to a carbonyl group (C=O).

Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydronaphthyl.

As used herein above and throughout this application, the terms "nitrogen" or "N" and "sulfur", "thio" or "S" include any oxidized form of nitrogen and sulfur, e.g., sulfoxide, sulfone, nitrone, nitro or N-oxide. The terms "nitrogen" or "N" also include quaternized forms of any basic nitrogen.

As used herein, the wording "and any derivative of each thereof" as contained in a recitation of a group of compounds, means that any of the compound can be present as a derivative. Such derivative can be any derivative disclosed herein and is more preferably any derivative specified in connection with said compounds and group of compounds, respectively. It is also within the present invention that any substitution of any compound can be attached to said compound at any position, preferably any position which allows the formation of a chemically stable compound.

As used herein a wording defining the limits of a range of length such as, e.g., "from 1 to 5" means any integer from 1 to 5, i.e., 1, 2, 3, 4 and 5. In other words, any range defined by two integers explicitly mentioned is meant to comprise any integer defining said limits and any integer comprised in said range.

As used herein the term substituted shall mean that one or more H atom of the group or compound which is substituted, is replaced by a different atom, a group of atoms, a molecule or a molecule moiety. Such atom, group of atoms, molecule or molecule moiety is also referred to herein as substituent.

It is also within the present invention that any substitutent may in turn be substituted by a substituent. A group, structure, moiety or the like which is substituted may comprise several substituents which may either be different or the same.

The substituent can be selected from any of the groups, moieties and substituents disclosed herein. However, the substituent is preferably selected from but is not limited to the group comprising H, alkyl, substituted alkyl, cycloalkyl, substituted cycloalkyl, heterocyclyl, substituted heterocyclyl, aryl, substituted aryl, heteroaryl, substituted heteroaryl, hydroxy, substituted hydroxy, thiol, substituted thiol, formyl, substituted formyl, aminocarbonyl, substituted aminocarbonyl, formylamino, substituted formylamino, aminocarbonylamino, substituted aminocarbonylamino, aminosulfonyl, substituted aminosulfonyl, substituted sulfonylamino, aminosulfonylamino, substituted aminosulfonylamino, aminocarbonyloxy, substituted aminocarbonyloxy, amino, substituted amino, substituted thiocarbonylamino, aminothiocarbonyl, substituted aminothiocarbonyl, aminothiocarbonylamino, substituted aminothiocarbonylamino, aminothiocarbonyloxy, substituted aminothiocarbonyloxy, substituted oxythiocarbonylamino, substituted sulfinyl, sulfonyl, substituted sulfonyl, substituted carbonyloxy, substituted oxycarbonyl, alkyloxy-heterocyclyl, substituted alkyloxy-heterocyclyl, halogen, trifluoromethyl, difluoromethyl, cyano, nitrone, ox, acyl, oxyacyl, carboxyl, carbamate, sulfonamide, sulfuryl, nitro, and substituted or unsubstituted cycloalkyalkyl, heterocyclylalkyl, arylalkyl, heteroarylalkyl, hydroxyalkyl, carbonylalkyl, aminocarbonylalkyl, carbonylaminoalkyl, aminocarbonylaminoalkyl, sulfonylaminoalkyl, aminosulfonylalkyl, aminosulfonylaminoalkyl, aminocarbonyloxyalkyl, oxycarbonylaminoalkyl, thioalkyl, sulfinylalkyl, sulfonylalkyl, carbonyloxyalkyl, oxycarbonyl alkyl, aminoalkyl, thiocarbonylaminoalkyl, aminothiocarbonylalkyl, aminothiocarbonyloxyalkyl, aminothiocarbonylaminoalkyl, oxythicarbonylaminoalkyl, alkylcycloalkyl, alkylheterocyclyl, alkylaryl, alkylheteroaryl, alkyloxy, alkylcarbonyl, alkylaminocarbonyl, alkylcarbonylamino, alkylaminocarbonylamino, alkylsulfonylamino, alkylaminosulfonyl, alkylaminosulfonylamino, alkylaminocarbonyloxy, alkyloxycarbonylamino, alkylthio, alkylsulfinyl, alkylsulfonyl, alkylcarbonyloxy, alkyloxycarbonyl, alkylamino, dialkylamino, alkylthiocarbonylamino, alkylaminothiocarbonyl, alkylaminothiocarbonyloxy, alkylaminothiocarbonylamino, alkyloxythicarbonylamino, arylalkylcycloalkyl, arylalkylheterocyclyl, arylalkylaryl, arylalkylheteroaryl, arylalkyloxy, arylalkylcarbonyl, arylalkylaminocarbonyl, arylalkylcarbonylamino, Arylalkylaminocarbonylamino, arylalkylsulfonylamino, arylalkylaminosulfonyl, arylalkylaminosulfonylamino, arylalkylaminocarbonyloxy, arylalkyloxycarbonylamino, arylalkylthio, arylalkylsulfinyl, arylalkylsulfonyl, arylalkylcarbonyloxy, arylalkyloxycarbonyl, arylalkylamino, arylalkylthiocarbonylamino, arylalkylaminothiocarbonyl, arylalkylaminothiocarbonyloxy, arylalkylaminothiocarbonylamino, arylalkyloxythicarbonylamino, arylcycloalkyl, arylheterocyclyl, arylaryl, arylheteroaryl, aryloxy, arylcarbonyl, arylaminocarbonyl, arylcarbonylamino, arylaminocarbonylamino, arylsulfonylamino, arylaminosulfonyl, arylaminosulfonylamino, arylaminocarbonyloxy, aryloxycarbonylamino, arylthio, arylsulfinyl, arylsulfonyl, arylcarbonyloxy, aryloxycarbonyl, arylamino, arylthiocarbonylamino, arylaminothiocarbonyl, arylaminothiocarbonyloxy, arylaminothiocarbonylamino, aryloxythicarbonylamino, cycloalkylalkylcycloalkyl, cycloalkylalkylheterocyclyl, cycloalkylalkylaryl, cycloalkylalkylheteroaryl, cycloalkylalkyloxy, cycloalkylalkylcarbonyl, cycloalkylalkylaminocarbonyl, cycloalkylalkylcarbonylamino, cycloalkylalkylaminocarbonylamino, cycloalkylalkylsulfonylamino, cycloalkylalkylaminosulfonyl, cycloalkylalkylaminosulfonylamino, cycloalkylalkylaminocarbonyloxy, cycloalkylalkyloxycarbonylamino, cycloalkylalkylthio, cycloalkylalkylsulfinyl, cycloalkylalkylsulfonyl, cycloalkylalkylcarbonyloxy, cycloalkylalkyloxycarbonyl, cycloalkylalkylamino, cycloalkylalkylthiocarbonylamino, cycloalkylalkylaminothiocarbonyl, cycloalkylalkylaminothiocarbonyloxy, cycloalkylalkylaminothiocarbonylamino, cycloalkylalkyloxythicarbonylamino, cycloalkylcycloalkyl, cycloalkylheterocyclyl, cycloalkylaryl, cycloalkylheteroaryl, cycloalkyloxy, cycloalkylcarbonyl, cycloalkylaminocarbonyl, cycloalkylcarbonylamino, cycloalkylaminocarbonylamino, cycloalkylsulfonylamino, cycloalkylaminosulfonyl, cycloalkylaminosulfonylamino, cycloalkylaminocarbonyloxy, cycloalkyloxycarbonylamino, cycloalkylthio, cycloalkylsulfinyl, cycloalkylsulfonyl, cycloalkylcarbonyloxy, cycloalkyloxycarbonyl, cycloalkylamino, cycloalkylthiocarbonylamino, cycloalkylaminothiocarbonyl, cycloalkylaminothiocarbonyloxy, cycloalkylaminothiocarbonylamino, cycloalkyloxythicarbonylamino, heterocyclylcycloalkyl, heterocyclylheterocyclyl, heterocyclylaryl, heterocyclylheteroaryl, heterocyclyloxy, heterocyclylcarbonyl, heterocyclylaminocarbonyl, heterocyclylcarbonylamino, heterocyclylaminocarbonylamino, heterocyclylsulfonylamino, heterocyclylaminosulfonyl, heterocyclylaminosulfonylamino, heterocyclylaminocarbonyloxy, heterocyclyloxycarbonylamino, heterocyclylthio, heterocyclylsulfinyl, heterocyclylsulfonyl, heterocyclylcarbonyloxy, heterocyclyloxycarbonyl, heterocyclylamino, heterocyclylthiocarbonylamino, heterocyclylaminothiocarbonyl, heterocyclylaminothiocarbonyloxy, heterocyclylaminothiocarbonylamino, heterocyclyloxythicarbonylamino, heterocyclylalkylcycloalkyl, heterocyclylalkylheterocyclyl, heterocyclylalkylaryl, heterocyclylalkylheteroaryl, heterocyclylalkyloxy, heterocyclylalkylcarbonyl, iheterocyclylalkylaminocarbonyl, heterocyclylalkylcarbonylamino, heterocyclylalkylaminocarbonylamino, heterocyclylalkylsulfonylamino, heterocyclylalkylaminosulfonyl, heterocyclylalkylaminosulfonylamino, heterocyclylalkylaminocarbonyloxy, heterocyclylalkyloxycarbonylamino, heterocyclylalkylthio, heterocyclylalkylsulfinyl, heterocyclylalkylsulfonyl, heterocyclylalkylcarbonyloxy, heterocyclylalkyloxycarbonyl, heterocyclylalkylamino, heterocyclylalkylthiocarbonylamino, heterocyclylalkylaminothiocarbonyl, heterocyclylalkylaminothiocarbonyloxy, heterocyclylalkylaminothiocarbonylamino, heterocyclylalkyloxythicarbonylamino, heteroarylcycloalkyl, heteroarylheterocyclyl, heteroarylaryl, heteroarylheteroaryl, heteroaryloxy, heteroarylcarbonyl, heteroarylaminocarbonyl, heteroarylcarbonylamino, heteroarylaminocarbonylamino, heteroarylsulfonylamino, heteroarylaminosulfonyl, heteroarylaminosulfonylamino, heteroarylaminocarbonyloxy, heteroaryloxycarbonylamino, heteroarylthio, heteroarylsulfinyl, heteroarylsulfonyl, heteroarylcarbonyloxy, heteroaryloxycarbonyl, heteroarylamino, heteroarylthiocarbonylamino, heteroarylaminothiocarbonyl, heteroarylaminothiocarbonyloxy, heteroarylaminothiocarbonylamino, heteroaryloxythicarbonylamino, heteroarylalkylcycloalkyl, heteroarylalkylheterocyclyl, heteroarylalkylaryl, heteroarylalkylheteroaryl, heteroarylalkyloxy, heteroarylalkylcarbonyl, heteroarylalkylaminocarbonyl, heteroarylalkylcarbonylamino, heteroarylalkylaminocarbonylamino, heteroarylalkylsulfonylamino, heteroarylalkylaminosulfonyl, heteroarylalkylaminosulfonylamino, heteroarylalkylaminocarbonyloxy, heteroarylalkyloxycarbonylamino, heteroarylalkylthio, heteroarylalkylsulfinyl, heteroarylalkylsulfonyl, heteroarylalkylcarbonyloxy, heteroarylalkyloxycarbonyl, heteroarylalkylamino, heteroarylalkylthiocarbonylamino, heteroarylalkylaminothiocarbonyl, heteroarylalkylaminothiocarbonyloxy, heteroarylalkylaminothiocarbonylamino, heteroarylalkyloxythicarbonylamino, alkylcycloalkylalkyl, alkylheterocyclylalkylalkyl, alkylarylalkylalkyl, alkylheteroarylalkylalkyl, alkyloxyalkylalkyl, alkylcarbonylalkylalkyl, alkylaminocarbonylalkylalkyl, alkylcarbonylaminoalkylalkyl, alkylaminocarbonylaminoalkylalkyl, alkylsulfonylaminoalkylalkyl, alkylaminosulfonylalkylalkyl, alkylaminosulfonylaminoalkylalkyl, alkylaminocarbonyloxyalkylalkyl, alkyloxycarbonylaminoalkylalkyl, alkylthioalkylalkyl, alkylsulfinylalkylalkyl, alkylsulfonylalkylalkyl, alkylcarbonyloxyalkylalkyl, alkyloxycarbonylalkylalkyl, alkylaminoalkylalkyl, alkylthiocarbonylaminoalkylalkyl, alkylaminothiocarbonylalkylalkyl, alkylaminothiocarbonyloxyalkylalkyl, alkylaminothiocarbonylaminoalkylalkyl, alkyloxythicarbonylaminoalkylalkyl, arylalkylcycloalkyalkylalkyl, arylalkylheterocyclylalkylalkyl, arylalkylarylalkylalkyl, arylalkylheteroarylalkylalkyl, arylalkyloxyalkyl, arylalkylcarbonylalkyl, arylalkylaminocarbonylalkyl, arylalkylcarbonylaminoalkyl, arylalkylaminocarbonylaminoalkyl, arylalkylsulfonylaminoalkyl, arylalkylaminosulfonylalkyl, arylalkylaminosulfonylaminoalkyl, arylalkylaminocarbonyloxyalkyl, arylalkyloxycarbonylaminoalkyl, arylalkylthioalkyl, arylalkylsulfinylalkyl, arylalkylsulfonylalkyl, arylalkylcarbonyloxyalkyl, arylalkyloxycarbonylalkyl, arylalkylaminoalkyl, arylalkylthiocarbonylaminoalkyl, arylalkylaminothiocarbonylalkyl, arylalkylaminothiocarbonyloxyalkyl, arylalkylaminothiocarbonylaminoalkyl, arylalkyloxythicarbonylaminoalkyl, arylcycloalkylalkyl, arylheterocyclylalkyl, arylarylalkyl, arylheteroarylalkyl, aryloxyalkyl, arylcarbonylalkyl, arylaminocarbonylalkyl, arylcarbonylaminoalkyl, arylaminocarbonylaminoalkyl, arylsulfonylaminoalkyl, arylaminosulfonylalkyl, arylaminosulfonylaminoalkyl, arylaminocarbonyloxyalkyl, aryloxycarbonylaminoalkyl, arylthioalkyl, arylsulfinylalkyl, arylsulfonylalkyl, arylcarbonyloxyalkyl, aryloxycarbonylalkyl, arylaminoalkyl, arylthiocarbonylaminoalkyl, arylaminothiocarbonylalkyl, arylaminothiocarbonyloxyalkyl, arylaminothiocarbonylaminoalkyl, aryloxythicarbonylaminoalkyl, cycloalkylalkylcycloalkylalkyl, cycloalkylalkylheterocyclylalkyl, cycloalkylalkylarylalkyl, cycloalkylalkylheteroarylalkyl, cycloalkylalkyloxyalkyl, cycloalkylalkylcarbonylalkyl, cycloalkylalkylaminocarbonylalkyl, cycloalkylalkylcarbonylaminoalkyl, Cycloalkylalkylaminocarbonylaminoalkyl, cycloalkylalkylsulfonylaminoalkyl, cycloalkylalkylaminosulfonylalkyl, cycloalkylalkylaminosulfonylaminoalkyl, cycloalkylalkylaminocarbonyloxyalkyl, cycloalkylalkyloxycarbonylaminoalkyl, cycloalkylalkylthioalkyl, cycloalkylalkylsulfinylalkyl, cycloalkylalkylsulfonylalkyl, cycloalkylalkylcarbonyloxyalkyl, cycloalkylalkyloxycarbonylalkyl, cycloalkylalkylaminoalkyl, cycloalkylalkylthiocarbonylaminoalkyl, cycloalkylalkylaminothiocarbonylalkyl, cycloalkylalkylaminothiocarbonyloxyalkyl, cycloalkylalkylaminothiocarbonylaminoalkyl, cycloalkylalkyloxythicarbonylaminoalkyl, cycloalkylcycloalkylalkyl, cycloalkylheterocyclylalkyl, cycloalkylarylalkyl, cycloalkylheteroarylalkyl, cycloalkyloxyalkyl, cycloalkylcarbonylalkyl, cycloalkylaminocarbonylalkyl, cycloalkylcarbonylaminoalkyl, cycloalkylaminocarbonylaminoalkyl, cycloalkylsulfonylaminoalkyl, cycloalkylaminosulfonylalkyl, cycloalkylaminosulfonylaminoalkyl, cycloalkylaminocarbonyloxyalkyl, cycloalkyloxycarbonylaminoalkyl, cycloalkylthioalkyl, cycloalkylsulfinylalkyl, cycloalkylsulfonylalkyl, cycloalkylcarbonyloxyalkyl, cycloalkyloxycarbonylalkyl, cycloalkylaminoalkyl, cycloalkylthiocarbonylaminoalkyl, cycloalkylaminothiocarbonylalkyl, cycloalkylaminothiocarbonyloxyalkyl, cycloalkylaminothiocarbonylaminoalkyl, cycloalkyloxythicarbonylaminoalkyl,
heterocyclylcycloalkylalkyl, heterocyclylheterocyclylalkyl, heterocyclylarylalkyl, heterocyclylheteroarylalkyl, heterocyclyloxyalkyl, heterocyclylcarbonylalkyl, heterocyclylaminocarbonylalkyl, heterocyclylcarbonylaminoalkyl, heterocyclylaminocarbonylaminoalkyl, heterocyclylsulfonylaminoalkyl, heterocyclylaminosulfonylalkyl, heterocyclylaminosulfonylaminoalkyl, heterocyclylaminocarbonyloxyalkyl, heterocyclyloxycarbonylaminoalkyl, heterocyclylthioalkyl, heterocyclylsulfinylalkyl, heterocyclylsulfonylalkyl, heterocyclylcarbonyloxyalkyl, heterocyclyloxycarbonylalkyl, heterocyclylaminoalkyl, heterocyclylthiocarbonylaminoalkyl, heterocyclylaminothiocarbonylalkyl, heterocyclylaminothiocarbonyloxyalkyl, heterocyclylaminothiocarbonylaminoalkyl, heterocyclyloxythicarbonylaminoalkyl,
heterocyclylalkylcycloalkylalkyl, heterocyclylalkylheterocyclylalkyl, heterocyclylalkylarylalkyl, heterocyclylalkylheteroarylalkyl, heterocyclylalkyloxyalkyl, heterocyclylalkylcarbonylalkyl, heterocyclylalkylaminocarbonylalkyl, heterocyclylalkylcarbonylaminoalkyl, heterocyclylalkylaminocarbonylaminoalkyl, heterocyclylalkylsulfonylaminoalkyl, heterocyclylalkylaminosulfonylalkyl, heterocyclylalkylaminosulfonylaminoalkyl, heterocyclylalkylaminocarbonyloxyalkyl, heterocyclylalkyloxycarbonylaminoalkyl, heterocyclylalkylthioalkyl, heterocyclylalkylsulfinylalkyl, heterocyclylalkylsulfonylalkyl, heterocyclylalkylcarbonyloxyalkyl, heterocyclylalkyloxycarbonylalkyl, heterocyclylalkylaminoalkyl, heterocyclylalkylthiocarbonylaminoalkyl, heterocyclylalkylaminothiocarbonylalkyl, heterocyclylalkylaminothiocarbonyloxyalkyl, heterocyclylalkylaminothiocarbonylaminoalkyl, heterocyclylalkyloxythicarbonylaminoalkyl,
heteroarylcycloalkylalkyl, heteroarylheterocyclylalkyl, heteroarylarylalkyl, heteroarylheteroarylalkyl, heteroaryloxyalkyl, heteroarylcarbonylalkyl, heteroarylaminocarbonylalkyl, heteroarylcarbonylaminoalkyl, heteroarylaminocarbonylaminoalkyl, heteroarylsulfonylaminoalkyl, heteroarylaminosulfonylalkyl, heteroarylaminosulfonylaminoalkyl, heteroarylaminocarbonyloxyalkyl, heteroaryloxycarbonylaminoalkyl, heteroarylthioalkyl, heteroarylsulfinylalkyl, heteroarylsulfonylalkyl, heteroarylcarbonyloxyalkyl, heteroaryloxycarbonylalkyl, heteroarylaminoalkyl, heteroarylthiocarbonylaminoalkyl, heteroarylaminothiocarbonylalkyl, heteroarylaminothiocarbonyloxyalkyl, heteroarylaminothiocarbonylaminoalkyl, heteroaryloxythicarbonylaminoalkyl,
heteroarylalkylcycloalkylalkyl, heteroarylalkylheterocyclylalkyl, heteroarylalkylarylalkyl, heteroarylalkylheteroarylalkyl, heteroarylalkyloxyalkyl, heteroarylalkylcarbonylalkyl, heteroarylalkylaminocarbonylalkyl, heteroarylalkylcarbonylaminoalkyl, heteroarylalkylaminocarbonylaminoalkyl, heteroarylalkylsulfonylaminoalkyl, heteroarylalkylaminosulfonylalkyl, heteroarylalkylaminosulfonylaminoalkyl,
heteroarylalkylaminocarbonyloxyalkyl, heteroarylalkyloxycarbonylaminoalkyl, heteroarylalkylthioalkyl, heteroarylalkylsulfinylalkyl, heteroarylalkylsulfonylalkyl, heteroarylalkylcarbonyloxyalkyl, heteroarylalkyloxycarbonylalkyl, heteroarylalkylaminoalkyl, heteroarylalkylthiocarbonylaminoalkyl, heteroarylalkylaminothiocarbonylalkyl, heteroarylalkylaminothiocarbonyloxyalkyl, heteroarylalkylaminothiocarbonylaminoalkyl, heteroarylalkyloxythicarbonylaminoalkyl,
alkyloxyaryl, substituted alkyloxyaryl,
alkyloxyheteroaryl, substituted alkyloxyheteroaryl,
alkylthiocycloalkyl and substituted alkylthiocycloalkyl.

Any of the substituents may be substituted itself by any of the aforementioned substituents. This applies preferably to cycloalkyl, heterocylic, aryl, heteroaryl and aryloxy. It is also preferred that alkoxy and mercapto are those of a lower alkyl group. It is to be acknowledged that any of the definition provided herein also applies to any substituent.

As used herein in connection with an embodiment of the various aspects of the present invention the term "each and independently selected from a group" or "are individually and independently from each other selected from the group" refers to two or more atoms, groups, substituents, moieties or whatsoever and describes that the single atom, group, substituent or moiety mentioned can be selected from the group. The wording used is a truncation which avoids unnecessary repetition as otherwise for each of the atoms, groups etc. the same group definition would have to be repeated.

As used herein in connection with an embodiment of the various aspects of the present invention the term "each and individually absent" refers to two or more atoms, groups, substituents, moieties or whatsoever and describes that the single atom, group, substituent or moiety mentioned can be absent regardless whether any of the other atoms, groups etc. mentioned is absent. The wording used is a truncation which avoids unnecessary repetition as otherwise for each of the atoms, groups etc. the fact that it may be absent in an embodiment of the invention would have to be repeated.

It is within the present invention that at least some of the substituents are non-symmetrical in their design and, therefore, provide different orientations and optionally reaction sites or positions which can be used to attach the substituent to another moiety of the compound. Based on this the linkage between the substituent and the respective moiety of the compound varies depending on the particular orientation and thus site(s) of the substituent used for such linkage in various embodiments of the compounds disclosed herein. It is within the present invention that any such orientation of the substituent and thus linkage is covered by the present disclosure and representations. The same applies also to other groups or moieties. It should therefore be understood that for example if B in a hypothetical molecule A-X—Y is NHCO, both orientations of X are included and the resulting molecules are A-NHCO—Y and A-CONH—Y.

It is within the present invention that the features of the various embodiments of the present invention can be realized either alone or in combination with the features of any other embodiment(s) of the present invention. Thus any combination of an/the individual feature or the combination of features of an embodiment of the present invention with an/the individual feature(s) or the combination of features of any other embodiment(s), either alone or in combination with (an) other embodiment(s), shall be disclosed by the present specification. This applies particularly to the various embodiments and features, respectively, of the compounds disclosed herein.

In a further aspect the present invention is related to a pharmaceutical composition comprising a compound according to any of the aspects of the present invention and a pharmaceutically acceptable carrier, diluent or excipient.

In compounds disclosed in the present invention stereogenic carbons may be in the R or S configuration and therefore compounds with one or more stereogenic carbons may occur as any possible stereoisomere or combination thereof. Consequently, any of the compounds according to the present invention containing one asymmetric carbon atom may occur as racemate, racemic mixture or as one of the two single enantiomers. In analogy, any of the compounds according to the present invention containing more than one asymmetric carbon atom may occur as racemate, racemic mixture, any enantiomer, diastereomeric mixture or as one of the possible individual diastereomers. All such isomeric forms of these compounds are expressly included in the present invention.

It shall be understood by the one of ordinary skill in the art that all compounds of the invention are preferably those which are chemically stable. This applies to any of the various uses of the compounds according to the present invention disclosed herein.

In a further aspect the compounds according to the present invention comprise a further moiety. Such further moiety preferably confers functional features to the compounds. It is to be acknowledged that such further moiety is preferably attached to or incorporated into any other part of the compounds according to the present invention, although it is also within the present invention that the moiety and moieties, more preferably the individual chemical or functional group or arrangement of such group, present in the compounds according to the present invention provides for the functional feature(s). More preferably such further moiety is an additional moiety, most preferably a compound on its own, which is attached, preferably conjugated to any of the compounds according to the present invention. Such further moiety is preferably selected from the group comprising a detection moiety, a targeted moiety and a delivery moiety. It is to be understood that the same moiety can have several functions. Accordingly, any specification in so far is not limiting the purpose for which such further moiety is incorporated into any of the compounds according to the present invention.

A detection moiety is preferably a moiety which allows the detection of the compound in vitro, ex vivo, in vivo and/or in situ. A preferred detection moiety is a label.

In a preferred embodiment the compound according to the present invention comprises a label and is also referred to herein as a labeled compound according to the present invention. By a "labeled compound according to the present invention" herein is meant a compound according to the present invention that has at least one element, isotope or chemical compound attached to or incorporated into enable the detection of the compound or the compound bound to a target such as an integrin. In general, labels as used herein, may be taken from any of the following classes: a) isotopic labels, which are preferably radioactive or heavy isotopes, including paramagnetic material; b) X-ray attenuating material; c) immune labels which comprise but are not limited to antibodies, antigens, or labels recognized by antibodies or other proteins such as biotin or antibody epitopes; d) colored, chemiluminescent, luminescent or fluorescent labels; e) enzyme substrates or enzymes; and f) other labels complexing detectable ions such as hexahistidine sequence. The labels may be incorporated into the compound at any position using well known methods, which are selected, in part, based on the chemical nature of the compound and the label. More preferred labels include $^{14}$C, $^{13}$C, $^{15}$N, $^{3}$H, $^{99}$Tc, biotin, and fluorescent labels as are well known in the art.

A specifically bound labeled compound could be detected by using in vivo imaging methods like radionucleotide imaging, positron emission tomography, computerized axial tomography, X-ray, infrared imaging, or magnetic imaging resonance methods. The specifically bound labeled compound could be also detected using ex vivo imaging methods, wherein, following the administration of such compound isolated cells or tissue probes are obtained from the individual and the integrin bound compound will be detected in these probes. Alternatively, the labeled compound could be applied to the isolated cells or tissue probes after obtaining the probes from the individuals. The specific binding of the labeled compound to the integrin could be detected directly or via the label moiety by radioactivity, fluorescence, luminescence, infrared imaging, X-ray, and immunological or enzymatic reactions. For example, the compound is directly coupled to an enzyme substrate, i.e., labeled with an enzyme substrate, which could be detected after incubation with the enzyme via a chromogenic, fluorescent or luminescent reaction, or the label could be recognized by an other molecule such as an antibody which is conjugated to an enzyme such as horseradish peroxidase, alkaline phosphatase, beta-galactosidase and others that are well known in the art.

In a further embodiment the further moiety is a targeted moiety. Preferably, the targeted moiety is a pharmaceutically active compound, which could be targeted by the compound according to the present invention to the site of action via specific interaction of the compound according to the present invention with the integrin, more preferably alpha5beta1. As mentioned above, the targeted moiety can also be active as detection moiety. The targeted moiety is preferably selected from the group comprising cytotoxins, radionuclides, chemotherapeutics, pharmaceutically active proteins like antibodies or cytotoxic proteins, linker molecules for delivery of gentherapeutic vectors, or liposomes.

More preferably and generally applicable to any further moiety described herein, the attachment of the chemical compound according to the present invention to the further moiety is achieved through a binding mechanism which is selected from the group comprising covalent binding, non-covalent binding. For example, where the pharmaceutical active agent is a cytotoxin coupled to the compounds according to the present invention. This complex should bind specifically to the integrin alpha5beta1, which is poorly expressed on quiescent vasculature, but significantly upregulated on endothelial cells in tumors and after stimulation with growth factors. Therefore this complex should bind only to activated endothelial cells, which are symptomatic for disorders connected with angiogenesis, kill these cells exclusively and stop consequently the pathological angiogenesis.

In a preferred embodiment the further moiety is a delivery moiety. Such delivery moiety is any agent which is suitable to improve the stability, solubility and pharmacokinetic properties of the compound to optimize the bioavailability after administration. Therefore, the compound shows improved properties through the moiety itself or in combination with a particular formulation. For example, the addition of a fluorine group to the molecule increases the solubility in polyfluorated vehicles and improves the bioavailability of the compound in combination with this special vehicle.

In an embodiment the composition comprises a further pharmaceutically active compound, preferably such further pharmaceutically active compound is selected from the group comprising chemotherapeutic agents, anti-hormones, agents influencing the vascular permeability, agents for photodynamic therapy, anti-inflammatory drugs, anti-fibrotic drugs, and anti-angiogenic drugs. The combination of integrin inhibiting drugs with different mechanisms of action may lead to additive or synergistic therapeutic effects.

Any of these agents are known to the ones skilled in the art. Preferred chemotherapeutic agents are 5-fluorouracil, gemcitabine, carboplatin, paclitaxel, taxol, oxaliplatin, irinotecan, and cisplatin. Preferred agents used as anti-hormones are cyproterone acetate and tamoxifen. Preferred agents influencing vascular permeability and/or angiogenesis are COX-2 inhibitors, NO-synthase inhibitors, bradykinin receptor antagonists, such as Icatibant, and others. Also preferred anti-angiogenic drugs are compounds effecting VEGF activity, such as, VEGF or VEGF-receptor antibodies or fragments, e.g., Avastin, Lucentis, soluble VEGF-receptor fragments, VEGF binding aptamers (Macugen, Eye001), VEGF-receptor-kinase inhibitors, e.g., SU5416, Bay 43-9006 or PTK787/ZK222584, VEGF or VEGF-receptor mRNA interfering drugs e.g. Cand5 or Sima 027 or agents affecting the action of other angiogenic growth factors such as PDGF and others. Other preferred anti-angiogenic drugs are inhibitors of matrix metalloproteases, endogenous inhibitors, such as endostatin and angiostatin, other integrin inhibitors, thalidomide and derivatives and others. A preferred agent used for photodynamic therapy is Visudyne. Preferred agents used as anti-inflammatory drugs are steroids, nonsteroidal anti-inflammatory drugs including aspirin, folic acid antagonists (e.g. methotrexate), hydroxychloroquine, sulfasalazine, pyrimidine synthesis inhibitors (leflunomide), COX-2 inhibitors as well as biologics such as compounds directed against cytokines (e.g. TNF antagonists like Enbrel, Infliximab, Adalimumab), compounds directed against T cells, antigen presenting cells (e.g. Alefacept, Efalizumab) and anti-inflammatory cytokines. Preferred agents used as anti-fibrotic drugs are interferons, TGFβ inhibitors (e.g. TGFβ antibodies or soluble TGFβ decoy receptor), inhibitors for other integrins (e.g. alphavbeta3 or alphavbeta6), Endothelin A receptor antagonists (e.g. LU135252), anti-oxidants (e.g. silymarin), phosphodiesterase inhibitors (e.g. pentoxifylline), thiazolidindiones, immunsuppressive agents (e.g. rapamycin and mycophenolate mofetil), halofuginone and inhibitors of the renin-angiotensin system.

In a preferred embodiment of the composition the compound is present as a pharmaceutically acceptable salt or a pharmaceutically active solvate.

In an even more preferred embodiment the pharmaceutically active compound is either alone or in combination with any of the ingredients of the composition present in a multitude of individualized dosages and/or administration forms.

It is also within the present invention that the pharmaceutical composition as well as the medicament which is manufactured using the compounds according to the present invention, is used with other therapies used in the prevention and/or treatment of any disease disclosed herein, preferably any disease for the prevention and/or treatment of which the pharmaceutical composition and/or the medicament which is manufactured using the compounds according to the present invention, is used. Such other therapies are selected from the group comprising chemotherapy, anti-hormone therapy, radiation therapy, photodynamic therapy, anti-angiogenic therapy and surgery. These other therapies are known to the ones skilled in the art. Basically chemotherapy means the standard chemotherapy usually applied to cancer patients as well as the metronomic therapy, the frequent application of low dose chemotherapeutics (Hahnfeldt, 2003, J Theor Biol., 220, 545). Anti-hormon therapy preferably means the standard hormon therapy usually applied to cancer patients with hormone dependent cancers such as breast or prostate cancer. Photodynamic therapy is the current standard treatment for defined stages of age related macular degeneration based on the photochemical injury of the blood vessels in the neovascular membranes of AMD patients, through the properties of a photo-active compound and a targeted laser treatment of the affected areas in the eye (Verteporfin in Visudyne, Novartis).

In a further aspect the present invention is related to the use of the compounds according to the present invention as a medicament and for the manufacture of a medicament, respectively. It is to be understood that any of the compounds according to the present invention can be used for the treatment of or for the manufacture of a medicament for the treatment of any of the diseases disclosed herein, irrespective of the mode of action or the causative agent involved as may be specified herein. Of course, it may particularly be used for any form of such disease where the particular causative agent is involved. Causative agent as used herein also means any agent which is observed in connection with the particular disease described and such agent is not necessarily causative in the sense that it causes the observed diseases or diseased condition. It is within the present invention that the medicament is preferably a pharmaceutical composition as described herein. The features disclosed in connection with the medicament and its manufacture are also applicable to the pharmaceutical composition and the features disclosed in connection with the pharmaceutical composition are also applicable to the medicament. More preferably, the pharmaceutical composition according to the present invention can be used for the treatment and/or prevention of any of the diseases disclosed herein.

The same applies also to each and any other use of the compounds according to the present invention, more particularly to the use of the compounds according to the present invention as diagnostic tools including in vivo and ex vivo diagnostics, the use of said compounds in the method for the treatment of any of the diseases disclosed herein and the use of said compounds as inhibitors, preferably as inhibitors to an integrin and more preferable the alpha5beta1 integrin.

As used herein, the term "disease" describes any disease, diseased condition or pathological condition including injuries, disabilities, syndromes, symptoms, deviant behaviors, and atypical variations of structure and function as well as conditions of unknown etiology. In connection with the present invention the terms disease and disorder shall be used and understood in an interchangeable way, if not explicitly indicated to the contrary. Such disease may also be defined as abnormal condition, preferably connected with pathological angiogenesis or pathological proliferation, migration and differentiation of cells. Also, in case of a pathogen, disease means a condition where a pathogen or an unwanted organism is present or present in a concentration or compartment where it is undesired and thus subject to reduction in numbers, removal, elimination, prevention of invasion and/or destruction by using the compounds according to the present invention.

The term "treatment" as used herein comprises both treatment and prevention of a disease. It also comprises follow-up treatment and a combination treatment of a disease. Follow-up treatment is realized upon a treatment of a disease using compounds preferably different from the one according to the present invention, for example, after a failed or insufficient pre-treatment of the targeted disease, such as chemotherapy, anti-hormone therapy, radiation therapy, photodynamic therapy, other anti-angiogenic therapy, anti-inflammatory therapy, anti-fibrotic therapy or surgical treatment. Follow-up treatment also means continuation of the same treatment preferably at lower dosage. Combination treatment means the treatment of a disease with a compound according to the present invention in combination with another therapeutically active compound or method. Such compounds could be for example chemotherapeutic agents, anti-hormones, an agent for photodynamic therapy, agents influencing the vascular permeability, anti-inflammatory agents, anti-fibrotic agents or anti-angiogenic compounds, like compounds affecting the VEGF activity, or agents affecting the action of other angiogenic growth factors, such as PDGF. Such methods could be radiation therapy, or photodynamic therapy.

The term "angiogenesis" includes hemangiogenesis, i.e. the process of formation of new blood vessels from sprouts of existing vessels, lymphangiogenesis, i.e. process of formation of lymphatic vessels, and vasculogenesis, i.e. vessels arise from endothelial cell precursors (Gasparini et al., 2005, J Clin Oncol, 23, 1295; Alitalo et al., 2005, Nature 438, 946).

The term "inhibition of angiogenesis" preferably means the inhibition of angiogenesis in a tissue in an individual, by administering a compound according to the present invention, whereby the compound interacts with an integrin, preferably alpha5beta1, thereby reducing or inhibiting angiogenesis in the tissue in the individual. Such inhibition provides the reduction of severity of a pathological condition associated with angiogenesis. Inhibition of angiogenesis means also the reduction of the amount of newly formed blood vessels in a tissue in the presence of the compound according to the present invention compared to the tissue in the absence of this compound. Methods for determining the amount of blood vessel formation in a tissue are described in the example and are well known in the art.

The term "inhibition of inflammation" preferably means the inhibition of processes connected with a chronic or acute pathological immune response such as vascular and cellular reactions mediated by chemical factors that are derived from plasma proteins or cells and are produced in response to or activated by the inflammatory stimulus, by administering a compound according to the present invention, whereby the compound interacts with an integrin, preferably alpha5beta1, thereby reducing or inhibiting inflammation in the tissue in the individual. Such inhibition provides the reduction of severity of a pathological condition associated with inflammation. Inhibition of inflammation additionally or alternatively means the reduction of the amount of immigrated and activated immune cells or the level of mediators of inflammation in the tissue in the presence of the compound according to the present invention compared to the tissue in the absence of this compound. Methods for determining the severity of inflammation in a tissue are well known in the art.

The term "inhibition of fibrosis" preferably means the inhibition of processes connected with a non-physiological wound healing or similar irritations following a persistent exogenous or endogenous stimulus, by administering a compound according to the present invention, whereby the compound interacts with an integrin, preferably alpha5beta1, thereby reducing or inhibiting fibrosis in the tissue in the individual. Such inhibition provides the reduction of severity of a pathological condition associated with tissue remodelling and hypertrophic scarring. Inhibition of fibrosis additionally or alternatively means the reduction of the amount of extracellular matrix protein deposits, profibrotic mediators and myofibroblasts in the tissue in the presence of the compound according to the present invention compared to the tissue in the absence of this compound. Methods for determining the severity of fibrosis in a tissue are well known in the art The compounds according to the present invention can be characterized by the $IC_{50}$ value, which is also referred to herein as $IC_{50}$. The term "$IC_{50}$" means the inhibition constant and describes the inhibition of the interaction between the integrin and the most preferred ligand of this integrin. The integrin is preferably alpha5beta1, but for determining the selectivity of the compound, also another integrin can be used. The term "selectivity" preferably means a more than 10-fold and more preferably a more than 100-fold lower $IC_{50}$ value for integrin alpha5beta1 in comparison to the other integrin(s).

The compounds according to the present invention are understood to bind to an integrin thus interfering with the binding of the integrin to a ligand. Preferably, such ligand is expressed in the extracellular matrix of a tissue or on a cell surface. The specificity of interaction of the compounds according to the present invention with the integrins, more preferably with alpha5beta1, defines the molecular environment where the compounds according to the present invention are active in terms of integrin inhibition and as compounds for the treatment of a disease. Integrins are crucial in mediating a number of biological processes, whereby particularly integrin alpha5beta1 is an integrin strongly associated with angiogenesis, and even more preferably related to pathological angiogenesis. As used herein, pathological angiogenesis is any angiogenesis which is undesired. An undesired angiogenesis is any angiogenesis which results in a disease or condition which is different from a desired condition, at least from a medical point of view. Additionally, alpha5beta1 is also strongly associated with other processes based on pathological migration, proliferation and differentiation of cells. Further diseases which can be addressed using the compounds according to the present invention are those which are connected with or where one of the following processes is involved: proliferation, migration and differentiation of alpha5beta1 expressing cells.

However, the mode of action of the compounds according to the present invention is not limited to competitive inhibition of the binding of an integrin and its ligand, but a compound according to the present invention can also change the binding characteristics of the integrin to the ligand and, optionally, also vice versa, preferably through a different mechanism, such as an allosteric mechanism, which includes uncompetitive and noncompetitive inhibition, upon which either the integrin or the ligand is changed so as to modulate the interaction between the integrin and a ligand thereof. Finally, in principle, the compounds according to the present invention can also induce partial antagonistic and/or agonistic effects on integrins (Humphries, 2000, Trends Pharmacol Science, 21, 29) or act via irreversible inhibition of integrins. Any of these situations, i.e., an inhibitory as well as a stimulatory situation with regard to the binding of an integrin and a ligand thereof regardless of the particular underlying mode of action, represent an integrin associated state, which can be influenced by the compounds according to the present invention and thus be a reduction or inhibition of angiogenesis or induction of agonistic effects on integrins, as used herein. The term integrin associated state is preferably any of the diseases disclosed herein. Also insofar a disease in the meaning of the present invention is angionesis, neovascularization, inflammation and fibrosis.

The wealth of potential applications in terms of medical conditions or diseases which may be treated using the compounds according to the present invention can also be explained by the impact of said compounds on the proliferation and migration of alpha5beta1 expressing cells. Beside the expression of alpha5beta1 on activated endothelial cells this integrin is also up-regulated on other types of proliferating cells such as tumor cells, retinal pigment epithelial cells, fibroblasts, inflammatory cells and others (WO2005/092073; Thannickal 2003, J. Biol. Chem. 278, 12384; Proulx, 2003, Molecular Vision, 9, 473; Kloss 1999, J Comp Neurol 411, 162; Shang 1998, J Imm 160, 467; Issekutz Inflam Res. 1998 47, S123; Burns 2001 J Imm 166, 4644; Dastych, 2001, Allergy and Immunology 125, 152; Furgeson 1991 PNAS 88, 8072). Furthermore, alpha5beta1 influences the differentiation of certain cell types during several pathogenetic processes, e.g., myofibroblast development during fibrosis (Thannickal 2003, J. Biol. Chem. 278, 12384), RPE cell transdifferentiation during AMD (US2005/0002930) and tumor cell immortalization during cancer. In several other diseases the alpha5beta1 ligand fibronectin is up-regulated in the affected tissue and therefore inhibition of alpha5beta1-fibronectin interaction could interfere with disease progression.

Therefore, given the bio distribution of the integrins and particularly of alpha5beta1 in tissues, organs and cells, respectively and the appearance of pathological angiogenesis, inflammation and fibrosis, the compounds according to the present invention can be used in the treatment of diseases of or involving various tissues and organs, respectively. Such tissues comprise but are not limited to ocular tissues, such as cornea, retina and macula and other tissues and organs such as the skin, the joints, liver, kidney, lung, heart, bladder, thyroid, brain, blood and neoplasms. Further tissues are the synovial tissue, intestinal tissues, connective tissue, reproductive tissue, and the bone tissue.

Based on this, the compounds according to the present invention are preferably used for the treatment of diabetic retinopathy and age related macular degeneration, as an example for diseases related to ocular tissues, preferably age related macular degeneration by neovascularization, for the treatment of skin diseases such as hemangioma and inflammatory diseases from the group comprising psoriasis, rosacea, gingivitis, arthritic conditions such as rheumatoid arthritis, psoriatric arthritis, juvenile arthritis and osteoarthritis, inflammatory bowel diseases, ulcerative colitis, Crohn's disease, and others. It will be acknowledged by the ones skilled in the art that some of the diseases can be grouped into different categories. In so far, the categorization presented is not limiting the actual use of the compounds according to the present invention. Rather, the compounds according to the present invention can be used for the treatment of any of the diseases disclosed herein.

Other ocular diseases contemplated to be treated using compounds according to the present invention are diseases which are connected with choroidal neovascularization such as, e.g., ocular histoplasmosis syndrome, high myopia, angoid streaks, choroidal rupture, optic disc drusen, optic pits, acute posterior multifocal placoid pigment epitheliopathy, serpiginous choroiditis, Harada's disease, Stargard's disease, toxoplasmosis, sarcoidosis, central serous retinopathy, congenital ribella, coloboma, morning glory synsdrome, choroidal hemangioma, choroidal melanoma, choroidal nevus, choroidal osteoma, toxocariasis, branch retinal vein occlusion, central retinal vein occlusion, parafoveal telangiectasis, retinitis pigmentosa, Best's disease, adult foveal macular dystrophy, problems after photocoagulation or retinal vascular diseases such as, e.g., hypertensive retinopathy, diabetic retinopathy, sickle cell retinopathy, retinopathy of prematurity, background retinopathy, or other eye diseases connected with neovascularization and/or integrin mediated interactions, such as, e.g., proliferative vitreoretinopathy, proliferative diabetic retinopathy, Behçet's disease, cavernous hemangioma of the retina, choroidal rupture, retinal telangiectasia, cystoid maculopathy, Eale's disease, idiopathic central serous choroidopathy, iris neovascularization, malignant choroidal melanoma, preretinal macula fibrosis, ocular histoplasmosis, retinal capillary hemangiomaretinal tumors, tumors of the iris and ciliary body, diseases with pathological corneal neovascularization, pterygiae.

In connection with these ocular diseases the pathological growth of new blood vessels causes the loss of vision. The leading cause of blindness in individuals over the age of 65 is the age related macular degeneration (AMD), characterized by the growth of new blood vessels from the choroid, which remain beneath the retinal pigment epithelium (RPE), or breach the RPE and enter the subretinal space, leading to hemorrhage, detachment of RPE and formation of subretinal scars followed by blindness (Ambati, 2003, Survey of Opthalmology, 48, 257). The leading cause of blindness in individuals under the age of 55 years is proliferative diabetic retinopathy (PDR), whereby retinal blood vessels proliferate along the surface of the retina and into the posterior vitreous due to ischaemic stimuli (Klein, 1994, Arch Opthalmol. 112, Friedlander, 1996, PNAS, 93, 9764).

Particularly in connection with AMD, a variety of different factors influence the pathogenesis thereof. Beside the pathological neovascularization vascular leakage, inflammation and fibrosis are connected with the progression of AMD. Macrophages and transdifferentiated RPE cells play an important role in triggering the inflammation and the following fibrosis as well as vascular leakage and angiogenesis by producing growth factors such as VEGF (Tezel, 2004, Trends Mol Med 10, 417; Lopez, 1996, IOVS 37, 855; Grossniklaus 2002, Mol V is 8, 119,). Proliferating fibroblasts and RPE cells, activated macrophages as well as myofibroblasts in fibrotic tissues have up-regulated the alpha5beta1 expression (Thannickal 2003, J. Biol. Chem. 278, 12384; Proulx, 2003, Molecular Vision, 9, 473; Shang 1998, J Imm 160, 467). Furthermore inhibition of integrin signaling in proliferating RPE cells in vitro caused a reduction of VEGF secretion (Jabali 2005 ARVO #462/B436). Therefore alpha5beta1 seems to play an important role for the proliferation of RPE cells outside the normal RPE cell layer, for the transdifferentiation of RPE cells to the pathological phenotype, for the secretion of growth factors from pathological RPE cells, for the infiltration of macrophages into the AMD lesion and the progression of fibrosis following inflammation and angiogenesis. Therefore, these in vitro and in vivo data indicate alpha5beta1 inhibitors may interfere with all processes important for the pathogenesis of AMD such as angiogenesis, inflammation, fibrosis and vascular leakage. Insofar, AMD also comprises aspects of inflammation and fibrosis which shall be dealt with herein separately again. Nevertheless, there are other—ocular—diseases which are connected to or which involve fibrosis and proliferation as well as transdifferentiation of RPE cells such as proliferative vitreoretinopathy which shall be discussed in more detail in the following.

In their normal state, RPE cells are strongly adherent to Bruch's membrane, but in certain pathological conditions such as retinal detachment, the RPE cell layer begins to dissociate from the membrane. This RPE-Bruch's membrane separation may be mediated by several stimuli or partly derived from the RPE themselves (Hiscott 1999, Prog Retin Eye Res 18, 167). Concomitant with the RPE disassociation, the cells begin to lose tertiary differentiation characteristics and gain macrophage-like features. These "free" RPE cells start to proliferate, migrate and create a provisional matrix triggering the formation of PVR membranes. Some of the cells adopt a fibroblast-like phenotype, similar to that of the dermal fibroblasts during cutaneous wound repair. These fibroblastic RPE cells synthesize ECM proteins like fibronectin, components found also in healing skin wounds. The ECM molecules in turn further modulate the activities of the cells via several families of cell surface receptors such as the integrin alpha5beta1. The resulting tissue (PVR membrane) displays many of the features of a contractile scar and is the hallmark of PVR. Thus the development of PVR, and the resulting tractional distortion of the neuroretina, could be dependent on RPE-matrix interactions such as alpha5beta1-fibronectin.

Several experimental data prove this fundamental role of alpha5beta1. Thus, alpha5beta1 is connected with proliferation, migration and fibrotic modifications of RPE cells in vitro whereas quiescent RPE have no alpha5beta1 expression (Proulx, 2003, Molecular Vision, 9, 473; Jin 2000, IOVS 41, 4324). The increase of alpha5beta1 expression in RPE cells is linked to an increase in mobility (Meitinger 2001 Exp Eye Res, 73, 681). In animal models for retinal detachment integrin inhibitors decreased the RPE cell induced tractional retinal detachment (Yang 1996, IOVS, 37, 843).

Other cells are also connected with the pathogenesis of PVR such as macrophages and fibroblasts. Macrophages could be derived from transdifferentiated RPE cells or come from the systemic circulation (Pastor 2002 Prog Ret Eye Res 21, 127). The fibroblasts and/or myofibroblasts as major component of pathological membranes originate probably also from the transformed RPE cells (Pastor 2002 Prog Ret Eye Res 21, 127). The inhibition of alpha5beta1 interaction could interfere with the proliferation, migration as well as transdifferentiation of RPE cells and infiltration of macrophages as well as development of myofibroblasts. Similar processes are obtained in the pathogenesis of proliferative diabetic retinopathy (P D R, Marano 1995, Exp Eye res 60, 5).

The compounds according to the present invention are also useful in inhibiting and thus in the treatment of diseases involving or comprising undesired cell proliferation, including but not limited to proliferative disorders in ocular tissues such as proliferative vitreoretinopathy.

The compounds according to the present invention are also useful for the treatment of neoplasms, whereby the neoplasm is the formation of a tumor, which is characterized, in part, by angiogenesis. The neoplasm can be benign such as hemangioma, glioma, teratoma or malignant such as sarcoma, carcinoma, osteosarcoma, adenocarcinoma, blastoma, myeloma, leukemia and lymphoma, whereby the malignant neoplasm may or may not be a metastatic. The malignant neoplasm can be solid tumors, and hematopoeitic cancers such as lymphoma and leukemia. More preferably, the solid tumor is selected from the group comprising carcinoma, sarcoma, osteoma, fibrosarcoma, chondrosarcoma, glioblastoma astrocytoma, neuroblastoma, retinoblastoma, and others.

More preferably, the malignant disorder is selected from the group comprising breast cancer, gynaecological cancers, pancreatic cancer, bladder cancer, brain cancer, mesothelioma, teratocarcinoma, astrocytoma, melanoma, angioma and glioblastoma, renal cancer, prostate cancer, lung cancer, head and neck cancer, parotid cancer, thyroid cancer, fibrosarcoma, gastrointestinal cancer, endocrine cancer, AIDS-related cancers, adrenal cancer, eye cancer, hepatocellular cancer, skin cancer, thymus cancer, and testicular cancer and sarcomas such as osteosarcoma and Kaposi's sarcoma. Preferably, the lung cancer is non-small cell lung cancer.

Without wishing to be bound by any theory, the reasons for the applicability of the compounds according to the present invention in this particular field resides in the following findings. In many types of tumors alpha5beta1 integrin is upregulated on the surface of tumor epithelial cells (in addition to endothelial cells of the tumor vasculature) as well as on tumor cells (WO2005/092073). Alpha5beta1 integrin is overexpressed on tumor cell lines originating from at least the following cancers: bladder cancer, breast cancer, colon cancer, fibrosarcoma, lung cancer, metastatic melanoma, pancreatic cancer, prostate cancer, ovarian cancer, and renal cell carcinoma. In addition, cancer cells and cancer cell lines of other origin and representing other tumor indications may also overexpress alpha5beta1. It has been shown that alpha5beta1 overexpressing tumor cells are susceptible to direct tumor cell killing using anti-alpha5beta1 antibodies. There is a direct anti-proliferative effect by anti-alpha5beta1 antibodies on the tumor cell proliferation (WO2005/092073). Furthermore, loss of the interaction between alpha5 and fibronectin diminished cell survival and induced apoptosis in tumor cells. The integrin alpha5beta1 was shown to be the most relevant receptor of tumor cells for binding to fibronectin (Nista et al 1997, Int. J. Cancer 72, 133). Function-blocking alpha5 antibodies attenuate tumor cell migration (Maschler 2005 Oncogene 24, 2032). Alpha5beta1 integrin has been reported to promote tumor cell invasion and metastasis (Qian et al. 2005, Biochem Biophys Res Commun. 333, 1269; Han et al. 2003 Lung Cancer 41, 65). High expression of alpha5 integrin subunit seems to be associated with the most invasive cancer phenotypes. Anti-alpha5beta1 antibodies inhibit tumor growth in vivo, e.g., in NW231 and LOX mouse tumor xenograft models as well as in a rabbit VX2 tumor model.

Additionally, alpha5beta1 is important for the survival, proliferation and migration of lymphatic endothelial cells (Zhang 2005, J Cell Physiol 202, 205). Therefore, the inhibition of alpha5beta1 on lymphatic endothelial cells is a promising approach for inhibition of lymphangiogenesis in many therapeutic areas. Lymphangiogenesis is a very important process in tumor progression. The extravasation of tumor cells via lymphatic vessels plays an essential role in tumor dissimination and therefore metastasis.

From a physiological point of view, the newly formed blood vessels in this kind of neovascular disorder provide the tumor cells with oxygen and nutrients. They are necessary for further tumor growth above 1-2 mm$^3$ and form a gateway for tumor cells to enter the circulation and to metastasize to distant sites of the body (Folkman and Shing, 1992, J. Biol. Chem., 267, 10931).

Thus, by acting through the above described multiple mechanisms, alpha5beta1 antagonists prevent tumor growth, invasiveness and metastasis.

Several other diseases also involve integrin mediated effects and processes, such as atherosclerosis progression and restenosis. Particularly, angiogenesis and migration are the critical steps of plaque development during atherosclerosis (Hoshiga, 1995, Circ. Res. 77, 1129), and undesired vascular repair processes in vessels of atherosclerotic patients cause coronary restenosis (Panda, 1997, PNAS, 94, 9308).

It is to be understood that the aforementioned diseases are particularly diseases which are based on pathological angiogenesis. However, the compounds according to the present invention are not limited to the use in connection with this kind of diseases but can in alternative embodiments also be used for the treatment of diseases which are generally based on the interaction of integrin with ligands such as fibronectin in the extracellular matrix or on a cell surface. Thereby the compounds are useful in the inhibition of cell adhesion and migration. The following diseases are currently understood as to be based on this kind of interaction. Accordingly, the compounds according to the present invention may also be used for the treatment of immune based and/or inflammatory diseases, more preferably rheumatoid arthritis, inflammatory bowel disease, Crohn's disease, psoriasis, osteoarthritis, ulcerative colitis, and infectious diseases which are caused by microbial infection, including fungal infections, bacterial infections and viral infections. Again, it is to be noted, that any of the diseases specifically disclosed herein can be treated by the compound according to the present invention without being limited to the particular mode of action.

In a still further embodiment the immune based and/or inflammatory disease is an autoimmune disease or autoimmune disorder. In a further embodiment, the immune based and/or inflammatory disease is selected from the group comprising rheumatoid arthritis, juvenile arthritis, osteoarthritis, psoriatric arthritis, glomerulonephritis, gingivitis, inflammatory bowel disease, ulcerative colitis, systemic lupus erythematosus associated glomerulonephritis, irritable bowel syndrome, bronchial asthma, multiple sclerosis, pemphigus, pemphigoid, scleroderma, myasthenia gravis, Wegener's Granulomatosis, Churg-Strauss-allergic granulomatosis, Sjögren's syndrome, Sicca syndrome, Goopasture's disease, autoimmune haemolytic and thrombocytopenic states, pulmonary hemorrhage, vasculitis, Crohn's disease, psoriasis, asthma, ankylosing spondylitis and dermatomyositis.

In a still further embodiment the immune based and/or inflammatory disease is selected from the group comprising inflammation associated with ankylosing spondylitis, burns, lung injury, myocardial infarction, coronary thrombosis, vascular occlusion, post-surgical vascular reocclusion, IgA nephropathy, sarcoidosis, eosinophilic granulomata, midline granuloma, arteritis temporalis, Takayasu's arteritis, pterygia, Kawasaki's disease, atherosclerosis, traumatic central nervous system injury, ischemic heart disease and ischemia-reperfusion injury, respiratory distress syndrome, systemic inflammatory response syndrome, multiple organ dysfunction syndrome, tissue graft rejection, burns, lung injury, uveitis, asthma, rosacea and hyperacute rejection of transplanted organs.

The following observations support the use of the compounds according to the present invention in connection with inflammatory diseases. Basically, the influx of inflammatory cells into the inflammatory region stimulates angiogenesis and following this, the increased vasculature enables a greater influx of leukocytes, which promote the inflammatory process, such as destruction of cartilage and bone in the joint during arthritis. Furthermore, the lymphatic system plays also an important role in initiating the immune response via directing leukocytes and antigens from the tissues to the lymphnodes (Pepper 2003, J. Biol. Chem. 163, 209) and is important during many inflammatory processes such as rejection reactions after transplantation (Cursiefen 2004, J Clin Invest 113, 1040). Expression of alpha5beta1 on immune cells such as activated macrophages, neutrophils, mast cells or T-lymphocytes points to an important role for migration of immune cells into the inflamed tissue (Kloss 1999, J Comp Neurol 411, 162; Shang 1998, J Imm 160, 467; Issekutz Inflam Res. 1998 47, S123; Burns 2001 J Imm 166, 4644; Dastych, 2001, Allergy and Immunology 125, 152; Furgeson 1991 PNAS 88, 8072).

Whereas the transendothelial migration of inflammatory cells depends mainly on the integrin alpha4beta1 the migration within the inflamed tissue is mediated by alpha5beta1 and its ligand fibronectin. (Loike 1999 J Cell Biol 144, 1047; Shang 1998 I Immunol 160, 467). Animal studies with an alpha5beta1 inhibitor have shown the protection against severe ischemia/reperfusion injury after liver transplantation via inhibition of macrophage invasion into the transplanted organ (Fondevila 2005 Transpl Proc 37, 1679). Therefore inflammatory diseases mediated by infiltrating macrophages and neutrophils could be treated by alpha5beta1 inhibition.

Many inflammatory diseases after granumloma formation develop toward fibrosis. Addressing the invasion of immune cells as well as the development of myofibroblasts provides a powerful approach for treating chronic inflammatory diseases. Many of them are connected with alpha5beta1 up-regulation such as sarcoidosis, psoriasis or other inflammatory diseases (Shigehara 1998 Virchows Ach 433, 55; Bata-Csorgo 1998 J Clin Inv 101, 1509).

The compounds according to the present invention are additionally useful in inhibiting pathogenic organisms and are, therefore, useful for treating infectious diseases. Many pathogens interact directly or mediated by extracellular matrix proteins with host cells, causing cell adhesion and invasion of these pathogens. This interaction is mediated by host cell integrins such as alpha5beta1 (Cue, 2000, PNAS, 97, 2858; Frankel, 1996, J. Biol. Chem., 271, 20359; van Putten, 1998, Mol. Microbiology, 29, 369; Finlay, 1997, Microbiol. Mol. Biol. Rev., 61, 136). Additionally pathogens can also express integrins themselves to enter the host cell.

In a preferred embodiment the infectious organism or agent is selected from the group comprising fungal, viral, bacterial and parasite infection.

Fungal infections contemplated for treatment using the compounds and methods according to the present invention include systemic fungal infections, dermatophytoses and fungal infections of the genito-urinary tract. Fungal infections, preferably systemic fungal infections, include those caused by *Histoplasma, Coccidioides, Cryptococcus, Blastomyces, Paracoccidioides, Aspergillus, Nocardia, Sporothrix, Rhizopus, Absidia, Mucor, Hormodendrum, Phialophora, Rhinosporidium*, and the like. Dermatophyte infections include those caused by *Microsporum, Trichophyton, Epidermophyton, Candida, Pityrosporum*, and the like. Fungal disorders of the genito-urinary tract include infections caused by *Candida, Cryptococcus, Aspergillus, Zygomycodoides*, and the like. Infection by such organisms causes a wide variety of disorders such as ringworm, thrush or candidiasis, San Joaquin fever or Valley fever or coccidiodomycosis, Gilchrist's disease or blastomycosis, aspergillosis, cryptococcosis, histioplasmosis, paracoccidiomycosis, zygomycosis, mycotic keratitis, nail hair and skin disease, Lobo's disease, lobomycosis, chromoblastomycosis, mycetoma, and the like. These infections can be particularly serious, and even fatal, in patients with a depressed immune system such as organ transplant recipients and persons with acquired immunodeficiency syndrome (AIDS). Insofar patient groups which can be treated using the inhibitors according to the present invention are persons with AIDS, particularly those suffering from any of the infectious diseases described herein.

In a further embodiment the bacterial infection is selected from the group comprising infections caused by both Gram-positive and Gram-negative bacteria, including infections caused by *Staphylococcus, Clostridium, Streptococcus, Enterococcus, Diplococcus, Hemophilus, Neisseria, Erysipelothricosis, Listeria, Bacillus, Salmonella, Shigella, Escherichia, Klebsiella, Enterobacter, Serratia, Proteus, Morganella, Providencia, Yersinia, Camphylobacter, Mycobacteria, Helicobacter, Legionalla, Nocardia* and the like.

In a preferred embodiment the bacterial infection causes a wide variety of diseases. Said disorders are selected, among others, from the group comprising pneumonia, diarrhea, dysentery, anthrax, rheumatic fever, toxic shock syndrome, mastoiditis, meningitis, gonorrhea, typhoid fever, brucellis, Lyme disease, gastroenteritis, tuberculosis, cholera, tetanus and bubonic plague.

In another embodiment the disease is a viral infection, more particularly a viral infection caused by a virus selected from the group comprising retrovirus, HIV, Papilloma virus, Epstein-Barr, Herpes virus, Hepatitis virus, Papova virus, Influenza virus, Rabies, JC, encephalitis causing virus, hemorrhagic fever causing virus such as Ebola Virus and Marburg Virus.

In a further embodiment the parasite infection is selected from the group comprising infections caused by *Trypanosoma, Leishmania, Trichinella, Echinococcus, Nematodes, Classes Cestoda, Trematoda, Monogenea, Toxoplasma, Giardia, Balantidium, Paramecium, Plasmodium* or *Entamoeba.*

In case the disease is a non-neoplastic cell proliferative disorder, it is preferably selected from the group comprising fibrotic disorder. Preferably, the fibrotic disorder is fibrosis.

A disease connected with non-neoplastic cell proliferation and/or tissue remodeling preferably means that the disease is associated in a causative or non-causative manner with the proliferation and/or differentiation of non-neoplastic cells.

The disease may also be a non-neoplastic cell proliferative disorder which is selected from the group comprising prostatic hypertrophy, preferably benign prostatic hypertrophy, endometriosis, uterine fibroid, keloid scar formation, scleroderma, psoriasis, tissue repair and wound healing.

Fibrotic disorders which may be treated using the compounds according to the present invention are generally characterized by inappropriate overproliferation or transdifferentiation of non-cancerous mostly fibroblastic cells. Examples thereof include fibromyalgia, fibrosis, more particularly cystic, hepatic, renal, ocular, lung, stomach, intestinal, skin, idopathic pulmonary, and pericardial fibrosis and the like, cardiac fibromas, fibromuscular hyperplasia, restenosis, atherosclerosis, fibromyositis, and the like.

In a preferred embodiment the fibrotic disorder is a hepatic disorder, preferably liver fibrosis, liver cirrhosis, reperfusion injury after hepatic transplantation, necrotizing hepatitis or renal disorders, preferably renal fibrosis, glomrulonephritis, IgA nephropathy, reperfusion injury after kidney transplantation, chronic renal allograft dysfunction, amyloidosis, diabetic nephropathy, mesangio proliferative glomrulonephritis, nephrosclerosis or other fibrotic disorders, preferably lung fibrosis comprising interstitial pulmonary fibrosis, idiophatic fibrosis, drug-induced fibrosis, sarcoidosis, diffuse alveolar damage disease, pulmonary hypertension, chronic obstructive pulmonary disease, respiratory distress syndrome; skin fibrosis such as scleroderma, keloid, hypertrophic scar, dermatofibroma, chronic wounds, psoriasis, dupuytren's contracture, pemphegoid, burn; stomach and intestinal fibrosis comprising abnormal intestinal motility, hypertrophic pyloric stenosis, Hirschsprung's disease, megacolon of piebaldism, idiopathic obstruction, collagenous colitis, villious atrophy and crypt hyperplasia, polyp formation, fibrosis of Crohn's disease, gastric ulcer; eye fibrosis comprising acute and fibrotic sympathetic ophthalmia, Grave's disease, fibrosis after glaucoma surgery, fibrosis after cataract surgery, anterior capsular cataract, corneal scarring, pemphigoid, diabetic microaneurism, capsule opacification; or any other fibrosis comprising systemic sclerosis, artherosclerosis, restenosis, chronic myeloproliferative disorders, fibrodysplsia ossificans progressive, myelodysplasia, osteoporosis, myelofibrosis, osteosclerosis, rheumatoid pannus formation in rheumatoid arthritis and osteoarthritis, peritoneal fibrosis, myocardial fibrosis, pancreatic fibrosis, chronic pancreatitis, glial scar tissue formation in HIV associated cognitive motor disease and spongiform encephalopathy, gingival hypertrophy secondary to drugs and fibrocystic disease.

Fibrosis is a pathological condition with non-physiological wound healing following a persistent exogenous or endogenous stimulus and is mostly mediated by or associated with an inflammatory response. During the fibrotic response tissue remodelling and hypertrophic scarring take place connected with excessive deposition of extracellular matrix proteins and transdifferentiation of certain cell types (tissue dependent) to myofibroblasts. The common endpoint of all fibrotic diseases is the development of myofibroblasts which trigger the fibrosis by secretion of pro-fibrotic factors such as cytokines, inflammatory mediators, growth factors as well as ECM proteins (Powell 1999, Am J Physiol 277, C1-C19). Myofibroblasts are active participants in normal wound repair, but persistence of these cells in injured tissues prevents normal healing and promotes a dysregulated repair process characterized by progressive connective tissue remodelling and fibrosis (Tomasek 2002, Nat Rev Mol Cell Biol 3, 349). Transformation of fibroblasts or other cells to myofibroblasts is primarily mediated by pro-fibrotic cytokines such as transforming growth factor (TGFβ) or PDGF (Border 1994, New Engl J Med 331, 1286; Friedman, 2000, J. Biol. Chem. 275, 2247). Due to the ubiquitous presence in all tissues, myofibroblasts play an important role in various organs such as liver, skin, lung, kidney, eye and others.

There are several hints for the involvement of alpha5beta1 in the pathogenesis of fibrotic disorders in several tissues. In vitro data have shown the up-regulation of alpha5beta1 expression after stimulation of fibroblast or other myofibroblast precursor cells with the profibrotic growth factor TGFβ, PDGF or connective growth factor (CTGF) and the promotion of fibrotic differentiation by fibronectin (Thannickal 2003, J. Biol. Chem. 278, 12384; Nesbit 2001 Lab Invest 81, 1263; Roberts, 1988, J. Biol. Chem., 263, 4586; Weston 2003 J Am Soc Nephrol 14, 601).

Many other data provide evidence for the important role of alpha5beta1 in vivo. Thus, alpha5beta1 is up-regulated in renal fibrotic disorders such as renal fibrosis (Norman 1999 Exp Nephrol 7, 167), glomerulonephritis (Roy-Chaudhury 1997 Kidney Int 52, 103) as well as IgA nephropathy (Wagrowska-Danilewicz 2004, Int Urol Nephr 36, 81), lung fibrosis and sacoidosis (Pilewski, 1997 Am J Physiol 273, L256; Shigehara 1998 Virchows Ach 433, 55). During the pathogenesis of liver fibrosis alpha5beta1 is up-regulated within the fibrotic tissue (Zhou 2000 Chin Med J 113, 272) and on activated hepatic stellate cells, the myofibroblast precursors, during fibrotic differentiation (Iwamoto 1998 J Hepatol 29, 752; Milliano 2003 J Hepatol 39, 32). Alpha5beta1 is also connected with the pathogenesis of skin fibrosis due to the up-regulation on fibroblasts, proliferating and migrating keratinocytes as well in fibrotic skin such as from Psoriasis patients (Frazier 1196 J Invest Dermatol 107, 404; Juhazs 1993 Am J Path 143, 1458; Bata-Csorgo 1998 J Clin Invest 101, 1509). Alpha5beta1 expression in synovial fibroblasts or articular chondrocytes indicates an essential role in rheumatoid arthritis and osteoarthritis (Kitagawa 2005, Ann. Rheum Dis, Fukumoto Osteoarthritis and Cartilage 2002 10, 135).

Other fibrotic disorders with involvement of alpha5beta1 are chronic myeloproliferative disorders (Schmitz 1998 J Cell Physiol 176, 445) or fibrodysplasia ossificans progressiva (Tang 2003, J Bone Min Res 18, 502; Moursi 1997 J Cell Sci 110, 2187; Gannon 2001 Human Path 32, 842) as well as Artherosclerosis (Yee 1999 Thromb Haemost 82, 762) or acute and fibrotic sympathetic ophthalmia (Kuppner 1993 Curr Eye res 12, 923).

In a further embodiment the compounds according to the present invention can be used as agonistic effectors on integrin thus promoting neovascularisation. Accordingly, the compounds according to the present invention are used in a preferred embodiment for the treatment of diseases which require or are treated by neovascularization or induction thereof. This kind of disease is a disease which can be selected from the group comprising wound healing, stroke, infertility, ulcer, scleroderma, transplantation, peripheral arterial disease and coronary heart disease.

It is also within the present invention that the compounds according to the present invention may be used for the treatment of a patient suffering from a disease or diseased condition as defined above. Such treatment comprises the administration of one or several of the compounds according to the present invention or a medicament or pharmaceutical composition described herein.

Toxicity and therapeutic efficacy of a compound can be determined by standard pharmaceutical procedures in vitro such as biochemical assays and in cell culture or experimental animals. Biochemical assays, cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Compounds which exhibit large therapeutic indices are preferred. The data obtained from these cell culture assays and animal studies can be used in formulating a range of dosages suitable for use in humans. The dosage may vary within this range depending upon a variety of factors, e.g., the dosage form employed, the route of administration utilized, the condition of the subject, and the disease, which has to be treated.

For any compound according to the present invention, the therapeutically effective dose can be estimated initially from protein binding and cell culture assays by determining an $IC_{50}$ (i.e., the concentration of the test substance which achieves a half-maximal inhibition of integrin binding or cell adhesion). A dose can then be formulated in animal models to achieve a circulating concentration range in plasma or other compartments such as, e.g., vitreous humor, synovial liquid or other, that includes the $IC_{50}$ as determined in binding assays. Such information can be used to more accurately determine useful doses in humans. Levels in plasma or other compartments may be measured, for example, by HPLC, LC/MS, or ELISA.

It should be noted that the attending physician would know how and when to terminate, interrupt, or adjust administration due to toxicity, to organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient. Typically, the dose will be between about 0.0001-100 mg/kg of body weight or 1 ng-1 mg per eye or comparable concentrations for other compartments. About 0.001 mg to about 1000 mg will preferably be administered to a child, and between 0.01 mg and about 7000 mg, more preferably 100 mg to 3000 mg, will preferably be administered to an adult.

A program comparable to that discussed above may be used in veterinary medicine. The exact dose will depend on the disorder to be treated and will be ascertainable by one skilled in the art using known techniques.

Depending on the specific conditions to be treated, such compounds may be formulated and administrated systemically or locally. Techniques for formulation and administration may be found in "Remington's Pharmaceutical Sciences", 1990, 18$^{th}$ ed., Mack Publishing Co., Easton, Pa. The administration of a compound according to the present invention can be done in a variety of ways, including, but not limited to, orally, subcutaneously, intravenously, intranasally, transdermally, intraperitoneally, intramuscularly, intrapulmonary, vaginally, rectally, or intraocularly, periocularly, intraorbitally, intracapsulary, intrasynovially, intracistemally, topically, just to name a few. In some instances, for example, in the treatment of wounds and inflammation, the compound according to the present invention may be directly applied as an ointment, powder, solution or spray. Topical administration also comprises passive or facilitated adsorption, preferably through the skin, including skin patches and iontophoresis.

Depending on the route of administration some formulations are particularly advantageous. For the administration of the compound to the eye and other tissues such as neoplastic and non-neoplastic tissues, fibrotic tissues, inflamed tissues the following formulations are preferred. In case of local administration, intraocular or periocular injection, local implants, drops and ointments are preferred. In case of systemic administration, injection and oral administration are preferred. In case of intraocular injection intravitreal, intracameral or sub-retinal injections are preferred. Periocular injections are selected from group comprising subconjunctival, para/retro bulbar, juxtascleral, sub-tenual, and others. In the case of local implants specialized sustained-release devices will be administered intraocular or periocular, to enable a constant, slow release of compound to the eye (Robinson, 2002, Exp. Eye Res, 74, 309; Geroski, 2000, 41, 961), other sustained release systems are microspheres, liposomes, nanoparticles or other polymer matrices (Bourlais, 1998, Prog. Retin Eye Res. 17, 33). In order to improve the stability and pharmacological properties of the compound for ocular administration, the compound could be modified, as described before, and/or administered in combination with a special formulation, addition of penetration enhancers, bioadhesives and/or biodegradable polymers (Clark, 2003, Nature Rev. Drug Discovery, 2, 448; Sasaki, 1999, Crit. Rev Ther Drug Carrier Syst., 16, 85; Kauer, 2002, Drug Dev Ind Pharm., 28, 473; Kimura, 2001, Opthalmologica, 215, 143). An example for a sustained release of compound in the eye is the preparation of a dry compound pellet which will be coated with a silicone layer. After implantation into the eye the pharmaceutically active compound will be released constantly over a long period of time (Robinson, 2002, Exp. Eye Res, 74, 309). Particulate drug carriers that offer unique opportunities to improve tumor, antifibrotic and anti-inflammatory therapy through several different mechanisms are preferred. Liposomes may (1) assist in formulation of poorly-soluble therapeutic agents, (2) provide a slow-release vehicle to achieve the pharmacokinetic profiles that maximize the therapeutic index, or (3) behave as long-circulating nanoparticulates that can, for instance, extravasate in the hyperpermeable regions of tumor vasculature. An example for the sustained systemic release of compounds for treatment of neoplasms is doxorubicin which, entrapped within sterically-stabilized liposomes (SSL-DXR), represents a long-circulating formulation that can extravasate within tumors and enhance drug deposition (Straubinger et al., 2004, Anticancer Res. 24, 397). Examples for sustained systemic release of compounds for treatment of precocious puberty, prostate and breast cancer, endometriosis, uterine leiomyoma, polycystic ovarian disease, and various other disorders are GNRH analogues (Filicori M, Flamigni C, 1988, Drugs 35, 63; Lahlou N., 2005, Ann Urol (Paris). 39 Suppl 3: S78).

In a further aspect the present invention is related to a medicament or a pharmaceutical composition comprising at least one active compound and at least one pharmaceutically acceptable carrier, excipient or diluent. As used herein, the active compound is a compound according to the present invention, a pharmaceutically salt or base thereof or a prodrug thereof, if not indicated to the contrary.

For injection, compounds of the invention may be formulated in aqueous solution, preferably in physiologically compatible buffers such as Hank's solution, Ringer's solution, or physiologically saline buffer. For transmucosal administration, penetrants appropriate to the barrier to be permeated are used in the formulation. Such penetrants are generally known in the art.

The use of pharmaceutical acceptable carriers to formulate the compounds according to the present invention into dosages or pharmaceutical compositions suitable for systemic administration is within the scope of the present invention. With proper choice of carrier and suitable manufacturing practice, the compositions of the present invention, in particular those formulated as solutions, may be administered parenterally, such as by intravenous injection. The compounds can be readily formulated using pharmaceutically acceptable carriers well known in the art into dosages suitable for oral administration. Such carriers enable the compounds according to the present invention to be formulated as tablets, pills, capsules, dragees, liquids, gels, syrups, slurries, suspensions and the like, for oral ingestion by a subject to be treated.

Compounds according to the present invention or medicaments comprising them, intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Delivery systems involving liposomes are disclosed in international patent application WO 91/19501, as well as U.S. Pat. No. 4,880,635 to Janoff et al. The publications and patents provide useful descriptions of techniques for liposome drug delivery and are incorporated by reference herein in their entirety.

Pharmaceutical compositions comprising a compound according to the present invention for parenteral administration include aqueous solutions of the active compound(s) in water-soluble form. Additionally, suspensions of the active compounds may be prepared as appropriate oily injection suspensions. Suitable lipophilic solvents or vehicles include fatty oils such as sesame oil or castor oil, or synthetic fatty acid esters, such as ethyl oleate or triglycerides, or liposomes. Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions.

Pharmaceutical compositions comprising a compound according to the present invention for oral use can be obtained by combining the active compound(s) with solid excipient, optionally grinding the resulting mixture, and processing the mixture of granules, after adding suitable auxiliaries, if desired, to obtain tablets or dragee cores.

Suitable excipients are, in particular, fillers such as sugars, including lactose, sucrose, mannitol, sorbitol, and the like; cellulose preparations, such as, for example, maize starch wheat starch, rice starch, potato starch, gelatin, gum tragacanth, methyl cellulose, hydroxypropylmethyl cellulose, sodium carboxymethyl cellulose, polyvinylpyrrolidone (PVP) and the like, as well as mixtures of any two or more thereof. If desired, disintegrating agents may be added, such as cross-linked polyvinyl pyrrolidone, agar, alginic acid or a salt thereof such as sodium alginate, and the like.

Dragee cores as a pharmaceutical composition comprising a compound according to the present invention are provided with suitable coatings. For this purpose, concentrated sugar solutions may be used, which may optionally contain gum arabic, talc, polyvinyl pyrrolidone, carbopol gel, polyethylene glycol, titanium dioxide, lacquer solutions, suitable organic solvents or solvent mixtures, and the like. Dyestuffs or pigments may be added to the tablets or dragee coatings for identification or to characterize different combinations of active compound doses.

Pharmaceutical preparations comprising a compound according to the present invention which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

A "patient" for the purposes of the present invention, i.e., to whom a compound according to the present invention or a pharmaceutical composition according to the present invention is or is to be administered, includes both humans and other animals and organisms. Thus the compounds, pharmaceutical compositions and methods are applicable to or in connection with both human therapy and veterinary applications including diagnostic(s), diagnostic procedures and methods as well as staging procedures and methods. For example, the veterinary applications include, but are not limited to, canine, bovine, feline, porcine, caprine, equine, and ovine animals, as well as other domesticated animals including reptiles, such as iguanas, turtles and snakes, birds such as finches and members of the parrot family, lagomorphs such as rabbits, rodents such as rats, mice, guinea pigs, monkeys, hamsters, amphibians, fish, and arthropods. Valuable non-domesticated animals, such as zoo animals, may also be treated. In the preferred embodiment the patient is a mammal, and in the most preferred embodiment the patient is human.

The pharmaceutical composition according to the present invention comprises at least one compound according to the present invention in a form suitable for administration to a patient. Preferably, a compound according to the present application is in a water soluble form, such as being present as a pharmaceutically acceptable salt, which is meant to include both acid and base addition salts which are also generally referred to herein as pharmaceutically acceptable salts. "Acid addition salt", and more particularly "pharmaceutically acceptable acid addition salts" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Base addition salts" and more particularly "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine. The pharmaceutical compositions according to the present invention may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The compounds according to the present invention are, in a further embodiment, administered to a subject either alone or in a pharmaceutical composition where the compound(s) is mixed with suitable carriers or excipient(s). In treating a subject, a therapeutically effective dose of compound (i.e. active ingredient) is administered. A therapeutically effective dose refers to that amount of the active ingredient that produces amelioration of symptoms or a prolongation of survival of a subject which can be determined by the one skilled in the art doing routine testing.

In an embodiment of the various aspects of the present invention, a compound according to the present invention is administered together with a further pharmaceutically active compound. More preferably, such further pharmaceutically active compound is selected from the group comprising chemotherapeutic agents such as, e.g., 5-fluorouracil, gemcitabine, carboplatin, paclitaxel, cisplatin, taxol, oxaliplatin, irinotecan and others, agents for anti-hormone therapy such as, e.g., acetate, tamoxifen and others, agents for photodynamic therapy, agents influencing the vascular permeability and/or angiogenesis such as, e.g., COX-2 inhibitors, NO-synthase inhibitors, bradykinin receptor antagonists or others, or anti-angiogenic compounds, like compounds affecting VEGF activity (like VEGF or VEGF-receptor antibodies, soluble VEGF-receptor fragments, VEGF-receptor-kinase inhibitors), or other agents affecting the action of angiogenic growth factors. The combination of compounds effecting different steps of angiogenic pathway or targeting different mechanism, which causes the diseases, could be beneficial for an optimal treatment of disease.

In addition the pharmaceutically active compound is preferably selected from the group consisting of anti-inflammatory agents such as, e.g., steroids, nonsteroidal anti-inflammatory drugs including aspirin, folic acid antagonists (e.g. methotrexate), hydroxychloroquine, sulfasalazine, pyrimidine synthesis inhibitors (leflunomide), COX-2 inhibitors as well as biologics such as compounds directed against cytokines (e.g. TNF antagonists like Enbrel, Infliximab, Adalimumab), compounds directed against T cells, antigen presenting cells (e.g. Alefacept, Efalizumab) and anti-inflammatory cytokines or anti-fibrotic agents such as, e.g., interferons, TGFβ inhibitors (e.g. TGFβ antibodies or soluble TGFβ decoy receptor), inhibitors for other integrins (e.g. alphavbeta3 or alphavbeta6) Endothelin A receptor antagonists (e.g. LU135252), anti-oxidants (e.g. silymarin), phosphodiesterase inhibitors (e.g. pentoxifylline), thiazolidinidiones, immunsuppressive agents (e.g. rapamycin and mycophenolate mofetil), halofuginone and inhibitors of the renin-angiotensin system.

According to the present invention the compounds disclosed herein, also referred to as compounds according to the present invention, may be used as a medicament or for the manufacture of medicament or in a method of treatment of a patient in need thereof. Insofar any of these compounds constitute a pharmaceutical compound. The use of this kind of compound also comprises the use of pharmaceutically acceptable derivatives of such compounds.

In addition, the compounds according to the present invention may be transformed upon application to an organism such as a patient, into the pharmaceutically active compound. Insofar the compounds according to the present invention may be prodrugs which, however, are nevertheless used for the manufacture of the medicaments as disclosed herein given the fact that at least in the organism they are changed in a form which allows the desired effect.

It is to be understood that any of the pharmaceutical compositions according to the present invention may be used for any of the diseases described herein.

The pharmaceutical compositions according to the present invention may be manufactured in a manner that is known as such, e.g., by means of conventional mixing, dissolving, granulating, dragee-mixing, levigating, emulsifying, encapsulating, entrapping, lyophilizing, processes, or the like.

In a further aspect, the present invention is related to the use of the compounds according to the present invention as a diagnostic means. As used herein, a diagnostic means is the same as a diagnostic or a diagnostic tool. More preferably, the compounds according to the present invention can be used for the manufacture of such diagnostic.

This use of the compounds according to the present invention is particularly based on the fact that said compounds interact specifically with integrins, more particularly alpha5beta1. Because of the very restricted expression of alpha5beta1 on activated endothelial cell in tumors, after stimulation with growth factors (Kim, 2000, Am. J. Path, 156, 1345; Collo, 1999, J. Cell Sc., 112, 569), on activated immune cells and myofibroblasts (Shang 1998, J Imm 160, 467, Thannickal 2003, J. Biol. Chem. 27), this molecule is a suitable marker for angiogenesis, inflammation and fibrosis in pathological conditions.

In preferred embodiments, the compounds according to the present invention are labeled compounds according to the present invention. The label is preferably a detectable label and allows the use of the respective compounds particularly in the performance of in vivo imaging methods such as radionuclide imaging, positron emission tomography, computerized axial tomography, infrared imaging and magnetic resonance imaging. Most preferably, a radionuclide or a paramagnetic material is used as a label in the aforementioned methods. Additionally the specific interaction of the compound with the integrin could be also detected ex vivo, e.g., on isolated cells and in tissues removed by biopsy.

The problem underlying the present invention is also solved by the technical teaching according to the attached independent claims. Preferred embodiments thereof may be taken from the dependent claims.

The invention is now further illustrated by reference to the following figures and examples from which further advantages, features and embodiments may be taken. It is understood that these examples are given for purpose of illustration only and not for purpose of limitation. All references cited herein are incorporated by reference.

Figure 1:
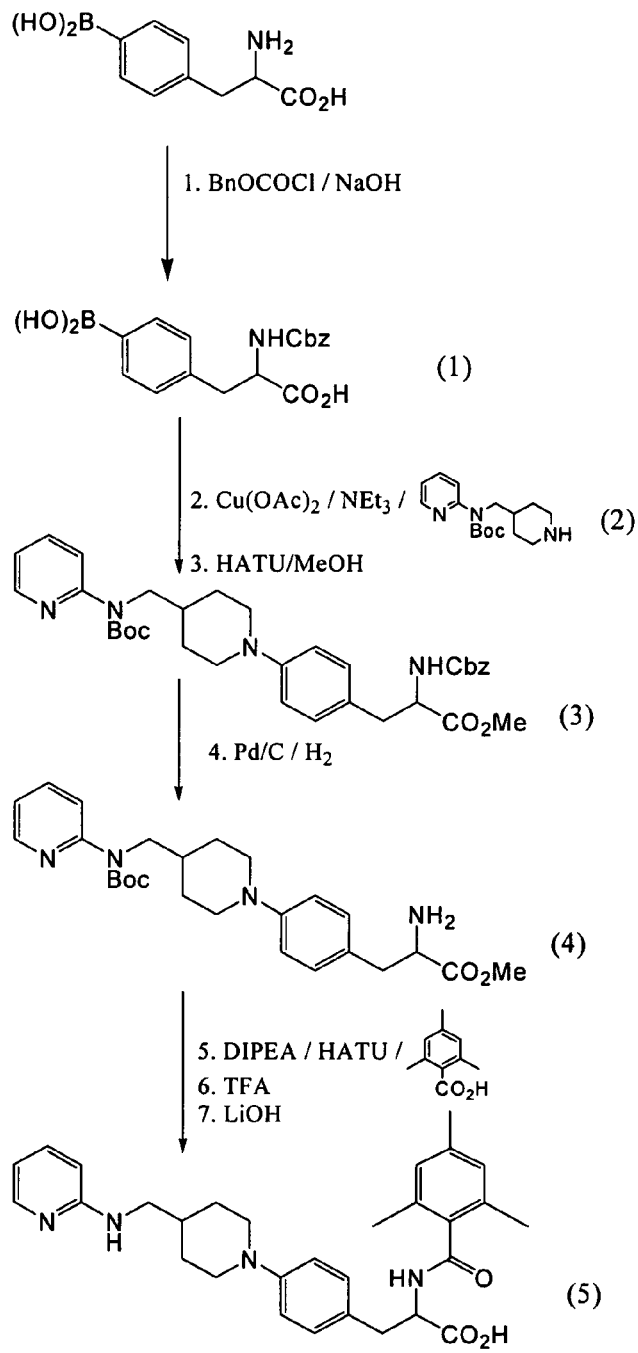
FIG. 1 shows the synthesis of 3-{4-[4-(pyridin-2-ylaminomethyl)-piperidin-1-yl]-phenyl}-2-(2,4,6-trimethyl-benzoylamino)-propionic acid (5)

Within the present application the following abbreviations are used:
Ac Acetyl
AIDS Acquired immunodefficiency syndrome
AMD Age related macular degeneration
bFGF Basic fibroblast growth factor
Boc tert-Buthoxycarbonyl
BSA Bovine serum albulmin
Cbz Benzyloxyformyl
CD31 Endothelial cell marker—platelet/endothelial cell adhesion molecule
Cox Cyclooxygenase
Cpd. Compound
d Doublet
dba Dibenzylidenaceton
DCE Dichloroethane
DCM Dichloromethane
DIC Diisopropylcarbodiimide
DIPEA N,N-Diisopropylethylamine
DMF N,N-Dimethylformamide
DMSO Dimethylsulfoxide
DMSZ Deutsche Sammlung von Mikroorganismen und Zellkulturen
EC Endothelial cells
ECM Extracellular matrix
EDTA Ethylenediaminetetra-acetate
ELISA Enzyme-linked immunosorbent assay
eq. Equivalent(s)
Et Ethyl
Fc Fragment of constant region of human immunoglobuline G1
FITC Fluorescein isothiocyanate
Fmoc 9-Fluorenylmethyloxycarbonyl
GnRH Gonadotropin releasing hormone
h Hour
HATU O-(7-Azabenzotriazol-1-yl)-1,1,3,3-tetramethyluronium-hexafluorophosphate
HBTU O-(Benzotriazol-1-yl)-1,1,3,3-tetramethyluronium-Hexafluorophosphat
Hepes N-2-Hydroxyethylpiperazine-N'-2-ethanesulfonic acid
HIV Human immuno-deficiency virus
HPLC high-pressure liquid chromatography
HRP Horseradish peroxidase
iPr 2-Propyl
KHMDS Potassium-hexamethyldisilazane
LC/MS Liquid chromatography-mass spectrometry
m Multiples
Me Methyl
Me Methyl
MES 2-(N-Morpholino)-ethanesulfonic acid
min Minute(n)
ml Milliliter
MTBE Methyl-tert-buthyl ether
NMR nuclear magnetic resonance
NO Nitric oxide
OD Optical density
OTf Trifluoromethanesulfonate
OTos Toluene-4-sulfonate
PBS Phosphate buffered saline
PDGF Platelet derived growth factor
PDR Proliferative diabetic retinopathy
PG Protecting group
PIDA Bisacetoxy iodobenzene
PMA Phorbol 12-myristate 13-acetate
PVP polyvinylpyrrolidone
PVR Proliferative vitreoretinopathy
RGD Argininyl-glycyl-aspartic acid
RNA Ribonucleic acid
RPE Retinal pigment epithelium
RPMI Medium developed at Roswell Park Memorial Institute
RT Room temperature
s Singulett
tBu tert-Butyl
TFA Trifluoroacetic acid
TGFβ Transforming growth factor beta
THF Tetrahydrofuran
TIBS Tributhylsilane
TMB 3,3,5,5'-tetramethylethylenediamine
TMSCl Chlorotrimethylsilane
Tris Tris(hydroxymethyl)-aminomethane
TRITC Tetramethylrhodamine isothiocyanate
VEGF Vascular endothelial growth factor
Xantphos 4,5-bis(diphenylphosphino)-9,9-dimethylxanthene

EXAMPLE 1

Materials and Methods

Solvents:
Solvents were used in the assigned quality without further purification. Acetonitrile (Gradient grade, J. T. Baker); dichlormethane (for synthesis, Merck Eurolab); diethylether (for synthesis, Merck Eurolab); N,N-dimethylformamide (LAB, Merck Eurolab); dioxane (for synthesis, Aldrich); methanol (for synthesis, Merck Eurolab).

Water:
Milli-Q Plus, Millipore, demineralized.

Reagents:

Reagents were synthesized according to or in analogy to literature procedures or purchased from Advanced ChemTech (Bamberg, Deutschland), Sigma-Aldrich-Fluka (Deisenhofen, Germany), Bachem (Heidelberg, Germany), J. T. Baker (Phillipsburg, USA), Lancaster (Muhlheimi/Main, Germany), Merck Eurolab (Darmstadt, Germany), Neosystem (Strasbourg, France), Novabiochem (Bad Soden, Germany, from 2003 Merck Biosciences, Darmstadt, Germany) und Acros (Geel, Belgium, Vertriebsgesellschaft Fisher Scientific GmbH, Schwerte, Germany), Peptech (Cambridge, Mass., USA), Synthetech (Albany, Oreg., USA), Pharmacore (High Point, N.C., USA), Anaspec (San Jose, Calif., USA) or other companies and used in the assigned quality without further purification.

Plastic ware for biochemical assays were purchased from Greiner Bio-one (Germany), Nunc (Nalge Europe Ltd)

General Remarks on the Synthesis of the Compounds According to the Present Invention The routes for the synthesis of compounds disclosed in this application by formula (I) mainly depend on the structures of the selected A- and Ar-moieties combined in a particular compound. The examples given below represent synthesis approaches that can be used to synthesize a wide range of compounds described in this application. Of course the following synthesis routes are examples and for any person skilled in the art, more particularly by any organic chemist many additional alternative routes for the synthesis of compounds described in this application are possible and feasible.

Synthesis of Compounds of Formula (I) Containing a Heterocycle A that is Linked to Ar Via a Ring N-Atom of A In a first class of compounds of formula (I) A is a nitrogen containing heterocyclic ring which is connected at a or the ring N-atom to Ar. In typical examples A is selected from, but is not restricted to the group comprising cyclic amines, cyclic carbamates, lactames or cyclic imides which are bond to Ar at their ring N-atoms. Such compounds can be prepared according to methods described in the literature. Some citations as well as experimental examples are given below.

Aromatic Amination

Figure 10:
FIG. 10 shows the compounds of formula (I) can be build up by the coupling of two building blocks.

In one approach the synthesis of theses compounds can be achieved by, but is not restricted to the coupling of two building blocks representing G-Z-A and Ar—Y-Ψ in formula (I) or precursors of them according to FIG. 10.

Figure 11:
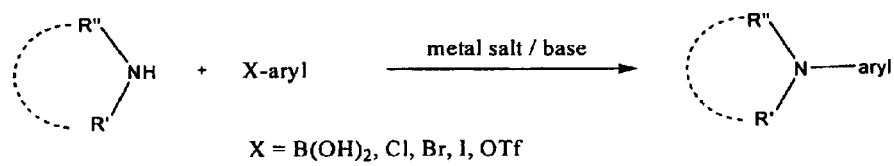
FIG. 11 shows a scheme for N-arylation reactions.

The key step in this synthesis of that class of compounds is the coupling of a G-Z-A-type building block at the NH of ring A with the aromate Ar of an Ar—Y-Ψ-type building block, i.e., a N-arylation of NH-containing substrates generally outlined in FIG. 11.

There are at least two different methods described for this in the literature, namely palladium catalyzed reactions of NH-substrates with aryl halides described by Hartwig and Buchwald (e.g. Hartwig, J. P. Synlett 1996, 329 or Wolfe, J. P.; Buchwald, S. L. J. Org. Chem. 1997, 62, 6066-6068) and copper salt promoted reactions of aryl boronic acids or salts thereof described by Chan et al. (e.g. in Tetrahedron Lett. 1998, 39, 2933-2936). Some copper mediated N-arylaton reactions are reviewed for example in Angew. Chem. 2003, 115, 5558-5607 by S. V. Ley and A. W. Thomas. In addition to the literature cited above recent examples can be found in the literature, e.g., R. Tatsumi et al., J. Med. Chem. 2005, 48, 2678-2686, M. V. Nandakumar, Adv. Synth. Catal. 2004, 346(8), 954-959 and S. Cacchi et al., Org. Lett. 2001, 3(16), 2539-2542 for the N-arylation of cyclic carbamates, E. T. Chemick et al., J. Org. Chem. 2005, 70, 1486-1489 for the N-arylation of cyclic imides and M. Vogler, Synthesis 2004, 1211-1228 or R. G. Browning, Tetrahedron 2004, 60(2), 359-366 for the N-arylation of lactames.

Typical examples of precursors of G-Z-A and Ar—Y-Ψ and their couplings are given in examples 2 to 8 with building blocks (2), (7), (10), (14), (17), (19), (22) and (1), (6), (12), (13), (30) in FIGS. 1 to 7.

Figure 2:
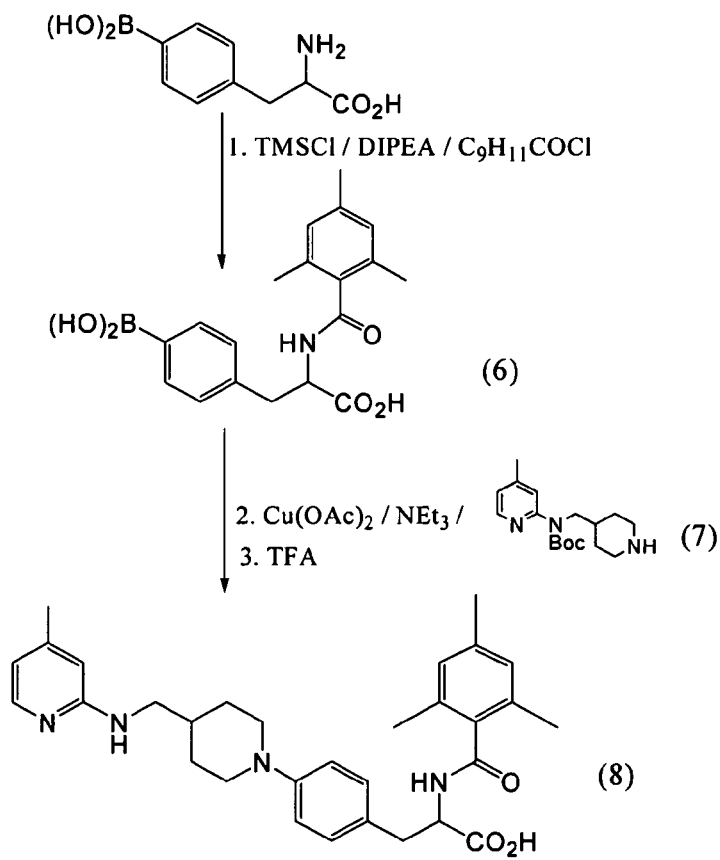
FIG. 2 shows the synthesis of 3-(4-{4-[(4-methyl-pyridin-2-ylamino)-methyl]-piperidin-1-yl}-phenyl)-2-(2,4,6-trimethyl-benzoylamino)-propionic acid (8)
Figure 3:
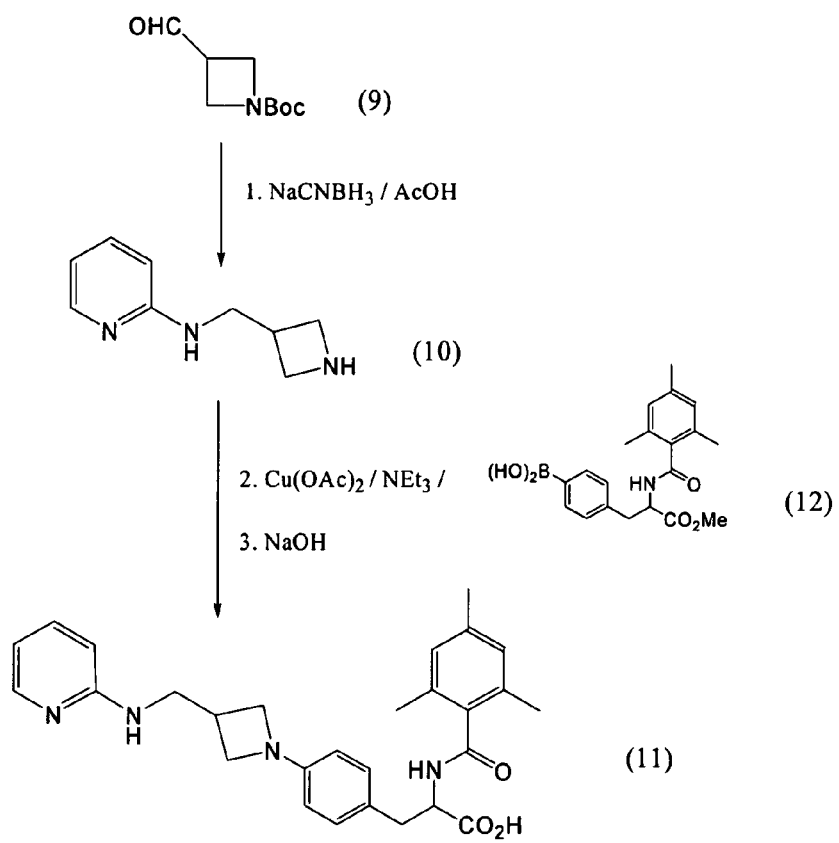
FIG. 3 shows the synthesis of 3-{4-[3-(Pyridin-2-ylaminomethyl)-azetidin-1-yl]-phenyl}-2-(2,4,6-trimethyl-benzoylamino)-propionic acid (11)
Figure 4:
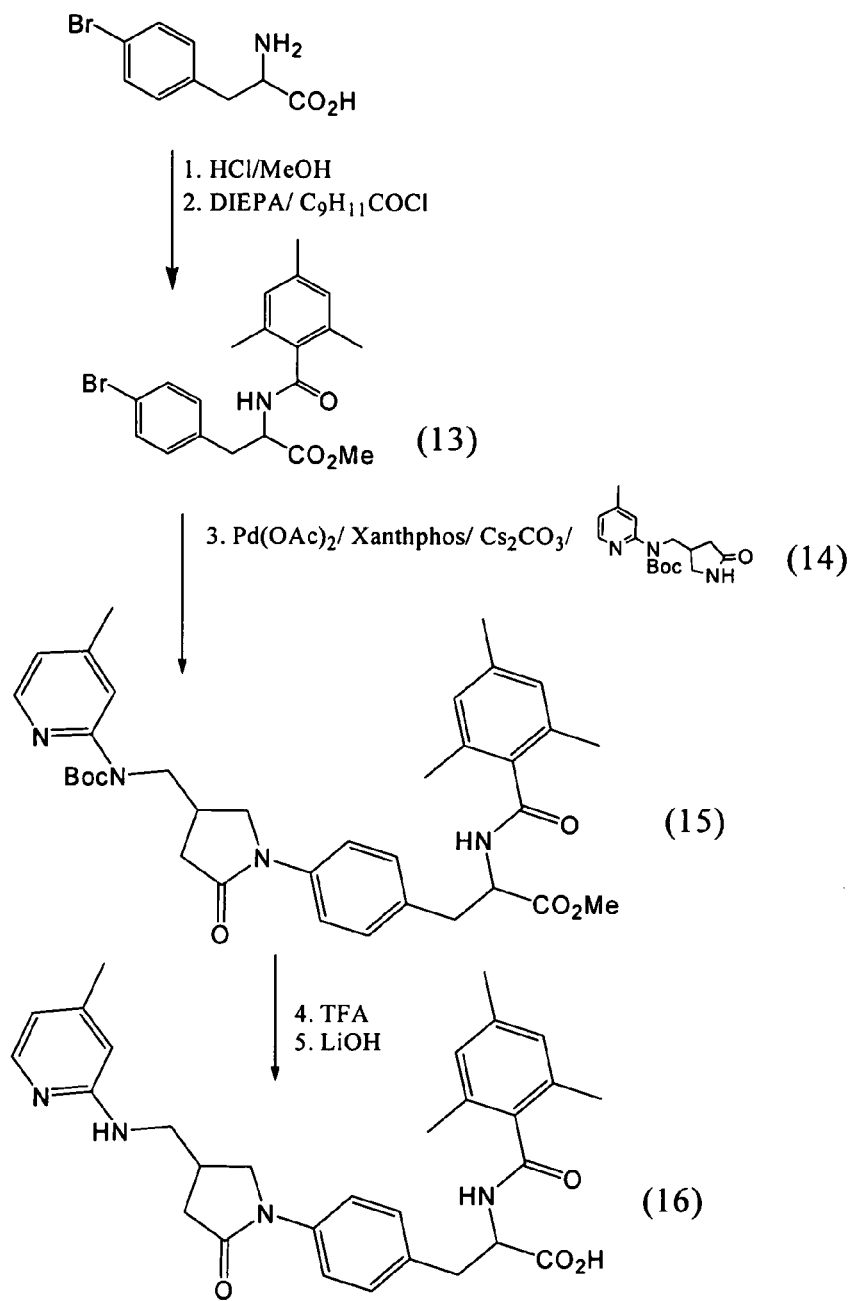
FIG. 4 shows the synthesis of 3-(4-{4-[(4-Methyl-pyridin-2-ylamino)-methyl]-2-oxo-pyrrolidin-1-yl}-phenyl)-2-(2,4,6-trimethyl-benzoylamino)-propionic acid (16)
Figure 5:
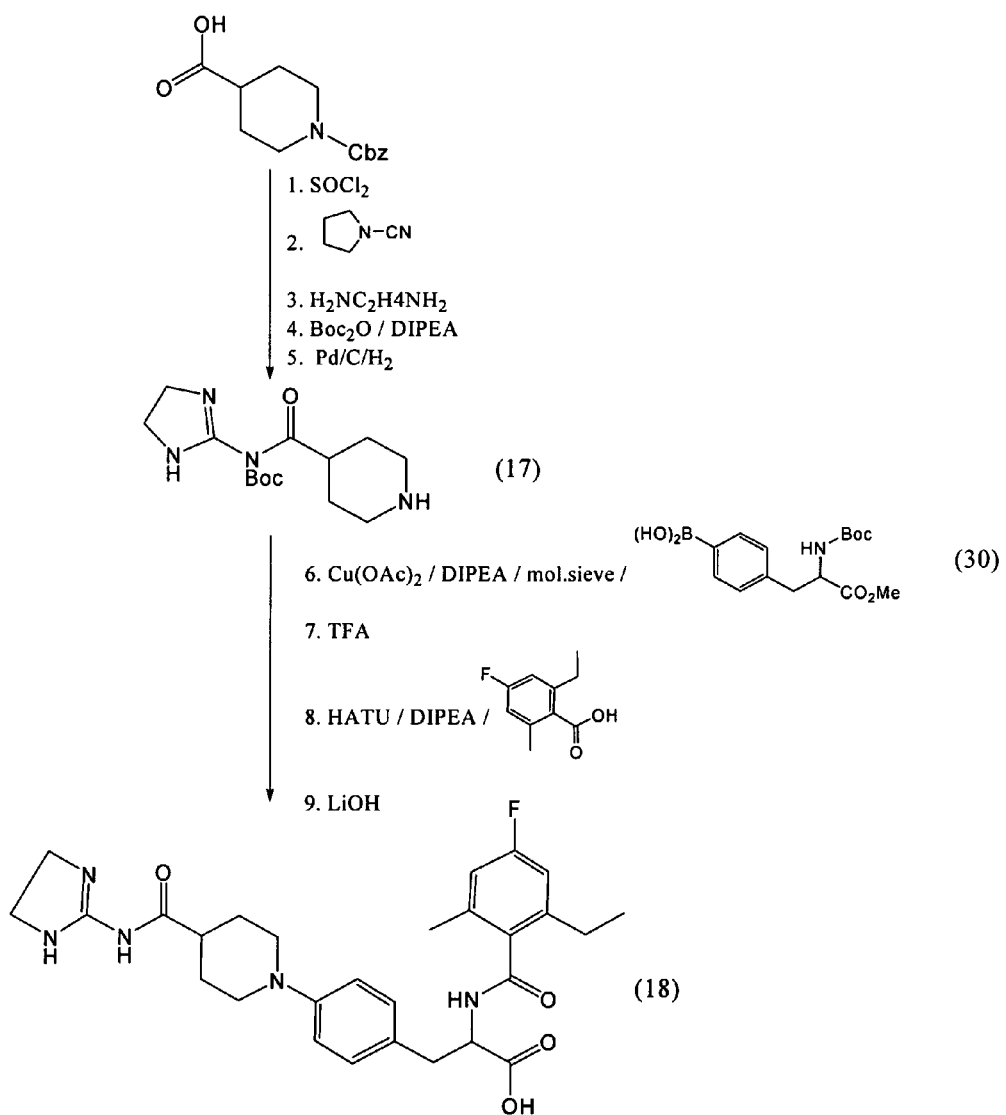
FIG. 5 shows the synthesis of 3-{4-[4-(4,5-dihydro-1H-imidazol-2-ylcarbamoyl)-piperidin-1-yl]-phenyl}-2-(2-ethyl-4-fluoro-6-methyl-benzoylamino)-propionic acid (18)
Figure 6:
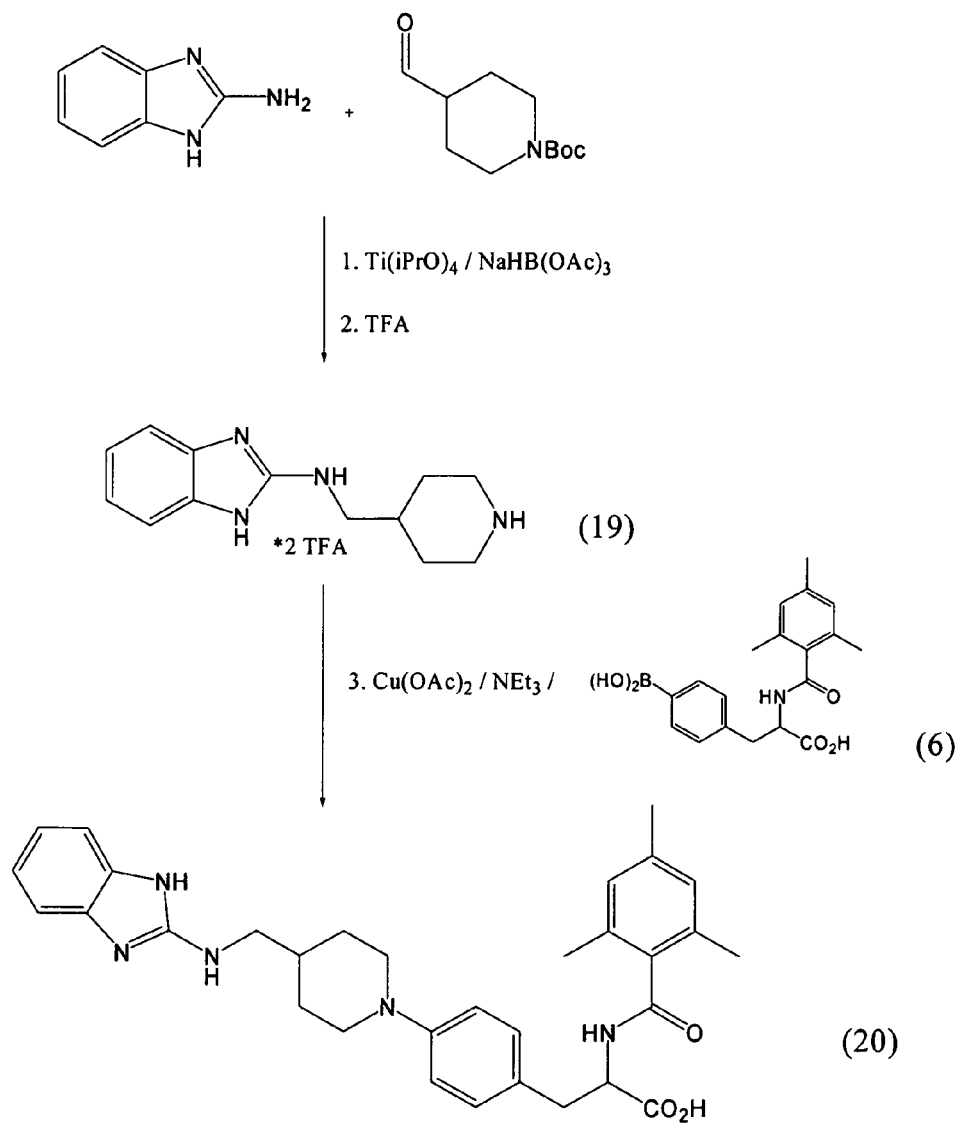
FIG. 6 shows the synthesis of 3-(4-{4-[(1H-benzoimidazol-2-ylamino)-methyl]-piperidin-1-yl}-phenyl)-2-(2,4,6-trimethyl-benzoylamino)-propionic acid (20)
Figure 7:
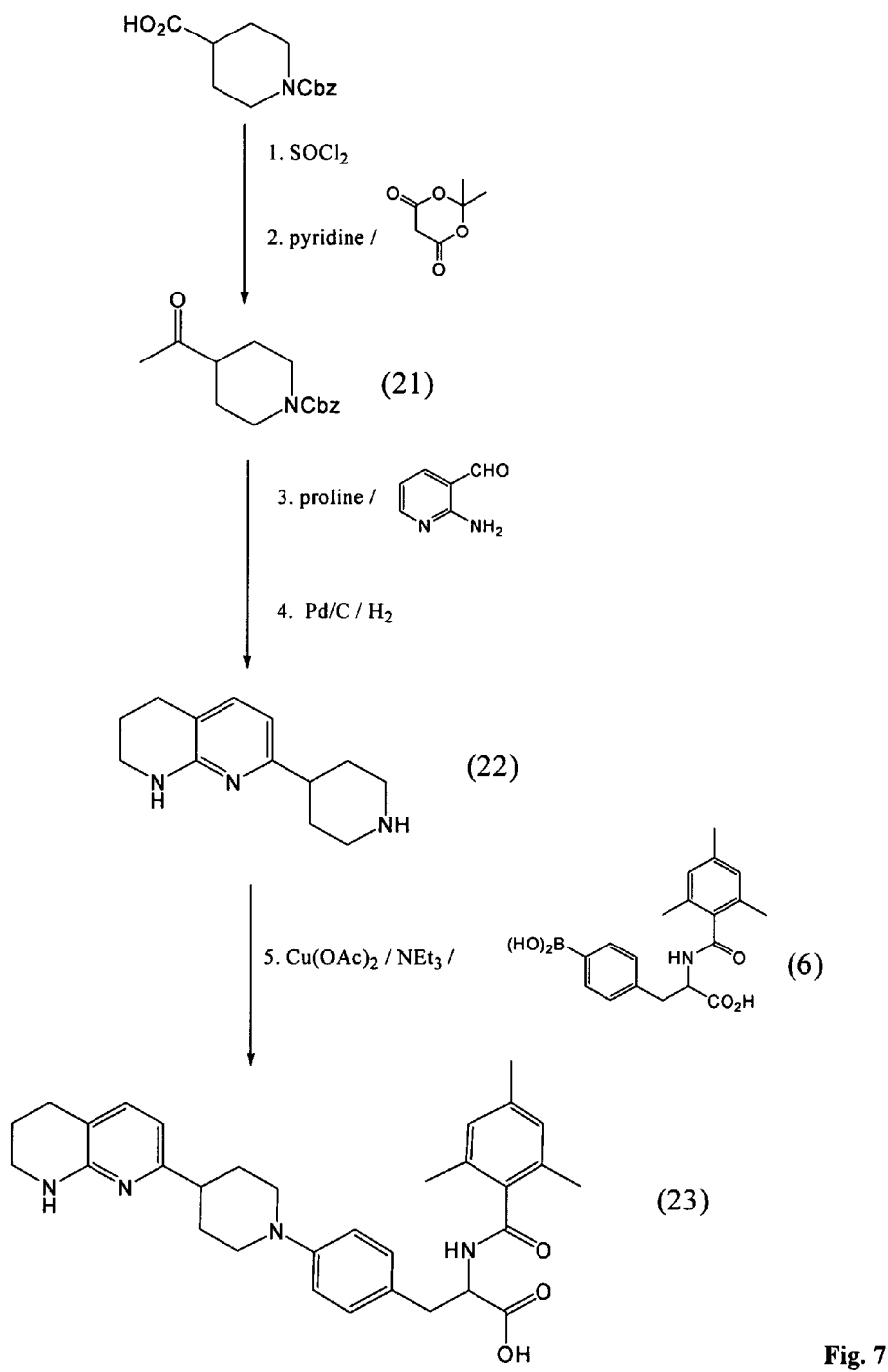
FIG. 7 shows the synthesis of 3-{4-[4-(5,6,7,8-tetrahydro-[1,8]naphthyridin-2-yl)-piperidin-1-yl]-phenyl}-2-(2,4,6-trimethyl-benzoylamino)-propionic acid (23)

In steps 2 of FIGS. 1 to 3 as well as in steps 6, 3 and 5 of FIGS. 5, 6 and 7 examples for the coupling of different building blocks representing G-Z-A or precursors of them with boronic acids representing Ar—Y-Ψ are given whereby the moieties A are cyclic amines. The experimental procedures are given in examples 2 to 4 and 6 to 8. Another method of N-arylation, i.e., the palladium catalyzed coupling of an NH-containing ring with an arylic halogenide or triflate ester is exemplified in example 5, i.e., step 3 in FIG. 4. Here lactame (14) is coupled to an aryl bromide (13).

Synthesis of Building Blocks G-Z-A

Building block (2) in FIG. 1 correlates to a Boc-protected G-Z-A-moiety in formula (I) wherein G is 2-pyridylamino, Z is methylene and A is piperidyl. Generally speaking this is an example for a group of G-Z-A-type building blocks wherein Z is an alkyl chain, G is of type $R_9$—NH and A is a non aromatic heterocycle. This class of building blocks can generally be obtained by methods described in the literature. Two examples for the synthesis are outlined in FIGS. 12 and 13.

Figure 12:
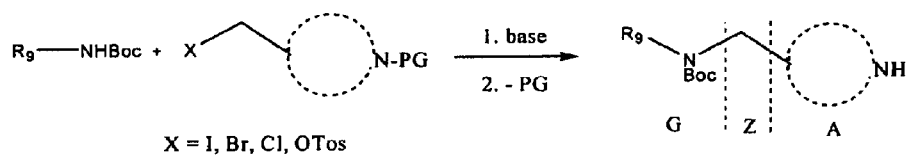
FIG. 12 shows the synthesis of G-Z-A-type building blocks by an alkylation procedure.
Figure 13:
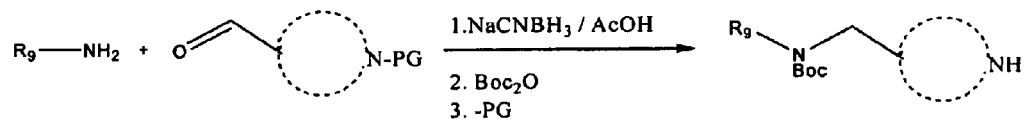
FIG. 13 shows the synthesis of G-Z-A-type building blocks by a reductive alkylation procedure.

FIG. 12 shows the alkylation of a Boc-protected aminoheterocycle after deprotonation with as strong base to give a G-Z-A-type building block. Examples for this procedure are the synthesis of building blocks (2), (7) and (14) in examples 2, 3 and 5, respectively. Building block (2) for example is obtained by the reaction of pyridin-2-yl-carbamic acid tert-butyl ester and 4-bromomethyl-piperidine-1-carboxylic acid benzyl ester with KHMDS as base.

In an alternative approach heterocycles with a free amino group, standing for moiety G in formula (I) become connected to an A or Z-A-derivative by a reductive alkylation procedure, followed by the optional introduction of a Boc-protection group and deprotection of the ring N-atom of ring A. This is outlined in FIG. 13. Examples for this procedure are the synthesis of building blocks (10) and (19) in examples 4 and 7. For example building block (10) in example 4 is obtained by a reductive amination reaction of 2-aminopyridine with 3-formyl-azetidine-1-carboxylic acid tert-butyl ester. In analogy building block (2) or derivatives could also be prepared by reductive amination of a 2-aminopyridine derivative with a N-protected 4-formylpiperidine.

Using one of these alkylation procedures almost every amino-heterocycle $R_9$—$NH_2$ representing moiety G can be connected to the ring systems described for moiety Z-A in formula (I) thereby generating a diverse set of optionally protected G-Z-A moieties. These can be used for the coupling with Ar—Y-Ψ-type building blocks.

And, of course, these two approaches can also be similarly applied to bromoalkyl- or formylalkyl heterocycles different from bromomethyl- or formylpiperidine as shown in examples 4 and 5. Together with the wide range of available heterocyclic amines numerous combinations can be selected to obtain a wide range of G-Z-A building blocks required for the synthesis of compounds described in this application.

Figure 14:
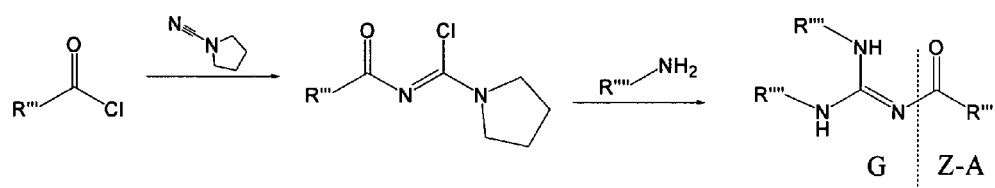
FIG. 14 shows a reaction scheme for the synthesis of N-acylguanidines.

Another group of G-Z moieties described in this application is the group providing N-acylguanidines. Beside other approaches described in the literature a general approach is outlined in FIG. 14. This approach can be used to synthesize related compounds described in this application. An example is given with the synthesis of building block (17) in example 6. It should be understood that the two R""-moieties in the final N-acylguanidine of FIG. 14 also can be joined to form a ring system, as exemplified by building block (17) in example 6.

It should be understood, that with the procedures for the synthesis of G-Z-A moieties given above not all related moieties described in this application can be synthesized but some need more individual synthesis strategies. An example for this is given with building block (22) in example 8 and FIG. 7 where G is 1,2,3,4-tetrahydro-[1,8]naphthyridyl, Z is a direct bond and A is piperidyl.

Synthesis of the Building Blocks Ar—Y-Ψ

For the synthesis of Ar—Y-Ψ-type building blocks preferably commercially available precursors are used, that need only few transformation steps to become suitable building blocks to be coupled with G-Z-A-type building blocks. In a preferred class of compounds disclosed in this application Ar—Y-Ψ-type building blocks can be described as substituted 2-amino-3-arylpropanoic acids. Examples wherein Ar is phenyl are given with building blocks (1), (6), (12), (13) and (30) that can easily be prepared from commercially available phenylalanine derivatives. Also for other derivatives wherein Ar is thienyl or pyridyl the related 2-amino-3-arylpropanoic acids precursors are commercially available. Synthesis approaches to substituted 2-amino-3-arylpropanoic acid derivatives include but are not limited to literatures procedures like palladium catalyzed couplings of aryl or heteroaryl iodides with protected iodo(2-amino-2-carboxy-ethyl)zinc derivatives (R. F. W. Jackson et al., Tetrahedron Letters 1989, 30(43), 5941-5944) or glycine enolate based approaches, e.g., bislactimether alkylation (U. Schollkopf, W. Hartwig, U. Groth, Angew. Chem. 1979, 91, 922-923) or alkylation of benzophenone imines prepared from glycine alkyl esters (M. J. O'Donnell et al., Tetrahedron Let. 1978, 19(30), 2641-2644). These and other procedures that can be found in the literature enable any person skilled in the art, more particularly an organic chemist to synthesize any Ar—Y-Ψ-type building block wherein Ar has such a structure.

Beside the possibility to synthesize Ar—Y-Ψ-type building blocks that differ in the structure of Ar it is also possible to vary the structure of the T-moiety which is defined by formula (II). For example in case of building block (6) this can be achieved by exchanging 2,4,6-trimethyl-benzoyl chloride of step 1 in FIG. 2 with another carboxylic acid chloride or sulfonyl chloride. This will affect changes in the structure of the Q-$R_2$-moiety which is a part of Ψ as shown by formula (II). In analogy it would be possible to introduce these changes closer to the last step of a synthesis of compounds of formula (I). For example it is possible to exchange the 2,4,6-trimethyl-benzoic acid in step 5 of FIG. 1 by other carboxylic or sulfonic acids or activated acid derivatives and couple them to intermediate (4) under appropriate conditions. By using this approach hundreds of derivatives of (5) differing in the structure of Q-$R_2$ can be prepared including those structures disclosed for $R_2$. In addition to the transformations of the primary amines like in compound (4) of FIG. 1 into amides or sulfonamides as described above, it is also possible to transform the primary amines with appropriate reactants into lactames as disclosed according to methods described in the literature.

Synthesis of Compounds of Formula (I) Containing a Heterocycle A that is Linked to Ar Via a Ring C-Atom of A In a second class of compounds A is connected at one of its ring C-atoms to Ar. In typical examples A is selected from, but is not restricted to the group comprising 4,5-dihydro-oxazole, 5,6-dihydro-4H-[1,3]oxazine, 4,5-dihydro-1H-imidazole or 1,4,5,6-tetrahydro-pyrimidine that are bond to Ar at the ring C-atom located between the two hetero atoms in these heterocycles, i.e., Ar is bond in position 2 of the above mentioned heterocycles. Such 2-substituted 5,6-dihydro-4H-[1,3]oxazines and oxazolines can be synthesized by methods described in the literature (e.g. for oxazolines A. I. Meyers et al., Angew. Chem. 1976, 88(10), 321-332 and references cited therein or P. Wimpf et al., J. Comb. Chem. 2002, 4, 656-660). As appropriate starting material for such compounds an analogue of building block (13) in FIG. 4 could be used where the bromine is replaced by a carboxylic acid moiety. The same starting building block could also be used for the synthesis of imidazolines (e.g. G. H. Merriman et al., Bioorg. Med. Chem. Lett. 2005, 15, 435-438). Amongst other suitable synthesis routes it is also possible to start with a derivative of building block (13) where the bromine atom is replaced by a formyl-moiety (H. Fujioka et al., Tetrahedron Lett. 2005, 46, 2197-2199) to build up compounds of formula (I) where A is a dihydroimidazole.

Synthesis of Compounds of Formula (I) where Ar is a Direct Bond

Figure 8:
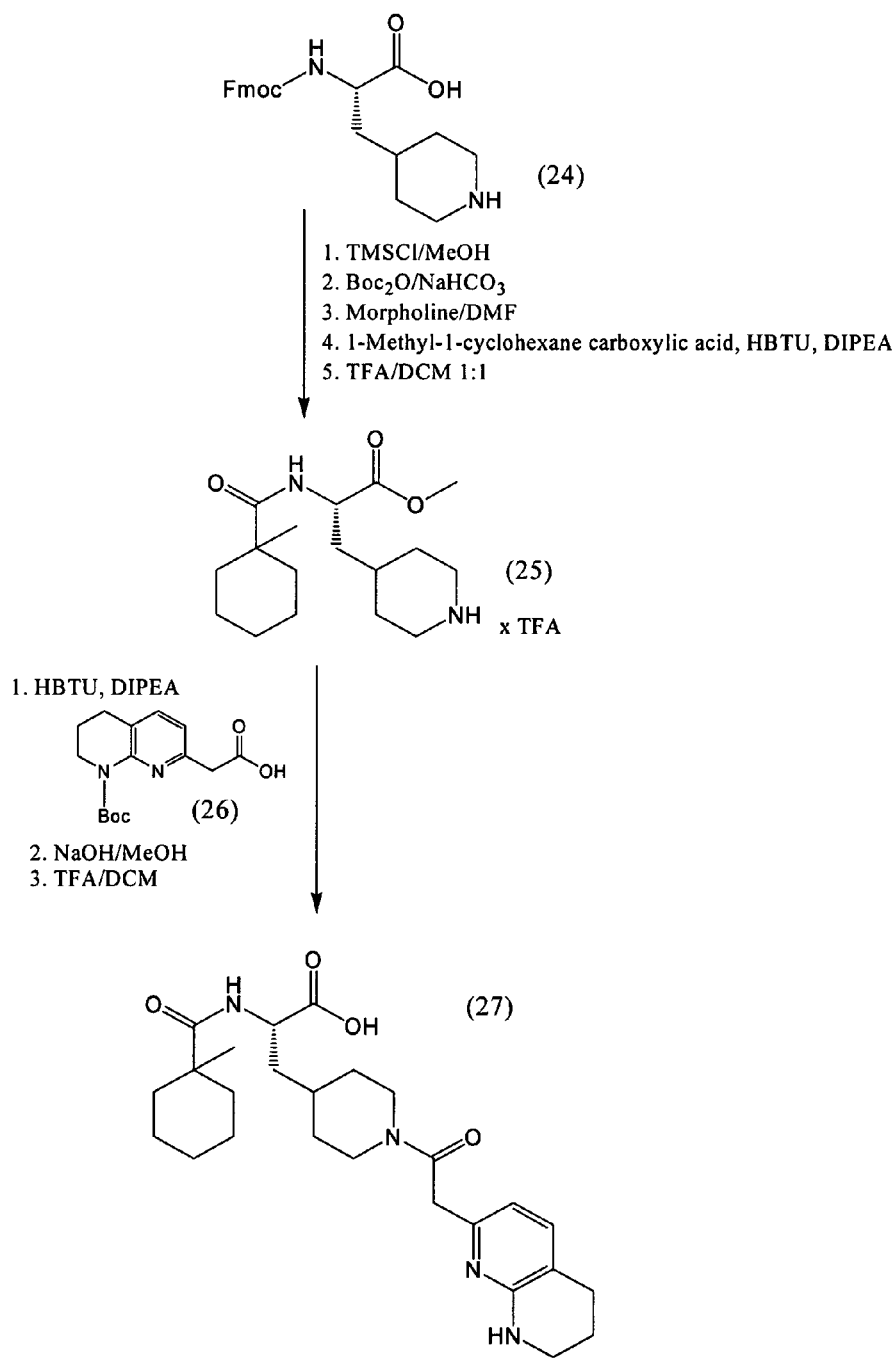
FIG. 8 shows the synthesis of 2-[(1-Methyl-cyclohexanecarbonyl)-amino]-3-[1-(2-5,6,7,8-tetrahydro-[1,8]naphthyridin-2-yl-acetyl)-piperidin-4-yl]-propionic acid (27)
Figure 9:
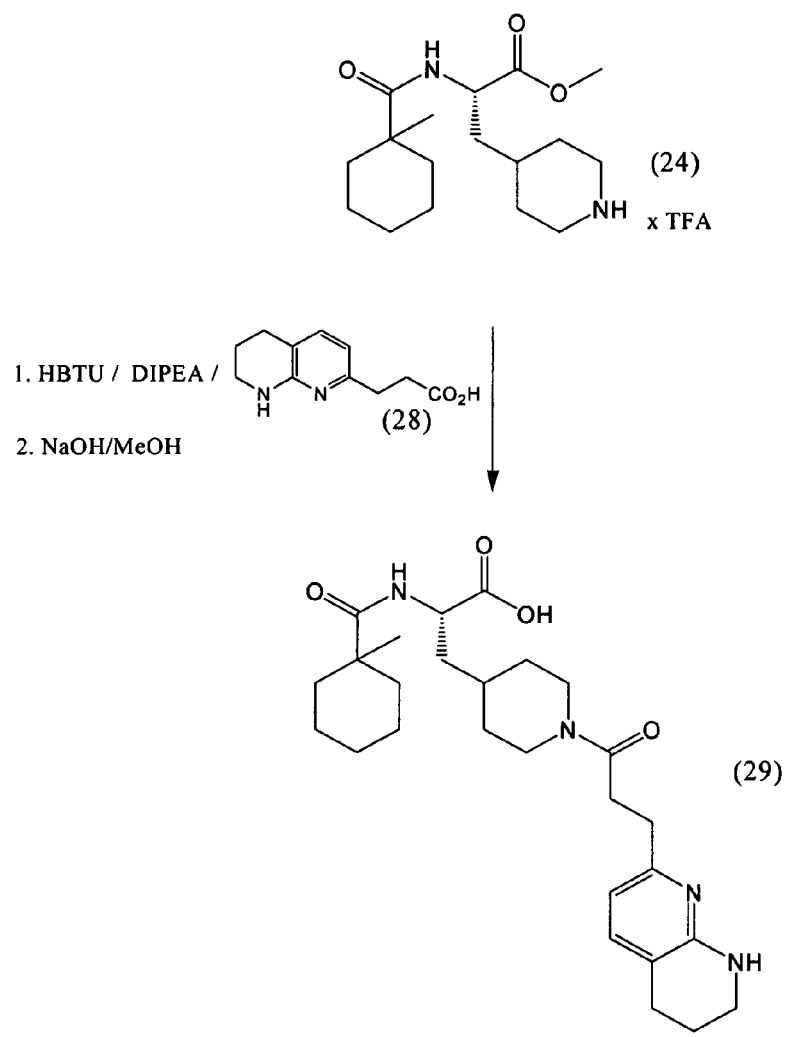
FIG. 9 shows the synthesis of 2-[(1-Methyl-cyclohexanecarbonyl)-amino]-3-[1-(3-5,6,7,8-tetrahydro-[1,8]naphthyridin-2-yl-propionyl)-piperidin-4-yl]-propionic acid (29)

In a third class of compounds Ar is not present and A is a ring system that is directly bond to Y. In a typical example Y is not present and A is a cyclic amine that is bond to Z at the ring N-atom. For two compounds detailed synthesis protocols are given in examples 9 and 10 which are outlined in FIGS. 8 and 9.

EXAMPLE 2

3-{4-[4-(Pyridin-2-ylaminomethyl)piperidin-1-yl]phenyl}-2-(2,4,6-trimethylbenzoylamino)propionic acid (5)

a) Synthesis of 2-benzyloxycarbonylamino-3-(4-boronophenyl)propionic acid (1)

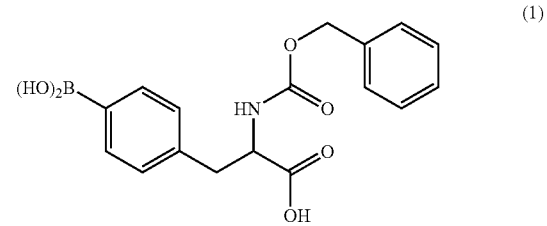 [SMILES: O=C(NC(Cc1ccc(B(O)O)cc1)C(=O)O)OCc1ccccc1]

(1)

3.0 g (14.4 mmol) of 2-amino-3-(4-boronophenyl)propionic acid were dissolved in 120 ml 0.4 N NaOH solution and diluted with 120 ml 1,4-dioxane. 2.05 ml benzyl chloroformate (14.4 mmol) in 15 ml 1,4-dioxane were added slowly at −15° C. The reaction mixture was allowed to come to room temperature over night and the organic solvent was removed under reduced pressure. After extracting the acidified remaining aqueous phase with ethyl acetate and drying this organic phase over $Na_2SO_4$ the solvent was removed under reduced pressure. The crude product was recrystallized from acetonitrile.

b) Synthesis of piperidin-4-ylmethyl-pyridin-2-yl-carbamic acid tert-butyl ester (2)

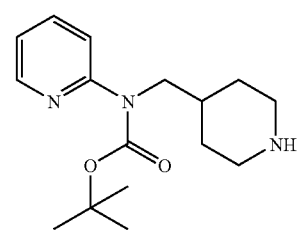

(2)

50 g 2-Aminopyridine (0.53 mol) was stirred with 127 g di-tert-butyl-dicarbonate (0.58 mol) in tert-butanol at 60° C. over night. The solvent was removed and the crude product was crystallized from toluene to give pyridin-2-yl-carbamic acid tert-butyl ester.

To a solution of 1.3 g (6.4 mmol) pyridin-2-yl-carbamic acid tert-butyl ester in dry DMF 16.6 ml (8.4 mmol) KHMDS (0.5 M in toluene) were added at 0° C. After complete addition 2.0 g (6.4 mmol) 4-bromomethylpiperidine-1-carboxylic acid benzyl ester were added and the reaction mixture was allowed to come to room temperature over night. 300 ml ethyl acetate were added and the mixture was washed 3 times with 2 N NaOH/brine (2:1) and once with brine. The organic phase was dried over sodium sulfate followed by evaporation under reduced pressure. Chromatography on silica gel with n-hexane/ethyl acetate afforded a Cbz-protected intermediate which was dissolved together with 10% palladium on carbon in methanol and stirred under an atmosphere of hydrogen for 4 h. Removal of the catalyst by filtration through a pad of Celite followed by evaporation of the solvent under reduced pressure yields the desired amine (2).

c) Synthesis of 2-benzyloxycarbonylamino-3-(4-{4-[(tert-butoxycarbonyl-pyridin-2-yl-amino)methyl]piperidin-1-yl}phenyl)propionic acid methyl ester (3)

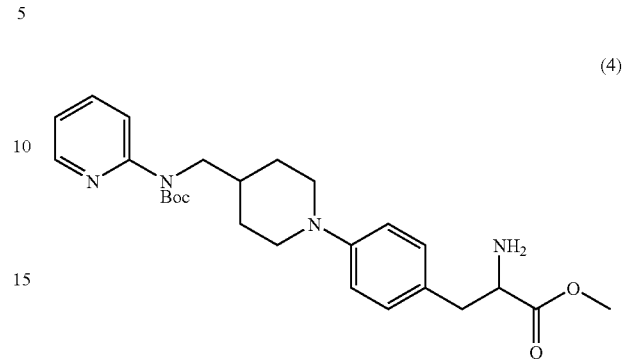

(3)

1.7 g (9.3 mmol) Cu(OAc)$_2$ and 26 ml NEt$_3$ together with 900 mg (3.1 mmol) of (2) were suspended in 300 ml DCE. After adding 1.7 g (9.3 mmol) of (1) the mixture was stirred 18 h and the solvent was removed. The remaining oil was dissolved in ethyl acetate, washed with sodium acetate buffer (pH 4) and dried over Na$_2$SO$_4$. The solvent was removed under reduced pressure. The crude product was dissolved in 50 ml DMF and stirred with 4.7 g (12.4 mmol) HATU, 3.18 ml (18.6 mmol) DIPEA and 10 ml MeOH for 4 hours. Same amounts of HATU and DIPEA were added and the reaction mixture was stirred for 4 h at room temperature. After diluting with 300 ml ethyl acetate and washing four times with 2 N NaOH/brine (2:1) and with brine the solution was dried over Na$_2$SO$_4$ and concentrated in vacuo. Chromatography on silica gel with hexane/ethyl acetate was used to obtain pure (3).

d) Synthesis of 2-amino-3-(4-{4-[(tert-butoxycarbonyl-pyridin-2-yl-amino)methyl]piperidin-1-yl}phenyl)propionic acid methyl ester (4)

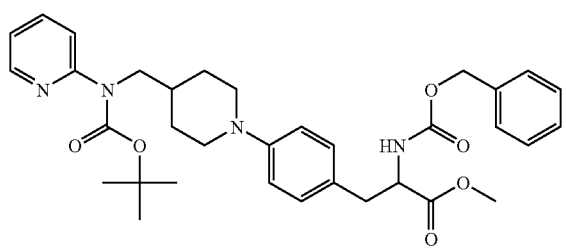

(4)

1.3 g (2.16 mmol) of (3) and 130 mg Pd/C (10%) in 50 ml methanol were stirred under a hydrogen atmosphere for 3 h. The reaction mixture was filtered over a pad of Celite and the solvent was evaporated to give crude (4) as oil which was used without further purification.

e) Synthesis of 3-{4-[4-(pyridin-2-ylaminomethyl)piperidin-1-yl]phenyl}-2-(2,4,6-trimethyl-benzoylamino)propionic acid (5)

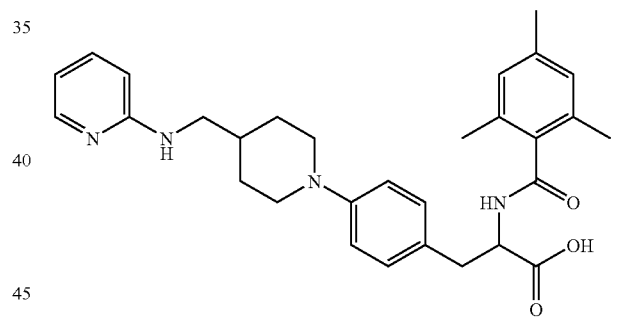

(5)

A solution of 202 mg (1.23 mmol) of 2,4,6-trimethylbenzoic acid, 467 mg (1.23 mmol) HATU, 300 mg (0.64 mmol) of (4) and 660 µl (3.85 mmol) DIPEA in 5 ml DMF were stirred at room temperature over night. The reaction mixture was diluted with 100 ml ethyl acetate, washed 3 times with 2 N NaOH/brine (2:1) and once with brine and dried over Na$_2$SO$_4$. The solvent was then removed under reduced pressure.

The remaining oil was dissolved in 20 ml TFA, stirred 30 min at room temperature, concentrated under reduced pressure and twice dissolved in acetone and evaporated. The methyl ester was hydrolyzed by stirring in 60 ml THF/water (2:1) and 10 ml 1 M LiOH till HPLC indicated complete conversion to the free carboxylic acid. At this point the reaction mixture was concentrated and purified by reversed phase HPLC using a water/acetonitrile gradient containing 0.1% TFA affording the TFA salt of (5) after lyophilization as a white powder.

ESI m/z obs.: 501.2 [M+H] (theor. 501.3)

EXAMPLE 3

3-(4-{(4-[(4-Methylpyridin-2-ylamino)methyl]piperidin-1-yl}phenyl)-2-(2,4,6-trimethylbenzoylamino)propionic acid a) Synthesis of 3-(4-boronophenyl)-2-(2,4,6-trimethylbenzoylamino)propionic acid (6)

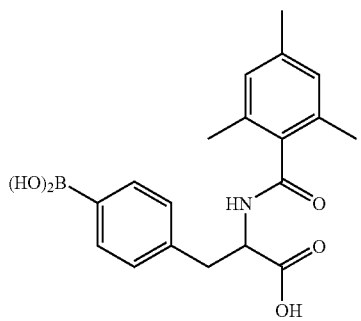

(6)

1.5 g (7.18 mmol) of 2-amino-3-(4-boronophenyl)propionic acid were suspended in 50 ml DCM and 7.4 ml (43.1 mmol) DIPEA and refluxed for 20 min together with 4.5 ml (35 mmol) TMSCl. The solution was cooled in an ice bath and a solution of 1.44 g (7.9 mmol) 2,4,6-trimethylbenzoyl chloride in 5 ml DCM were added dropwise. The reaction mixture was stirred 2 h at room temperature, diluted with 100 ml DCM and washed with 2 N aqueous HCl. During this washing some product precipitated which was collected. The organic phase was extracted with 2 N NaOH twice. Upon acidifying of the combined basic phases the product precipitated, which was collected and dried together with the first precipitate. The crude product was used without further purification.

b) Synthesis of (4-methyl-pyridin-2-yl)piperidin-4-ylmethyl-carbamic acid tert-butyl ester (7)

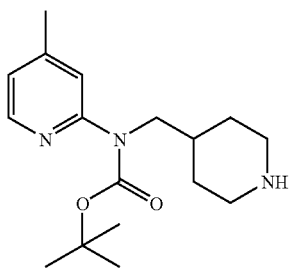

(7)

15 g 2-Amino-4-methylpyridine (0.14 mol) was stirred with 36.4 g di-tert-butyl-dicarbonate (0.17 mol) in THF at room temperature over night. The solvent was removed and the crude product was crystallized from 2-propanol to give 4-methylpyridin-2-yl-carbamic acid tert-butyl ester.

To a solution of 0.33 g (1.6 mmol) 4-methylpyridin-2-yl-carbamic acid tert-butyl ester in 10 ml dry DMF 3.84 ml (1.92 mmol) KHMDS (0.5 M in toluene) were added at 0° C. After complete addition 0.5 g (1.6 mmol) 4-bromomethyl-piperidine-1-carboxylic acid benzyl ester were added and the reaction mixture was allowed to come to room temperature over night. 200 ml ethyl acetate were added and the mixture was washed twice with saturated aqueous Na$_2$CO$_3$ and once with brine. The organic phase was dried over sodium sulfate followed by evaporation under reduced pressure. Chromatography on silica gel with n-hexane/ethyl acetate afforded a Cbz-protected intermediate which was dissolved together with 10% palladium on carbon in methanol and stirred under an atmosphere of hydrogen for 4 h. Removal of the catalyst by filtration through a pad of Celite followed by evaporation of the solvent under reduced pressure yielded the desired amine (7).

c) Synthesis of 3-(4-{4-[(4-methylpyridin-2-ylamino)methyl]piperidin-1-yl}phenyl)-2-(2,4,6-trimethylbenzoylamino)propionic acid (8)

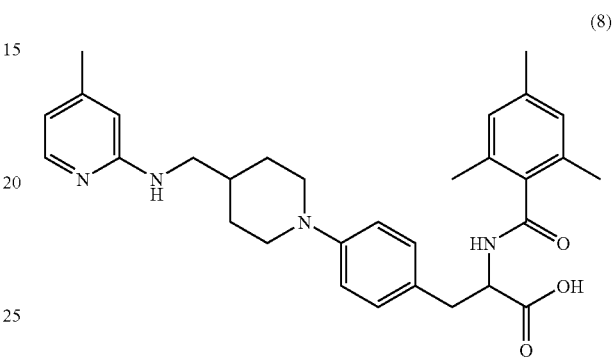

(8)

200 mg (1.1 mmol) Cu(OAc)$_2$ and 260 µl (2.2 mmol) Et$_2$NMe together with 223 mg (0.73 mmol) of amine (7) were suspended in 20 ml DCE and stirred with 520 mg (1.46 mmol) boronic acid (6) over night at room temperature. Additional 100 mg Cu(OAc)$_2$ and 1.1 ml Et$_2$NMe were added and stirring was continued for 40 h. The reaction mixture was washed with sodium acetate buffer (pH≈4), dried over Na$_2$SO$_4$ and evaporated at reduced pressure. The resulting oil was dissolved in TFA/DCM (5:1), stirred 4 h at room temperature and concentrated under reduced pressure. Purification by reversed phase HPLC using a water/acetonitrile gradient containing 0.1% TFA yielded the TFA salt of (8) after lyophilization as a white powder.

ESI m/z obs.: 515.5 [M+H] (theor. 515.3)

EXAMPLE 4

3-{4-[3-(Pyridin-2-ylaminomethyl)azetidin-1-yl]phenyl}-2-(2,4,6-trimethylbenzoylamino)propionic acid (11)

a) Synthesis of azetidin-3-ylmethyl-pyridin-2-yl-amine (10)

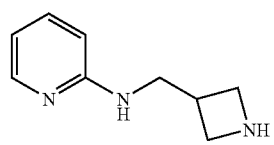

(10)

570 mg (3.08 mmol) 3-formylazetidine-1-carboxylic acid tert-butyl ester were dissolved in 20 ml methanol containing 1% acetic acid. After adding 370 mg (3.88 mmol) 2-aminopyridine and 348 mg (5.54 mmol) NaCNBH$_3$ the reaction mixture was stirred at room temperature over night followed by evaporation under reduced pressure. Chromatography on silica gel with hexane/ethyl acetate was used to obtain the pure intermediate. Its Boc-protection group was removed by stirring in 8 ml DCM/TFA (1:1) for 2 h. After evaporation and drying building block (10) was obtained as TFA salt.

b) Synthesis of 3-{4-[3-(pyridin-2-ylaminomethyl) azetidin-1-yl]phenyl}-2-(2,4,6-trimethylbenzoylamino)propionic acid (11)

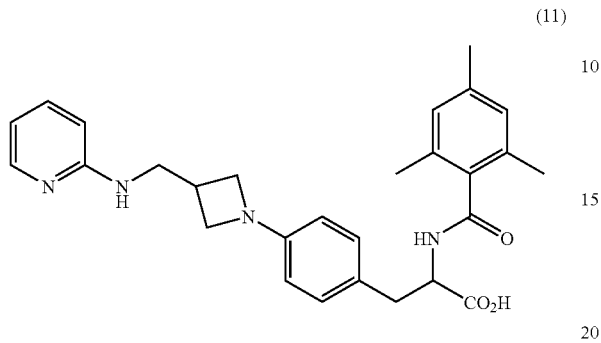

(11)

153 mg (0.203 mmol) TFA salt of (10) together with 150 mg (0.406 mmol) 2-(2,4,6-trimethylbenzoylamino)-3-(4-boronophenyl)propionic acid methyl ester (12), 844 µl (6.1 mmol) triethylamine and 74 mg (0.406 mmol) Cu(OAc)$_2$ were stirred in 2.5 ml DCE for 20 min under ultrasonification and then stirring was continued for another 20 h at room temperature. The reaction mixture was filtered over a pad of Celite, the solvent was removed under reduced pressure and the residue was dissolved in acetonitrile to be filtered over another pad of Celtite. After the solvent was removed, the crude methyl ester was dissolved in 9 ml methanol and stirred with 4 ml 0.5 M NaOH over the weekend. Solids were removed by filtration and the reaction mixture was purified by reversed phase HPLC using a water/acetonitrile gradient containing 0.1% TFA yielding the TFA salt of (11) after lyophilization as a white powder.

ESI m/z obs.: 473.4 [M+H] (theor. 473.3)

EXAMPLE 5

3-(4-{(4-[(4-Methylpyridin-2-ylamino)methyl]-2-oxo-pyrrolidin-1-yl}phenyl)-2-(2,4,6-trimethylbenzoylamino)propionic acid (16)

a) Synthesis of 3-(4-bromophenyl)-2-(2,4,6-trimethylbenzoylamino)propionic acid methyl ester (13)

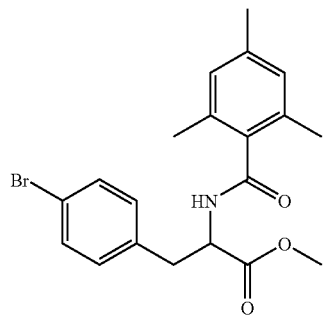

(13)

1.0 g (4.01 mmol) H-Phe(4-Br)—OH were refluxed in 20 ml methanol with 2.1 ml HCl (4 M in 1,4-dioxane) over night. Evaporation of the solvent gave H-Phe(4-Br)—OMe*HCl as white solid. 1.0 g (3.4 mmol) of this hydrochloride and 1.7 ml (10.2 mmol) DIPEA were suspended in 8 ml THF and 0.41 ml (3.4 mmol) 2,4,6-trimethylbenzoyl chloride were added dropwise at 0° C. After 18 h at room temperature the reaction was quenched with water and the solvent was removed. The residue was suspended in ethyl acetate, washed with saturated Na$_2$SO$_4$ and brine to give compound (13) as an oil.

b) Synthesis of (4-methylpyridin-2-yl)-(5-oxo-pyrrolidin-3-ylmethyl)carbamic acid tert-butyl ester (14)

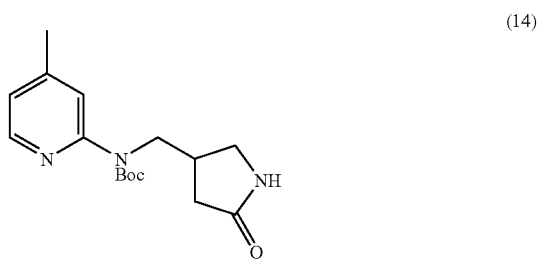 [SMILES: Cc1ccnc(N(CC2CNC(=O)C2)C(=O)OC(C)(C)C)c1]

(14)

(4-Methylpyridin-2-yl)carbamic acid tert-butyl ester was alkylated with 4-bromomethylpyrrolidin-2-one by deprotonation in DMF at 0° C. with NaH and treating the sodium salt with the bromide at room temperature. After dilution of the reaction mixture with ethyl acetate and washing with saturated aqueous NaHCO$_3$ the crude product was purified by chromatography on silica gel (ethyl acetate/hexane) to yield (14) as yellow oil.

c) Synthesis of 3-[4-(4-{[tert-butoxycarbonyl(4-methylpyridin-2-yl)amino]methyl}-2-oxo-pyrrolidin-1-yl)phenyl]-2-(2,4,6-trimethylbenzoylamino)propionic acid methyl ester (15)

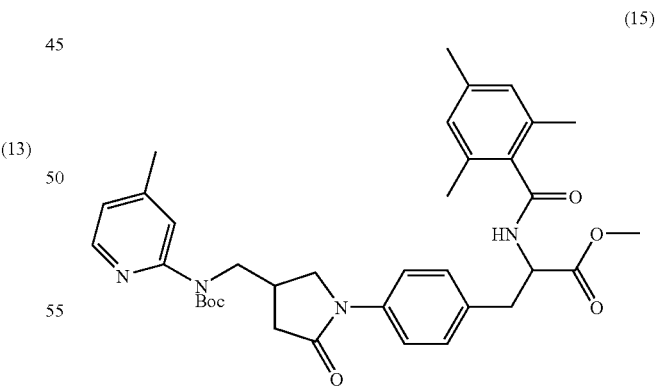

(15)

45 mg (0.074 mmol) of (8), 50 mg (0.123 mmol) of (7), 48 mg (0.148 mmol) of Cs$_2$CO$_3$, 16 mg (0.024 mmol) of Pd(dba)$_2$-CHCl$_3$ and 43 mg (0.074 mmol) of Xantphos were heated under argon for 3 hours. After diluting with 50 ml ethyl acetate and washing two times with saturated aqueous NaHCO$_3$ and one time with brine the solution was dried over Na$_2$SO$_4$ and concentrated in vacuo. 70 mg of crude (15) were obtained as yellow foam.

d) Synthesis of 3-(4-{4-[(4-methylpyridin-2-ylamino)methyl]-2-oxo-pyrrolidin-1-yl}phenyl)-2-(2,4,6-trimethylbenzoylamino)propionic acid (16)

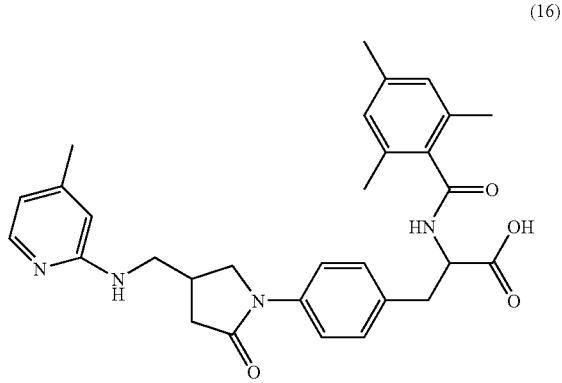 [SMILES: Cc1ccnc(NCC2CC(=O)N(c3ccc(CC(NC(=O)c4c(C)cc(C)cc4C)C(=O)O)cc3)C2)c1]

70 mg of crude (15) were diluted in 2 ml of DCM. 0.2 ml of TFA were added and the solution was stirred for 1 hour at room temperature. After evaporation of the solvent the crude reaction mixture was dissolved in 1 ml of dioxane/water (1:1) cooled to 0° C. and 20 mg of LiOH were added. The solution was stirred for 2 hours and subsequently submitted to reversed phase HPLC purification using a water/acetonitrile gradient containing 0.1% TFA. The required fractions were collected and lyophilized to yield the TFA salt of (16) as white solid.

ESI m/z obs.: 515.2 [M+H] (theor. 515.2)

EXAMPLE 6

3-{4-[4-(4,5-Dihydro-1H-imidazol-2-ylcarbamoyl)piperidin-1-yl]phenyl}-2-(2-ethyl-4-fluoro-6-methyl-benzoylamino)propionic acid a) Synthesis of (4,5-dihydro-1H-imidazol-2-yl)-(piperidine-4-carbonyl)carbamic acid tert-butyl ester (17)

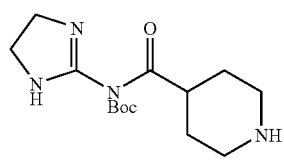

1.0 g (3.8 mmol) piperidine-1,4-dicarboxylic acid monobenzyl ester and 830 µl (11.4 mmol) SOCl$_2$ in 20 ml DCE were stirred under argon for 3.5 h at 50° C. Then the volatile components were removed under reduced pressure. To this crude acid chloride 438 mg (4.56 mmol) pyrrolidine-1-carbonitrile were added and the mixture was stirred 1 h at 50° C. Then 30 ml 1,4-dioxane were added and the resulting suspension was added slowly to a solution of 5.1 ml (76 mmol) ethane-1,2-diamine in 15 ml 1,4-dioxane. After 30 min at 60° C. ethyl acetate was added. The mixture was washed with saturated aqueous NaHCO$_3$ and dried over Na$_2$SO$_4$. After removing the solvent under reduced pressure the crude product was purified by chromatography on silica gel using n-hexane/ethyl acetate as eluents. 370 mg (1.12 mmol) of this 4-(4,5-dihydro-1H-imidazol-2-ylcarbamoyl)piperidine-1-carboxylic acid benzyl ester were Boc-protected by stirring 18 h at room temperature together with 717 µl (3.35 mmol) Boc$_2$O and 383 µl (2.24 mmol) DIPEA in 5 ml tert-butanol. The solvent was then removed under reduced pressure and the crude product was purified by chromatography on silica gel using n-hexane/ethyl acetate as eluents. The resulting product was dissolved in 7 ml methanol and stirred with Pd(OH)$_2$/C (82 mg) under a hydrogen atmosphere for 1 h to remove the Cbz-protection group. The reaction mixture was filtered over a pad of Celite, concentrated under reduced pressure, dissolved in ethyl acetate, filtered and concentrated again to yield (17) as colorless oil.

a) Synthesis of 3-{4-[4-(4,5-dihydro-1H-imidazol-2-ylcarbamoyl)piperidin-1-yl]phenyl}-2-(2-ethyl-4-fluoro-6-methylbenzoylamino)propionic acid (18)

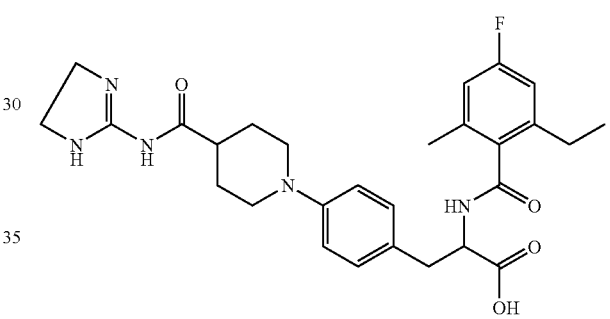

265 mg (1.01 mmol) of piperidine derivative (17), 490 mg (1.52 mmol) boronic acid (30), 367 mg (2.02 mmol) Cu(OAc)$_2$, 1.21 ml (7.07 mmol) DIPEA and 3 g molecular sieve (3 Å, dried) were suspended in 40 ml DCE and stirred at room temperature over night. The reaction mixture was concentrated under reduced pressure, diluted with ethyl acetate and filtered over a pad of Celite. The solution was washed three times with saturated aqueous NaHCO$_3$, dried over Na$_2$SO$_4$ and concentrated under reduced pressure. Chromatography on silica gel with n-hexane/ethyl acetate was used to obtain a purified product which was treated 1 h at room temperature with 10 ml of DCM containing 20% TFA. Volatile components were removed under reduced pressure to remove surplus TFA. The obtained product was added to a stirred solution of HATU (87 mg; 0.23 mmol), 2-ethyl-4-fluoro-6-methyl-benzoic acid (42 mg; 0.23 mmol) and DIPEA (149 mg; 1.15 mmol) in 2 ml DMF. After stirring over night the reaction mixture was diluted with ethyl acetate and washed with saturated aqueous NaHCO$_3$ and brine. The solvent was removed under reduced pressure. The resulting product was dissolved in 600 µl 1,4-dioxane and 400 µl water and stirred with 20 mg LiOH*H$_2$O 2 h at room temperature. The reaction mixture was subsequently submitted to reversed phase HPLC purification using a water/acetonitrile gradient containing 0.1% TFA. The required fractions were collected and lyophilized to yield the TFA salt of (18) as white solid.

ESI m/z obs.: 524.2 [M+H] (theor. 524.3)

EXAMPLE 7

3-(4-{4-[(1H-Benzoimidazol-2-ylamino)methyl]piperidin-1-yl}phenyl)-2-(2,4,6-trimethylbenzoylamino)propionic acid (20)

a) Synthesis of (1H-benzoimidazol-2-yl)piperidin-4-ylmethylamine trifluoroacetate (19)

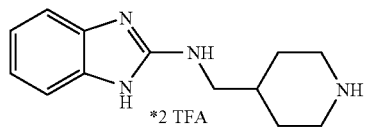

(19)

100 mg 4-Formylpiperidine-1-carboxylic acid tert-butyl ester (0.47 mmol) and 125 mg 1H-benzoimidazol-2-ylamine (0.94 mmol) together with Ti(iPrO)$_4$ (280 μl; 0.94 mmol) were dissolved in 5 ml DCE and stirred over night. The solution was then diluted with 60 ml methanol/acetic acid (5:1) and 1.49 g (7.04 mmol) NaHB(OAc)$_3$ were added. After 24 h the reaction mixture was diluted with 200 ml 2 N aqueous NaOH and extracted three times with ethyl acetate. The combined organic phases were dried over Na$_2$SO$_4$ and the solvent was removed under reduced pressure. The crude product was subsequently submitted to reversed phase HPLC purification using a water/acetonitrile gradient containing 0.1% TFA. The required fractions were collected, brought to pH>10 with 2 N aqueous NaOH and extracted with ethyl acetate. The combined organic phases were dried over Na$_2$SO$_4$ and evaporated under reduced pressure. The residue was dissolved in 10 ml TFA, stirred 1 h at room temperature and evaporated under reduced pressure to give the TFA salt (19) as an oil.

b) Synthesis of 3-(4-{4-[(1H-benzoimidazol-2-ylamino)methyl]piperidin-1-yl}phenyl)-2-(2,4,6-trimethylbenzoylamino)propionic acid (20)

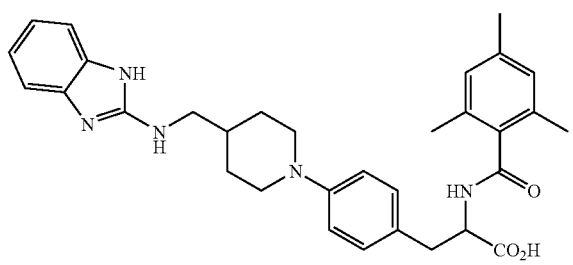

(20)

95 mg (0.207 mmol, calculated as bistrifluoroacetate salt) of crude piperidine derivative (19), 113 mg (0.621 mmol) Cu(OAc)$_2$, 147 mg (0.415 mmol) boronic acid (6) and 1.72 ml (12.42 mmol) NEt$_3$ were mixed in 10 ml DCE and stirred at room temperature for 20 h. The reaction mixture was concentrated under reduced pressure and the residue was dissolved in methanol and subsequently submitted to reversed phase HPLC purification using a water/acetonitrile gradient containing 0.1% TFA. The required fractions were collected and lyophilized to yield (20) as white solid.

ESI m/z obs.: 540.3 [M+H] (theor. 540.3)

EXAMPLE 8

3-{4-[4-(5,6,7,8-Tetrahydro-[1,8]naphthyridin-2-yl)piperidin-1-yl]phenyl}-2-(2,4,6-trimethylbenzoylamino)propionic acid (23)

a) Synthesis of 4-acetylpiperidine-1-carboxylic acid benzyl ester (21)

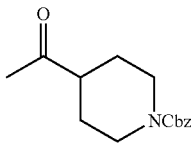

(21)

5.0 g (19.0 mmol) piperidine-1,4-dicarboxylic acid monobenzyl ester were dissolved in 200 ml DCM and 4.16 ml SOCl$_2$. After heating 2 h to reflux the volatile components were removed under reduced pressure. The residue was dissolved in 200 ml DCM and 3.29 g (22.8 mmol) 2,2-dimethyl-[1,3]dioxane-4,6-dione as well as 4.6 ml (57 mmol) pyridine were added. The reaction mixture was stirred at room temperature over night, washed twice with 1 N aqueous HCl and brine, dried over Na$_2$SO$_4$ and concentrated under reduced pressure to be subsequently submitted to column chromatography on silica gel with n-hexane/ethyl acetate to yield a product, which was dissolved in 50 ml DMSO/water (95:5) and heated to 70° C. for 3 h. The solvent was removed under reduced pressure and the residue was dissolved in ethyl acetate, washed twice with 0.1 N aqueous HCl, saturated aqueous Na$_2$CO$_3$ and brine, dried over Na$_2$SO$_4$ and evaporated under reduced pressure. The residue was purified by chromatography on silica gel using n-hexane/ethyl acetate as eluents to yield ketone (21).

b) Synthesis of 7-piperidin-4-yl-1,2,3,4-tetrahydro-[1,8]naphthyridine (22)

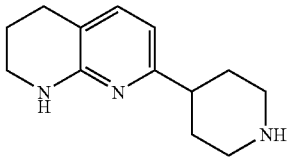

(22)

100 mg (0.383 mmol) ketone (21), 47 mg (0.383 mmol) 2-aminopyridine-3-carbaldehyde and 22 mg (0.192 mmol) proline were refluxed in ethanol for 3 days. The solvent was removed under reduced pressure. The crude product was purified by chromatography on silica gel (ethyl acetate/hexane) to yield 4-[1,8]naphthyridin-2-yl-piperidine-1-carboxylic acid benzyl ester as an oil. 210 mg (0,605 mmol) of this intermediate were dissolved together with 50 mg 10% Pd/C in 50 ml methanol and stirred under an atmosphere of hydrogen for 18 h. Removal of the catalyst by filtration through a pad of Celite followed by evaporation of the solvent under reduced pressure gave the desired amine (22).

c) Synthesis of 3-{4-[4-(5,6,7,8-tetrahydro-[1,8]naphthyridin-2-yl)piperidin-1-yl]phenyl}-2-(2,4,6-trimethylbenzoylamino)propionic acid (23)

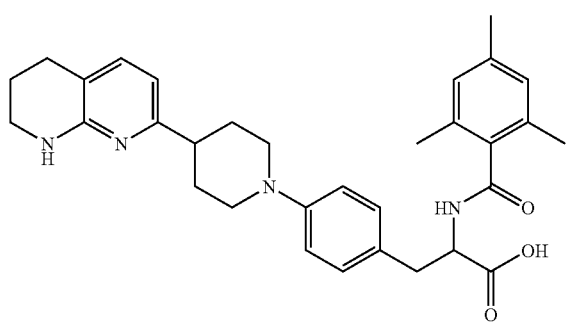

(23)

131 mg (0.605 mmol) piperidine derivative (22), 430 mg (1.21 mmol) boronic acid (6), 330 mg (1.82 mmol) Cu(OAc)$_2$ and 5.0 ml (36.3 mmol) NEt$_3$ were stirred 2 days at room temperature. The solvent was removed under reduced pressure and the residue was diluted with ethyl acetate. Washing with 0.2 M sodium acetate buffer was followed by drying over Na$_2$SO$_4$ and evaporation under reduced pressure. The residue was dissolved in methanol and subsequently submitted to reversed phase HPLC purification using a water/acetonitrile gradient containing 0.1% TFA. The required fractions were collected and lyophilized to yield the TFA salt of (23) as white solid.

ESI m/z obs.: 527.3 [M+H] (theor. 527.3)

EXAMPLE 9

2-[(1-Methylcyclohexanecarbonyl)amino]-3-[1-(2-5,6,7,8-tetrahydro-[1,8]naphthyridin-2-yl-acetyl)piperidin-4-yl]propionic acid (27)

a) Synthesis of 2-[(1-methylcyclohexanecarbonyl)amino]-3-piperidin-4-yl-propionic acid methyl ester as trifluoro acetic acid salt (24)

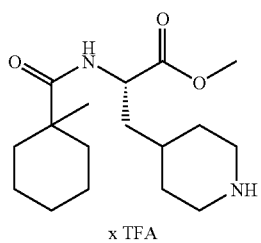

(24)

x TFA 500 mg (1.27 mmol) of 2-N-Fmoc-amino-3-piperidin-4-yl-propionic acid in 6.5 ml methanol were treated 15 h at room temperature with 710 µl (5.6 mmol) trimethyl chlorosilane. The solvent was evaporated. The crude product was dissolved in 3 ml 1,4-dioxane and 3 ml of 5% aqueous NaHCO$_3$. A solution of 555 mg (2.54 mmol) di-tert-butyl dicarbonate in 0.7 ml 1,4-dioxane was added dropwise and the reaction mixture was stirred 15 h at room temperature. The organic solvent was removed under reduced pressure. After diluting with 100 ml ethyl acetate and washing two times with saturated aqueous NaHCO$_3$ and one time with brine the solution was dried over Na$_2$SO$_4$ and concentrated in vacuo. The crude material was dissolved in 2 ml THF and treated 2 h at room temperature with 2 ml morpholine. The reaction mixture was evaporated in vacuo and evaporated again with 5 ml toluene. The remaining residue was suspended in methanol and filtrated. The filtrate gave a yellow foam after evaporation.

This foam was dissolved in 4 ml THF and 1 ml DMF. 181 mg (1.27 mmol) 1-methylcyclohexane-1-carboxylic acid, 431 µl (2.54 mmol) DIPEA and 481 mg (1.27 mmol) HBTU were added and this mixture was stirred 24 h at room temperature. After diluting with 100 ml ethyl acetate and washing one time with 2% aqueous citric acid, two times with half saturated aqueous NaHCO$_3$ and one time with brine the solution was dried over Na$_2$SO$_4$ and concentrated in vacuo. The crude product was purified by chromatography on silica gel (ethyl acetate/n-hexane) to yield the Boc-protected derivative of (24) as yellow foam. This material was dissolved in 3 ml dichloromethane and 3 ml TFA and was evaporated after 2 h to yield the TFA salt (24) quantitatively.

b) Synthesis of 2-[(1-methylcyclohexanecarbonyl)amino]-3-[1-(2-5,6,7,8-tetrahydro-[1,8]naphthyridin-2-yl-acetyl)piperidin-4-yl]propionic acid (27)

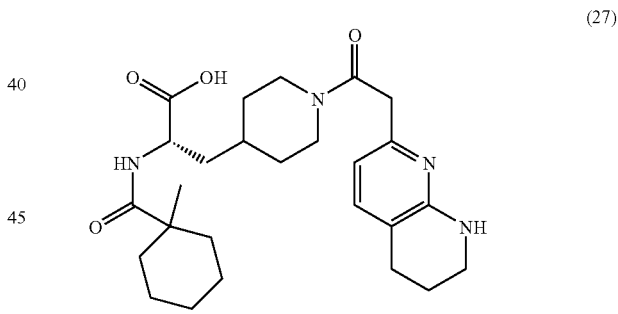

(27)

To a solution of 36 mg (0.085 mmol) of (24) and 27 mg (8-N-Boc-5,6,7,8-tetrahydro[1,8]naphthyridin-2-yl)acetic acid (26) in 1.5 ml DMF 58 µl (0.34 mmol) DIPEA and 35 mg (0.094 mmol) HBTU were added. After 15 h at room temperature the mixture was diluted with 10 ml ethyl acetate and washed two times with half saturated aqueous NaHCO$_3$ and with brine. After evaporation of the solvent the residue was redissolved in 2 ml methanol and 0.85 ml 0.5 N aqueous NaOH. After 20 h stirring at room temperature the solvent was completely removed in vacuo. The residual material was dissolved in 2 ml dichloromethane and 2 ml TFA and was evaporated after 2 h. The crude product was purified by reversed phase HPLC using a water/acetonitrile gradient containing 0.1% TFA to yield the TFA salt of (27) as a white lyophylizate.

ESI m/z obs.: 471.3 [M+H] (theor. 471.6)

EXAMPLE 10

2-[(1-Methylcyclohexanecarbonyl)amino]-3-[1-(2-5,6,7,8-tetrahydro-[1,8]naphthyridin-2-yl-propionyl)piperidin-4-yl]propionic acid (29)

a) Synthesis of 2-[(1-methylcyclohexanecarbonyl)amino]-3-[1-(3-5,6,7,8-tetrahydro[1,8]naphthyridin-2-yl-propionyl)piperidin-4-yl]propionic acid (29)

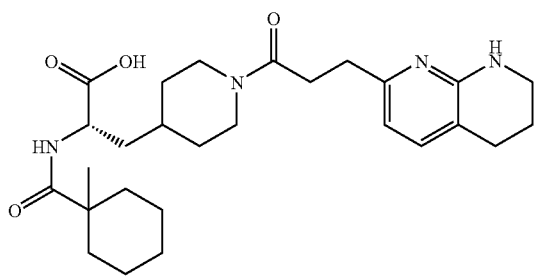
(29)

To a solution of 21 mg (0.05 mmol) of (11) and 27 mg (5,6,7,8-tetrahydro[1,8]naphthyridin-2-yl)propionic acid (28) in 1.0 ml DMF was added 34 μl (0.20 mmol) DIPEA and 21 mg (0.055 mmol) HBTU. After 5 h at room temperature the mixture was diluted with 25 ml ethyl acetate and washed two times with half saturated aqueous $NaHCO_3$ and one time with brine. After evaporation of the solvent the residue was redissolved in 2 ml methanol and 0.55 ml 0.5 N aqueous NaOH solution. After stirring 5 h at room temperature the pH of the solution was adjusted to 6 with 1 M aqueous HCl and the solvent was completely removed in vacuo. The crude product was purified by reversed phase HPLC using a water/acetonitrile gradient containing 0.1% TFA to yield the TFA salt of (29) as a white lyophylizate.

ESI m/z obs.: 485.3 [M+H] (theor. 485.3)

It is to be acknowledged that according to the protocols described herein any of the compounds as specified in Table 1 and also many others comprised in this application, can be synthesized using derivatives of the staring materials. These minor changes in the starting material can be preformed by any person skilled in the art, more particularly by any organic chemist.

Some of the more preferred compounds according to the present invention are summarised in table 1 and include any pharmaceutically acceptable salt, solvate or prodrug thereof.

TABLE 1

| structure | formula | name | synthesis in analogy to example |
|---|---|---|---|
| (5) | $C_{30}H_{36}N_4O_3$ | 3-(4-(4-((pyridin-2-ylamino)methyl)piperidin-1-yl)phenyl)-2-(2,4,6-trimethylbenzamido)propanoic acid | 2 |
| (8) | $C_{31}H_{38}N_4O_3$ | 3-(4-(4-((4-methylpyridin-2-ylamino)methyl)piperidin-1-yl)phenyl)-2-(2,4,6-trimethylbenzamido)propanoic acid | 3 |
| (11) | $C_{28}H_{32}N_4O_3$ | 3-(4-(3-((pyridin-2-ylamino)methyl)azetidin-1-yl)phenyl-2-(2,4,6-trimethylbenzamido)propanoic acid | 4 |

TABLE 1-continued

| Structure | Formula | Name | # |
|---|---|---|---|
| 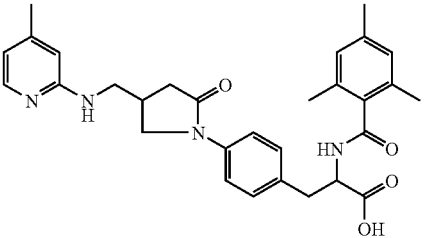 16 | C₃₀H₃₄N₄O₄ | 3-(4-{4-[(4-Methyl-pyridin-2-ylamino)-methyl]-2-oxo-pyrrolidin-1-yl}-phenyl)-2-(2,4,6-trimethyl-benzoylamino)-propionic acid | 5 |
| 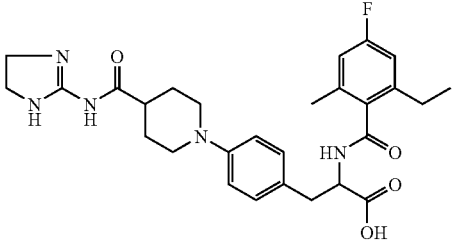 18 | C₂₈H₃₄FN₅O₄ | 3-{4-[4-(4,5-Dihydro-1H-imidazol-2-ylcarbamoyl)-piperidin-1-yl]-phenyl}-2-(2-ethyl-4-fluoro-6-methyl-benzoylamino)-propionic acid | 6 |
| 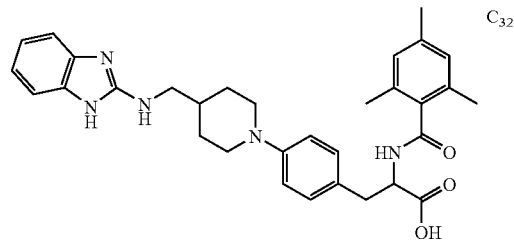 20 | C₃₂H₃₇N₅O₃ | 3-(4-(4-((1H-benzo[d]imidazol-2-ylamino)methyl)piperidin-1-yl)phenyl)-2-(2,4,6-trimethylbenzamido)propanoic acid | 7 |
| 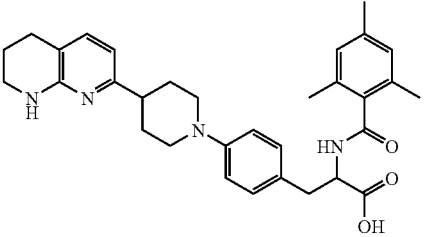 23 | C₃₂H₃₈N₄O₃ | 3-(4-(4-(5,6,7,8-tetrahydro-1,8-naphthyridin-2-yl)piperidin-1-yl)phenyl)-2-(2,4,6-trimethylbenzamido)propanoic acid | 8 |
| 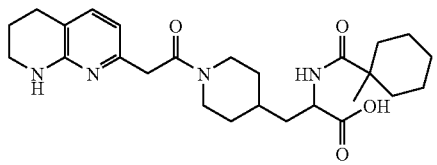 27 | C₂₆H₃₈N₄O₄ | 2-[(1-Methyl-cyclohexanecarbonyl)-amino]-3-[1-(2-5,6,7,8-tetrahydro-[1,8]naphthyridin-2-yl-acetyl)-piperidin-4-yl]-propionic acid | 9 |
| 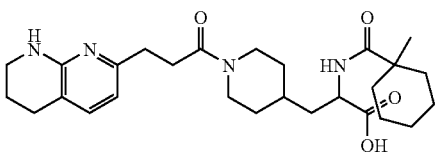 29 | C₂₇H₄₀N₄O₄ | 2-(1-methylcyclohexanecarboxamido)-3-(1-(3-(5,6,7,8-tetrahydro-1,8-naphthyridin-2-yl)propanoyl)piperidin-4-yl)propanoic acid | 10 |

TABLE 1-continued

| | | | |
|---|---|---|---|
| 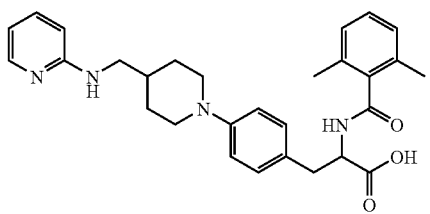 58 | C29H34N4O3 | 2-(2,6-dimethylbenzamido)-3-(4-(4-((pyridin-2-ylamino)methyl)piperidin-1-yl)phenyl)propanoic acid | 2 |
| 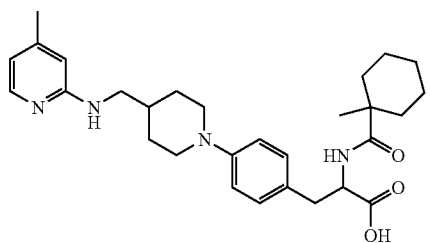 75 | C29H40N4O3 | 2-(1-methylcyclohexanecarboxamido)-3-(4-(4-((4-methylpyridin-2-ylamino)methyl)piperidin-1-yl)phenyl)propanoic acid | 3 |
| 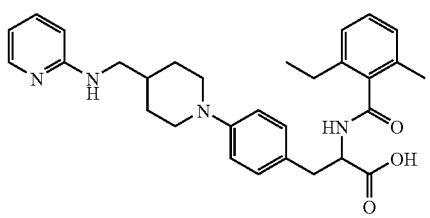 84 | C30H36N4O3 | 2-(2-ethyl-6-methylbenzamido)-3-(4-(4-((pyridin-2-ylamino)methyl)piperidin-1-yl)phenyl)propanoic acid | 2 |
| 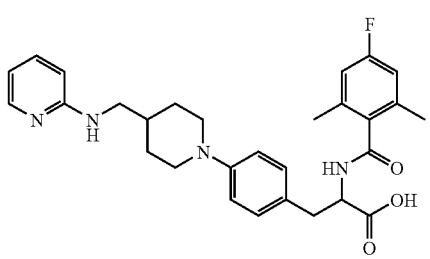 90 | C29H33FN4O3 | 2-(4-fluoro-2,6-dimethylbenzamido)-3-(4-(4-((pyridin-2-ylamino)methyl)piperidin-1-yl)phenyl)propanoic acid | 2 |
| 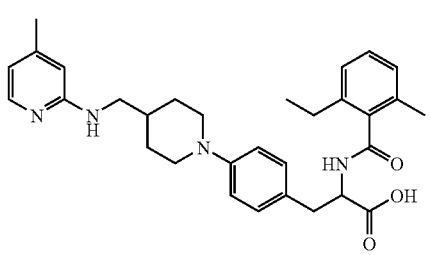 117 | C31H38N4O3 | 2-(2-ethyl-6-methylbenzamido)-3-(4-(4-((4-methylpyridin-2-ylamino)methyl)piperidin-1-yl)phenyl)propanoic acid | 3 |

| | | | |
|---|---|---|---|
| 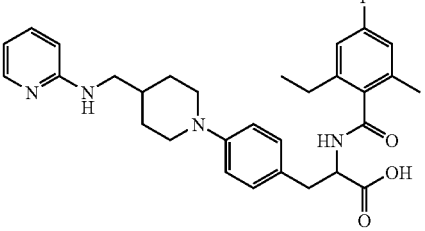 120 | $C_{30}H_{35}FN_4O_3$ | 2-(2-ethyl-4-fluoro-6-methylbenzamido)-3-(4-(4-((pyridin-2-ylamino)methyl)piperidin-1-yl)phenyl)propanoic acid | 2 |
| 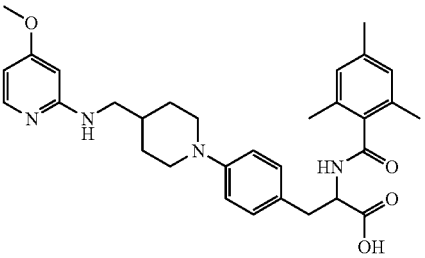 147 | $C_{31}H_{38}N_4O_4$ | 3-(4-(4-((4-methoxypyridin-2-ylamino)methyl)piperidin-1-yl)phenyl)-2-(2,4,6-trimethylbenzamido)propanoic acid | 3 |
| 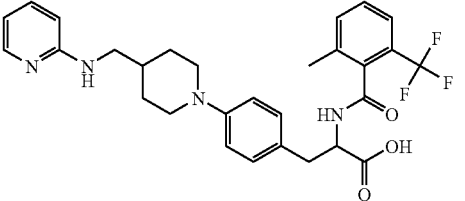 166 | $C_{29}H_{31}F_3N_4O_3$ | 2-(2-methyl-6-(trifluoromethyl)benzamido)-3-(4-(4-((pyridin-2-ylamino)methyl)piperidin-1-yl)phenyl)propanoic acid | 2 |
| 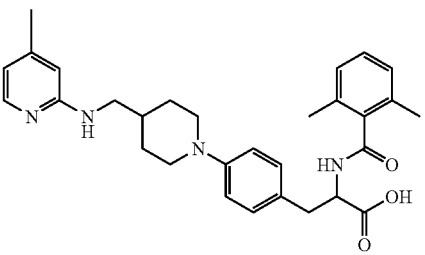 259 | $C_{30}H_{36}N_4O_3$ | 2-(2,6-Dimethyl-benzoylamino)-3-(4-{4-[(4-methyl-pyridin-2-ylamino)-methyl]-piperidin-1-yl}-phenyl)-propionic acid | 3 |
| 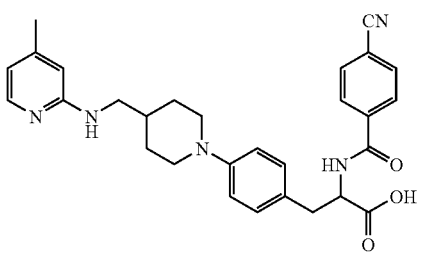 260 | $C_{29}H_{31}N_5O_3$ | 2-(4-Cyano-benzoylamino)-3-(4-{4-[(4-methyl-pyridin-2-ylamino)-methyl]-piperidin-1-yl}-phenyl)-propionic acid | 3 |

TABLE 1-continued

| | | | |
|---|---|---|---|
| 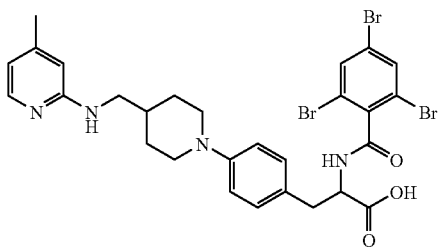 261 | $C_{28}H_{29}Br_3N_4O_3$ | 3-(4-{4-[(4-Methyl-pyridin-2-ylamino)-methyl]-piperidin-1-yl}-phenyl)-2-(2,4,6-tribromo-benzoylamino)-propionic acid | 3 |
| 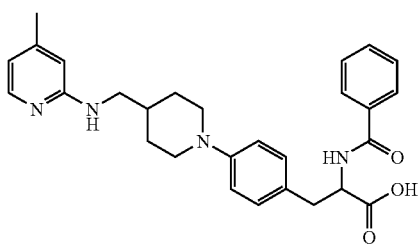 262 | $C_{28}H_{32}N_4O_3$ | 2-Benzoylamino-3-(4-{4-[(4-methyl-pyridin-2-ylamino)-methyl]-piperidin-1-yl}-phenyl)-propionic acid | 3 |
| 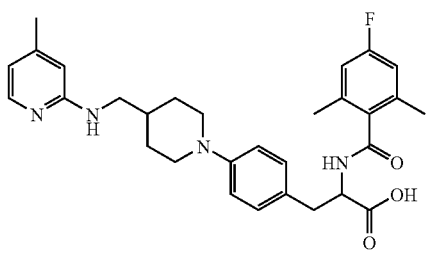 263 | $C_{30}H_{35}FN_4O_3$ | 2-(4-Fluoro-2,6-dimethyl-benzoylamino)-3-(4-{4-[(4-methyl-pyridin-2-ylamino)-methyl]-piperidin-1-yl}-phenyl)-propionic acid | 3 |
| 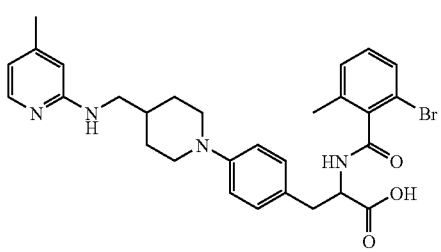 264 | $C_{29}H_{33}BrN_4O_3$ | 2-(2-Bromo-6-methyl-benzoylamino)-3-(4-{4-[(4-methyl-pyridin-2-ylamino)-methyl]-piperidin-1-yl}-phenyl)-propionic acid | 3 |
| 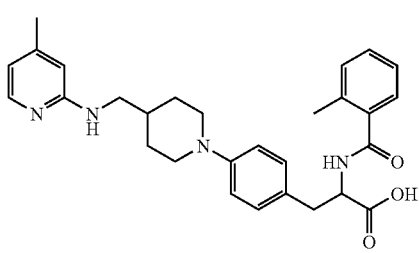 265 | $C_{29}H_{34}N_4O_3$ | 2-(2-Methyl-benzoylamino)-3-(4-{4-[(4-methyl-pyridin-2-ylamino)-methyl]-piperidin-1-yl}-phenyl)-propionic acid | 3 |

TABLE 1-continued

| structure | formula | | | |
|---|---|---|---|---|
| 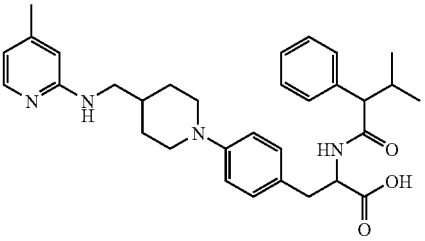 266 | C₃₂H₄₀N₄O₃ | 2-(3-Methyl-2-phenyl-butyrylamino)-3-(4-{4-[(4-methyl-pyridin-2-ylamino)-methyl]-piperidin-1-yl}-phenyl)-propionic acid | | 3 |
| 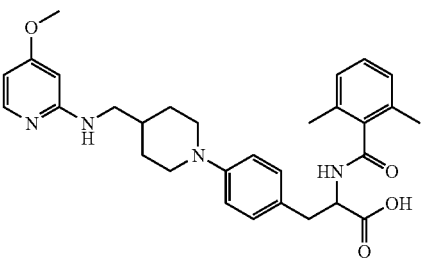 267 | C₃₀H₃₆N₄O₄ | 2-(2,6-Dimethyl-benzoylamino)-3-(4-{4-[(4-methoxy-pyridin-2-ylamino)-methyl]-piperidin-1-yl}-phenyl)-propionic acid | | 3 |
| 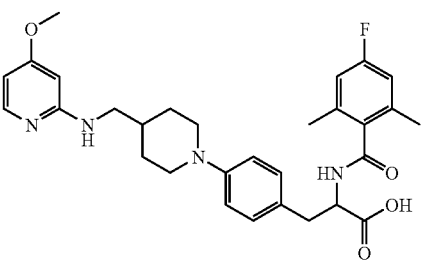 268 | C₃₀H₃₅FN₄O₄ | 2-(4-Fluoro-2,6-dimethyl-benzoylamino)-3-(4-{4-[4-methoxy-pyridin-2-ylamino)-methyl]-piperidin-1-yl}-phenyl)-propionic acid | | 3 |

| structure | formula | molecular weight | exact mass | LCMS |
|---|---|---|---|---|
| 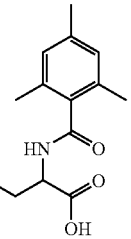 5 | C₃₀H₃₆N₄O₃ | 500.6 | 500.3 | 501.2 |
|  8 | C₃₁H₃₈N₄O₃ | 514.7 | 514.3 | 515.5 |

TABLE 1-continued
| | | | | |
|---|---|---|---|---|
| 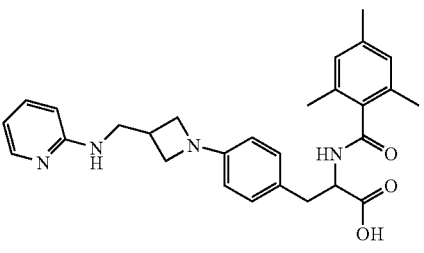 11 | $C_{28}H_{32}N_4O_3$ | 472.6 | 472.2 | 473.4 |
| 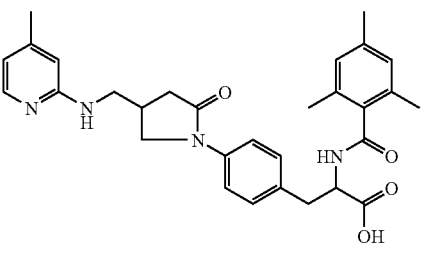 16 | $C_{30}H_{34}N_4O_4$ | 514.6 | 514.2 | 512.2 |
| 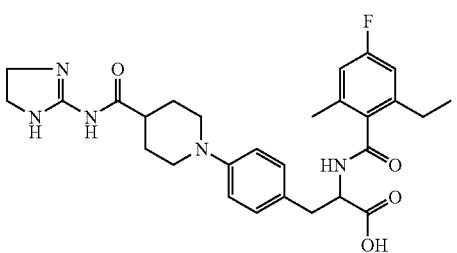 18 | $C_{28}H_{34}FN_5O_4$ | 523.6 | 523.3 | 524.2 |
| 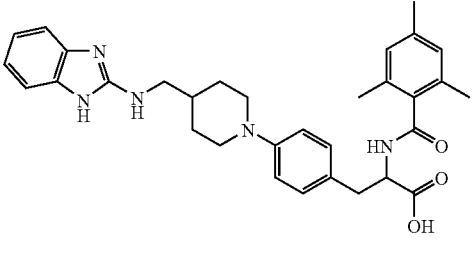 20 | $C_{32}H_{37}N_5O_3$ | 539.7 | 539.3 | 540.3 |
| 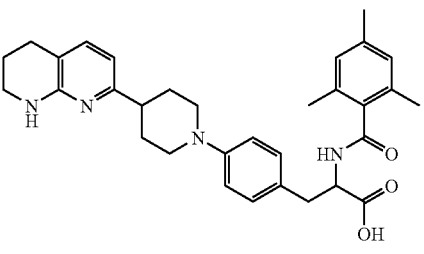 23 | $C_{32}H_{38}N_4O_3$ | 526.7 | 526.3 | 527.3 |
| 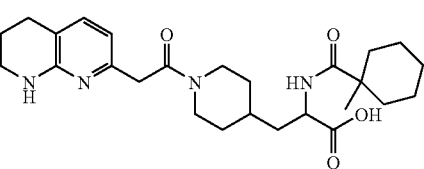 27 | $C_{26}H_{38}N_4O_4$ | 470.6 | 470.3 | 471.3 |

TABLE 1-continued
| Structure | Formula | | | |
|---|---|---|---|---|
| 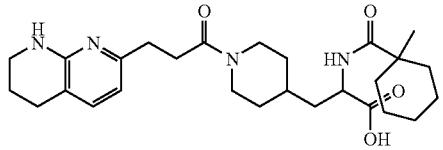 29 | C₂₇H₄₀N₄O₄ | 484.6 | 484.3 | 485.3 |
| 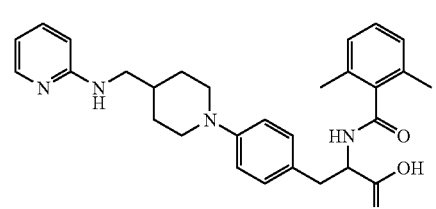 58 | C₂₉H₃₄N₄O₃ | 486.6 | 486.3 | 487.3 |
| 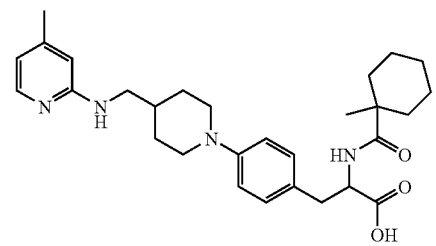 75 | C₂₉H₄₀N₄O₃ | 492.7 | 492.3 | 493.3 |
| 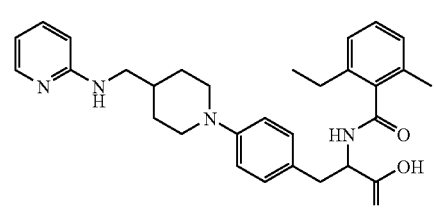 84 | C₃₀H₃₆N₄O₃ | 500.6 | 500.3 | 501.4 |
| 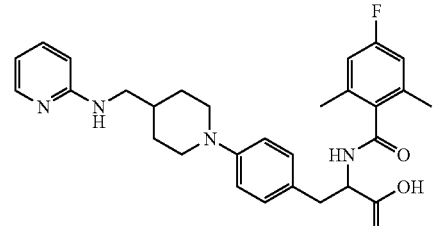 90 | C₂₉H₃₃FN₄O₃ | 504.6 | 504.3 | 505.2 |
| 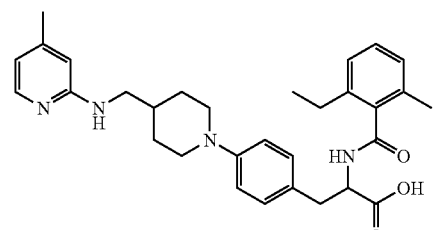 117 | C₃₁H₃₈N₄O₃ | 514.7 | 514.3 | 515.2 |

TABLE 1-continued
| Structure | Formula | MW calc | MW found | M+H |
|---|---|---|---|---|
| 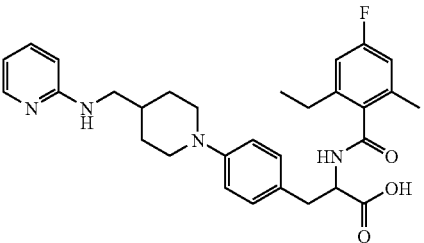 120 | C₃₀H₃₅FN₄O₃ | 518.6 | 518.3 | 519.3 |
| 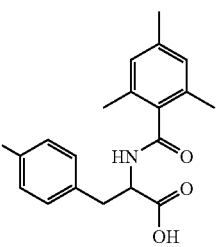 147 | C₃₁H₃₈N₄O₄ | 530.7 | 530.3 | 531.4 |
| 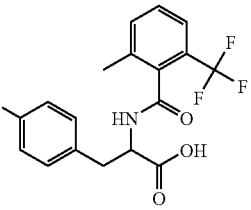 166 | C₂₉H₃₁F₃N₄O₃ | 540.6 | 540.2 | 541.3 |
| 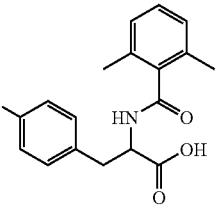 259 | C₃₀H₃₆N₄O₃ | 500.6 | 500.3 | 501.2 |
| 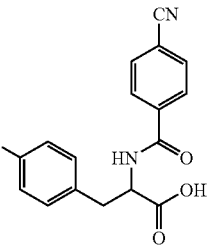 260 | C₂₉H₃₁N₅O₃ | 497.6 | 497.2 | 498.2 |

TABLE 1-continued
| Structure | Formula | MW | Calc | Found |
|---|---|---|---|---|
| 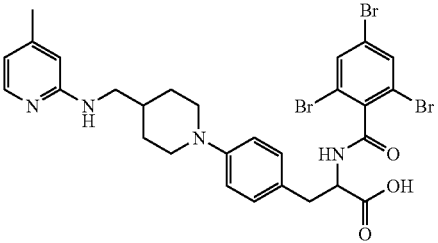 261 | C₂₈H₂₉Br₃N₄O₃ | 709.3 | 708.0 | 709.0 |
| 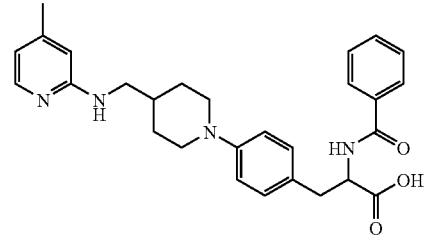 262 | C₂₈H₃₂N₄O₃ | 472.6 | 472.3 | 473.2 |
| 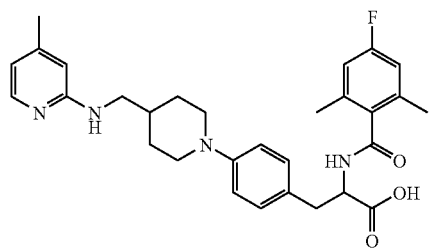 263 | C₃₀H₃₅FN₄O₃ | 518.6 | 518.3 | 519.5 |
| 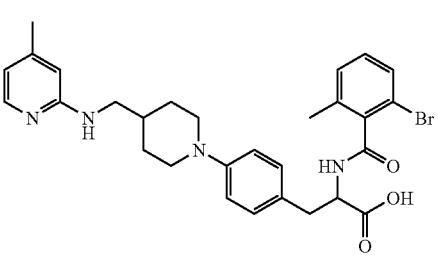 264 | C₂₉H₃₃BrN₄O₃ | 565.5 | 566.2 | 567.2 |
| 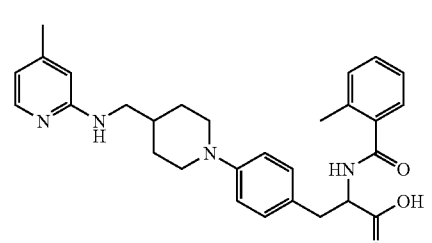 265 | C₂₉H₃₄N₄O₃ | 486.6 | 486.3 | 487.2 |

TABLE 1-continued

| Structure | Formula | | | |
|---|---|---|---|---|
| 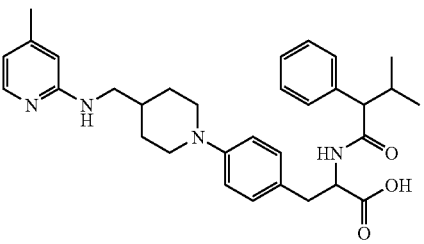 266 | $C_{32}H_{40}N_4O_3$ | 528.7 | 528.3 | 529.3 |
| 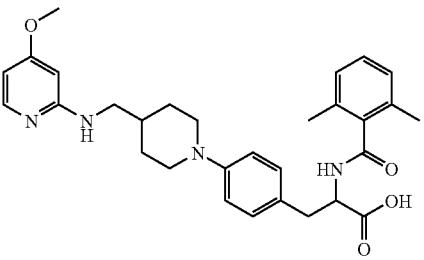 267 | $C_{30}H_{36}N_4O_4$ | 516.6 | 516.3 | 517.4 |
| 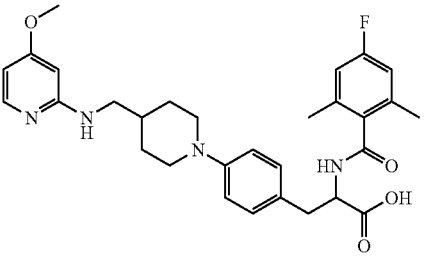 268 | $C_{30}H_{35}FN_4O_4$ | 534.3 | 534.6 | 535.5 |

EXAMPLE 11

Biological Characterization of the Compounds

1. Integrin Receptor Binding Assays

The $IC_{50}$ values of selected inhibitors were determined using competitive ELISA studies by inhibition of binding of integrin to the most active ligand of the integrin. The optimal concentrations of integrin and ligand were selected from ELISA binding studies with variable concentrations of both to obtain optimal signal noise ratio for further studies. $IC_{50}$ studies were performed with fixed concentration of ligand and integrin and a serial dilution of inhibitor. The plates were measured with SpectraMax Plus reader (Molecular Devices). The resulting inhibition curves were analyzed using Soft-MaxPro 4.0 software, the turning point describes the $IC_{50}$ value.

Fibronectin was purchased from Sigma and fibrinogen from Calbiochem. (EMD Biosciences, Darmstadt, Germany). The integrin alpha5beta1 extracellular domain Fc-fusion was expressed and purified as described (Coe, 2001, J. Biol. Chem., 276, 35854). Integrin alphaIIbbeta3 was purchased form Kordia (Kordia Life Science, Leiden, Netherlands)

1.1. alpha5beta1-Fibronectin Binding Assay

Fibronectin was diluted with coating buffer (15 mM $Na_2CO_3$, 35 mM $NaHCO_3$, pH 9.6) and coated with 100 μL/well to Nunc-Immuno maxisorp plates (Nalge Nunc Europe Ltd) over night at 4° C. After discarding the coating solution plates were washed 3 times with buffer 1 (25 mM Tris, pH 7.6, 150 mM NaCl, 1 mM $MnCl_2$, 1 mg/ml BSA) and blocked with 100 μL blocking buffer (3% BSA in PBS 0.1% Tween20) for 1 hour at room temperature. After washing the blocked plates (3 times) with buffer 1, integrin (50 μL) and either inhibitor (serial dilution in buffer 1) or buffer 1 (50 μL) were added to the wells and incubated for one hour at RT. Plates were then washed (3 times) with buffer 1 and incubated with 100 μL of anti-human-Fc-HRP antibody conjugate (Sigma-Aldrich, Taufkirchen, Germany) in buffer 1 for 1 hour at RT. After additional washing steps (3 times) with buffer 1 50 μL of HRP substrate solution TMB (Seramun, Germany) were added to the wells. Color development was stopped after 3-5 minutes with 50 μL 1 M $H_2SO_4$. The developed color was measured at 450 nm and analyzed as described above.

1.2. alphaIIbbeta3-Fibrinogen Binding Assay

Fibrinogen was diluted with coating buffer (15 mM $Na_2CO_3$, 35 mM $NaHCO_3$, pH 9.6) and coated with 100 μL/well to Nunc-Immuno maxisorp plates over night at 4° C. After discarding the coating solution plates were washed 3 times with buffer 1 (25 mM Tris, pH 7.6, 150 mM NaCl, 1 mM $MnCl_2$, 1 mg/ml BSA) and blocked with 100 μL blocking buffer (3% BSA in PBS 0.1% Tween20) for 1 hour at room temperature. After washing the blocked plates (3 times) with buffer 1, integrin alphaIIbbeta3 (50 μL) and either inhibitor (serial dilution in buffer 3, 25 mM Tris, pH 7.6, 150 mM NaCl, 1 mM $MnCl_2$, 1 mg/ml BSA 1 mM $MgCl_2$, 1 mM $CaCl_2$,) or buffer 3 (50 μL) were added to the wells and incubated for one hour at RT. Plates were then washed (3 times) with buffer 3 and incubated with 100 μL of anti-alphaIIbbeta3 antibody (anti CD41b, Pharmingen) in buffer 3 for 1 hour at RT. Plates were washed (3 times) with buffer 3 and incubated for 1 hour with 100 μL secondary antibody (anti-mouse-HRP conjugate, Sigma) in buffer 3. After additional washing steps (3 times) with buffer 350 μL of HRP substrate solution TMB (Seramun) were added to the wells. Color development was stopped after 3-5 minutes with 50 μL 1 M $H_2SO_4$. The developed color was measured at 450 nm and analyzed as described above.

The results of the various assays performed on some of the compounds according to the present invention are depicted as $IC_{50}$ values in table 2.

2. Cellular Inhibition Assays 2.1. Cell Adhesion Assay with HEK293

Cryopreserved cells were thawed and grown for 72 h in DMEM medium with 10% FCS, 2 mM glutamine, 100 U/ml penicillin and 100 μg/ml streptomycin before use.

Cells were detached with cell dissociation solution (Sigma) and suspended in growth medium, centrifuged and resuspended in buffer A (150 mM NaCl, 25 mM HEPES, 2 mM EDTA, pH 7.4). Cells were incubated for 30 min at 37° C. in a 5% $CO_2$. Subsequently, cells were washed with prewarmed buffer B (150 mM NaCl, 25 mM HEPES pH 7.4) and resuspended in buffer B. 96-well Maxisorp-plate were coated with 0.01% poly-L-lysine, 10 μg/ml fibronectin (Chemicon; #F1904) in carbonate buffer or carbonate buffer alone (15 mM $Na_2CO_3$, 35 mM $NaHCO_3$, pH 9.6) for 1 h at RT. Plates were washed and blocked with 1% BSA for 30 min at RT. Cells were preincubated with test compound and adjusted DMSO concentrations for 10 min at RT. $7 \times 10^4$ cells per well were plated in triplicate and allowed to attach for 1 h at 37° C. in the presence of 2 mM $MgCl_2$. Cells were washed with PBS and adherent cells were fixed with 5% glutaraldehyde for 30 min.

Cells were subsequently washed and stained with 0.1% Crystal Violet for 1 hr at 37° C. Plates were washed and incorporated dye was solubilized with 10% acetic acid. Absorbance was measured at 570 nm using a Spectramax Plus 384 microtiter plate reader and analyzed with SoftMax-Pro (Molecular Devices). Minimal binding on BSA was subtracted. $IC_{50}$ values were determined using XL-FIT.

2.2. Migration Assay with HUVEC

Migration assays are carried out using modified Boyden chambers consisting of Fluoroblock Transwell membrane filter (8 μm pores) in 24 well companion tissue plates (BD). Three wells per group are used.

The underfaces of the transwell membranes are coated with chymotryptic fibronectin fragment (10 μg/ml; Chemicon) and blocked with 2% BSA for 1 h at room temperature. After rinsing with PBS transwells are placed into companion plates containing 700 μl serumfree medium with indicated compound concentrations and chemoattractant (10 ng/ml bFGF; Promocell).

HUVEC are maintained in standard culture medium (Endothelial Cell Growth Medium; Promocell, containing supplement mix and 2% FCS) in a humified 5% $CO_2$ incubator at 37° C. Cells are grown to 70-90% confluency and are made quiescent in culture medium containing 0.5% FCS, 0.1% BSA, no supplements for 16 h. Medium is removed and serum-free medium (0% FCS; 0.1% BSA, no supplements) is added for 1.5 h. Cells are detached with trypsin and cell suspension is adjusted to $1 \times 10^5$/ml. Indicated compound concentrations are added to cells. Cells are preincubated with compounds for 15 min, before seeding of 250 μl of the cell suspensions into the transwells. Cells are allowed to migrate for 3 h in 37° C. incubator with 5% $CO_2$. Then, transwells are transferred to 24 well companion tissue plates containing Calcein AM (4 μM; Molecular Probes) in HBSS and incubated for another 2 h. Plates are read at excitation/emission 585/538 nm in a fluorescence reader.

Results are expressed as percent of control (cells in serum-free medium without compound and chemoattractant.

2.3. Tube Formation Assay in Fibrin Gel

Experiments were pursued in modification of the originally published protocol described in Korff and Augustin 1999 J Cell Sci 112, 3249. In brief, spheroids were prepared as described (Korff and Augustin 1998 J Cell Biol 143, 1341) by pipetting 500 endothelial cells (HUVEC, PromoCell, Heidelberg, Germany) in a hanging drop on plastic dishes to allow overnight spheroidal aggregation. Spheroids were harvested and 50 spheroids were seeded in 900 μl of a fibrin solution (2 mg/ml) and pipetted into individual wells of a 24 well plate to allow fibrin gel polymerization. Test compound was added in different concentrations after 30 min by pipetting 100 μl of a 10 fold concentrated working dilution on top of the gel. Endothelial cell spheroids were additionally stimulated with VEGF [25 ng/ml] or bFGF [25 ng/ml]. Plates were incubated at 37° C. for 24 h. Dishes were fixed at the end of the experimental incubation period by addition of paraformaldehyde. Sprouting intensity of endothelial cells was quantitated by an automated image analysis system determining the cumulative sprout length per spheroid using an Olympus IX50 inverted microscope and the digital imaging software analySIS (Soft imaging system, Munster, Germany). The mean of the cumulative sprout length of 10 randomly selected spheroids was analyzed as an individual data point.

Table 2: In vitro activities of selected compounds in different functional assays described in section 1.1-2.2.

| Compound Nr. | $IC_{50}$ alpha5beta1 [nM] | $IC_{50}$ alphabIIbbeta3 [μM] | $IC_{50}$ alpha5beta1 in cell adhesion assay [μM] | Migration (HUVEC) [μM] |
|---|---|---|---|---|
| 8 | <100 | >1 | <2 | <10 |
| 11 | >100 | >1 | >20 | — |
| 20 | >100 | >1 | 2-20 | — |
| 23 | <100 | >1 | <2 | <10 |
| 29 | <100 | >1 | 2-20 | >20 |
| 75 | <100 | >1 | <2 | — |
| 114 | <100 | >1 | <2 | <10 |
| 120 | <100 | >1 | <2 | <10 |
| 147 | <100 | >1 | <2 | — |
| 262 | <100 | >1 | 2-20 | — |
| 266 | <100 | >1 | <2 | — |
| 269 | <100 | >1 | >20 | — |

The features of the present invention disclosed in the specification, the sequence listing, the claims and/or the drawings may both separately and in any combination thereof be material for realizing the invention in various forms thereof.

The invention claimed is:

1. A compound selected from the group consisting of
 compound (5): 3-(4-(4-((pyridin-2-ylamino)methyl)piperidin-1-yl)phenyl)-2-(2,4,6-trimethylbenzamido)propanoic acid;
 compound (8): 3-(4-(4-((4-methylpyridin-2-ylamino)methyl)piperidin-1-yl)phenyl)-2-(2,4,6-trimethylbenzamido)propanoic acid;
 compound (11): 3-(4-(3-((pyridin-2-ylamino)methyl)azetidin-1-yl)phenyl)-2-(2,4,6-trimethylbenzamido)propanoic acid;

compound (16): 3-(4-{4-[(4-methyl-pyridin-2-ylamino)methyl]-2-oxo-pyrrolidin-1-yl}phenyl)-2-(2,4,6-trimethyl-benzoylamino)propionic acid;

compound (18): 3-{4-[4-(4,5-Dihydro-1H-imidazol-2-yl-carbamoyl)piperidin-1-yl]phenyl}-2-(2-ethyl-4-fluoro-6-methyl-benzoylamino)propionic acid;

compound (20): 3-(4-(4-((1H-benzo[d]imidazol-2-ylamino)methyl)piperidin-1-yl)phenyl)-2-(2,4,6-trimethylbenzamido)propanoic acid;

compound (23): 3-(4-(4-(5,6,7,8-tetrahydro-1,8-naphthyridin-2-yl)piperidin-1-yl)phenyl)-2-(2,4,6-trimethylbenzamido)propanoic acid;

compound (31): 2-(1-methylcyclohexanecarboxamido)-3-(4-(3-((pyridin-2-ylamino)methyl)azetidin-1-yl)phenyl)propanoic acid;

compound (32): 2-(2,2-dimethylbutanamido)-3-(4-(4-((pyridin-2-ylamino)methyl)piperidin-1-yl)phenyl)propanoic acid;

compound (33): 2-(picolinamido)-3-(4-(4-((pyridin-2-ylamino)methyl)piperidin-1-yl)phenyl)propanoic acid;

compound (34): 2-(1-oxo-2-azaspiro[3.4]octan-2-yl)-3-(4-(4-((pyridin-2-ylamino)methyl)piperidin-1-yl)phenyl)propanoic acid;

compound (35): 2-(1-methylcyclohexanecarboxamido)-3-(4-(4-((pyridin-2-ylamino)methyl)-4,5-dihydrooxazol-2-yl)phenyl)propanoic acid;

compound (36): 2-(1-methylcyclohexanecarboxamido)-3-(4-(3-((pyridin-2-ylamino)methyl)pyrrolidin-1-yl)phenyl)propanoic acid;

compound (37): 2-(2-ethyl-2-methylbutanamido)-3-(4-(4-((pyridin-2-ylamino)methyl)piperidin-1-yl)phenyl)propanoic acid;

compound (38): 2-(1-oxoisoindolin-2-yl)-3-(4-(4-((pyridin-2-ylamino)methyl)piperidin-1-yl)phenyl)propanoic acid;

compound (39): 2-(2-oxoindolin-1-yl)-3-(4-(4-((pyridin-2-ylamino)methyl)piperidin-1-yl)phenyl)propanoic acid;

compound (40): 2-(2-methylbenzamido)-3-(4-(4-((pyridin-2-ylamino)methyl)piperidin-1-yl)phenyl)propanoic acid;

compound (41): 2-(2-ethyl-6-methylbenzamido)-3-(4-(3-((pyridin-2-ylamino)methyl)azetidin-1-yl)phenyl)propanoic acid;

compound (42): 2-(2-methylnicotinamido)-3-(4-(4-((pyridin-2-ylamino)methyl)piperidin-1-yl)phenyl)propanoic acid;

compound (43): 3-(4-(4-((4-methylpyridin-2-ylamino)methyl)piperidin-1-yl)phenyl)-2-(1-oxo-2-azaspiro[3.4]octan-2-yl)propanoic acid;

compound (44): 2-(1-oxo-2-azaspiro[3.5]nonan-2-yl)-3-(4-(4-((pyridin-2-ylamino)methyl)piperidin-1-yl)phenyl)propanoic acid;

compound (45): 2-(1-oxo-2-azaspiro[4.4]nonan-2-yl)-3-(4-(4-((pyridin-2-ylamino)methyl)piperidin-1-yl)phenyl)propanoic acid;

compound (46): 2-(3,5-dimethylisoxazole-4-carboxamido)-3-(4-(4-((pyridin-2-ylamino)methyl)piperidin-1-yl)phenyl)propanoic acid;

compound (47): 2-(1-methylcyclohexanecarboxamido)-3-(4-(4-((pyridin-2-ylamino)methyl)piperidin-1-yl)phenyl)propanoic acid;

compound (48): 2-(3,3-diethyl-2-oxopyrrolidin-1-yl)-3-(4-(4-((pyridin-2-ylamino)methyl)piperidin-1-yl)phenyl)propanoic acid;

compound (49): 2-(1-methylcyclohexanecarboxamido)-3-(4-(5-((pyridin-2-ylamino)methyl)-5,6-dihydro-4H-1,3-oxazin-2-yl)phenyl)propanoic acid;

compound (50): 2-(1-methylcyclohexanecarboxamido)-3-(4-(2-oxo-4-((pyridin-2-ylamino)methyl)pyrrolidin-1-yl)phenyl)propanoic acid;

compound (51): 2-(4-cyanobenzamido)-3-(4-(4-((pyridin-2-ylamino)methyl)piperidin-1-yl)phenyl)propanoic acid;

compound (52): 3-{4-[4-(4,5-dihydro-1H-imidazol-2-yl-carbamoyl)piperidin-1-yl]phenyl}-2-[(1-methyl-cyclohexanecarbonyl)-amino]propionic acid;

compound (53): 3-(4-(4-((4-methylpyridin-2-ylamino)methyl)piperidin-1-yl)phenyl)-2-(1-oxoisoindolin-2-yl)propanoic acid;

compound (54): 3-(4-(4-((4-methylpyridin-2-ylamino)methyl)piperidin-1-yl)phenyl)-2-(2-oxoindolin-1-yl)propanoic acid;

compound (55): 2-(1-oxo-3,4-dihydroisoquinolin-2(1H)-yl)-3-(4-(4-((pyridin-2-ylamino)methyl)piperidin-1-yl)phenyl)propanoic acid;

compound (56): 2-(3-oxo-3,4-dihydroisoquinolin-2(1H)-yl)-3-(4-(4-((pyridin-2-ylamino)methyl)piperidin-1-yl)phenyl)propanoic acid;

compound (57): 2-(2-oxo-3,4-dihydroquinolin-1(2H)-yl)-3-(4-(4-((pyridin-2-ylamino)methyl)piperidin-1-yl)phenyl)propanoic acid;

compound (58): 2-(2,6-dimethylbenzamido)-3-(4-(4-((pyridin-2-ylamino)methyl)piperidin-1-yl)phenyl)propanoic acid;

compound (59): 3-(4-(4-((pyridin-2-ylamino)methyl)-4,5-dihydrooxazol-2-yl)phenyl)-2-(2,4,6-trimethylbenzamido)propanoic acid;

compound (60): 2-(2-ethyl-6-methylbenzamido)-3-(4-(4-((pyridin-2-ylamino)methyl)-4,5-dihydrooxazol-2-yl)phenyl)propanoic acid;

compound (61): 3-(4-(3-((pyridin-2-ylamino)methyl)pyrrolidin-1-yl)phenyl)-2-(2,4,6-trimethylbenzamido)propanoic acid;

compound (62): 2-(2-ethyl-6-methylbenzamido)-3-(4-(3-((pyridin-2-ylamino)methyl)pyrrolidin-1-yl)phenyl)propanoic acid;

compound (63): 2-(2,4-dimethylnicotinamido)-3-(4-(4-((pyridin-2-ylamino)methyl)piperidin-1-yl)phenyl)propanoic acid;

compound (64): 3-(4-(4-((4-methylpyridin-2-ylamino)methyl)piperidin-1-yl)phenyl)-2-(1-oxo-2-azaspiro[3.5]nonan-2-yl)propanoic acid;

compound (65): 3-(4-(4-((4-methylpyridin-2-ylamino)methyl)piperidin-1-yl)phenyl)-2-(1-oxo-2-azaspiro[4.4]nonan-2-yl)propanoic acid;

compound (66): 2-(1-oxo-2-azaspiro[4.5]decan-2-yl)-3-(4-(4-((pyridin-2-ylamino)methyl)piperidin-1-yl)phenyl)propanoic acid;

compound (67): 2-(6-oxo-7-azaspiro[4.5]decan-7-yl)-3-(4-(4-((pyridin-2-ylamino)methyl)piperidin-1-yl)phenyl)propanoic acid;

compound (68): 2-(2-ethyl-4-fluoro-6-methylbenzamido)-3-(4-(3-((pyridin-2-ylamino)methyl)azetidin-1-yl)phenyl)propanoic acid;

compound (69): 2-(5-ethyl-3-methylisoxazole-4-carboxamido)-3-(4-(4-((pyridin-2-ylamino)methyl)piperidin-1-yl)phenyl)propanoic acid;

compound (70): 2-(2,4-dimethylthiophene-3-carboxamido)-3-(4-(4-((pyridin-2-ylamino)methyl)piperidin-1-yl)phenyl)propanoic acid;

compound (71): 2-(1-methylcyclohexanecarboxamido)-3-(4-(4-((4-methylpyridin-2-ylamino)methyl)-2-oxopyrrolidin-1-yl)phenyl)propanoic acid;

compound (74): 2-(3,3-diethyl-2-oxopyrrolidin-1-yl)-3-(4-(4-((4-methylpyridin-2-ylamino)methyl)piperidin-1-yl)phenyl)propanoic acid;

compound (75): 2-(1-methylcyclohexanecarboxamido)-3-(4-(4-((4-methylpyridin-2-ylamino)methyl)piperidin-1-yl)phenyl)propanoic acid;

compound (76): 2-(4-fluoro-2,6-dimethyl-benzoylamino)-3-[1-(2-5,6,7,8-tetrahydro-[1,8]naphthyridin-2-yl-acetyl)piperidin-4-yl]propionic acid;

compound (77): 2-(4-cyano-2-ethyl-6-methylbenzamido)-3-(4-(3-((pyridin-2-ylamino)methyl)azetidin-1-yl)phenyl)propanoic acid;

compound (78): 2-(1-methylcyclohexanecarboxamido)-3-(4-(4-((4-oxo-1,4,5,6-tetrahydropyrimidin-2-ylamino)methyl)piperidin-1-yl)phenyl)propanoic acid;

compound (79): 2-[(1-methyl-cyclohexanecarbonyl)-amino]-3-{4-[4-(1,4,5,6-tetrahydro-pyrimidin-2-ylcarbamoyl)piperidin-1-yl]phenyl}propionic acid;

compound (80): 3-(4-(4-((4-methylpyridin-2-ylamino)methyl)piperidin-1-yl)phenyl)-2-(1-oxo-3,4-dihydroisoquinolin-2(1H)-yl)propanoic acid;

compound (81): 3-(4-(4-((4-methylpyridin-2-ylamino)methyl)piperidin-1-yl)phenyl)-2-(3-oxo-3,4-dihydroisoquinolin-2(1H)-yl)propanoic acid;

compound (82): 3-(4-(4-((4-methylpyridin-2-ylamino)methyl)piperidin-1-yl)phenyl)-2-(2-oxo-3,4-dihydroquinolin-1(2H)-yl)propanoic acid;

compound (83): 2-(2-oxo-3-phenylpyrrolidin-1-yl)-3-(4-(4-((pyridin-2-ylamino)methyl)piperidin-1-yl)phenyl)propanoic acid;

compound (84): 2-(2-ethyl-6-methylbenzamido)-3-(4-(4-((pyridin-2-ylamino)methyl)piperidin-1-yl)phenyl)propanoic acid;

compound (85): 2-(2-methyl-2-phenylpropanamido)-3-(4-(4-((pyridin-2-ylamino)methyl)piperidin-1-yl)phenyl)propanoic acid;

compound (86): 3-(4-(5-((pyridin-2-ylamino)methyl)-5,6-dihydro-4H-1,3-oxazin-2-yl)phenyl)-2-(2,4,6-trimethylbenzamido)propanoic acid;

compound (87): 2-(2-ethyl-6-methylbenzamido)-3-(4-(5-((pyridin-2-ylamino)methyl)-5,6-dihydro-4H-1,3-oxazin-2-yl)phenyl)propanoic acid;

compound (88): 2-(2-ethyl-6-methylbenzamido)-3-(4-(2-oxo-4-((pyridin-2-ylamino)methyl)pyrrolidin-1-yl)phenyl)propanoic acid;

compound (89): 2-(2-ethyl-4-methylnicotinamido)-3-(4-(4-((pyridin-2-ylamino)methyl)piperidin-1-yl)phenyl)propanoic acid;

compound (90): 2-(4-fluoro-2,6-dimethylbenzamido)-3-(4-(4-((pyridin-2-ylamino)methyl)piperidin-1-yl)phenyl)propanoic acid;

compound (91): 2-(2-ethyl-4-fluoro-6-methylbenzamido)-3-(4-(4-((pyridin-2-ylamino)methyl)-4,5-dihydrooxazol-2-yl)phenyl)propanoic acid;

compound (92): 2-(2-ethyl-4-fluoro-6-methylbenzamido)-3-(4-(3-((pyridin-2-ylamino)methyl)pyrrolidin-1-yl)phenyl)propanoic acid;

compound (93): 3-(4-(4-((4-methylpyridin-2-ylamino)methyl)piperidin-1-yl)phenyl)-2-(1-oxo-2-azaspiro[4.5]decan-2-yl)propanoic acid;

compound (94): 3-(4-(4-((4-methylpyridin-2-ylamino)methyl)piperidin-1-yl)phenyl)-2-(6-oxo-7-azaspiro[4.5]decan-7-yl)propanoic acid;

compound (95): 2-(1-oxo-2-azaspiro[5.5]undecan-2-yl)-3-(4-(4-((pyridin-2-ylamino)methyl)piperidin-1-yl)phenyl)propanoic acid;

compound (96): 2-(1-methylcyclohexanecarboxamido)-3-(4-(4-(5,6,7,8-tetrahydro-1,8-naphthyridin-2-yl)piperidin-1-yl)phenyl)propanoic acid;

compound (97): 3-{4-[4-(4,5-dihydro-1H-imidazol-2-ylcarbamoyl)piperidin-1-yl]phenyl}-2-(2,4,6-trimethylbenzoylamino)propionic acid;

compound (98): 2-(3,5-diethylisoxazole-4-carboxamido)-3-(4-(4-((pyridin-2-ylamino)methyl)piperidin-1-yl)phenyl)propanoic acid;

compound (99): 3-{4-[4-(4,5-Dihydro-1H-imidazol-2-ylcarbamoyl)piperidin-1-yl]phenyl}-2-(2-ethyl-6-methyl-benzoylamino)propionic acid;

compound (102): 3-(4-(4-((pyridin-2-ylamino)methyl)piperidin-1-yl)phenyl)-2-(2,4,6-trimethylcyclohexanecarboxamido)propanoic acid;

compound (103): 2-(4-chloro-2-ethyl-6-methylbenzamido)-3-(4-(3-((pyridin-2-ylamino)methyl)azetidin-1-yl)phenyl)propanoic acid;

compound (104): 3-(4-(4-((4-methoxypyridin-2-ylamino)methyl)piperidin-1-yl)phenyl)-2-(1-methylcyclohexanecarboxamido)propanoic acid;

compound (105): 2-(2-oxo-1',3'-dihydrospiro[azetidine-3,2'-indene]-1-yl)-3-(4-(4-((pyridin-2-ylamino)methyl)piperidin-1-yl)phenyl)propanoic acid;

compound (108): 2-(4-cyano-2,6-dimethylbenzamido)-3-(4-(4-((pyridin-2-ylamino)methyl)piperidin-1-yl)phenyl)propanoic acid;

compound (109): 2-(4-cyano-2-ethyl-6-methylbenzamido)-3-(4-(4-((pyridin-2-ylamino)methyl)-4,5-dihydrooxazol-2-yl)phenyl)propanoic acid;

compound (110): 2-(4-cyano-2-ethyl-6-methylbenzamido)-3-(4-(3-((pyridin-2-ylamino)methyl)pyrrolidin-1-yl)phenyl)propanoic acid;

compound (111): 3-(4-(4-((4-methylpyridin-2-ylamino)methyl)piperidin-1-yl)phenyl)-2-(2-oxo-3-phenylpyrrolidin-1-yl)propanoic acid;

compound (113): 2-(4-acetyl-2-ethyl-6-methylbenzamido)-3-(4-(3-((pyridin-2-ylamino)methyl)azetidin-1-yl)phenyl)propanoic acid;

compound (114): 3-(4-(4-((4-methylpyridin-2-ylamino)methyl)-2-oxopyrrolidin-1-yl)phenyl)-2-(2,4,6-trimethylbenzamido)propanoic acid;

compound (115): 2-(2-ethyl-6-methylbenzamido)-3-(4-(4-((4-methylpyridin-2-ylamino)methyl)-2-oxopyrrolidin-1-yl)phenyl)propanoic acid;

compound (116): 2-(2-isopropyl-6-methylbenzamido)-3-(4-(4-((pyridin-2-ylamino)methyl)piperidin-1-yl)phenyl)propanoic acid;

compound (117): 2-(2-ethyl-6-methylbenzamido)-3-(4-(4-((4-methylpyridin-2-ylamino)methyl)piperidin-1-yl)phenyl)propanoic acid;

compound (119): 3-(4-(4-((1H-benzo[d]imidazol-2-ylamino)methyl)piperidin-1-yl)phenyl)-2-(1-methylcyclohexanecarboxamido)propanoic acid;

compound (120): 2-(2-ethyl-4-fluoro-6-methylbenzamido)-3-(4-(4-((pyridin-2-ylamino)methyl)piperidin-1-yl)phenyl)propanoic acid;

compound (121): 2-(2-ethyl-4-fluoro-6-methylbenzamido)-3-(4-(5-((pyridin-2-ylamino)methyl)-5,6-dihydro-4H-1,3-oxazin-2-yl)phenyl)propanoic acid;

compound (122): 2-(2-ethyl-4-fluoro-6-methylbenzamido)-3-(4-(2-oxo-4-((pyridin-2-ylamino)methyl)pyrrolidin-1-yl)phenyl)propanoic acid;

compound (123): 2-(2-methyl-6-(methylthio)benzamido)-3-(4-(4-((pyridin-2-ylamino)methyl)piperidin-1-yl)phenyl)propanoic acid;

compound (124): 3-(4-(4-((4-methylpyridin-2-ylamino)methyl)piperidin-1-yl)phenyl)-2-(1-oxo-2-azaspiro[5.5]undecan-2-yl)propanoic acid;

compound (125): 3-(4-(4-((4-oxo-1,4,5,6-tetrahydropyrimidin-2-ylamino)methyl)piperidin-1-yl)phenyl)-2-(2,4,6-trimethylbenzamido)propanoic acid;

compound (126): 2-(2-ethyl-6-methylbenzamido)-3-(4-(4-((4-oxo-1,4,5,6-tetrahydropyrimidin-2-ylamino)methyl)piperidin-1-yl)phenyl)propanoic acid;

compound (127): 2-(2-ethyl-6-methyl-benzoylamino)-3-{4-[4-(1,4,5,6-tetrahydro-pyrimidin-2-ylcarbamoyl)piperidin-1-yl]phenyl}propionic acid;

compound (128): 3-{4-[4-(1,4,5,6-Tetrahydro-pyrimidin-2-ylcarbamoyl)piperidin-1-yl]phenyl}-2-(2,4,6-trimethyl-benzoylamino)propionic acid;

compound (129): 3-(4-(4-((pyridin-2-ylamino)methyl)piperidin-1-yl)phenyl)-2-(2,2,6,6-tetramethylcyclohexanecarboxamido)propanoic acid;

compound (130): 2-(4-chloro-2-ethyl-6-methylbenzamido)-3-(4-(4-((pyridin-2-ylamino)methyl)-4,5-dihydrooxazol-2-yl)phenyl)propanoic acid;

compound (131): 2-(4-chloro-2,6-dimethylbenzamido)-3-(4-(4-((pyridin-2-ylamino)methyl)piperidin-1-yl)phenyl)propanoic acid;

compound (132): 2-(4-chloro-2-ethyl-6-methylbenzamido)-3-(4-(3-((pyridin-2-ylamino)methyl)pyrrolidin-1-yl)phenyl)propanoic acid;

compound (134): 3-(4-(4-((4-methylpyridin-2-ylamino)methyl)piperidin-1-yl)phenyl)-2-(2-oxo-1',3'-dihydrospiro[azetidine-3,2'-indene]-1-yl)propanoic acid;

compound (135): 2-(2'-oxo-1,3-dihydrospiro[indene-2,3'-pyrrolidine]-1'-yl)-3-(4-(4-((pyridin-2-ylamino)methyl)piperidin-1-yl)phenyl)propanoic acid;

compound (136): 2-(4-cyano-2-ethyl-6-methylbenzamido)-3-(4-(5-((pyridin-2-ylamino)methyl)-5,6-dihydro-4H-1,3-oxazin-2-yl)phenyl)propanoic acid;

compound (137): 2-(4-cyano-2-ethyl-6-methylbenzamido)-3-(4-(2-oxo-4-((pyridin-2-ylamino)methyl)pyrrolidin-1-yl)phenyl)propanoic acid;

compound (138): 2-(4-cyano-2-ethyl-6-methylbenzamido)-3-(4-(4-((pyridin-2-ylamino)methyl)piperidin-1-yl)phenyl)propanoic acid;

compound (141): 2-(4-acetyl-2-ethyl-6-methylbenzamido)-3-(4-(4-((pyridin-2-ylamino)methyl)-4,5-dihydrooxazol-2-yl)phenyl)propanoic acid;

compound (142): 2-(4-acetyl-2,6-dimethylbenzamido)-3-(4-(4-((pyridin-2-ylamino)methyl)piperidin-1-yl)phenyl)propanoic acid;

compound (143): 2-(4-acetyl-2-ethyl-6-methylbenzamido)-3-(4-(3-((pyridin-2-ylamino)methyl)pyrrolidin-1-yl)phenyl)propanoic acid;

compound (144): 2-(4-carbamoyl-2,6-dimethyl-benzoylamino)-3-{4-[4-(pyridin-2-ylaminomethyl)piperidin-1-yl]phenyl}propionic acid;

compound (145): 2-(4-cyano-2-ethyl-6-methyl-benzoylamino)-3-{4-[4-(4,5-dihydro-1H-imidazol-2-ylcarbamoyl)piperidin-1-yl]phenyl}propionic acid;

compound (146): 2-(2-ethyl-6-methylbenzamido)-3-(4-(4-((4-methoxypyridin-2-ylamino)methyl)piperidin-1-yl)phenyl)propanoic acid;

compound (147): 3-(4-(4-((4-methoxypyridin-2-ylamino)methyl)piperidin-1-yl)phenyl)-2-(2,4,6-trimethylbenzamido)propanoic acid;

compound (149): 2-(2,6-dimethyl-4-nitrobenzamido)-3-(4-(4-((pyridin-2-ylamino)methyl)piperidin-1-yl)phenyl)propanoic acid;

compound (150): 2-(2-ethyl-4-fluoro-6-methylbenzamido)-3-(4-(4-((4-methylpyridin-2-ylamino)methyl)-2-oxopyrrolidin-1-yl)phenyl)propanoic acid;

compound (151): 2-(4-fluoro-2-isopropyl-6-methylbenzamido)-3-(4-(4-((pyridin-2-ylamino)methyl)piperidin-1-yl)phenyl)propanoic acid;

compound (152): 2-(2-ethyl-4-fluoro-6-methylbenzamido)-3-(4-(4-((4-methylpyridin-2-ylamino)methyl)piperidin-1-yl)phenyl)propanoic acid;

compound (154): 2-(4-chloro-2-ethyl-6-methylbenzamido)-3-(4-(5-((pyridin-2-ylamino)methyl)-5,6-dihydro-4H-1,3-oxazin-2-yl)phenyl)propanoic acid;

compound (155): 2-(4-chloro-2-ethyl-6-methylbenzamido)-3-(4-(2-oxo-4-((pyridin-2-ylamino)methyl)pyrrolidin-1-yl)phenyl)propanoic acid;

compound (156): 2-(4-chloro-2-ethyl-6-methylbenzamido)-3-(4-(4-((pyridin-2-ylamino)methyl)piperidin-1-yl)phenyl)propanoic acid;

compound (157): 2-(4-fluoro-2-methyl-6-(methylthio)benzamido)-3-(4-(4-((pyridin-2-ylamino)methyl)piperidin-1-yl)phenyl)propanoic acid;

compound (158): 2-(2-ethyl-4-fluoro-6-methylbenzamido)-3-(4-(4-((4-oxo-1,4,5,6-tetrahydropyrimidin-2-ylamino)methyl)piperidin-1-yl)phenyl)propanoic acid;

compound (159): 2-(2-ethyl-4-fluoro-6-methyl-benzoylamino)-3-{4-[4-(1,4,5,6-tetrahydro-pyrimidin-2-ylcarbamoyl)piperidin-1-yl]phenyl}propionic acid;

compound (160): 3-(4-(4-((4-methylpyridin-2-ylamino)methyl)piperidin-1-yl)phenyl)-2-(2'-oxo-1,3-dihydrospiro[indene-2,3'-pyrrolidine]-1'-yl)propanoic acid;

compound (161): 2-(2-ethyl-4-(1H-imidazol-1-yl)-6-methylbenzamido)-3-(4-(3-((pyridin-2-ylamino)methyl)azetidin-1-yl)phenyl)propanoic acid;

compound (162): 2-(4-cyano-2-ethyl-6-methylbenzamido)-3-(4-(4-((4-methylpyridin-2-ylamino)methyl)-2-oxopyrrolidin-1-yl)phenyl)propanoic acid;

compound (163): 3-(4-(4-((1H-benzo[d]imidazol-2-ylamino)methyl)piperidin-1-yl)phenyl)-2-(2-ethyl-6-methylbenzamido)propanoic acid;

compound (164): 2-(4-cyano-2-ethyl-6-methylbenzamido)-3-(4-(4-((4-methylpyridin-2-ylamino)methyl)piperidin-1-yl)phenyl)propanoic acid;

compound (165): 2-(4-chloro-2-ethyl-6-methyl-benzoylamino)-3-{4-[4-(4,5-dihydro-1H-imidazol-2-ylcarbamoyl)piperidin-1-yl]phenyl}propionic acid;

compound (166): 2-(2-methyl-6-(trifluoromethyl)benzamido)-3-(4-(4-((pyridin-2-ylamino)methyl)piperidin-1-yl)phenyl)propanoic acid;

compound (167): 2-(2-ethyl-6-methyl-4-(trifluoromethyl)benzamido)-3-(4-(3-((pyridin-2-ylamino)methyl)azetidin-1-yl)phenyl)propanoic acid;

compound (169): 2-(2-methyl-4-(trifluoromethyl)nicotinamido)-3-(4-(4-((pyridin-2-ylamino)methyl)piperidin-1-yl)phenyl)propanoic acid;

compound (170): 2-(4-acetyl-2-ethyl-6-methylbenzamido)-3-(4-(5-((pyridin-2-ylamino)methyl)-5,6-dihydro-4H-1,3-oxazin-2-yl)phenyl)propanoic acid;

compound (171): 2-(4-acetyl-2-ethyl-6-methylbenzamido)-3-(4-(2-oxo-4-((pyridin-2-ylamino)methyl)pyrrolidin-1-yl)phenyl)propanoic acid;

compound (172): 2-(4-acetyl-2-ethyl-6-methylbenzamido)-3-(4-(4-((pyridin-2-ylamino)methyl)piperidin-1-yl)phenyl)propanoic acid;

compound (173): 2-(4-carbamoyl-2-ethyl-6-methyl-benzoylamino)-3-{4-[4-(pyridin-2-ylaminomethyl)piperidin-1-yl]phenyl}propionic acid;

compound (174): 2-(4-cyano-2-methyl-6-(methylthio)benzamido)-3-(4-(4-((pyridin-2-ylamino)methyl)piperidin-1-yl)phenyl)propanoic acid;

compound (175): 2-(2,6-dimethyl-4-(methylcarbamoyl)benzamido)-3-(4-(4-((pyridin-2-ylamino)methyl)piperidin-1-yl)phenyl)propanoic acid;

compound (176): 2-(4-(methoxycarbonyl)-2,6-dimethylbenzamido)-3-(4-(4-((pyridin-2-ylamino)methyl)piperidin-1-yl)phenyl)propanoic acid;

compound (177): 2-(4-cyano-2-ethyl-6-methylbenzamido)-3-(4-(4-((4-oxo-1,4,5,6-tetrahydropyrimidin-2-ylamino)methyl)piperidin-1-yl)phenyl)propanoic acid;

compound (178): 2-(4-cyano-2-ethyl-6-methyl-benzoylamino)-3-{4-[4-(1,4,5,6-tetrahydro-pyrimidin-2-ylcarbamoyl)piperidin-1-yl]phenyl}propionic acid;

compound (180): 2-(4-acetyl-2-ethyl-6-methyl-benzoylamino)-3-{4-[4-(4,5-dihydro-1H-imidazol-2-ylcarbamoyl)piperidin-1-yl]phenyl}propionic acid;

compound (181): 2-(2-ethyl-4-fluoro-6-methylbenzamido)-3-(4-(4-((4-methoxypyridin-2-ylamino)methyl)piperidin-1-yl)phenyl)propanoic acid;

compound (183): 2-(4-chloro-2-ethyl-6-methylbenzamido)-3-(4-(4-((4-methylpyridin-2-ylamino)methyl)-2-oxopyrrolidin-1-yl)phenyl)propanoic acid;

compound (184): 2-(4-chloro-2-ethyl-6-methylbenzamido)-3-(4-(4-((4-methylpyridin-2-ylamino)methyl)piperidin-1-yl)phenyl)propanoic acid;

compound (185): 2-(2-bromo-6-methylbenzamido)-3-(4-(4-((pyridin-2-ylamino)methyl)piperidin-1-yl)phenyl)propanoic acid;

compound (186): 2-(2-ethyl-4-(1H-imidazol-1-yl)-6-methylbenzamido)-3-(4-(4-((pyridin-2-ylamino)methyl)-4,5-dihydrooxazol-2-yl)phenyl)propanoic acid;

compound (187): 2-(4-(1H-imidazol-1-yl)-2,6-dimethylbenzamido)-3-(4-(4-((pyridin-2-ylamino)methyl)piperidin-1-yl)phenyl)propanoic acid;

compound (188): 2-(4-(1H-imidazol-2-yl)-2,6-dimethylbenzamido)-3-(4-(4-((pyridin-2-ylamino)methyl)piperidin-1-yl)phenyl)propanoic acid;

compound (189): 2-(2-ethyl-4-(1H-imidazol-1-yl)-6-methylbenzamido)-3-(4-(3-((pyridin-2-ylamino)methyl)pyrrolidin-1-yl)phenyl)propanoic acid;

compound (190): 2-(4-chloro-2-methyl-6-(methylthio)benzamido)-3-(4-(4-((pyridin-2-ylamino)methyl)piperidin-1-yl)phenyl)propanoic acid;

compound (191): 2-(2,6-dimethyl-4-(oxazol-2-yl)benzamido)-3-(4-(4-((pyridin-2-ylamino)methyl)piperidin-1-yl)phenyl)propanoic acid;

compound (192): 2-(4-chloro-2-ethyl-6-methylbenzamido)-3-(4-(4-((4-oxo-1,4,5,6-tetrahydropyrimidin-2-ylamino)methyl)piperidin-1-yl)phenyl)propanoic acid;

compound (193): 2-(4-chloro-2-ethyl-6-methyl-benzoylamino)-3-{4-[4-(1,4,5,6-tetrahydro-pyrimidin-2-ylcarbamoyl)piperidin-1-yl]phenyl}propionic acid;

compound (194): 2-(2,6-dimethyl-4-(trifluoromethyl)benzamido)-3-(4-(4-((pyridin-2-ylamino)methyl)piperidin-1-yl)phenyl)propanoic acid;

compound (195): 2-(2-ethyl-6-methyl-4-(trifluoromethyl)benzamido)-3-(4-(4-((pyridin-2-ylamino)methyl)-4,5-dihydrooxazol-2-yl)phenyl)propanoic acid;

compound (196): 2-(2-ethyl-6-methyl-4-(trifluoromethyl)benzamido)-3-(4-(3-((pyridin-2-ylamino)methyl)pyrrolidin-1-yl)phenyl)propanoic acid;

compound (197): 2-(4-cyano-2-ethyl-6-methylbenzamido)-3-(4-(4-((4-methoxypyridin-2-ylamino)methyl)piperidin-1-yl)phenyl)propanoic acid;

compound (198): 2-(2-methyl-4-(trifluoromethoxy)benzamido)-3-(4-(4-((pyridin-2-ylamino)methyl)piperidin-1-yl)phenyl)propanoic acid;

compound (199): 2-(4-acetyl-2-ethyl-6-methylbenzamido)-3-(4-(4-((4-methylpyridin-2-ylamino)methyl)-2-oxopyrrolidin-1-yl)phenyl)propanoic acid;

compound (200): 2-(4-acetyl-2-ethyl-6-methylbenzamido)-3-(4-(4-((4-methylpyridin-2-ylamino)methyl)piperidin-1-yl)phenyl)propanoic acid;

compound (201): 2-(2-ethyl-6-methyl-4-(methylcarbamoyl)benzamido)-3-(4-(4-((pyridin-2-ylamino)methyl)piperidin-1-yl)phenyl)propanoic acid;

compound (202): 2-(4-(dimethylcarbamoyl)-2,6-dimethylbenzamido)-3-(4-(4-((pyridin-2-ylamino)methyl)piperidin-1-yl)phenyl)propanoic acid;

compound (203): 3-(4-(4-((1H-benzo[d]imidazol-2-ylamino)methyl)piperidin-1-yl)phenyl)-2-(2-ethyl-4-fluoro-6-methylbenzamido)propanoic acid;

compound (208): 2-(4-chloro-2-ethyl-6-methylbenzamido)-3-(4-(4-(5,6,7,8-tetrahydro-1,8-naphthyridin-2-yl)piperidin-1-yl)phenyl)propanoic acid;

compound (209): 2-(4-acetyl-2-ethyl-6-methylbenzamido)-3-(4-(4-((4-oxo-1,4,5,6-tetrahydropyrimidin-2-ylamino)methyl)piperidin-1-yl)phenyl)propanoic acid;

compound (210): 2-(4-acetyl-2-ethyl-6-methyl-benzoylamino)-3-{4-[4-(1,4,5,6-tetrahydro-pyrimidin-2-ylcarbamoyl)piperidin-1-yl]phenyl}propionic acid;

compound (211): 2-(4-(benzyloxy)benzamido)-3-(4-(4-((pyridin-2-ylamino)methyl)piperidin-1-yl)phenyl)propanoic acid;

compound (212): 2-(2,6-dimethyl-4-(methylsulfonyl)benzamido)-3-(4-(4-((pyridin-2-ylamino)methyl)piperidin-1-yl)phenyl)propanoic acid;

compound (213): 3-(4-(4-((1H-benzo[d]imidazol-2-ylamino)methyl)piperidin-1-yl)phenyl)-2-(4-cyano-2-ethyl-6-methylbenzamido)propanoic acid;

compound (214): 2-(4-chloro-2-ethyl-6-methylbenzamido)-3-(4-(4-((4-methoxypyridin-2-ylamino)methyl)piperidin-1-yl)phenyl)propanoic acid;

compound (215): 2-(2,6-dimethyl-4-sulfamoyl-benzoylamino)-3-{4-[4-(pyridin-2-ylaminomethyl)piperidin-1-yl]phenyl}propionic acid;

compound (216): 2-(2-ethyl-4-(1H-imidazol-1-yl)-6-methylbenzamido)-3-(4-(4-((pyridin-2-ylamino)methyl)piperidin-1-yl)phenyl)propanoic acid;

compound (217): 2-[2-ethyl-4-(1H-imidazol-2-yl)-6-methyl-benzoylamino]-3-{4-[4-(pyridin-2-ylaminomethyl)piperidin-1-yl]phenyl}propionic acid;

compound (218): 2-(2-ethyl-4-(1H-imidazol-1-yl)-6-methylbenzamido)-3-(4-(5-((pyridin-2-ylamino)methyl)-5,6-dihydro-4H-1,3-oxazin-2-yl)phenyl)propanoic acid;

compound (219): 2-(2-ethyl-4-(1H-imidazol-1-yl)-6-methylbenzamido)-3-(4-(2-oxo-4-((pyridin-2-ylamino)methyl)pyrrolidin-1-yl)phenyl)propanoic acid;

compound (220): 2-(2-ethyl-6-methyl-4-(oxazol-2-yl)benzamido)-3-(4-(4-((pyridin-2-ylamino)methyl)piperidin-1-yl)phenyl)propanoic acid;

compound (221): 2-(2-ethyl-6-methyl-4-(trifluoromethyl)benzamido)-3-(4-(4-((pyridin-2-ylamino)methyl)piperidin-1-yl)phenyl)propanoic acid;

compound (222): 2-(2-ethyl-6-methyl-4-(trifluoromethyl)benzamido)-3-(4-(5-((pyridin-2-ylamino)methyl)-5,6-dihydro-4H-1,3-oxazin-2-yl)phenyl)propanoic acid;

compound (223): 2-(2-ethyl-6-methyl-4-(trifluoromethyl) benzamido)-3-(4-(2-oxo-4-((pyridin-2-ylamino)methyl)pyrrolidin-1-yl)phenyl)propanoic acid;

compound (224): 2-(4-acetyl-2-ethyl-6-methylbenzamido)-3-(4-(4-(5,6,7,8-tetrahydro-1,8-naphthyridin-2-yl)piperidin-1-yl)phenyl)propanoic acid;

compound (225): 2-(4-(dimethylcarbamoyl)-2-ethyl-6-methylbenzamido)-3-(4-(4-((pyridin-2-ylamino)methyl)piperidin-1-yl)phenyl)propanoic acid;

compound (226): 3-{4-[4-(4,5-dihydro-1H-imidazol-2-ylcarbamoyl)piperidin-1-yl]phenyl}-2-[2-ethyl-4-(1H-imidazol-2-yl)-6-methyl-benzoylamino]propionic acid;

compound (227): 2-(4-acetyl-2-ethyl-6-methylbenzamido)-3-(4-(4-((4-methoxypyridin-2-ylamino)methyl)piperidin-1-yl)phenyl)propanoic acid;

compound (228): 2-(2-ethyl-4-(1H-imidazol-1-yl)-6-methylbenzamido)-3-(1-(3-(5,6,7,8-tetrahydro-1,8-naphthyridin-2-yl)propanoyl)piperidin-4-yl)propanoic acid;

compound (229): 3-{4-[4-(4,5-dihydro-1H-imidazol-2-ylcarbamoyl)piperidin-1-yl]phenyl}-2-(2-ethyl-6-methyl-4-trifluoromethyl-benzoylamino)propionic acid;

compound (230): 3-(4-(4-((1H-benzo[d]imidazol-2-ylamino)methyl)piperidin-1-yl)phenyl)-2-(4-chloro-2-ethyl-6-methylbenzamido)propanoic acid;

compound (232): 2-(2-ethyl-4-methanesulfonyl-6-methyl-benzoylamino)-3-{4-[4-(pyridin-2-ylaminomethyl)piperidin-1-yl]phenyl}propionic acid;

compound (233): 2-(2-ethyl-4-(1H-imidazol-1-yl)-6-methylbenzamido)-3-(4-(4-(((4-methylpyridin-2-ylamino)methyl)-2-oxopyrrolidin-1-yl)phenyl)propanoic acid;

compound (234): 2-(2-ethyl-4-(1H-imidazol-1-yl)-6-methylbenzamido)-3-(4-(4-((4-methylpyridin-2-ylamino)methyl)piperidin-1-yl)phenyl)propanoic acid;

compound (235): 3-(4-(4-((1H-benzo[d]imidazol-2-ylamino)methyl)piperidin-1-yl)phenyl)-2-(4-acetyl-2-ethyl-6-methylbenzamido)propanoic acid;

compound (236): 2-(2,6-dimethyl-4-(2,2,2-trifluoroacetyl)benzamido)-3-(4-(4-((pyridin-2-ylamino)methyl)piperidin-1-yl)phenyl)propanoic acid;

compound (237): 2-(2-ethyl-6-methyl-4-(trifluoromethyl) benzamido)-3-(4-(4-((4-methylpyridin-2-ylamino)methyl)-2-oxopyrrolidin-1-yl)phenyl)propanoic acid;

compound (238): 2-(2-ethyl-6-methyl-4-(trifluoromethyl) benzamido)-3-(4-(4-((4-methylpyridin-2-ylamino)methyl)piperidin-1-yl)phenyl)propanoic acid;

compound (239): 2-(2-ethyl-6-methyl-4-(trifluoromethoxy)benzamido)-3-(4-(4-((pyridin-2-ylamino) methyl)piperidin-1-yl)phenyl)propanoic acid;

compound (240): 2-(2-ethyl-4-(1H-imidazol-1-yl)-6-methylbenzamido)-3-(4-(4-((4-oxo-1,4,5,6-tetrahydropyrimidin-2-ylamino)methyl)piperidin-1-yl)phenyl)propanoic acid;

compound (241): 2-[2-ethyl-4-(1H-imidazol-2-yl)-6-methyl-benzoylamino]-3-{4-[4-(1,4,5,6-tetrahydro-pyrimidin-2-ylcarbamoyl)piperidin-1-yl]phenyl}propionic acid;

compound (242): 2-(2-methyl-6-(methylthio)-4-(trifluoromethyl)benzamido)-3-(4-(4-((pyridin-2-ylamino) methyl)piperidin-1-yl)phenyl)propanoic acid;

compound (243): 2-(2-ethyl-6-methyl-4-(trifluoromethyl) benzamido)-3-(4-(4-((4-oxo-1,4,5,6-tetrahydropyrimidin-2-ylamino)methyl)piperidin-1-yl)phenyl)propanoic acid;

compound (244): 2-(2-ethyl-6-methyl-4-trifluoromethyl-benzoylamino)-3-{4-[4-(1,4,5,6-tetrahydro-pyrimidin-2-ylcarbamoyl)piperidin-1-yl]phenyl}propionic acid;

compound (245): 2-(2-ethyl-6-methyl-4-methylsulfamoyl-benzoylamino)-3-{4-[4-(pyridin-2-ylaminomethyl)piperidin-1-yl]phenyl}propionic acid;

compound (246): 2-(4-(N,N-dimethylsulfamoyl)-2,6-dimethylbenzamido)-3-(4-(4-((pyridin-2-ylamino)methyl) piperidin-1-yl)phenyl)propanoic acid;

compound (247): 2-(2-ethyl-6-methyl-4-(trifluoromethyl) benzamido)-3-(4-(4-(5,6,7,8-tetrahydro-1,8-naphthyridin-2-yl)piperidin-1-yl)phenyl)propanoic acid;

compound (248): 2-[2-ethyl-6-methyl-4-(2,2,2-trifluoroacetyl)benzoylamino]-3-{4-[4-(pyridin-2-ylaminomethyl)piperidin-1-yl]phenyl}propionic acid;

compound (249): 2-(2-ethyl-4-(1H-imidazol-1-yl)-6-methylbenzamido)-3-(4-(4-((4-methoxypyridin-2-ylamino)methyl)piperidin-1-yl)phenyl)propanoic acid;

compound (250): 2-(2-ethyl-6-methyl-4-(trifluoromethyl) benzamido)-3-(4-(4-((4-methoxypyridin-2-ylamino) methyl)piperidin-1-yl)phenyl)propanoic acid;

compound (251): 2-(2,6-dimethyl-4-(trichloromethyl) benzamido)-3-(4-(4-((pyridin-2-ylamino)methyl)piperidin-1-yl)phenyl)propanoic acid;

compound (252): 3-(4-(4-((1H-benzo[d]imidazol-2-ylamino)methyl)piperidin-1-yl)phenyl)-2-(2-ethyl-4-(1H-imidazol-1-yl)-6-methylbenzamido)propanoic acid;

compound (253): 3-(4-(4-((1H-benzo[d]imidazol-2-ylamino)methyl)piperidin-1-yl)phenyl)-2-(2-ethyl-6-methyl-4-(trifluoromethyl)benzamido)propanoic acid;

compound (254): 2-(4-dimethylsulfamoyl-2-ethyl-6-methyl-benzoylamino)-3-{4-[4-(pyridin-2-ylaminomethyl)piperidin-1-yl]phenyl}propionic acid;

compound (255): 2-(2-ethyl-6-methyl-4-trichloromethyl-benzoylamino)-3-{4-[4-(pyridin-2-ylaminomethyl)piperidin-1-yl]phenyl}propionic acid;

compound (256): 2-(2,6-dimethyl-4-(trifluoromethylsulfonyl)benzamido)-3-(4-(4-((pyridin-2-ylamino)methyl)piperidin-1-yl)phenyl)propanoic acid;

compound (257): 2-(2-ethyl-6-methyl-4-trifluoromethanesulfonyl-benzoylamino)-3-{4-[4-(pyridin-2-ylaminomethyl)piperidin-1-yl]phenyl}propionic acid;

compound (258): 3-(4-(4-((pyridin-2-ylamino)methyl)piperidin-1-yl)phenyl)-2-(2,4,6-tribromobenzamido)propanoic acid;

compound (259): 2-(2,6-dimethyl-benzoylamino)-3-(4-{4-[(4-methyl-pyridin-2-ylamino)methyl]piperidin-1-yl}phenyl)propionic acid;

compound (260): 2-(4-cyano-benzoylamino)-3-(4-{4-[(4-methyl-pyridin-2-ylamino)methyl]piperidin-1-yl}phenyl)propionic acid;

compound (261): 3-(4-{4-[(4-methyl-pyridin-2-ylamino) methyl]piperidin-1-yl}phenyl)-2-(2,4,6-tribromo-benzoylamino)propionic acid;

compound (262): 2-benzoylamino-3-(4-{4-[(4-methyl-pyridin-2-ylamino)methyl]piperidin-1-yl}phenyl)propionic acid;

compound (263): 2-(4-fluoro-2,6-dimethyl-benzoylamino)-3-(4-{4-[(4-methyl-pyridin-2-ylamino)methyl]piperidin-1-yl}phenyl)propionic acid;

compound (264): 2-(2-bromo-6-methyl-benzoylamino)-3-(4-{4-[(4-methyl-pyridin-2-ylamino)methyl]piperidin-1-yl}phenyl)propionic acid;

compound (265): 2-(2-methyl-benzoylamino)-3-(4-{4-[(4-methyl-pyridin-2-ylamino)methyl]piperidin-1-yl}phenyl)propionic acid;

compound (266): 2-(3-methyl-2-phenyl-butyrylamino)-3-(4-{4-[(4-methyl-pyridin-2-ylamino)methyl]piperidin-1-yl}phenyl)propionic acid;

compound (267): 2-(2,6-dimethyl-benzoylamino)-3-(4-{4-[(4-methoxy-pyridin-2-ylamino)methyl]piperidin-1-yl}phenyl)propionic acid;

compound (268): 2-(4-fluoro-2,6-dimethyl-benzoylamino)-3-(4-{4-[(4-methoxy-pyridin-2-ylamino)methyl]piperidin-1-yl}phenyl)propionic acid;

compound (269): 3-(4-{4-[(3-propyl-ureido)methyl]piperidin-1-yl}phenyl)-2-(2,4,6-trimethyl-benzoylamino)propionic acid;

compound (270): 3-{4-[4-(3-cyclopropylmethyl-ureidomethyl)piperidin-1-yl)phenyl}trimethyl-benzoylamino)propionic acid;

compound (271): 3-(4-{4-[(3-cyclobutyl-ureido)methyl]piperidin-1-yl}phenyl)-2-(2,4,6-trimethyl-benzoylamino)propionic acid;

compound (272): 3-(4-{4-[3-(2,2,2-trifluoro-ethyl)ureidomethyl]piperidin-1-yl}phenyl)-2-(2,4,6-trimethyl-benzoylamino)propionic acid; and compound (273): 3-(4-{4-[3-(2,2,3,3,3-pentafluoro-propyl)ureidomethyl]piperidin-1-yl}phenyl)-2-(2,4,6-trimethyl-benzoylamino)propionic acid.

2. A pharmaceutical composition comprising a compound according to claim 1 and a pharmaceutically acceptable carrier, diluent or excipient.

3. A method of treating a disease based on pathological angiogenesis, comprising administering a pharmaceutical composition according claim 2 to a patient suffering from a disease based on pathological angiogenesis.

4. The method according to claim 3, wherein treating a disease based on pathological angiogenesis further comprises performing a sequential or combination therapy selected from the group consisting of chemotherapy, anti-proliferative therapy, anti-hormone therapy, radiation therapy, photodynamic therapy, surgery, anti-fibrotic therapy, anti-inflammatory therapy, immunosuppressive therapy and anti-angiogenic therapy.

* * * * *

UNITED STATES PATENT AND TRADEMARK OFFICE
CERTIFICATE OF CORRECTION

PATENT NO. : 8,927,534 B2
APPLICATION NO. : 12/162798
DATED : January 6, 2015
INVENTOR(S) : Gunther Zischinsky et al.

Page 1 of 1

It is certified that error appears in the above-identified patent and that said Letters Patent is hereby corrected as shown below:

In the Claims:

Column 127, claim 1, lines 11-12, the word "phenyl}trimethyl-benzoylamino)" should read "phenyl}-2-(2,4,6-trimethyl-benzoylamino)".

Signed and Sealed this
Fourteenth Day of July, 2015

Michelle K. Lee
*Director of the United States Patent and Trademark Office*